(12) United States Patent
Climax et al.

(10) Patent No.: US 12,076,304 B2
(45) Date of Patent: Sep. 3, 2024

(54) COMPOSITIONS COMPRISING 15-HEPE AND METHODS OF TREATING OR PREVENTING HEMATOLOGIC DISORDERS, AND/OR RELATED DISEASES

(71) Applicant: Afimmune Limited, Dublin (IE)

(72) Inventors: John Climax, Dublin (IE); Moayed Hamza, Dublin (IE); Markus Weissbach, Dublin (IE); David Coughlan, Dublin (IE)

(73) Assignee: Afimmune Limited (IE)

( * ) Notice: Subject to any disclaimer, the term of this patent is extended or adjusted under 35 U.S.C. 154(b) by 124 days.

(21) Appl. No.: 17/738,181

(22) Filed: May 6, 2022

(65) Prior Publication Data
US 2022/0265593 A1    Aug. 25, 2022

Related U.S. Application Data

(63) Continuation of application No. 16/839,899, filed on Apr. 3, 2020, now abandoned.

(51) Int. Cl.
*A61K 31/202* (2006.01)
*A61K 9/00* (2006.01)
*A61K 31/232* (2006.01)

(52) U.S. Cl.
CPC .......... *A61K 31/202* (2013.01); *A61K 31/232* (2013.01); *A61K 9/0053* (2013.01)

(58) Field of Classification Search
CPC .. A61K 31/202; A61K 31/232; A61K 9/0053; A61P 1/00
See application file for complete search history.

(56) References Cited

U.S. PATENT DOCUMENTS

| | | |
|---|---|---|
| 3,055,923 A | 9/1962 | Ginger et al. |
| 4,273,763 A | 6/1981 | Horrobin |
| 4,309,415 A | 1/1982 | Horrobin |
| 4,386,072 A | 5/1983 | Horrobin et al. |
| 4,388,324 A | 6/1983 | Horrobin |
| 4,415,554 A | 11/1983 | Horrobin |
| 4,444,755 A | 4/1984 | Horrobin |
| 4,681,896 A | 7/1987 | Horrobin |
| 4,776,984 A | 10/1988 | Traitler et al. |
| 4,826,877 A | 5/1989 | Stewart et al. |
| 4,888,326 A | 12/1989 | Horrobin |
| 4,898,885 A | 2/1990 | Horrobin |
| 4,965,075 A | 10/1990 | Horrobin et al. |
| 4,970,076 A | 11/1990 | Horrobin |
| 4,996,233 A | 2/1991 | Horrobin |
| 4,997,657 A | 3/1991 | Horrobin et al. |
| 5,106,542 A | 4/1992 | Traitler et al. |
| 5,198,468 A | 3/1993 | Horrobin |
| 5,318,991 A | 6/1994 | Horobin et al. |
| 5,324,748 A | 6/1994 | Horrobin |
| 5,380,757 A | 1/1995 | Horrobin |
| 5,562,913 A | 10/1996 | Horrobin |
| 5,580,556 A | 12/1996 | Horrobin |
| 5,583,159 A | 12/1996 | Horrobin et al. |
| 5,589,509 A | 12/1996 | Horrobin |
| 5,618,558 A | 4/1997 | Horrobin et al. |
| 5,663,202 A | 9/1997 | Horrobin et al. |
| 5,696,166 A | 12/1997 | Yanni |
| 5,709,885 A | 1/1998 | Hellen et al. |
| 5,789,441 A | 8/1998 | Gosselin et al. |
| 5,888,541 A | 3/1999 | Horrobin et al. |
| 6,069,168 A | 5/2000 | Horrobin et al. |
| 6,140,304 A | 10/2000 | Sears |
| 6,177,470 B1 | 1/2001 | Horrobin et al. |
| 6,359,158 B1 | 3/2002 | Falck et al. |
| 6,368,621 B1 | 4/2002 | Engel et al. |
| 6,479,544 B1 | 11/2002 | Horrobin |
| 6,602,690 B2 | 8/2003 | Kawashima et al. |
| 6,630,157 B1 | 10/2003 | Horrobin et al. |
| 6,670,396 B2 | 12/2003 | Serhan et al. |
| 7,202,276 B2 | 4/2007 | Buchanan et al. |
| 7,579,362 B2 | 8/2009 | Feuerbach et al. |
| 7,666,447 B2 | 2/2010 | Rockway |
| 7,888,393 B2 | 2/2011 | Bettle |
| 7,893,106 B2 | 2/2011 | Arterburn et al. |
| 8,293,790 B2 | 10/2012 | Manku et al. |
| 8,455,035 B2 | 6/2013 | Rein et al. |
| 8,536,223 B2 | 9/2013 | Kelliher et al. |
| 8,729,126 B2 | 5/2014 | Kelliher et al. |
| 8,936,803 B2 | 1/2015 | Manku et al. |
| 8,945,886 B2 | 2/2015 | Katano et al. |
| 9,006,287 B2 | 4/2015 | Tateishi et al. |
| 9,050,308 B2 | 6/2015 | Maines et al. |
| 9,056,086 B2 | 6/2015 | Manku et al. |
| 9,096,815 B2 | 8/2015 | Manku et al. |
| 9,682,055 B2 | 6/2017 | Manku et al. |

(Continued)

FOREIGN PATENT DOCUMENTS

| | | |
|---|---|---|
| AU | 2011253846 | 1/2012 |
| CA | 1334002 | 1/1995 |
| DE | 4238869 | 5/1994 |
| EP | 0035856 | 9/1981 |
| EP | 0037175 | 10/1981 |
| EP | 0087863 | 9/1983 |
| EP | 0087864 | 9/1983 |
| EP | 0087865 | 9/1983 |
| EP | 0115419 | 8/1984 |
| EP | 0132089 | 1/1985 |
| EP | 0139480 | 5/1985 |
| EP | 0173478 | 3/1986 |
| EP | 0309086 | 3/1989 |
| EP | 0334507 | 9/1989 |
| EP | 0409559 | 1/1991 |
| EP | 0416855 | 3/1991 |
| EP | 1571195 | 9/2005 |

(Continued)

OTHER PUBLICATIONS

JohnsHopkinsMedicine, 2023 (Year: 2023).*

(Continued)

*Primary Examiner* — Umamaheswari Ramachandran
(74) *Attorney, Agent, or Firm* — Perkins Coie LLP

(57) ABSTRACT

The present disclosure relates to methods of treating or preventing hematologic disorders by administration of 15-HEPE or compositions thereof.

9 Claims, 71 Drawing Sheets

Specification includes a Sequence Listing.

(56) References Cited

U.S. PATENT DOCUMENTS

| | | |
|---|---|---|
| 9,855,238 B2 | 1/2018 | Coughlan et al. |
| 9,889,106 B2 | 2/2018 | Kelliher et al. |
| 10,105,333 B2 | 10/2018 | Manku et al. |
| 10,154,977 B2 | 12/2018 | Serhan et al. |
| 10,231,945 B2 | 3/2019 | Coughlan et al. |
| 10,363,235 B2 | 7/2019 | Rowe et al. |
| 2002/0052000 A1 | 5/2002 | Parthasarathy et al. |
| 2002/0055538 A1 | 5/2002 | Serhan et al. |
| 2004/0043013 A1 | 3/2004 | McCleary |
| 2005/0032757 A1 | 2/2005 | Cho |
| 2005/0239889 A1 | 10/2005 | Gosselin et al. |
| 2005/0282781 A1 | 12/2005 | Ghosal |
| 2006/0009522 A1 | 1/2006 | Dana et al. |
| 2006/0078625 A1 | 4/2006 | Rockway |
| 2006/0160095 A1 | 7/2006 | Hayes et al. |
| 2007/0105954 A1 | 5/2007 | Puri |
| 2007/0248586 A1 | 10/2007 | Arterburn et al. |
| 2008/0108699 A1 | 5/2008 | Tateishi et al. |
| 2010/0056486 A1 | 3/2010 | Gras Escardo et al. |
| 2010/0216882 A1 | 8/2010 | Serhan et al. |
| 2010/0233724 A1 | 9/2010 | Watkins et al. |
| 2010/0317735 A1 | 12/2010 | Hong et al. |
| 2011/0016585 A1 | 1/2011 | Pereira et al. |
| 2011/0039010 A1 | 2/2011 | Rein et al. |
| 2011/0059885 A1 | 3/2011 | Lea et al. |
| 2011/0105510 A1 | 5/2011 | Ishikawa |
| 2012/0142773 A1 | 6/2012 | Kelliher et al. |
| 2012/0213824 A1 | 8/2012 | Kelliher et al. |
| 2012/0232147 A1 | 9/2012 | Manku et al. |
| 2012/0264705 A1 | 10/2012 | Manku et al. |
| 2012/0264824 A1 | 10/2012 | Mizuguchi et al. |
| 2013/0101533 A1 | 4/2013 | Manku et al. |
| 2013/0102575 A1 | 4/2013 | Manku et al. |
| 2013/0150602 A1 | 6/2013 | Kelliher et al. |
| 2013/0267598 A1 | 10/2013 | Manku et al. |
| 2013/0274338 A1 | 10/2013 | Manku et al. |
| 2013/0310422 A1 | 11/2013 | Brown et al. |
| 2013/0331448 A1 | 12/2013 | Manku et al. |
| 2014/0079631 A1 | 3/2014 | Serhan et al. |
| 2015/0079164 A1 | 3/2015 | Fraser et al. |
| 2015/0196521 A1 | 7/2015 | Manku et al. |
| 2015/0224076 A1 | 8/2015 | Rowe et al. |
| 2018/0104207 A1 | 4/2018 | Coughlan et al. |
| 2018/0256597 A1 | 9/2018 | Serhan et al. |

FOREIGN PATENT DOCUMENTS

| | | |
|---|---|---|
| EP | 1852114 | 11/2007 |
| EP | 2762143 | 8/2014 |
| GB | 2504061 | 1/2014 |
| JP | A-S52-64452 | 5/1977 |
| JP | A-S52-66659 | 6/1977 |
| JP | 4-290820 | 10/1992 |
| JP | A-H05-186342 | 7/1993 |
| JP | H05201924 | 8/1993 |
| JP | H06128154 | 5/1994 |
| JP | H07126160 | 5/1995 |
| JP | H09505562 | 6/1997 |
| JP | AH10500111 | 1/1998 |
| JP | 2000191525 | 7/2000 |
| JP | 2002047176 | 2/2002 |
| JP | A2003513949 | 4/2003 |
| JP | A2003525880 | 9/2003 |
| JP | 2004528360 | 9/2004 |
| JP | 2005179211 | 7/2005 |
| JP | 2006219454 | 8/2006 |
| JP | 2006306812 | 11/2006 |
| JP | 2008167721 | 7/2008 |
| JP | 2008-543865 | 12/2008 |
| JP | 2013517304 | 5/2013 |
| JP | 2015508094 | 3/2015 |
| JP | A2015140323 | 8/2015 |
| RU | 94002337 | 8/1996 |
| RU | 2205004 | 5/2003 |
| WO | WO 1990/014824 | 12/1990 |
| WO | WO 1997/029751 | 8/1997 |
| WO | WO 1998/016215 | 4/1998 |
| WO | WO 1998/052556 | 11/1998 |
| WO | WO 99/45916 | 9/1999 |
| WO | WO 01/03696 | 1/2001 |
| WO | WO 01/34549 | 5/2001 |
| WO | WO 2001/049282 | 7/2001 |
| WO | WO 2001/060778 | 8/2001 |
| WO | WO 02/096408 | 12/2002 |
| WO | WO 2003/063793 | 8/2003 |
| WO | WO 2004/072013 | 8/2004 |
| WO | WO 2007118335 | 10/2007 |
| WO | WO 2008/114141 | 9/2008 |
| WO | WO 2009/098454 | 8/2009 |
| WO | WO 2010/125330 | 11/2010 |
| WO | WO 2012/023254 | 2/2012 |
| WO | WO 2012/087745 | 6/2012 |
| WO | WO 2012/135032 | 10/2012 |
| WO | WO 2013/057287 | 4/2013 |
| WO | WO 2013057284 | 4/2013 |
| WO | WO 2013/082265 | 6/2013 |
| WO | WO 2013/090833 | 6/2013 |
| WO | WO 2013/103902 | 7/2013 |
| WO | WO 2013/112876 | 8/2013 |
| WO | WO 2013/124479 | 8/2013 |
| WO | WO 2013/170006 | 11/2013 |
| WO | WO 2014/019919 | 2/2014 |
| WO | WO 2014/022816 | 2/2014 |
| WO | WO 2014/040921 | 3/2014 |
| WO | WO 2014/105576 | 7/2014 |
| WO | WO 2014/118097 | 8/2014 |
| WO | WO 2014/142364 | 9/2014 |
| WO | WO 2014/170504 | 10/2014 |
| WO | WO 2015071766 | 5/2015 |
| WO | WO 2015/106215 | 7/2015 |
| WO | WO 2015/185698 | 12/2015 |
| WO | WO 2016/090030 | 6/2016 |
| WO | WO 2016/113635 | 7/2016 |
| WO | WO 2016/181221 | 11/2016 |
| WO | WO 2017/013492 | 1/2017 |
| WO | WO 2017/118911 | 7/2017 |

OTHER PUBLICATIONS

MedicalNewsToday, Nov. 2021 (Year: 2021).*
VerywellHealth, 2022 (Year: 2022).*
Healthline (Year: 2018).*
"Blood sample volumes," National Centre for the Replacement Refinement & Reduction of Animals in Research (adapted Wolfensohn & Lloyd, 2003, Handbook of Laboratory Animal Management and Welfare, 3rd Edition) (publication date: Nov. 28, 2003) (https://www.nc3rs.org.uk/blood-sample-volumes; accessed Mar. 27, 2019).
AASLD Abstracts. Hepatology, 598A-702A (publication date: Oct. 2005).
Araujo et al., "Evaluation of a Rapid Method for the Quantitative Analysis of Fatty Acids in Various Matrices," J. Chromatogr A., 1212(1-2):106-113 (publication date: Nov. 28, 2008, epublication date: Oct. 8, 2008).
Argo et al., "Effects of N-3 Fish Oil on Metabolic and Histological Parameters in NASH:A Double-Blind, Randomized, Placebo-Controlled Trial," Journal of Hepatology, (publication date: Jan. 2015, epublication date: Sep. 6, 2014).
Armstrong et al., "Inhibitory and mechanistic investigations of oxo-lipids with humanlipoxygenase isozymes," Bioorganic & Medicinal Chemistry. 22(15):4293-4297 (publication date: Aug. 1, 2014, epublication date: May 21, 2014).
Astarita, et al., "Targeted lipidomic strategies for oxygenated metabolites ofpolyunsaturated fatty acids," Biochimica et Biophysica Acta 1851, pp. 456-468 (publication date: Apr. 2015, epublication date: Dec. 5, 2014).
Ballard et al., "Alzheimer's disease," Lancet. 377:1019-1031 (publication date: Mar. 19, 2011, epublication date: Mar. 2, 2011).
Banno, "Diversified Approach to Acne Care by Using Natural Raw Materials," Fragrance Journal, 35(5):36-41 (publication date: May 2007) (with English translation).

(56) References Cited

OTHER PUBLICATIONS

Barnes, "Mediators of Chronic Obstructive Pulmonary Disease," Pharmacol Rev 56(4):515-48 (publicaiton date: Dec. 2004).
Baskin-Bey et al., "Constitutive androstane receptor agonist, TCPOBOP, attenuates steatohepatitis in the methionine choline-deficient diet-fed mouse," World J Gastroenterol, 13(42): pp. 5635-5641 (publication date: Nov. 14, 2007).
Boston et al., "Ethyl-EPA in Alzheimer's disease—a pilot study," Prostaglandins, Leukotrienes and Essential Fatty Acids. 71(5):341-346 (publication date: Nov. 2004).
Boyd, "Thiazolidinediones in dermatology," 46(6):557-63 (publication date: Jun. 2007) Abstract only.
Brooks et al., "The fatty acid oxidation product 15-A3t-isoprostane is a potent inhibitor of NFκB transcription and macrophage transformation," Journal of Neurochemistry 119:604-616 (publication date: Nov. 2011, epublication date: Sep. 23, 2011).
Cardoso et al., "Insulin and Insulin-Sensitizing Drugs in Neurodegeneration: Mitochondria as Therapeutic Targets," Pharmaceuticals (Base) 2(3):250-286 (publication date: Dec. 2009).
Cayman Chemical, Product Information: Dihomo-γ-Linolenic Acid, Item No. 90230 (publication date: Jul. 7, 2011).
Center for Drug Evaluation and Research, "Guidance for Industry Estimating the Maximum Safe Starting Dose in Initial Clinical Trials for Therapeutics in Adult Healthy Volunteers," Pharmacology and Toxicology (publication date: Jul. 2005).
Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology, 55(6):,2005-2023 (publication date: Jun. 2012).
Chen et al., "Peroxisome proliferator-activated receptor gamma (PPAR-γ) and neurodegenerative disorders," Mol Neurobiol 46(1):114-24 (publication date: Aug. 2012) Abstract only.
Chen et al.; "Therapeutic Effect of Topical Gamma-Linolenic Acid on Refractory Uremic Pruritus"; American Journal of Kidney Diseases 48(1):69-76 (publication date: Jul. 2006).
Cho et al., "A novel 15-hydroxyeicosatienoic acid-substituted diacylglycerol (15-HETrE-DAG) selectively inhibits epidermal protein kinase C-[beta],"Biochimica ET Biophysica Acta (BBA)-Lipids and Lipid Metabolism, 1349(1):67-71 (publication date: Nov. 8, 1997).
Chronic Obstructive Airway Disease, Merck Manual, Japanese edition, Japan, Nikkei Business Publications, Inc., 17th edition, pp. 558-586 (publication date: Dec. 10, 1999) (with English translation).
Conrow et al., "Manufacture of (5Z,8Z,11Z,13E)(15S)-15-Hydroxyeicosa-5,8,11,13-tetraenoic Acid Sodium Salt of Clinical Trials,:" Org. Proc. Res. & Dev. 15:301-304 (epublication date: Dec. 2, 2010).
Contrera et al., "Estimating the safe starting dose in phase I clinical trials and no observed effect level based on QSAR modeling ofthe human maximum recommended daily dose," Regulatory Toxicology and Pharmacology (publication date: Dec. 2004, epublication date: Oct. 2, 2004).
Cooper GM, "Regulation of Programmed Cell Death," The Cell: A Molecular Approach. 2nd Edition. Sunderland MA). Sinauer Associates. (2002).
D'Amelio et al., "Caspase-3 in the central nervous system: beyond apoptosis," Trends in Neuroscience 35(11):700-09 (publication date: Nov. 2012, epublication date: Jul. 14, 2012).
Das, "A defect in the activities of $\Delta^6$ and $\Delta^5$ desaturases and pro-resolution bioactive lipids in the pathobiology of non-alcoholic fatty liver disease," World Journal of Diabetes 2g112:176-188 (publication date: Nov. 15, 2011).
Deng et al., "Organ fibrosis inhibited by blocking transforming growth factor-β signaling via peroxisome proliferator-activated receptor γ agonists," Hepatobiliary Pancreat Dis Int. 11(5):467-78 (publication date: Oct. 2012).
Depner et al., "Docosahexaenoic Acid Attenuates Hepatic Inflammation, Oxidative Stress, and Fibrosis without Decreasing Hepatosteatosis in a Ldlr2/2 Mouse Model of Western Diet-Induced Nonalcoholic Steatohepatitis/\(1-3)," The Journal of Nutrition 143(3):315-23 (publication date: Mar. 2013, epublication date: Jan. 9, 2013).
Desbois et al., "Antibacterial Activity of Long-Chain Polyunsaturated Fatty Acids against Propionibacterium acnes and *Staphylococcus aureus*," Marine Drugs, 11(11):4544-57 (publication date: Nov. 13, 2013).
Di Minno et al., "Omega-3 fatty acids forthe treatment of non-alcoholic fatty liver disease," World Journal of Gastroenterology 18(41): pp. 5839-5847 (epublication date: Nov. 7, 2012).
Dignity Sciences Limited, "Oral DS107G in Moderate to Severe Atopic Dermatitis," ClinicalTrials.gov (Study start date: Jan. 2015).
Ding et al., "Regulation of Adipokines by Polyunsaturated Fatty Acids in a Rat Model of Non-alcoholic Steatohepatitis," Arch Iran Med, 17(8): pp. 563-568. (publication date: Aug. 2014).
Ehlayel et al., "Montelukast Treatment in Children with Moderately Severe Atopic Dermatitis," European Annals of Allergey and Clinical Immunology 39(7):232-236 (publication date: Sep. 2007).
Elshof et al. "Biocatalytic hydroxylation of linoleic acid in a double-fed batch system with lipoxygenase and cystine," European Journ. Lipid Sci. and Tech., 100(6):246-251 (publication date: Jun. 1998, epublication date: Jan. 28, 1999).
Elshof et al. "Biocatalytic large-scale production of13(S)-hydroperoxy-9(Z), 11(E)-octadecadienoic acid from hydrolysed safflower oil by a crude soybean-flour extract as lipoxygenase source," Rec. Trav. Chim Pays-Bas, 115(11-12):499-504 (publication date: Nov./Dec. 1996).
Ericksen et al., "Open trial of supplements of omega 3 and 6 fatty acids, vitamins and minerals in atopic dermatitis," Journal of Dermatological Treatment 17(2):82-85 (2006).
Feldlaufer et al., "Antimicrobial activity of fatty acids against Bacillus larvae, the causative agent of American Foulbrood disease," Apidologie 24:95-99 (publication date: Nov. 2, 1993).
Flachs et al., "Synergistic induction of lipid catabolism and anti-inflammatory lipids in white fat of dietary obese mice in response to calorie restriction and n-3 fatty acids," Diabetologia, 54(10):2626-2638 (publication date: Oct. 2011, epublication date: Jul. 21, 2011).
Frank, "Treatment of Huntington's Disease," Neurotherapeutics. 11(1):153-160 (publication date: Jan. 2014, epublication date: Dec. 24, 2013).
Freudlsperger et al., "The Critical Role of PPARγ in Human Malignant Melanoma," PPAR Research 2008:503797 (epublication date: May 11, 2008).
Frocchi et al., "The Efficacy and Safety of γ-Linolenic Acid in the Treatment of Infantile Atopic Dermatitis," Journal of International Medical Research 22(1):24-32 (publication date: Jan.-Feb. 1994).
Granlund et al., "Effects of structural changes of fatty acids on lipid accumulation in adipocytes and primary hepatocytes," Biochimica et Biophysica Acta 1687(1-3):23-30 (publication date: Feb. 21, 2005, epublication date: Nov. 28, 2004).
Grigoriev et al., "Expression of Caspase-3 and -7 Does Not Correlate with the Extent of Apoptosis in Primary Breast Carinomas," Cell Cycle 1(5):337-342 (publication date: Sep./Oct. 2002).
Guil-Guerrero et al., "Gamma-linolenic and stearidonic acids: Purification and upgrading of C18-PUFA oils," European J. Lipid Sci. and Tech., 112(10):1068-1081 (publication date: Oct. 2010, epublication date: Sep. 20, 2010).
Han et al., "Combined treatment with peroxisome proliferator-activated receptor (PPAR) gamma ligands and gamma radiation induces apoptosis by PPARγ-independent up-regulation of reactive oxygen species-induced deoxyribonucleic acid damage signals in non-small cell lung cancer cells," Int J Radiat Oncol Biol Phys 85(5):e239-48 (publication date: Apr. 1, 2013, epublication date: Jan. 17, 2013).
Hashiramoto et al., "Drug Seminar," Life Style Medicine, 2(2):168-175 (2008) (with English machine translation of Summary).
Heshiki et al., "Constitutive Activation of Caspase-3 in Non-Apoptotic Oral Squamous Cell Carcinoma Cells," Journal of Cancer Science & Therapy 7(2):75-80 (publication date: Feb. 28, 2015).
Hirahashi et al., "Immunomodulation with eicosapentaenoic acid supports the treatment of autoimmune small-vessel vasculitis," Scientific Reports. vol. 4 (publication date: Sep. 18, 2014).

(56) References Cited

OTHER PUBLICATIONS

Horrobin DF, "Nutritional And Medical Importance Of Gamma-Linolenic Acid"; Prog. lipid Res. vol. 31(2):163-194 (publication date: Aug. 1992).
Huang et al., "Antimicrobial activity of n-6, n-7 and n-9 fatty acids and their esters for oral microorganisms," Archives of Oral Biology, 55(8):555-560 (publication date: Aug. 2010, epublication Jun. 11, 2010).
International Search Report and Written Opinion dated Aug. 5, 2015 for International Application No. PCT/EP2015/062518.
International Search Report and Written Opinion dated Dec. 15, 2015 for International Application No. PCT/US2015/011054.
International Search Report and Written Opinion dated Feb. 3, 2016 for International Application No. PCT/US2015/63488.
International Search Report and Written Opinion dated Jul. 12, 2020 for International Application No. PCT/EP2020/059682.
International Search Report and Written Opinion dated Jun. 6, 2016 for International Application No. PCT/IB2016/000202.
International Search Report and Written Opinion dated Mar. 27, 2014 for PCT/EP14/51455.
International Search Report and Written Opinion dated May 17, 2017 for International Application No. PCT/IB2016/001878.
International Search Report and Written Opinion dated Sep. 14, 2018 for International Application No. PCT/IB2018/000623.
International Search Report and Written Opinion dated Sep. 5, 2016 for International Application No. PCT/IB16/00732.
Ishii et al., "Eicosapentaenoic acid ameliorates steatohepatitis and hepatocellular carcinoma in hepatocyte-specific Pten-deficient mice", Journal of Hepatology, 2009, pp. 562-571 (publication date: Mar. 1, 2009, epublication date: Dec. 27, 2008).
Iversen et al.,"Effect of dihomogammalinolenic acid and its 15-lipoxygenase metabolite on eicosanoid metabolism by human mononuclear leukocytes in vitro: selective inhibition of the 5-lipoxygenase pathway," Arch Dermatol Res 284(4):222-226 (publication date: Aug. 1992.
Ivy et al., "Approaches to Phase 1 Clinical Trail Design Focused on Safety, Efficiency, and Selected Patient Populations: A Report from the Clinical Trail Design Task Force of the National Cancer Institute Investigational Drug Steering Committee," Clin Cancer Res (publication date: Mar. 15, 2010, epublication date: Mar. 9, 2010).
Jancin et al., "Bioactive lipid shows promise in atopic dermatitis," Dermatology News (publication date: Nov. 9, 2016).
Jareonkitmongkol et al., "A Novel Δ5-Desaturase-Defective Mutant of Mortierella alpina 1S-4 and Its Dihomo-γ-Linolenic Acid Productivity," Applied Environmental Microbiology 56(12):4300-4304 (publication date: Dec. 1993).
Johnson et al., "Dietary Supplementation with γ-Linolenic Acid Alters Fatty Acid Content and Eicosanoid Production in Healthy Humans," The Journal of Nutrition 127(8):1435-1444 (publication date: Aug. 1, 1997).
Kajikawa et al., "Eicosapentaenoic acid attenuates progression of hepatic fibrosis with inhibition of reactive oxygen species production in rats fed methionine- and choline-deficient diet," Dig Dis Sci 56(4):1065-74 (publication date: Apr. 2011, epublication date: Sep. 17, 2010).
Kalia et al., "Pakinson's disease," Lancet. 386:896-912 (publication date: Aug. 29, 2015, epublication date: Apr. 20, 2015).
Kanehara, S. et al., "Undershirts coated with borage oil alleviate the symptoms of atopic dermatitis in children," Eur J Dermatol, 17(5):448-9 (publication date: Sep.-Oct. 2007, epublication date: Aug. 2, 2007).
Kang et al., "A Simplified Method for Analysis of Polyunsaturated Fatty Acids," BMC Biochemistry (publication date: Mar. 24, 2005).
Kawamura et al.; "Dietary Supplementation of Gamma-Linolenic Acid Improves Skin Parameters in Subjects with Dry Skin and Mild Atopic Dermatitis"; Journal of Oleo Science; vol. 60(12):597-607 (2011).
Kawashima et al. "Oral Administration of Dihomo-γ-Linolenic Acid Prevents Development of Atopic Dermatitis in NC/Nga Mice," Lipids 43(1):37-43 (publication date: Jan. 2008, epublication date: Nov. 6, 2007).

Kawashima et al., "Subchronic (13-week) oral toxicity study of dihomo-y-linolenic acid (DGLA) oil in rats," Food and Chemical Toxicology 47(6):1280-6 (publication date: Jun. 2009, epublication date: Mar. 9, 2009).
Kawashima et al., "Industrial Production of Dihomo-γ-linolenic Acid by a Δ5 Desaturase-defective Mutant of Mortierella alpina 1S-4 Fungus," JAOCS 77:1135-1139 (publication date: Nov. 2000).
Kelavkar et al., "Prostate tumor growth can be modulated by dietarily targeting the 15-lipoxygenase-1 and cyclooxygenase-Z enzymes," Neoplasia, 11(7):692-9 (publication date: Jul. 2009).
Kendall et al., "Distribution of Bioactive Lipid Mediators in Human Skin," Journal of Investigative Dermatology, 00:1-11 (epublication date: Mar. 12, 2015).
Kernoff et al., "Antithrombotic potential of dihomo-gamma-linolenic acid in man," British Medical Journal 2(6100):1441-1444 (publication date: Dec. 3, 1977).
Kim, "M867, a Novel Selective Inhibitor of Caspase-3 Enhances Cell Death and Extends Tumor Growth Delay in Irradiated Lung Cancer Models," PloS One (publication date: May 28, 2008).
Kubota et al., "PPARγ and adiposcience," Adiposcience, Fuji Medical Publishing, 7(2):156-161 (publication date: Dec. 2010) English translation.
Kucera, Otto et al., "Experimental models of non-alcoholic fatty liver disease in rats," World J Gastroenterol, 20(26): pp. 8364-8376 (epublication date: Jul. 14, 2014).
Lam et al., "Transformation of 15-Hydroperoxyeicosapentaenoic acid into mono-and dihydroeicosapentaenoic acids by human platelets," Drugs Affecting Leukotrienes and Other Eicosanoid Pathways 95:167-180 1985.
Larsson et al., "Dietary long-chain n-3 fatty acids for the prevention of cancer: a review of potential mechanisms," The American Journal of Clinical Nutrition 79(6):935-45 (publication date: Jun. 2004).
Liu et al., Water-Insoluble Drug Formulation (CRC Press 2008) Chapter 15, "Pharmaceutical Salts," pp. 417-435 (publication date: Jan. 18, 2008).
Lodish et al., "Section 5.3 Biomembranes: Structural Organization and Basic Functions," Molecular Cell Biology. 4th Edition. New York. W.H. Freeman. (2002).
Lovell et al., "Treatment of Atopic Eczema With Evening Primrose Oil," The Lancet. 278 (publication date: Jan. 31, 1981).
Lundström et al., "Lipid Mediator Profiling in Pulmonary Disease," Current Pharmaceutical Biotechnology, 12(7):1026-1052 (publication date: Jul. 2011).
Mahady et al., "Management of Nonalcoholic Steatohepatitis, An Evidence-Based Approach," Clin Liver Dis 16(3):631-645 (publication date: Aug. 2012, epublication date: Jun. 20, 2012).
Makrides et al., "Changes in the polyunsaturated fatty acids of breast milk from mothers of full-term infants over 30 wk of lactation," Am J Clin Nutr. 61(6):231-1233 (publication date: Jun. 1995).
Malholtra et al., "Management of non-alcoholic fatty liver disease in 2015," World Journal of Hegatology, 7(30):2962-2967 (epublication date: Dec. 28, 2015).
Martinez-Clemente et al., "5-Lipoxygenase Deficiency Reduces Hepatic Inflammation and Tumor Necrosis Factor α-Induced Hepatocyte Damage in Hyperlipidemia-Prone AgoE-Null Mice," Hepatology 51(3):817-27 (publication date: Mar. 2010).
Masterton et al., "Review article: omega-3 fatty acids—a promising novel therapy for non-alcoholic fatty liver disease," Alimentary Pharmacology & Therapeutics 31(7):679-692 (publication date: Apr. 30, 2010, epublication date: Mar. 1, 2010).
Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. Of Invest. Dermatol 96(1):98-103 (publication date: Jan. 1991).
Miller et al., "Guinea Pig Epidermis Generates Putative Anti-Inflammatory Metabolites from Fish Oil Polyunsaturated Acids," Lipids 24(12):998-1003 (publication date: Dec. 1989).
Miller et al., "Guinea pig epidermis synthesizes 15-hydroxy-8,11,13-eicosatrienoic acid (15-OH-20:3n6) from dihomogammalinolenic

(56) References Cited

OTHER PUBLICATIONS acid (DGLA): a potent lipoxygenase inhibitor derived from dietary primrose oil," Clinical Research 35(3):704A (publication date: Apr. 1987).
Miller et al.; "Induction of Epidermal Hyperproliferation by Topical n-3 Polyunsaturated Fatty Acids on Guinea Pig Skin Linked to Decreased Levels of 13-Hydroxyoctadecadienoic Acid (13-Hode)," The Journal of Investigative Dermatology 94(3):353-8 (publication date: Mar. 1990).
Ming-Chang Chiang et al., "PPARgamma rescue of the mitochondrial dysfunction in Huntington's disease," Neurobiology of Disease 45:322-328 (publication date: Jan. 2020, epublication date: Aug. 25, 2011).
Minoura et al., "Mechanism by which a novel non-thiazolidinedione peroxisome proliferator-activated receptor gamma agonist, FK614, ameliorates insulin resistance in Zucker fatty rats," Diabetes Obes Metab, 9(3):369-78 (publication date: May 2007).
Mitchell et al., "Inhibition of platelet 12-lipoxygenase by hydroxy-fatty acids," Biochemical Society Transactions, 12(5):839-841 (publication date: Oct. 1, 1984).
Morse et al., "A Meta-Analysis of Randomized, Placebo-Controlled Clinical Trials of Efamol® Evening Primrose Oil in Atopic Eczema. Where Do We Go From Here in Light of More Recent Discoveries?" Current Pharmaceutical Biotechnology, 7(6):503-524 (publication date: Dec. 2006).
NCT02211417 (CIinicalTriaIs.gov, Aug. 6, 2014) (Accessed from https://www.clinicaltrials.gov/ct2/history/NCT02211417?V_1 on Aug. 26, 2019) (Year: 2014).
Nguyen et al., "Mechanisms for anti-inflammatory effects of 1-[15(S)-hydroxyeicosapentaenoyl] lysophosphatidylcholine, administered intraperitoneally, in zymosan A-induced peritonitis," British Journal of Pharmacology 162(5):1119-1135 (publication date: Mar. 2011, epublication date: Nov. 22, 2010).
Nijs et al. "Adult-onset asthma: is it really different?" Eur. Respir. Rev., 22(127):44-52 (publication date: Mar. 1, 2013).
Nu-Chek Prep, Inc. Catalog, The Home of Fine Lipid Organics, 85 pages (publication date: Mar. 18, 2009).
Olsson et al., "Caspases and cancer," Cell Death and Differentiation, 18:1441-1449 (epublication date: Apr. 1, 2011).
Osmundsen et al. "Effects of dietary treatment of rats with eicosapentaenoic acid or docosahexaenoic acid on hepatic lipid metabolism," Biochemical Journal 331(1):153-160 (publication date: Apr. 1, 1998).
Parker et al., "Omega-3 supplementation and non-alcoholic fatty liver disease: a systematic review and meta-analysis," J Hepatol. 56(4):944-51 (publication date: Apr. 2012, epublication date: Oct. 21, 2011).
Pauwels et al., "Role of IL-1α and the Nlrp3/caspase-1/IL-1β axis in cigarette smoke-induced pulmonary inflammation and COPD," The European Respiratory Journal 38(5):1019-1028 (publication date: Nov. 2011, epublication date: May 26, 2011).
PCT Application No. PCT/IB2014/003027, International Search Report and Written Opinion, Apr. 28, 2015.
Pereira et al., "Identification of two novel microalgae enzymes involved in the conversion of the omega3-fatty acid, eicosapentaenoic acid, into docosahexaenoic acid," Biochem J. 384:357-366 (publication date: Dec. 1, 2004, epublication date: Aug. 13, 2004).
Powell et al., "Metabolism of eicosapentaenoic acid by aorta: formation of a novel 13-hydroxylated prostaglandin," Biochim Biophys Acta 835(2):201-11 (publication date: Jul. 9, 1985) (Abstract only).
Proteau et al., "Divinyl ethers and hydroxy fatty acids from three species of *Laminaria* (brown algae)," Lipids 28(9):783-7 (publication date: Sep. 1993) (Abstract only).
Ramchurren et al., "Effects of Gamma-linolenic and Dihomo-gamma-linolenic Acids on 7,12-Dimethylbenz(α)anthracene-Induced Mammary Tumors in Rats," Prostaglandins Leukotrienes and Essential Fatty Acids 53(2):95-101 (publication date: Aug. 1995).
Reddy et al., "Conversion of Dihomo-β-Linolenic Acid to Mono- and Dihydroxy Acids by Potato Lipoxygenase: Evidence for the Formation of 8,9-Leukotriene A3," Archives of Biochemistry and Bioghysics 279(2):211-217 (publication date: May 15, 1990).
Román, Studies of anti-cancer and anti-inflammatory activity of bioactive compounds isolated from terrestrial and marine aqueous media, abstract accessed at: https://idus.us.es/xmlui/handle/11441/51306, (publication date: Mar. 21, 2014) (Abstract only).
Ruocco et al., "Diatom-derived oxylipins induce cell death in sea urchin embryos activating caspase-8 and caspase 3/7," Aquatic Toxicology (publication date: Jul. 2016, epublication date: Apr. 22, 2016).
Rusu E. et al., "Medical nutrition therapy in non-alcoholic fatty liver disease—a review of literature," Journal of Medicine and Life, ol. 8, Issue 3, pp. 258-262 (publication date: Jul.-Sep. 2015).
Sanyal et al., "No Significant Effects of Ethyl-Eicosapentanoic Acid on Histologic Features of Nonalcoholic Steatohepatitis in a Phase 2 Trial," Gastroenterology 147(2):377-384 (publication date: Aug. 2014, epublication date: May 9, 2014).
Schaefer, "Synthesized Omega-6 DGLA for Anti-inflammatories," Cosmetics & Toiletries (publication date: Feb. 11, 2009).
Schuchardt et al., "Bioavailability of long-chain omega-3 fatty acids," Prostaglandins, Leukotrienes and Essential Fatty Acids 89(1):1-8 (publication date: Jul. 2013).
Scollan et al., "Manipulating the fatty acid composition of muscle and adipose tissue in beef cattle," British Journal of Nutrition 85(1):115-124 (publication date: Jan. 2001).
Serhan et al., "Novel Pro-resolving Aspirin-Triggered DHA Pathway," Chem. Biol. 18(8):976-987 (publication date: Aug. 26, 2011).
Serhan et al., "Resolvins and Protectins in Inflammation-Resolution," Chem Rev. 111(10):5922-5943 (publication date: Oct. 12, 2011, epublication date: Jul. 18, 2011).
Serhan et al., "Resolvins: A Family of Bioactive Products of Omega-3 Fatty Acid Transformation Circuits Initiated by Aspirin Treatment that Counter Proinflammation Signals," J. Exp. Med. 196(8):1025-1037 (publication date: Oct. 21, 2002).
Shinohara et al., "Functional metabolomics reveals novel active products in the DHA metabolome," Front Immunol 3:81, pp. 1-9 (publication date: Apr. 17, 2012).
Siersbaek et al., "PPARgamma in adipocyte differentiation and metabolism—novel insights from genome-wide studies," FEBS Letters 584:3242-3249 (epublication date: Jun. 11, 2010).
Simon "Eosinophils and atopic dermatitis," Allergy 59:561-70 (publication date: Jun. 2004).
Simon et al., "Gamma-Linolenic Acid Levels Correlate with Clinical Efficacy of Evening Primrose Oil in Patients with Atopic Dermatitis," Adv Ther 31(2):180-188 (publication date: Feb. 2014, epublication date: Jan. 17, 2014).
Stone et al., "The Metabolism of Dihomo-γ-Linolenic Acid in Man," Lipids. 14(2):174-180 (publication date: Feb. 1979).
Swarbrick et al., "Salt Forms of Drugs and Absorption," Encyclopedia of Pharmaceutical Technology 13, Marcel Dekker, NY, pp. 453-499 (48 pages) (publication date: Oct. 24, 1995).
Tanaka et al., "Highly-purified eicosapentaenoic acid treatment improves nonalcoholicsteatohepatitis," Journal of Clinical Gastroenterology, 42(4):413-418 (publication date: Apr. 1, 2008).
Tanaka et al., "Oral Supplementation with Dihomo-γ-Linolenic Acid (DGLA)-Enriched Oil Increases Serum DGLA Content in Healthy Adults," Lipids 47(6):643-6 (publication date: Jun. 2012, epublication date: Mar. 14, 2012).
Teraoka et al., "Oral Supplementation with Dihomo-γ-linolenic Acid-Enriched Oil Altered Serum Fatty Acids in Healthy Men," Biosci. Biotechnol. Biochem, 73(6):1453-1455 (epublication date: Jun. 7, 2009).
Tyagi et al., "The peroxisome proliferator-activated receptor: A family of nuclear receptors role in various diseases," J Adv Pharm Technol Res 2(4):236-40 (publication date: Oct.-Dec. 2011).
Uehara et al., "Blood eosinophilia in atopic dermatitis," Clinical and Experimental Dermatology 15(4):264-266 (publication date: Jul. 1990).
Umeda-Sawada et al., "Distribution and Metabolism of Dihomo-γ-linolenic Acid (DGLA, 20:3n-6) by Oral Supplementation in Rats," Biosci. Biotechnol. Biochem. 70(9):2121-2130 (publication date: Sep. 7, 2006).

(56) References Cited

OTHER PUBLICATIONS

Vang et al., "15-lipoxygenase metabolites of gamma-linolenic acid/eicosapentaenoic acid suppress growth and arachidonic acid metabolism in human prostatic adenocarcinoma cells: Possible implications ofdietary fatty acids", Prostaglandins Leukot Essent Fatty Acids 72(5):363-372 (publication date: May 2005).

Wheelock et al, "Allergic Asthmatics exhibit altered response in oxylipin profile as compared to healthy and asthmatic controls after allergen provocation," American Journal of Respiratory and Critical Care Medicine, 183:1 (2011) (Abstract only).

Wright et al., "Oral Evening-Primrose-Seed Oil Improves Atopic Eczema," The Lancet, 2(8308):1120-1122 (publication date: Nov. 20, 1982).

Yazawa et al., "Heterologous Production of Dihomo-γ-Linolenic Acid in *Saccharomyces cerevisiae*" Applied and Environmental Microbiology, 73(21):6965-71 (publication date: Nov. 2007, epublication date: Sep. 14, 2007).

Yin et al., "Identification of Novel Autoxidation Products of the ω-3 Fatty Acid Eicosapentaenoic Acid in Vitro and in Vivo," Journal of Biological Chemistry 282(41):29890-29901 (publication date: Oct. 12, 2007, epublication date: Aug. 21, 2007).

Ziboh et al., "Significance of lipoxygenase-derived monohydroxy fatty acids in cutaneous biology," Prostaglandins & other Lipid Mediators 63(1-2):3-13 (publication date: Nov. 2000).

Ziboh et al., "Metabolism of polyunsaturated fatty acids by skin epidermal enzymes: generation of anti-inflammatory and antiproliferative metabolites," The American Journal of Clinical Nutrition, 71(1 Suppl):361S-366S (publication date: Jan. 2000).

Zou et al., "Inhibition of the HER2 pathway by n-3 polyunsaturated fatty acids prevents breast cancer in fat-1 transgenic mice," Journal of Lipid Research 54(12):3453-3463 (publication date: Dec. 2013, epublication date: Sep. 19, 2013).

Borba et al., "Reticulocyte Parameters and Hemoglobin F Production in Sickle Cell Disease Patients Undergoing Hydroxyurea Therapy," Journal of Clinical Laboratory Analysis 17:66-72 (2003).

Conran et al., "Inflammation in Sickle Cell Disease," Clin Hemorheol Microcirc. 68(2-3):263-299 (2018).

Gao et al., "Red Blood Cell/Hemoglobin Disorders," Hematopathology, Third Ed. 3-56 (2018).

Vanderhoek et al., "Inhibitory potencies of fish oil hydroxy fatty acids on cellular lipoxygenases and platelet aggregation," Biochemical Pharmacology (publication date: Jul. 25, 1991).

\* cited by examiner

| Class | Metabolite | Code OWL | Week 8 vs. Baseline log₂ (fold-change) | Week 8 vs. Baseline Student's t-test (p-value) | Week 16 vs. Baseline log₂ (fold-change) | Week 16 vs. Baseline Student's t-test (p-value) |
|---|---|---|---|---|---|---|
| AA | Phenylalanine | AA18 | -0.02 | 4.09E-01 | -0.14 | |
| | Glutamic Acid | AA02 | -0.01 | 7.04E-01 | -0.13 | 2.85E-01 |
| | Serine | AA05 | -0.14 | | -0.03 | 1.51E-01 |
| | Taurine | AA09 | 0.25 | 5.99E-03 | -0.10 | |
| | Sarcosine | AA22 | 0.01 | 5.17E-02 | -0.08 | |
| | Hypotaurine | AA26 | -0.33 | 9.78E-04 | -0.20 | 2.75E-01 |
| | Asp-Phe | AA31 | -0.33 | 5.11E-03 | -0.19 | 7.31E-01 |
| | Gly-DL-Phe | AA25 | -0.15 | | 0.12 | |
| | AC(18:2n:6) | AC10 | -0.11 | 5.70E-02 | -0.06 | |
| DG | DG(32:2) | DG04 | 0.50 | 1.57E-01 | -0.13 | |
| | DG(34:1) | DG06 | 0.19 | 7.18E-01 | -0.12 | |
| | DG(34:2) | DG07 | 0.20 | 7.70E-01 | -0.08 | |
| | DG(36:3) | DG09 | 0.05 | 6.67E-01 | -0.22 | |
| | DG(36:4) | DG10 | -0.08 | 1.21E-01 | -0.21 | |
| | DG(36:4) | DG11 | 0.33 | | 0.11 | 8.46E-01 |
| ChoE | ChoE(18:3) | ChoE_09 | 0.56 | 1.50E-02 | 0.44 | |
| BA | Glycochenodeoxycholic acid | BA16H | 0.33 | 6.37E-01 | -0.12 | |
| | Glycoursodeoxycholic acid | BA17H | 0.89 | 2.72E-01 | 0.34 | |
| PE | PE(O-16:0/18:1) | MEMAPE01 | 0.30 | 4.78E-01 | 0.49 | |
| | PE(P-18:/18:2) | MEMAPE17 | 0.49 | 1.18E-01 | 0.64 | 8.09E-02 |
| LPE | PE(18:3/0:0) | MAPE21 | 1.14 | | 0.35 | |
| | PE(P-20:0/0:0) | MEPE18 | 0.31 | 3.48E-01 | 0.28 | 5.20E-01 |
| PC | PC(30:0) | DAPC47 | 0.50 | 8.23E-03 | 0.22 | 7.51E-02 |
| | PC(31:0) | DAPC45 | 0.31 | | 0.17 | 3.45E-01 |
| | PC(16:0/18:0) | DAPC06 | 0.18 | 2.55E-03 | 0.58 | 1.06E-01 |
| | PC(17:0/18:1) | DAPC39_DAPC40 | 0.63 | | 0.27 | 7.42E-02 |
| | PC(34:3) | DAPE14 | 0.23 | 8.56E-03 | 0.44 | |
| | PC(37:2) | DAPE23 | 0.41 | | 0.53 | 1.11E-01 |
| | PC(O-16:0/18:2) | MEMAPC07 | 0.35 | | 0.68 | |
| | PC(O-18:0/18:2) | MEMAPC12 | 0.45 | 2.45E-03 | 0.40 | 1.17E-01 |
| | PC(O-18:1/18:2) | MEMAPC13 | 0.26 | | 0.21 | 4.69E-01 |
| | PC(O-18:2/20:4) | MEMAPC28 | 0.34 | 3.57E-03 | 0.17 | 5.39E-01 |
| | PC(P-16:0/22:6) | MEMAPC29 | 0.32 | | 0.46 | |
| | PC(18:3/0:0) | MAPC22 | 0.49 | 4.11E-01 | 0.64 | |
| | PC(0:0/18:3) | MAPC21 | 0.76 | 2.36E-01 | 0.33 | |
| LPC | PC(O-18:0/0:0) | MEPC04 | 0.19 | 4.42E-01 | 0.42 | |
| | PC(P-18:0/0:0) | MEPC07 | 0.27 | 2.36E-01 | 0.46 | |
| | PC(P-18:1/0:0) | MEPC08 | 0.28 | 1.14E-01 | 0.46 | |
| | PC(P-20:1/0:0) | MEPC14 | 0.37 | 3.77E-01 | 0.60 | |
| | PC(P-20:2/0:0) | MEPC15 | 0.38 | 1.46E-01 | 0.65 | |
| PI | PI(18:0/18:2) | DAPI04 | 0.33 | | 0.36 | 1.74E-01 |
| LPI | LPI(18:1) | MAPI06 | 0.53 | 2.32E-01 | 0.60 | 4.32E-03 |
| | LPI(22:6) | MAPI13 | 0.46 | | 0.33 | 1.65E-01 |
| FSB | Sphingosine-1-phosphate | FSB01 | -0.08 | | 0.09 | 9.40E-01 |

Figure 26 ion to U.S. patent application Ser. No. 16/839,899, filed Apr. 3, 2020, entitled "COMPOSITIONS COMPRISING 15-HEPE AND METHODS OF TREATING OR PREVENTING HEMATOLOGIC DISORDERS, AND/OR RELATED DISEASES".

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: 36B4 MA057856 forward primer

<400> SEQUENCE: 1
ttccaggctt tgggcatca                                              19

<210> SEQ ID NO 2
<211> LENGTH: 24
<212> TYPE: DNA
<213> ORGANISM: Artificial Sequence
<220> FEATURE:
<223> OTHER INFORMATION: 36B4 MA057856 reverse primer

<400> SEQUENCE: 2
atgttcagca tgttcagcag tgtg                                        24

<210> SEQ ID NO 3
<211> LENGTH: 22
<212> TYPE: DNA
<213> ORGANISM: Artificial Sequence
<220> FEATURE:
<223> OTHER INFORMATION: Alpha-SMA MA057911 forward primer

<400> SEQUENCE: 3
aagagcatcc gacactgctg ac                                          22

<210> SEQ ID NO 4
<211> LENGTH: 24
<212> TYPE: DNA
<213> ORGANISM: Artificial Sequence
<220> FEATURE:
<223> OTHER INFORMATION: Alpha-SMA MA057911 reverse primer

<400> SEQUENCE: 4
agcacagcct gaatagccac atac                                        24

<210> SEQ ID NO 5
<211> LENGTH: 20
<212> TYPE: DNA
<213> ORGANISM: Artificial Sequence
<220> FEATURE:
<223> OTHER INFORMATION: TIMP-1 MA098519 forward primer

<400> SEQUENCE: 5
tgagccctgc tcagcaaaga                                             20

<210> SEQ ID NO 6
<211> LENGTH: 21
<212> TYPE: DNA
<213> ORGANISM: Artificial Sequence
<220> FEATURE:
<223> OTHER INFORMATION: TIMP-1 MA098519 reverse primer

<400> SEQUENCE: 6
gaggacctga tccgtccaca a                                           21

<210> SEQ ID NO 7
<211> LENGTH: 25
<212> TYPE: DNA
<213> ORGANISM: Artificial Sequence

```
<220> FEATURE:
<223> OTHER INFORMATION: TGF-beta MA030397 forward primer

<400> SEQUENCE: 7
gtgtggagca acatgtggaa ctcta                                         25

<210> SEQ ID NO 8
<211> LENGTH: 20
<212> TYPE: DNA
<213> ORGANISM: Artificial Sequence
<220> FEATURE:
<223> OTHER INFORMATION: TGF-beta MA030397 reverse primer

<400> SEQUENCE: 8
ttggttcagc cactgccgta                                               20

<210> SEQ ID NO 9
<211> LENGTH: 24
<212> TYPE: DNA
<213> ORGANISM: Artificial Sequence
<220> FEATURE:
<223> OTHER INFORMATION: Collagen Type 1 MA075477 forward primer

<400> SEQUENCE: 9
ccaacaagca tgtctggtta ggag                                          24

<210> SEQ ID NO 10
<211> LENGTH: 23
<212> TYPE: DNA
<213> ORGANISM: Artificial Sequence
<220> FEATURE:
<223> OTHER INFORMATION: Collagen Type 1 MA075477 reverse primer

<400> SEQUENCE: 10
gcaatgctgt tcttgcagtg gta                                           23
```

COMPOSITIONS COMPRISING 15-HEPE AND METHODS OF TREATING OR PREVENTING HEMATOLOGIC DISORDERS, AND/OR RELATED DISEASES

CROSS-REFERENCE TO RELATED APPLICATION(S)

This application is a continuation of U.S. patent application Ser. No. 16/839,899, filed Apr. 3, 2020, entitled "COMPOSITIONS COMPRISING 15-HEPE AND METHODS OF TREATING OR PREVENTING HEMATOLOGIC DISORDERS, AND/OR RELATED DISEASES".

TECHNICAL FIELD

The present application relates generally to compositions comprising 15-HEPE, and to methods of using the same.

SEQUENCE LISTING

This disclosure includes a sequence listing, which was submitted in ASCII format via EFS-Web, and is hereby incorporated by reference in its entirety. The ASCII copy, created on Apr. 1, 2020, is named Sequence Listing 124318-8014. US00_ST25.txt and is 3 kilobytes in size.

BACKGROUND

Hematologic disorders include red blood cell disorders and thrombophilia. Red blood cell disorders are a class of conditions that affect the production, life-span, and shape of red blood cells (RBCs) and its oxygen transport molecule, hemoglobin. These conditions inhibit the transport of oxygen from the lungs to the rest of the body. Thrombophilia is a class of disorders that increase a subject's risk of developing blood clots in veins and arteries. These clots can break loose from the blood vessel and travel through the blood stream to an organ thereby preventing blood flow to that organ resulting in ischemia. These conditions lead to an increased risk of stroke and/or pulmonary embolism.

SUMMARY

The application relates to compositions comprising 15-hydroxyeicosapentaenoic acid (15-HEPE) and to methods of using such compositions in the treatment of a variety of diseases and disorders.

In some aspects, the present disclosure provides methods of treating and/or preventing a hematologic disorder in a subject in need thereof, the method comprising administering to the subject 15-HEPE or a composition comprising 15-HEPE.

In some aspects, the present disclosure provides methods of treating and/or preventing a hematologic disorder in a subject in need thereof, the method comprising administering to the subject up to about 8 g of a composition comprising 15-HEPE, wherein the 15-HEPE represents at least about 90% by weight, of all fatty acids in the composition.

In yet another aspect, the present disclosure provides methods of treating and/or preventing a hematologic disorder in a subject in need thereof, the method comprising administering to the subject up to about 8 g of a composition comprising 15-HEPE, wherein the 15-HEPE represents at least about 90% by weight, of all fatty acids in the composition, and the subject exhibits one or more of: (a) an increase in red blood cell count; (b) a decrease in red cell distribution width; and/or (c) a decrease in reticulocyte count.

In various embodiments, the hematologic disorder is selected from the group consisting of inherited hemolytic anemia, acquired hemolytic anemia, Fanconi anemia, iron deficiency anemia, folate deficiency, B12 deficiency, and myelodysplastic syndrome.

In some aspects, the present disclosure provides methods of treating and/or preventing a hemoglobin disorder in a subject in need thereof, the method comprising administering to the subject 15-HEPE or a composition comprising 15-HEPE.

In other aspects, the present disclosure provides methods of treating and/or preventing a red blood cell disorder in a subject in need thereof, the method comprising administering to the subject 15-HEPE or a composition comprising 15-HEPE.

In another aspect, the present disclosure provides methods of treating and/or preventing a hemoglobin disorder and/or a red blood cell disorder in a subject in need thereof, the method comprising administering to the subject up to about 8 g of a composition comprising 15-HEPE, wherein the 15-HEPE represents at least about 90% by weight, of all fatty acids in the composition.

In yet another aspect, the present disclosure provides methods of treating and/or preventing a hemoglobin disorder and/or a red blood cell disorder in a subject in need thereof, the method comprising administering to the subject up to about 8 g of a composition comprising 15-HEPE, wherein the 15-HEPE represents at least about 90% by weight, of all fatty acids in the composition, and the subject exhibits one or more of: (a) an increase in red blood cell count; (b) a decrease in red cell distribution width; and/or (c) a decrease in reticulocyte count.

In various embodiments, the hematologic disorder, the hemoglobin disorder, and/or the red blood cell disorder are selected from the group consisting of inherited hemolytic anemia, acquired hemolytic anemia, Fanconi anemia, iron deficiency anemia, folate deficiency, B12 deficiency, and myelodysplastic syndrome.

In yet another aspect, the present disclosure provides methods of treating and/or preventing hemolytic anemia in a subject in need thereof, the method comprising administering to the subject up to about 8 g of a composition comprising 15-HEPE, wherein the 15-HEPE represents at least about 90% by weight, of all fatty acids in the composition.

In some embodiments, the hemolytic anemia is inherited hemolytic anemia or acquired hemolytic anemia. In another embodiment, the acquired hemolytic anemia is acquired as secondary to infection, from a medication, from a hematological malignancy, from autoimmune disease, from hypersplenism, following placement of a mechanical heart valve, a blood transfusion, or a combination thereof. In yet another embodiment, the sickle cell disease and sickle cell anemia are associated with sickle cell crisis, a vaso-occlusive crisis, a splenic sequestration, or a combination thereof.

In some embodiments, the subject exhibits an increase in red blood cell count, a decrease in red blood cell distribution width, and a decrease in reticulocyte count. In some aspects, the present disclosure provides methods of treating and/or preventing thrombophilia disorders in a subject in need thereof, the method comprising administering to the subject 15-HEPE or a composition comprising 15-HEPE.

In other aspects, the present disclosure provides methods of treating and/or preventing thrombophilia in a subject in need thereof, the method comprising administering to the subject up to about 8 g of a composition comprising 15-HEPE, wherein the 15-HEPE represents at least about 90% by weight, of all fatty acids in the composition.

In another aspect, the present disclosure provides method of treating and/or preventing thrombophilia in a subject in need thereof, the method comprising administering to the subject up to about 8 g of a composition comprising 15-HEPE, wherein the 15-HEPE represents at least about 90% by weight, of all fatty acids in the composition, and the subject exhibits one or more of: (a) an increase in prothrombin time; (b) an increase in activated partial thromboplastin time; and/or (c) a decrease in fibrinogen concentration.

In yet another aspect, the present disclosure provides methods of treating and/or preventing a venous thromboembolism in a subject in need thereof, the method comprising administering to the subject up to about 8 g of a composition comprising 15-HEPE, wherein the 15-HEPE represents at least about 90% by weight, of all fatty acids in the composition.

In one aspect, the present disclosure provides methods of treating and/or preventing an arterial thrombosis in a subject in need thereof, the method comprising administering to the subject up to about 8 g of a composition comprising 15-HEPE, wherein the 15-HEPE represents at least about 90% by weight, of all fatty acids in the composition.

In another aspect, the present disclosure provides methods of preventing an embolism in a subject in need thereof, the method comprising administering to the subject up to about 8 g of a composition comprising 15-HEPE, wherein the 15-HEPE represents at least about 90% by weight, of all fatty acids in the composition.

In some embodiments, the subject exhibits an increase in prothrombin time, an increase in activated partial thromboplastin time, and a decrease in fibrinogen concentration.

In another embodiment, the 15-HEPE is in a free acid form, esterified form, or salt form. In yet another embodiment, the esterified form is an alkyl ester form or a triglyceride form. In some embodiments, the 15-HEPE comprises 15(S)-HEPE, 15(R)-HEPE, or combinations thereof.

In some embodiments, the 15-HEPE is in the form of an ethyl ester (15-HEPE EE) or the 15-HEPE is in the form of an optically active ester (15(S)-HEPE EE).

In some embodiments, the composition comprises about 10 mg to about 10,000 mg of 15-HEPE. In another embodiment, the composition comprises about 1 g to about 2 g of 15-HEPE. In another embodiment, the composition comprises about 2 g or more of 15-HEPE. In yet another embodiment, the composition is formulated to provide about 5 mg 15-HEPE per kg of bodyweight (mg/kg), about 50 mg/kg, about 250 mg/kg, or about 500 mg/kg to the subject. In various embodiments, the 15-HEPE represents at least about 90%, by weight, of all fatty acids present in the composition.

In some embodiments, the 15-HEPE is orally administered. In various embodiments, the composition is administered in 1 to 8 capsules per day.

BRIEF DESCRIPTION OF THE FIGURES

FIGS. 18C-8G show DS102 effects on membrane translocation and degradation of Type I TGF-β receptor, Type II TGF-β receptor, Type III TGF-β receptor, EGFR and Caveolin-1 according to the study described in Example 3, respectively.

FIG. 26 is a chart depicting the changes in hepatoxic lipid profile of patients administered DS102.

DETAILED DESCRIPTION

Figure 1:
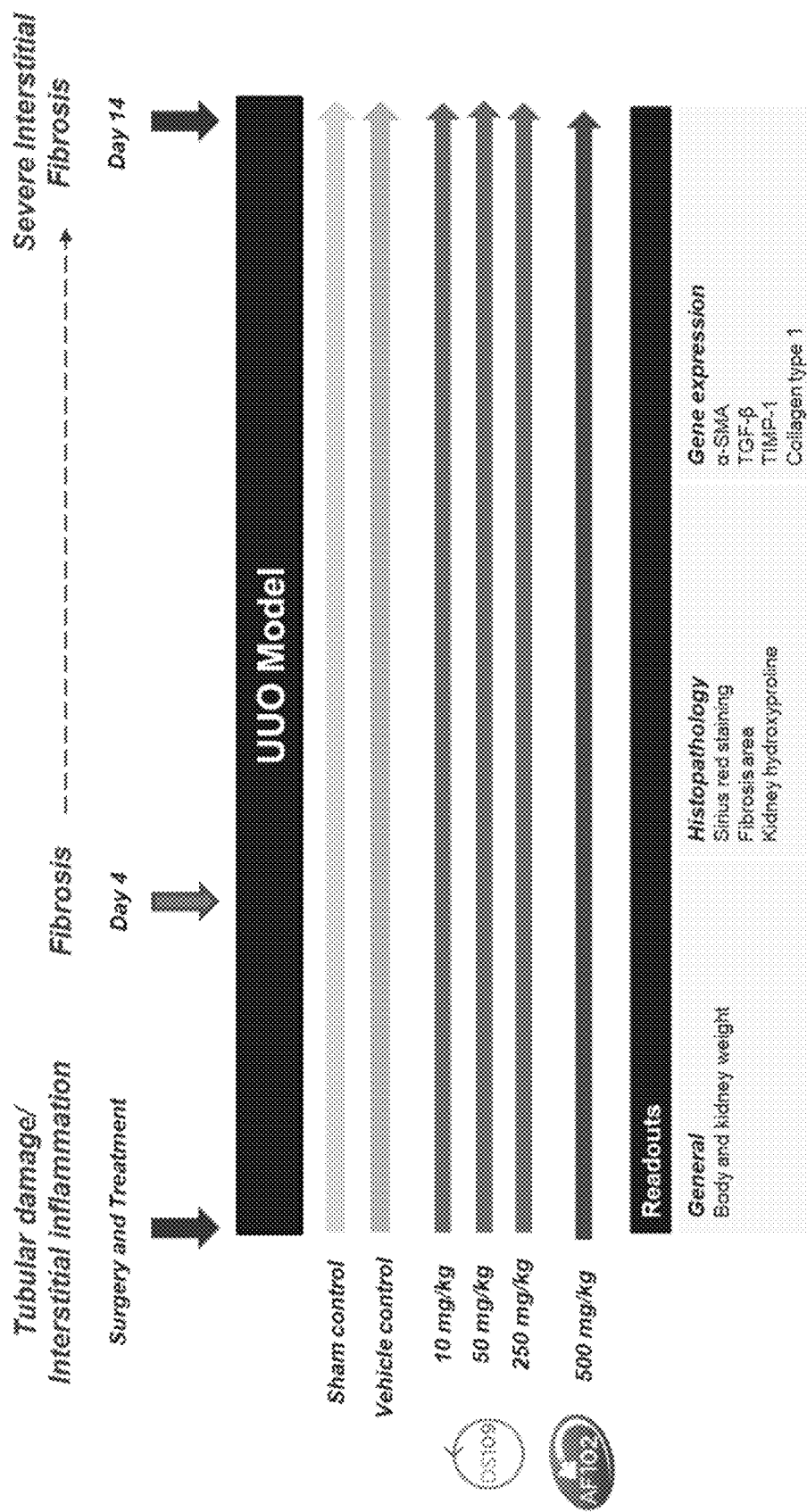
FIG. 1 is a schematic diagram of the study described in Example 1 and its duration.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited, as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein; and, in all instances, such ratios, ranges, and ranges of ratios represent various embodiments of the present invention.

Unless otherwise defined, all technical and scientific terms used herein have the same meaning as commonly understood by one of ordinary skill in the art to which this disclosure pertains. Although methods and materials similar or equivalent to those described herein can be used in the practice of the present disclosure, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Definitions

As used herein, "15-HEPE" is 15-hydroxy-eicosa-5Z,8Z, 11Z,13E,17Z-pentaenoic acid. 15-HEPE, also occasionally referred to as 15-OHEPA, can be synthesized from eicosapentaenoic acid ("EPA," eicosa-5,8,11,14,17-pentaenoic acid or 20:5n-3), an omega-3 fatty acid according to methods known in the art. For example, 15-HEPE can be synthesized by exposure of EPA to the enzyme 15-lipoxygenase. As used herein, the term "15-HEPE" refers to 15-HEPE in its free acid form (e.g., 15-hydroxy-eicosa-5Z, 8Z,11Z,13E,17Z-pentaenoic acid) and/or a pharmaceutically acceptable ester, conjugate or salt thereof, or mixtures of any of the foregoing. A derivative of 15-HEPE may be used instead, though this does not include any derivative compound missing the hydroxy group of 15-HEPE. In some embodiments, the 15-HEPE is used in the free acid form. Alternatively, pharmaceutically acceptable esters or salts of 15-HEPE are used in the disclosure. In some embodiments, the 15-HEPE is in the form of a 01-4 alkyl ester such as methyl ester, ethyl ester, or a combination of methyl ester and ethyl ester. In yet another embodiment, the 15-HEPE is in a form of a glyceride (e.g., diglyceride or triglyceride). In another embodiment, the 15-HEPE is in the form of an ethyl ester (also referred to herein as E-15-HEPE, 15-HEPE EE, or ethyl-15-HEPE).

15-HEPE is a chiral molecule and may be used in the (S)- or (R)-enantiomeric form, or as a racemic mixture. Used herein, "15-HEPE" includes all such forms, with no limitation as to stereospecificity. In another embodiment, the 15-HEPE comprises the (S) form: 15(S)-hydroxy-(5Z,8Z, 11Z,13E,17Z)-eicosapentaenoic acid or the (R) from: 15(R)-hydroxy-(5Z,8Z,11Z,13E,17Z)-eicosapentaenoic acid. In yet another embodiment, the 15-HEPE EE comprises the (S) form: 15(S)-HEPE EE.

As used herein, "DS102" refers to 15-HEPE, 15-HEPE EE, a composition comprising 15-HEPE, a composition comprising 15-HEPE EE, or a composition comprising 15-HEPE and 15-HEPE EE.

As used herein, "Epeleuton" refers to 15-HEPE, 15-HEPE EE, a composition comprising 15-HEPE, a composition comprising 15-HEPE EE, or a composition comprising 15-HEPE and 15-HEPE EE.

As used herein, "treating" or "treatment" of a disease, disorder, or condition includes at least partially: (1) inhibiting the disease, disorder, or condition, i.e., arresting or reducing the development of the disease, disorder, or condition or its clinical symptoms; or (2) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Other features and advantages of the disclosure will be apparent from the following detailed description.

Compositions

In one embodiment, compositions of the disclosure comprise 15-HEPE as an active ingredient. The term "pharmaceutically acceptable" in the present context means that the substance in question does not produce unacceptable toxicity to the subject or interaction with other components of the composition.

In one embodiment, the 15-HEPE is in the form of an ester (also referred to herein as E-15-HEPE, ethyl-15-HEPE, or 15-HEPE EE). In another embodiment, the 15-HEPE comprises a $C_1$-$C_5$ alkyl ester of 15-HEPE. In another embodiment, the 15-HEPE comprises 15-HEPE methyl ester, 15-HEPE propyl ester, or 15-HEPE butyl ester. In still another embodiment, the 15-HEPE comprises the optically active 15(S)-Hydroxy-(5Z,8Z,11Z,13E,17Z)-eicosapentaenoic acid. This isomer may be used in any of the forms discussed above.

In another embodiment, the 15-HEPE comprises lithium 15-HEPE, mono, di- or triglyceride 15-HEPE or any other ester or salt of 15-HEPE, or the free acid form of 15-HEPE.

In various embodiments, the disclosure provides pharmaceutical compositions, for example orally deliverable compositions, comprising 15-. In one embodiment, the compositions comprise a therapeutically effective amount of 15-HEPE. In one embodiment, the pharmaceutical composition comprises about 0.1% to about 99%, about 1% to about 95%, about 5% to about 90%, by weight, of 15-HEPE. As provided herein the "composition" and the phrase "pharmaceutical composition" are used interchangeably.

In one embodiment, the pharmaceutical composition comprises about at least about 70%, at least about 80% or at least about 90%, by weight, of 15-HEPE. In one embodiment, the pharmaceutical composition comprises at least about 50%, at least about 60%, at least about 70%, at least about 80% or at least about 90%, by weight, of 15-HEPE.

In another embodiment, 15-HEPE is present in a composition of the disclosure in an amount of about 1 mg to about 10,000 mg, about 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, 15-HEPE present in a composition of the disclosure comprises at least about 90%, by weight, 15-HEPE (as the term "15-HEPE" is defined and exemplified herein). 15-HEPE compositions can comprise even higher purity 15-HEPE, for example at least about 95%, by weight, 15-HEPE or at least about 97%, by weight, 15-HEPE, wherein the 15-HEPE is any form of 15-HEPE as set forth herein. The purity of 15-HEPE can further be defined (e.g., impurity profile) by any of the descriptions of 15-HEPE provided herein.

Above are discussed the amounts of the 15-HEPE in the pharmaceutical composition and their purity. The nature of the essential fatty acids and their synthesis is such that the 15-HEPE composition may include moieties from other essential fatty acids in the essential fatty acid metabolic cascade.

In one embodiment, a composition of the disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-HEPE represents at least about 60%, at least about 70%, at least about 80%, at least about 90%, at least about 95%, at least about 97%, at least about 98%, at least about 99%, or 100%, by weight, of all fatty acids present in a composition of the disclosure.

In one embodiment, the salt form of 15-HEPE present in a composition of the invention comprises at least 90%, by weight, of the salt form of 15-HEPE. Compositions containing the salt form of 15-HEPE can comprise even higher purity, for example at least 91% by weight, at least 92% by weight, at least 93% by weight, at least 94% by weight, at least 95% by weight, at least 96% by weight or at least 97% by weight of the salt form of 15-HEPE.

There may be present some residual eicosapentaenoic acid from the synthesis of the 15-HEPE. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight EPA. Alternatively, there is substantially no, or no, EPA in a form which has not been modified to the hydroxyl-form.

In one embodiment, the present disclosure provides a pharmaceutical composition comprising 15-HEPE or derivative thereof encapsulated in a capsule shell. In one embodiment, the composition is administered to the subject in an amount sufficient to provide up to about 1 g, about 2 g, about 3 g, about 4 g, about 5 g, about 6 g, about 7 g, about 8 g, about 9 g, or about 10 g of 15-HEPE E or a derivative thereof per day. In one embodiment, the composition is administered to the subject in an amount sufficient to provide about 4 g to about 8 g, about 1 g to about 2 g, about 2 g to about 4 g, about 3 g to about 8 g, about 4 g to about 6 g of 15-HEPE or a derivative thereof per day. In one embodiment, about 500 mg to about 1 g of 15-HEPE or derivative thereof is encapsulated in the capsule shell.

In one embodiment, the capsule shell comprises gelatin (for example, Gelatin RXL or lime bone gelatin with a lower molecular weight). In another embodiment, the capsule shell comprises Gelatin RXL that has been treated by proteolytic enzyme to cut the gelatin pattern and effectively decrease its molecular weight. In another embodiment, the pharmaceutical composition comprises 15-HEPE esters of D-Sorbitol and 1,4-sorbitan. In one embodiment, the capsule shell comprises (a) gelatin and (b) plasticizers selected from one or more of D-Sorbitol and 1,4-sorbitans. In one embodiment, the gelatin is as described in U.S. Pat. No. 7,485,323, and is hereby incorporated by reference herein in its entirety.

In one embodiment, the plasticizer comprises 1,4-sorbitans in an amount from about 20% to about 30%, for example, about 24% to about 28%, 24%, or 28% (on a dry basis), and a D-Sorbitol content of about 30% to about 50%, for example, about 35% to about 45% (on a dry basis).

In some embodiments, the capsule is a hard gelatin capsule. In another embodiment, the capsule is a soft gelatin capsule.

In some embodiments, the capsule shell comprises modified starch, carrageenan (e.g., extract of red seaweed), disodium phosphate, glycerol and/or sorbitol. In some embodiments, the capsule shell further comprises water. In some embodiments, the capsule shell is stable up to a temperature of about 65° C. and/or pH of about 12.

In some embodiments, the capsule shell is odorless and has a neutral color (e.g., colorless, white, or transparent).

In some embodiments, the capsule shell further comprises glycerol, purified water, titanium dioxide, medium chain triglycerides and lecithin.

Additional Active Agents

In one embodiment, the pharmaceutical composition further comprises one or more additional active agent(s). In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent. If an additional active agent is to be used, the 15-HEPE can be co-formulated as a single dosage unit or can be formulated as two to a plurality of dosage units for coordinated, combination or concomitant administration.

EPA itself has beneficial properties in treating fatty liver disease and/or cardiovascular disease and it is possible to combine the 15-HEPE with EPA in an alternative embodiment.

In one embodiment, 15-HEPE and one or more active agent(s) are present in a composition of the disclosure, or are co-administered in a weight ratio of 15-HEPE: additional agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

Dosage Forms

A composition for use in accordance with the disclosure can be formulated as one or more dosage units. The terms "dose unit" and "dosage unit" herein refer to a portion of a composition that contains an amount of a therapeutic agent suitable for a single administration to provide a therapeutic effect. Such dosage units may be administered one to a plurality (e.g., 1 to about 10, 1 to 8, 1 to 6, 1 to 4 or 1 to 2) of times per day, or as many times as needed to elicit a therapeutic response.

In some embodiments, compositions of the disclosure are in the form of orally deliverable dosage forms or units. Non-limiting examples of suitable dosage forms include tablets (e.g., suspension tablets, bite suspension tablets, rapid dispersion tablets, chewable tablets, etc), caplets, capsules (e.g., a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophageal administration.

Alternatively, compositions of the disclosure can also be formulated for rectal, topical, or parenteral (e.g., subcutaneous, intramuscular, intravenous and intradermal or infusion) delivery.

In discussing the amount of 15-HEPE in a composition of the disclosure, this may be split over several dosage forms. There is a limit as to the size for oral administration. If a subject is to be administered about 1 to about 4 g 15-HEPE a day, this may be by up to 4 capsules, each providing about 1 g of 15-HEPE.

Compositions of the disclosure can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the disclosure comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavoring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment and/or prevention of a hematologic disorder in a subject in need thereof. In some embodiments, the hematologic disorder is a hemoglobin disorder, a red blood cell disorder, hemolytic anemia, a thrombophilia disorder, a venous thromboembolism, an arterial thrombosis, an embolism, or a combination thereof. In some embodiments, the methods comprise administering to the subject 15-hydroxyeicosapentaenoic acid (15-HEPE) or a composition comprising 15-hydroxyeicosapentaenoic acid (15-HEPE).

The compositions and formulations disclosed herein may be used in the treatment and/or prevention of hematologic disorders, hemoglobin disorders, and/or red blood cell disorders. Hematologic disorders refer to a class of conditions that affect the blood and blood-forming organs. While hemoglobin disorders and red blood cells disorders are similar to hematologic disorders, both hemoglobin disorders and red blood cell disorders define a narrower class of disorders. Specifically, hemoglobin disorders refer to defects in hemoglobin, the oxygen transport protein in red blood cells. And red blood cell disorders, refer to defects in the red blood cell itself. Non-limiting examples of risk factors of hematologic disorders, hemoglobin disorders, and red blood cell disorders include reduced red blood cell counts, increased red blood cell distribution widths, and increased reticulocyte counts. Non-limiting examples of hematologic disorders, hemoglobin disorders, and red blood cell disorders include anemia (nutritional anemias and non-nutritional anemias, inherited hemolytic anemia such as sickle cell disease, sickle cell anemia, β-thalassemia, and hereditary spherocytosis, acquired hemolytic anemia such as secondary to infection, medication, hematological malignancy, autoimmune disease, hypersplenism, mechanical heart valves, and blood transfusions, Fanconi anemia, iron deficiency anemia), blood cancer (lymphoma, leukemia, and myeloma), coagulation defects (thrombophilia, hemophilia, Von Willebrand disease, and thrombocytopenia), folate deficiency, B12 deficiency, and myelodysplastic syndrome. In some embodiments, sickle cell disease and sickle cell anemia are associated with sickle cell crisis, vaso-occlusive crisis, and/or splenic sequestration.

In some embodiments, the subject has a reduced red blood cell count of at least 10% below normal, at least 15% below normal, at least 20% below normal, at least 25% below normal, or at least 30% below normal.

In some embodiments, the subject has an increased red blood cell distribution width, where the red blood cells vary in size by about 15-20%, by about 20-25%, by about 25-30%, by about 30-35%, or by about 35-40%.

In another embodiment, the subject has an increased reticulocyte count of at least about 5% of the total amount of red blood cells, at least about 10% of the total amount of red blood cells, at least about 15% of the total amount of red blood cells, or at least about 20% of the total amount of red blood cells.

In some embodiments, the subject has elevated baseline triglyceride levels of about 135 mg/dL to about 2000 mg/dL, for example about 135 mg/dL to about 500 mg/dL, about 150 mg/dL to about 500 mg/dL, about 200 mg/dL to about 499 mg/dL, about 200 mg/dL to <500 mg/dL, about 300 mg/dL to about 1800 mg/dL, about 500 mg/dL to about 1500 mg/dL, about 500 mg/dL to about <2000 mg/dL, or about 500 mg/dL to about 2000 mg/dL. In some embodiments, the subject has a fasting baseline triglyceride level of about 50 mg/dL to about 2000 mg/dL, for example about 50 mg/dL to about 1500 mg/dL, about 80 mg/dL to about 1500 mg/dL, about 50 mg/dL to about 190 mg/dl, about 80 mg/dL to about 190 mg/dl, about 190 mg/dL to about 250 mg/dL, about 250 mg/dL to about 1400 mg/dL, about 500 mg/dL to about 1200 mg/dL, about 500 mg/dL to about 1500 mg/dL, about 500 mg/dL to about <2000 mg/dL, or about 500 mg/dL to about 2000 mg/dL. In one embodiment, the subject has a fasting baseline triglyceride level of about 80 mg/dL to about 1400 mg/dL. In some embodiments, the subject or subject group has a baseline triglyceride level (or median baseline triglyceride level in the case of a subject group), fed or fasting, of about 50 mg/dL, about 55 mg/dL, about 60 mg/dL, about 65 mg/dL, about 70 mg/dL, about 75 mg/dL, about 80 mg/dL, about 85 mg/dL, about 90 mg/dL, about 95 mg/dL, about 100 mg/dL, about 105 mg/dL, about 110 mg/dL, about 115 mg/dL, about 120 mg/dL, about 125 mg/dL, about 130 mg/dL, about 135 mg/dL, about 140 mg/dL, about 145 mg/dL, about 150 mg/dL, about 155 mg/dL, about 160 mg/dL, about 165 mg/dL, about 170 mg/dL, about 175 mg/dL, about 180 mg/dL, about 185 mg/dL, about 190 mg/dL, about 195 mg/dL, about 200 mg/dL, about 205 mg/dL, about 210 mg/dL, about 215 mg/dL, about 220 mg/dL, about 225 mg/dL, about 230 mg/dL, about 235 mg/dL, about 240 mg/dL, about 245 mg/dL, about 250 mg/dL, about 255 mg/dL, about 260 mg/dL, about 265 mg/dL, about 270 mg/dL, about 275 mg/dL, about 280 mg/dL, about 285 mg/dL, about 290 mg/dL, about 295 mg/dL, about 300 mg/dL, about 305 mg/dL, about 310 mg/dL, about 315 mg/dL, about 320 mg/dL, about 325 mg/dL, about 330 mg/dL, about 335 mg/dL, about 340 mg/dL, about 345 mg/dL, about 350 mg/dL, about 355 mg/dL, about 360 mg/dL, about 365 mg/dL, about 370 mg/dL, about 375 mg/dL, about 380 mg/dL, about 385 mg/dL, about 390 mg/dL, about 395 mg/dL, about 400 mg/dL, about 405 mg/dL, about 410 mg/dL, about 415 mg/dL, about 420 mg/dL, about 425 mg/dL, about 430 mg/dL, about 435 mg/dL, about 440 mg/dL, about 445 mg/dL, about 450 mg/dL, about 455 mg/dL, about 460 mg/dL, about 465 mg/dL, about 470 mg/dL, about 475 mg/dL, about 480 mg/dL, about 485 mg/dL, about 490 mg/dL, about 495 mg/dL, about 500 mg/dL, about 1000 mg/dL, about 1100 mg/dL, about 1200 mg/dL, about 1300 mg/dL, about 1400 mg/dL, about 1500 mg/dL, about 2000 mg/dL, about 2500 mg/dL, about 3000 mg/dL, about 3500 mg/dL, about 4000 mg/dL, about 4500 mg/dL, about 5000 mg/dL, or greater than about 5000 mg/dL. In some embodiments, the subject or subject group has a baseline triglyceride level (or median baseline triglyceride level in the case of a subject group), fed or fasting, greater than or equal to 80 mg/dL, greater than or equal to about 100 mg/dL, greater than or equal to about 120 mg/dL greater than or equal to about 150 mg/dL, greater than or equal to about 175 mg/dL, greater than or equal to about 250 mg/dL, or greater than equal to about 500 mg/dL, for example about 190 mg/dL to about 250 mg/dL, about 80 mg/dL to about 190 mg/dL, about 250 mg/dL to about 1400 mg/dL, about 200 mg/dL to about 500 mg/dL, about 300 mg/dL to about 1800 mg/dL, about 500 mg/dL to about 1500 mg/dL, about 80 mg/dL to about 1500 mg/dL, about 80 mg/dL to less than about 2000 mg/dL, about 80 mg/dL to about 2000 mg/dL, about 500 mg/dL to less than about 2000 mg/dL or about 500 mg/dL to about 2000 mg/dL.

In another embodiment, the subject has an elevated baseline blood pressure of at least about 100 mmHg, at least about 115 mmHg, at least about 120 mmHg, at least about 125 mmHg, at least about 130 mmHg, at least about 135 mmHg, at least about 140 mmHg, at least about 145 mmHg, at least about 150 mmHg, at least about 155 mmHg, at least about 160 mmHg, at least about 165 mmHg, or at least about 170 mmHg.

In some embodiments, the subject has elevated baseline fasting glucose levels of at least about 100 mg/dL, at least about 115 mg/dL, at least about 120 mg/dL, at least about 125 mg/dL, at least about 130 mg/dL, at least about 135 mg/dL, at least about 140 mg/dL, at least about 145 mg/dL, at least about 150 mg/dL, at least about 155 mg/dL, at least about 160 mg/dL, at least about 165 mg/dL, or at least about 170 mg/dL.

In some embodiments, the subject has reduced baseline HDL-C levels of less than about 60 mg/dL, less than about 55 mg/dL, less than about 50 mg/dl, less than about 45 mg/dL, less than about 40 mg/dL, less than about 35 mg/dL, less than about 30 mg/dL, less than about 25 mg/dL, less than about 20 mg/dL, less than about 15 mg/dL, less than about 10 mg/dL, or less than about 5 mg/dL.

In some embodiments, the present disclosure provides a method of treating and/or preventing hematologic disease in a subject, the method comprising administering to the subject 15-HEPE. In another embodiment, the method comprises administering to the subject up to about 8 g of 15-HEPE. In yet another embodiment, the 15-HEPE represents at least about 90%, by weight, all fatty acids in the composition.

In some embodiments, the present disclosure provides a method of treating and/or preventing hematologic disease in a subject, the method comprising administering to the subject 15-HEPE or a composition comprising 15-HEPE. In another embodiment, the method comprises administering to the subject up to about 8 g of 15-HEPE or a composition comprising 15-HEPE. In yet another embodiment, the 15-HEPE represents at least about 90%, by weight, all fatty acids in the composition.

In some embodiments, the present disclosure provides methods of treating and/or preventing a hematologic disorder in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides a method of treating and/or preventing hematologic disease in a subject, the method comprising administering to the subject 15-HEPE or a composition comprising 15-HEPE. In some embodiments, the method further comprises determining that the subject has at least one risk factor for hematologic disease before administering the 15-HEPE, or a composition comprising 15-HEPE. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count. In another embodiment, the method comprises administering to the subject up to about 8 g of 15-HEPE or a composition comprising 15-HEPE. In yet another embodiment, the 15-HEPE represents at least about 90%, by weight, of all fatty acids in the composition.

In some embodiments, the present disclosure provides methods of treating and/or preventing a hematologic disorder in a subject in need thereof, the method comprising administering to the subject 15-hydroxyeicosapentaenoic acid (15-HEPE) or a composition comprising 15-HEPE. In some embodiments, the method further comprises determining that the subject has at least one risk factor for hematologic disease before administering the 15-HEPE, or a composition comprising 15-HEPE. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a hemoglobin disorder in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a hemoglobin disorder in a subject in need thereof, the method comprising administering to the subject 15-hydroxyeicosapentaenoic acid (15-HEPE) or a composition comprising 15-HEPE. In some embodiments, the method further comprises determining that the subject has at least one risk factor for the hemoglobin disorder before administering the 15-HEPE, or a composition comprising 15-HEPE. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a red blood cell disorder in a subject in need thereof, the method comprising administering to the subject 15-HEPE or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a red blood cell disorder in a subject in need thereof, the method comprising administering to the subject 15-HEPE or a composition comprising 15-HEPE. In some embodiments, the method further comprises determining that the subject has at least one risk factor for the red blood cell disorder before administering the 15-HEPE, or a composition comprising 15-HEPE. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a hematologic disorder, a hemoglobin disorder, and/or a red blood cell disorder in a subject in need thereof, the method comprising administering to the subject 15-HEPE or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a hematologic disorder, a hemoglobin disorder, and/or a red blood cell disorder in a subject in need thereof, the method comprising administering to the subject 15-HEPE or a composition comprising 15-HEPE. In some embodiments, the method further comprises determining that the subject has at least one risk factor for a hematologic disorder, a hemoglobin disorder, and/or a red blood cell disorder before administering the 15-HEPE, or a composition comprising 15-HEPE. In some embodiments, at least one risk factor is reduced red blood cell counts, increased red blood cell distribution widths, and/or increased reticulocyte counts. In some embodiments, the subject exhibits one or more of an increase in red blood cell count, a decrease in red blood cell distribution width and/or a reduced reticulocyte count.

In some embodiments, the present disclosure provides methods of treating and/or preventing a hematologic disorder, a hemoglobin disorder, and/or a red blood cell disorder in a subject in need thereof, the method comprising administering to the subject 15-HEPE or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition. In another embodiment, the hematologic disorder, the hemoglobin disorder, and/or the red blood cell disorder are selected from the group consisting of inherited hemolytic anemia, acquired hemolytic anemia, Fanconi anemia, iron deficiency anemia, folate deficiency, B12 deficiency, and myelodysplastic syndrome. In some embodiments, the method further comprises determining that the subject has at least one risk factor for inherited hemolytic anemia, acquired hemolytic anemia, Fanconi anemia, iron deficiency anemia, folate deficiency, B12 deficiency, and/or myelodysplastic syndrome before administering the 15-HEPE, or a composition comprising 15-HEPE. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count.

In some embodiments, the present disclosure provides methods of treating and/or preventing hemolytic anemia in a subject in need thereof, the method comprising administering to the subject 15-HEPE or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing hemolytic anemia in a subject in need thereof, the method comprising administering to the subject 15-HEPE or a composition comprising 15-HEPE. In some embodiments, the method further comprises determining that the subject has at least one risk factor for hemolytic anemia before administering the 15-HEPE, or a composition comprising 15-HEPE. In some embodiments, at least one risk factor is reduced red blood cell counts, increased red blood cell distribution widths, and/or increased reticulocyte counts. In some embodiments, the subject exhibits one or more of an increase in red blood cell count, a decrease in red blood cell distribution width and/or a reduced reticulocyte count.

In some embodiments, the present disclosure provides methods of treating and/or preventing hemolytic anemia in a subject in need thereof, the method comprising administering to the subject up to about 8 g of a composition comprising 15-HEPE. In some embodiments, the 15-HEPE represents at least about 90% by weight, of all fatty acids in the composition. In some embodiments, the hemolytic anemia is inherited hemolytic anemia or acquired hemolytic anemia. In another embodiment, the inherited hemolytic anemia is selected from the group consisting of sickle cell disease, sickle cell anemia, β-thalassemia, and hereditary spherocytosis. In yet another embodiment, the acquired hemolytic anemia is selected from the group consisting of secondary to infection, medication, hematological malignancy, autoimmune disease, hypersplenism, mechanical heart valves, and blood transfusions. In various embodiments, the sickle cell disease and sickle cell anemia are associated with sickle cell crisis, vaso-occlusive crisis, and/or splenic sequestration. In some embodiments, the subject exhibits an increase in red blood cell count, a decrease in red blood cell distribution width, and a decrease in reticulocyte count following administration.

In some embodiments, the present disclosure provides methods of treating and/or preventing hemolytic anemia in a subject in need thereof, the method comprising administering to the subject up to about 8 g of a composition comprising 15-HEPE. In some embodiments, the 15-HEPE represents at least about 90% by weight, of all fatty acids in the composition. In some embodiments, the hemolytic anemia is inherited hemolytic anemia or acquired hemolytic anemia. In another embodiment, the inherited hemolytic anemia is selected from the group consisting of sickle cell disease, sickle cell anemia, β-thalassemia, and hereditary spherocytosis. In some embodiments, the method further comprises determining that the subject has at least one risk factor for inherited hemolytic anemia or acquired hemolytic anemia before administering the 15-HEPE, or a composition comprising 15-HEPE. In yet another embodiment, the acquired hemolytic anemia is selected from the group consisting of secondary to infection, medication, hematological malignancy, autoimmune disease, hypersplenism, mechanical heart valves, and blood transfusions. In various embodiments, the sickle cell disease and sickle cell anemia are associated with sickle cell crisis, vaso-occlusive crisis, and/or splenic sequestration. In some embodiments, the method further comprises determining a baseline red blood cell count, a red blood cell distribution width, and/or a reticulocyte count of the subject before administering the 15-HEPE. In one embodiment, the subject exhibits an increase in the red blood cell count, a decrease in the red blood cell distribution width, and/or a decrease in the reticulocyte count.

The compositions and formulations disclosed herein may further be used in the treatment and/or prevention of a thrombophilia disorder. Thrombophilia disorders refer to a class of conditions characterized by abnormal blood coagulation that increases the risk of thrombosis. Non-limiting examples of risk factors of thrombophilia disorders include decreased prothrombin times, decreased activated partial thromboplastin times, and increased fibrinogen concentration.

In some embodiments, the subject has a reduced prothrombin time of at least 10% below normal, at least 15% below normal, at least 20% below normal, at least 25% below normal, or at least 30% below normal.

In some embodiments, the subject has a reduced activated partial thromboplastin time of at least 10% below normal, at least 15% below normal, at least 20% below normal, at least 25% below normal, or at least 30% below normal.

In some embodiments, the subject has an increased fibrinogen concentration of at least 10% below normal, at least 15% below normal, at least 20% below normal, at least 25% below normal, or at least 30% below normal.

In some embodiments, the present disclosure provides methods of treating and/or preventing a thrombophilia disorder in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a thrombophilia disorder in a subject in need thereof, the method comprising administering to the subject 15-HEPE or a composition comprising 15-HEPE. In some embodiments, the method further comprises determining that the subject has at least one risk factor for a thrombophilia disorder before administering the 15-HEPE, or a composition comprising 15-HEPE. In some embodiments, at least one risk factor is decreased prothrombin times, decreased activated partial thromboplastin times, and/or increased fibrinogen concentration. In some embodiments, the subject exhibits one or more of an increase in prothrombin time, an increase in activated partial thromboplastin time and/or a decrease in fibrinogen concentration after administering the 15-HEPE, or a composition comprising 15-HEPE.

In some embodiments, the present disclosure provides methods of treating and/or preventing a venous thromboembolism in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing a venous thromboembolism in a subject in need thereof, the method comprising administering to the subject 15-HEPE or a composition comprising 15-HEPE. In some embodiments, the method further comprises determining that the subject has at least one risk factor for venous thromboembolism before administering the 15-HEPE, or a composition comprising 15-HEPE. In some embodiments, at least one risk factor is decreased prothrombin times, decreased activated partial thromboplastin times, and/or increased fibrinogen concentration. In some embodiments, the subject exhibits one or more of an increase in prothrombin time, an increase in activated partial thromboplastin time and/or a decrease in fibrinogen concentration.

In some embodiments, the present disclosure provides methods of treating and/or preventing an arterial thrombosis in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of treating and/or preventing an arterial thrombosis in a subject in need thereof, the method comprising administering to the subject 15-HEPE or a composition comprising 15-HEPE. In some embodiments, the method further comprises determining that the subject has at least one risk factor for an arterial thrombosis before administering the 15-HEPE, or a composition comprising 15-HEPE. In some embodiments, at least one risk factor is decreased prothrombin times, decreased activated partial thromboplastin times, and/or increased fibrinogen concentration. In some embodiments, the subject exhibits one or more of an increase in prothrombin time, an increase in activated partial thromboplastin time and/or a decrease in fibrinogen concentration.

In some embodiments, the present disclosure provides methods of preventing an embolism in a subject in need thereof, the method comprising administering to the subject 15-hydroxyeicosapentaenoic acid (15-HEPE) or a composition comprising 15-HEPE. In another embodiment, the method comprises administering to the subject up to about 8 g of a composition comprising 15-HEPE. In another embodiment, the 15-HEPE represents at least about 90% by weight, of all fatty acids in the composition.

In some embodiments, the present disclosure provides methods of preventing an embolism in a subject in need thereof, the method comprising administering to the subject 15-HEPE or a composition comprising 15-HEPE. In some embodiments, the method further comprises determining that the subject has at least one risk factor for developing an embolism before administering the 15-HEPE, or a composition comprising 15-HEPE. In some embodiments, at least one risk factor is decreased prothrombin times, decreased activated partial thromboplastin times, and/or increased fibrinogen concentration. In some embodiments, the subject exhibits one or more of an increase in prothrombin time, an increase in activated partial thromboplastin time and/or a decrease in fibrinogen concentration.

In some embodiments, the present disclosure provides a method of treating and/or preventing endothelial dysfunction in a subject, the method comprising administering to the subject 15-HEPE. In another embodiment, the method comprises administering to the subject up to about 8 g of 15-HEPE. In yet another embodiment, the 15-HEPE represents at least about 90%, by weight, all fatty acids in the composition.

In some embodiments, the present disclosure provides a method of treating and/or preventing endothelial dysfunction in a subject, the method comprising administering to the subject 15-HEPE or a composition comprising 15-HEPE. In another embodiment, the method comprises administering to the subject up to about 8 g of 15-HEPE or a composition comprising 15-HEPE. In yet another embodiment, the 15-HEPE represents at least about 90%, by weight, all fatty acids in the composition.

In some embodiments, the present disclosure provides a method of treating, preventing, or reducing cell stress apoptosis, the method comprising administering to the subject 15-HEPE or a composition comprising 15-HEPE. In some embodiments the subject exhibits a reduction in markers associated with apoptosis such as proteins from the Bcl-2 family, activated fragments of caspases and/or cleaved PAR P-1.

In some embodiments, the present disclosure provides a method of treating, preventing, and/or reducing inflammation, the method comprising administering to the subject 15-HEPE or a composition comprising 15-HEPE. In some embodiments the subject exhibits a reduction T cell activation, B cell activation, and/or chemotaxis.

The compositions and formulations disclosed herein may be used in the treatment or prevention of cardiovascular disease or disorder. In one embodiment the cardiovascular disease or disorder is selected from: dyslipidemia, hyperlipidemia, hypercholesterolemia, hypertriglyceridemia, primary hypercholesterolemia, primary hyperlipidemia, common primary hyperlipidemia, common hypercholesterolemia, familial hyperlipidemia, familial primary hyperlipidemia, familial hypercholesterolemia, familial hypertriglyceridemia, familial combined hyperlipidemia, familial defective apolipoprotein b-100, secondary hyperlipidemia, mixed hyperlipidemia, cardiovascular disease, residual cardiovascular risk, prevention of atherosclerotic plaque formation/progression, microvascular disease, macrovascular disease, atherosclerosis, coronary atherosclerosis, diastolic dysfunction, reduction of cardiovascular risk, prevention of major coronary events, prevention of major adverse cardiovascular events, prevention of ischemic events, secondary/primary prevention of cardiovascular events, prevention of cardiovascular death, myocardial infarction, stroke, angina, restoration of normal endothelial function, diabetes, diabetes mellitus, insulin resistance, hyperinsulinemia, hyperglycemia, dysglycemia, induction of glycemic control, impaired glucose tolerance, and impaired fasting glucose. Non-limiting examples of microvascular disease include retinopathy, nephropathy, and neuropathy. Non-limiting examples of macrovascular disease include stroke, peripheral vascular disease, limb ischemia, and heart disease. In some embodiments, the subject has non-alcoholic liver disease, cholestatic liver disease, kidney disease, or metabolic syndrome. Any of the aforementioned examples of cardiovascular disease may also refer to non-limiting examples of cardiometabolic disease.

In one embodiment, the present disclosure provides a method of treating and/or preventing cardiovascular disease in a subject, the method comprising administering to the subject 15-HEPE.

In one embodiment, the present disclosure provides a method of treating and/or preventing cardiovascular disease in a subject, the method comprising administering to the subject 15-HEPE or a composition comprising 15-HEPE.

In another embodiment, the present disclosure provides a method of preventing hematologic disorder in a subject having diabetes (e.g., Type I or Type II), the method comprising administering to the subject 15-HEPE. In some embodiments, the method further comprises determining the subject has diabetes before administering the 15-HEPE. In another embodiment, the method comprises administering to the subject about 10 mg per weight of the subject (mg/kg), about 50 mg/kg, about 250 mg/kg, or about 500 mg/kg 15-HEPE. In yet another embodiment, the 15-HEPE represents at least about 90%, by weight, all fatty acids in the composition.

In another embodiment, the present disclosure provides a method of preventing hematologic disorder in a subject having diabetes (e.g., Type I or Type II), the method comprising administering to the subject 15-HEPE or a composition comprising 15-HEPE. In some embodiments, the method further comprises determining the subject has diabetes before administering the 15-HEPE or composition comprising 15-HEPE. In another embodiment, the method comprises administering to the subject about 10 mg per weight of the subject (mg/kg), about 50 mg/kg, about 250 mg/kg, or about 500 mg/kg 15-HEPE or composition comprising 15-HEPE. In yet another embodiment, the 15-HEPE represents at least about 90%, by weight, all fatty acids in the composition.

In another embodiment, the present disclosure provides a method of treating and/or preventing hematologic disorder in a subject having cardiovascular disease, the method comprising administering to the subject 15-HEPE. In some embodiments, the method further comprises determining the subject has cardiovascular before administering the 15-HEPE. In another embodiment, the method comprises administering to the subject about 10 mg per weight of the subject (mg/kg), about 50 mg/kg, about 250 mg/kg, or about 500 mg/kg 15-HEPE. In yet another embodiment, the 15-HEPE represents at least about 90%, by weight, all fatty acids in the composition.

In another embodiment, the present disclosure provides a method of treating and/or preventing hematologic disorder in a subject having cardiovascular disease, the method comprising administering to the subject 15-HEPE or a composition comprising 15-HEPE. In some embodiments, the method further comprises determining the subject has cardiovascular before administering the 15-HEPE or composition comprising 15-HEPE. In another embodiment, the method comprises administering to the subject about 10 mg per weight of the subject (mg/kg), about 50 mg/kg, about 250 mg/kg, or about 500 mg/kg 15-HEPE or composition comprising 15-HEPE. In yet another embodiment, the 15-HEPE represents at least about 90%, by weight, all fatty acids in the composition.

In another embodiment, the present disclosure provides a method of treating and/or preventing hematologic disorder in a subject having high blood pressure, the method comprising administering to the subject 15-HEPE. In some embodiments, the method further comprises determining the subject has high blood pressure before administering the 15-HEPE. In some embodiments, the subject has a high blood pressure of at least about 130 mmHg, at least about 135 mmHg, at least about 140 mmHg, at least about 145 mmHg, at least about 150 mmHg, at least about 155 mmHg, at least about 160 mmHg, at least about 165 mmHg, or at least about 170 mmHg. In another embodiment, the method comprises administering to the subject about 10 mg/kg, about 50 mg/kg, about 250 mg/kg, or about 500 mg/kg 15-HEPE. In yet another embodiment, the 15-HEPE represents at least about 90%, by weight, all fatty acids in the composition.

In another embodiment, the present disclosure provides a method of treating and/or preventing hematologic disorder in a subject having high blood pressure, the method comprising administering to the subject 15-HEPE or a composition comprising 15-HEPE. In some embodiments, the method further comprises determining the subject has high blood pressure before administering the 15-HEPE or composition comprising 15-HEPE. In some embodiments, the subject has a high blood pressure of at least about 130 mmHg, at least about 135 mmHg, at least about 140 mmHg, at least about 145 mmHg, at least about 150 mmHg, at least about 155 mmHg, at least about 160 mmHg, at least about 165 mmHg, or at least about 170 mmHg. In another embodiment, the method comprises administering to the subject about 10 mg/kg, about 50 mg/kg, about 250 mg/kg, or about 500 mg/kg 15-HEPE or composition comprising 15-HEPE. In yet another embodiment, the 15-HEPE represents at least about 90%, by weight, all fatty acids in the composition.

The compositions and formulations disclosed herein may also be used for reducing cytokines and/or chemokines in a subject having cardiovascular disease, and/or hematologic disease. Non-limiting cytokines and/or chemokines include α-smooth muscle action (α-SMA), metallopeptidase inhibitor-1 (TIMP-1), transforming growth factor beta-β (TGF-β), and Collagen Type 1.

In another embodiment, upon treatment with a composition of the present invention, the subject or subject group exhibits one or more of the following outcomes:

(a) no increase or a reduction in serum aminotransferase (ALT) and/or aspartate aminotransferase (AST) levels relative to baseline, placebo control, and/or untreated patient;
(b) no increase or a reduction in bilirubin (BUN) levels relative to baseline, placebo control, and/or untreated patient;
(c) no increase or a reduction in fibrosis area relative to baseline, placebo control, and/or untreated patient;
(d) no increase or a reduction in fasting glucose levels relative to baseline, placebo control, and/or untreated patient;
(e) no increase or a reduction in insulin levels relative to baseline, placebo control, and/or untreated patient;
(f) no increase or a reduction in alkaline phosphate (ALP) levels relative to baseline, placebo control, and/or untreated patient;
(g) no increase or a reduction in hemoglobin A1C (HbA1C) levels relative to baseline, placebo control, and/or untreated patient;
(h) no increase or a reduction in homeostatic model assessment of insulin resistance (HOMA-IR) levels relative to baseline, placebo control, and/or untreated patient;
(i) no increase or a reduction in adipose tissue insulin resistance (adipo-IR) levels relative to baseline, placebo control, and/or untreated patient;
(j) no increase or a reduction in total cholesterol levels relative to baseline, placebo control, and/or untreated patient;
(k) no increase or a reduction in triglyceride levels relative to baseline, placebo control, and/or untreated patient;
(l) no increase or a reduction in diglyceride levels relative to baseline, placebo control, and/or untreated patient;
(m) no increase or a reduction in very low-density lipoprotein cholesterol (VLDL-C) levels relative to baseline, placebo control, and/or untreated patient;
(n) no increase or a reduction in remnant-like particle cholesterol (RLP-C) levels relative to baseline, placebo control, and/or untreated patient;
(o) no increase or a reduction in non-high-density lipoprotein cholesterol (non-HDL-C) levels relative to baseline, placebo control, and/or untreated patient;
(p) no reduction or an increase in high density lipoprotein cholesterol (HDL-C) levels relative to baseline, placebo control, and/or untreated patient;
(q) no increase or a reduction in low density lipoprotein cholesterol (LDL-C) levels relative to baseline, placebo control, and/or untreated patient;
(r) no increase or a reduction in kidney hydroxyproline levels relative to baseline, placebo control, and/or untreated patient;
(s) no increase or a reduction in interleukin-33 (IL-33) levels relative to baseline, placebo control, and/or untreated patient;
(t) no increase or a reduction in interleukin-17 (IL-17) levels relative to baseline, placebo control, and/or untreated patient;
(u) no increase or a reduction in aryl hydrocarbon receptor (AhR) levels relative to baseline, placebo control, and/or untreated patient;
(v) no increase or a reduction in TNF-like ligand 1A (TL1A) levels relative to baseline, placebo control, and/or untreated patient;
(w) no increase or a reduction in tumor necrosis factor (TNF-α) levels relative to baseline, placebo control, and/or untreated patient;
(x) no increase or a reduction in interleukin-13 (IL-13) levels relative to baseline, placebo control, and/or untreated patient;
(y) no increase or a reduction in interleukin-6 (IL-6) levels relative to baseline, placebo control, and/or untreated patient;
(z) no increase or a reduction in interleukin 1 beta-β (IL-1β) levels relative to baseline, placebo control, and/or untreated patient;
(aa) no increase or a reduction in Collagen Type 1 levels relative to baseline, placebo control, and/or untreated patient;
(bb) no increase or a reduction in transforming growth factor-β (TGF-β) levels relative to baseline, placebo control, and/or untreated patient;
(cc) no increase or a reduction in α-smooth muscle action (α-SMA) levels relative to baseline, placebo control, and/or untreated patient;
(dd) no increase or a reduction in tumor necrosis factor ligand superfamily member 11A (TNRSF11A) levels relative to baseline, placebo control, and/or untreated patient;
(ee) no increase or a reduction in serine protease 2 (PRSS2) levels relative to baseline, placebo control, and/or untreated patient;

(ff) no increase or a reduction in amine oxidase, copper containing 3 (AOC3) levels relative to baseline, placebo control, and/or untreated patient;
(gg) no increase or a reduction in leukocyte immunoglobulin like receptor B1 (LILBR1) levels relative to baseline, placebo control, and/or untreated patient;
(hh) no increase or a reduction in transferrin receptor protein 1 (TR) levels relative to baseline, placebo control, and/or untreated patient;
(ii) no increase or a reduction in elafin (PI3) levels relative to baseline, placebo control, and/or untreated patient;
(jj) no increase or a reduction in serum amyloid A4 (SAA4) levels relative to baseline, placebo control, and/or untreated patient;
(kk) no increase or a reduction in monocyte chemoattractant protein-1 (MCP-1) levels relative to baseline, placebo control, and/or untreated patient;
(ll) no increase or a reduction in chemokine (C—C motif) ligand 16 (CCL16) levels relative to baseline, placebo control, and/or untreated patient;
(mm) no increase or a reduction in trem-like transcript 2 (TLT2) levels relative to baseline, placebo control, and/or untreated patient;
(nn) no increase or a reduction in dipeptidyl peptidase 4 (DPP4) levels relative to baseline, placebo control, and/or untreated patient; and
(oo) no increase or a reduction in metalloproteinase inhibitor-1 (TIMP-1) levels relative to baseline, placebo control, and/or untreated patient;
(pp) no increase or a reduction in plasminogen activator inhibitor-1 (PAI-1) levels relative to baseline, placebo control, and/or untreated patient;
(qq) no increase or a reduction in a NAFLD score (NFS) relative to baseline, placebo control, and/or untreated patient; and
(rr) no increase or a reduction in fibrosis-4 (FIB-4) levels relative to baseline, placebo control, and/or untreated patient;
(ss) no increase or a reduction in liver stiffness levels relative to baseline, placebo control, and/or untreated patient;
(tt) no increase or a reduction in hepatic fat content relative to baseline, placebo control, and/or untreated patient;
(uu) no reduction or an increase in glycerophospholipid levels relative to baseline, placebo control, and/or untreated patient;
(w) no increase or a reduction in blood pressure relative to baseline, placebo control, and/or untreated patient;
(ww) no increase or a reduction in an enhanced liver fibrosis (ELF) score relative to baseline, placebo control, and/or untreated patient;
(xx) no increase or a reduction in collagen production in lung and/or dermal fibroblasts relative to baseline, placebo control, and/or untreated patient;
(yy) no reduction or an increase in glucose uptake relative to baseline, placebo control, and/or untreated patient;
(zz) an increase in lung and/or dermal fibroblast viability relative to baseline, placebo control, and/or untreated patient;
(ab) no change or a reduction in interleukin-8 (IL-8) levels relative to baseline, placebo control, and/or untreated patient;
(ac) no change or a reduction in interleukin-23 (IL-23) levels relative to baseline, placebo control, and/or untreated patient;
(ad) no change or a reduction in interlekin-11 (IL-11) levels relative to baseline, placebo control, and/or untreated patient; and/or
(ae) no change or a reduction in interferon γ (IFNγ) levels relative to baseline, placebo control, and/or untreated patient;
(af) no change or a reduction in T and/or B cell activation relative to baseline, placebo control, and/or untreated patient;
(ag) no change or a reduction in chemotaxis relative to baseline, placebo control, and/or untreated patient;
(ah) no change or a reduction in phosphorylated B-cell lymphoma 2 (Bcl-2) family members relative to baseline, placebo control, and/or untreated patient;
(ai) no change or a reduction in activated fragments of caspases levels relative to baseline, placebo control, and/or untreated patient;
(aj) no change or a reduction in cleaved poly (ADP-ribose) polymerase-1 (PARP-1) levels relative to baseline, placebo control, and/or untreated patient;
(ak) no change or a reduction in waist circumference relative to baseline, placebo control, and/or untreated patient;
(al) no change or a reduction in an AST to platelet ration index (ARPI) relative to baseline, placebo control, and/or untreated patient;
(am) no change or a reduction in a liver inflammation and fibrosis (LIF) score relative to baseline, placebo control, and/or untreated patient;
(an) no change or a reduction in a Lok score relative to baseline, placebo control, and/or untreated patient;
(ao) no change or a reduction in a fibrosis score relative to baseline, placebo control, and/or untreated patient;
(ap) no change or a reduction in a King score relative to baseline, placebo control, and/or untreated patient;
(aq) no change or a reduction in a Bonacini score relative to baseline, placebo control, and/or untreated patient;
(ar) no change or a reduction in a transient elastography (TE) score relative to baseline, placebo control, and/or untreated patient.
(as) no increase or a reduction in vascular adhesion molecules relative to baseline, placebo control, and/or untreated patient;
(at) no increase or a reduction in cardiovascular risk proteins relative to baseline, placebo control, and/or untreated patient;
(au) no increase or a reduction in chemokines relative to baseline, placebo control, and/or untreated patient;
(av) no increase or a reduction in tumor necrosis factor receptor superfamily members relative to baseline, placebo control, and/or untreated patient;
(aw) no change or an increase in red blood cell count relative to baseline, placebo control, and/or untreated patient;
(ax) no change or an increase in white blood cell count relative to baseline, placebo control, and/or untreated patient;
(ay) no change or an increase in platelet count relative to baseline, placebo control, and/or untreated patient;
(az) no change or an increase in prothrombin time relative to baseline, placebo control, and/or untreated patient;
(ba) no change or an increase in activated partial thromboplastin time relative to baseline, placebo control, and/or untreated patient;
(bc) no change or an increase in hemoglobin production relative to baseline, placebo control, and/or untreated patient;

(bd) no change or an increase in the synthesis of the beta globin chains of the hemoglobin tetramer relative to baseline, placebo control, and/or untreated patient;
(be) no change or a reduction in red blood cell hemolysis relative to baseline, placebo control, and/or untreated patient;
(bf) no change or a reduction in shortness of breath relative to baseline, placebo control, and/or untreated patient;
(bg) no change or a reduction in heart rate relative to baseline, placebo control, and/or untreated patient;
(bh) no change or a reduction in spleen size relative to baseline, placebo control, and/or untreated patient;
(bi) no change or a reduction in liver size relative to baseline, placebo control, and/or untreated patient;
(bj) no change or a reduction in dactylitis relative to baseline, placebo control, and/or untreated patient;
(bk) no change or a reduction in pain crises relative to baseline, placebo control, and/or untreated patient;
(bl) no change or a reduction in abnormal blood clot development relative to baseline, placebo control, and/or untreated patient;
(bm) no change or a reduction in red cell distribution width relative to baseline, placebo control, and/or untreated patient;
(bn) no change or a reduction in reticulocyte count relative to baseline, placebo control, and/or untreated patient; and/or
(bo) no change or a reduction in fibrinogen concentration relative to baseline, placebo control, and/or untreated patient.

In one embodiment, methods of the present invention comprise measuring baseline levels of one or more markers or parameters set forth in (a)-(bo) above prior to dosing the subject or subject group. In another embodiment, the methods comprise administering a composition as disclosed herein to the subject after baseline levels of one or more markers or parameters set forth in (a)-(bo) are determined, and subsequently taking an additional measurement of said one or more markers.

In another embodiment, upon treatment with a composition of the present invention, for example, over a period of about 1 to about 12 weeks, about 1 to about 8 weeks, or about 1 to about 4 weeks, the subject or subject group exhibits any 5 or more of, any 10 or more of, any 15 or more of, any 20 or more of, any 25 or more of, any 30 or more of, any 35 or more of, any 40 or more of, any 45 or more of, any 50 or more of, any 55 or more of, any 60 or more of, any 65 or more of, any 70 or more of, any 75 or more of, any 80 or more of, any 85 or more of, any 90 or more of, or all 91 of outcomes (a)-(bo) described immediately above.

In another embodiment, upon treatment with a composition of the present invention, the subject or subject group exhibits one or more of the following outcomes:
(a) no increase or a reduction in serum ALT and/or AST levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(b) no increase or a reduction in BUN levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(c) no increase or a reduction in fibrosis area of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(d) no increase or a reduction in fasting glucose levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(e) no increase or a reduction in insulin of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(f) no increase or a reduction in ALP levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(g) no increase or a reduction in HB1Ac levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(h) no increase or a reduction in HOMA-IR levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(i) no increase or a reduction in adipo-IR levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(j) no increase or a reduction in total cholesterol levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(k) no increase or a reduction in triglyceride levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(l) no increase or a reduction in diglyceride levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(m) no increase or a reduction in VLDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(n) no increase or a reduction in RLP-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(o) no increase or a reduction in non-HDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(p) no reduction or an increase in HDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(q) no increase or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(r) no increase or a reduction in kidney hydroxyproline levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(s) no increase or a reduction in IL-33 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(t) no increase or a reduction in IL-17 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(u) no increase or an reduction in AhR levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(v) no increase or a reduction in TL1A levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%; relative to baseline, placebo control, and/or untreated patient;

(w) no increase or a reduction in TNF-α levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(x) no increase or a reduction in IL-13 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(y) no increase or a reduction in IL-6 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(z) no increase or a reduction IL-1β levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(aa) no increase or a reduction in Collagen Type 1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(bb) no increase or a reduction in TGF-β levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(cc) no increase or a reduction in α-SMA of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(dd) no increase or a reduction in TNRSF11A of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ee) no increase or a reduction in PRSS2 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient.

(ff) no increase or a reduction in AOC3 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(gg) no increase or a reduction in LILBR1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(hh) no increase or a reduction in TR levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ii) no increase or a reduction in PI3 of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(jj) no increase or a reduction in SAA4 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(kk) no increase or a reduction in MCP-1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ll) no increase or a reduction in CCL16 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(mm) no increase or a reduction in TLT2 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(nn) no increase or a reduction in DPP4 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(oo) no increase or a reduction in TIMP-1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(pp) no increase or a reduction in PAI-1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(qq) no increase or a reduction in a NFS of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(rr) no increase or a reduction in FIB-4 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ss) no increase or a reduction in liver stiffness of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(tt) no increase or a reduction in hepatic fat content of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(uu) no reduction or an increase in glycerophospholipid levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(w) no increase or a reduction in blood pressure of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ww) no increase or a reduction in an ELF score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(zz) no increase or a reduction in collagen production in lung and/or dermal fibroblasts score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(yy) no reduction or an increase in glucose uptake of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(zz) an increase in lung and/or dermal fibroblast viability of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ab) no change or a reduction in IL-8 levels score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ac) no change or a decrease in IL-23 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% levels relative to baseline, placebo control, and/or untreated patient; and/or
(ad) no change or a reduction in IL-11 levels score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ae) no change or a reduction in IFNγ levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(af) no change or a reduction in T and/or B cell activation at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ag) no change or a reduction in chemotaxis of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ah) no change or a reduction in Bcl-2 family members of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ai) no change or a reduction in activated fragments of caspases levels relative of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% to baseline, placebo control, and/or untreated patient;
(aj) no change or a reduction in cleaved PARP-1 levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ak) no change or a reduction in waist circumference of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(al) no change or a reduction in an ARPI of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(am) no change or a reduction in a LIF score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(an) no change or a reduction in a Lok score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ao) no change or a reduction in a fibrosis score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(ap) no change or a reduction in a King score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(aq) no change or a reduction in a Bonacini score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient; and/or (ar) no change or a reduction in a TE score of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient.

(as) an increase in vascular adhesion molecules of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(at) an increase in cardiovascular risk proteins of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(au) an increase in chemokines of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient; and (av) an increase in tumor necrosis factor receptor superfamily members of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient.

(aw) no change or an increase in red blood cell count of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ax) no change or an increase in white blood cell count of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ay) no change or an increase in platelet count of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(az) no change or an increase in prothrombin time of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(ba) no change or an increase in activated partial thromboplastin time of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(bc) no change or an increase in hemoglobin production of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(bd) no change or an increase in the synthesis of the beta globin chains of the hemoglobin tetramer of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;

(be) no change or a reduction in red blood cell hemolysis of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bf) no change or a reduction in shortness of breath of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bg) no change or a reduction in heart rate of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bh) no change or a reduction in spleen size of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bi) no change or a reduction in liver size of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bj) no change or a reduction in dactylitis of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bk) no change or a reduction in pain crises of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bl) no change or a reduction in abnormal blood clot development of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bm) no change or a reduction in red blood cell distribution of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient;
(bn) no change or a reduction in reticulocyte count of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient; and/or
(bo) no change or a reduction in fibrinogen concentration of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% relative to baseline, placebo control, and/or untreated patient.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Unilateral Ureteral Obstruction-Induced Renal Interstitial Fibrosis

The objective of this study was to examine the effects of DS109 (15-HETrE) and DS102 (15-HEPE) on UUO-induced renal interstitial fibrosis.

FIG. 1 depicts the study design from surgery and treatment to day 14 of the study.

1.1 Materials and Methods

Test Substances: The test substances for this study were DS109 (15-HETrE) and DS102 (15-HEPE). To prepare dosing solutions of each substance, DS109 was first weighed and then dissolved in a vehicle of 0.5% hydroxypropyl methyl cellulose (HPMC) and DS102 was diluted in a vehicle of 0.5% HPMC.

UUO Surgery: On day 0 of the study, UUO surgery was performed on mice under pentobarbital sodium anesthesia. The mouse's hair was first shaved and then abdomen cut open to exteriorize the mouse's left ureter. The ureter was ligated 4-0 nylon sutures at two points. The mouse's peritoneum and skin were then closed with sutures, and the mouse transferred to a clean cage until recovered from the anesthesia. Sham operated mice had their left ureter exposed but not ligated.

Drug Administration: DS109 and DS102 were administered to the mice orally in a volume of 10 milliliters (mL)/kilogram (Kg).

Treatment Doses: DS109 was administered at 3 dose levels of 5, 50, and 250 milligram (mg)/Kg once daily from Day 0 to Day 13 of the study. DS102 was administered at 2 doses levels of 50 and 500 mg/kg once daily from Day 0 to Day 13 of the study.

Animals: Seven-week-old female C57BL/6 mice (i.e., animals) were obtained from Japan SLC, Inc. (Japan) and were housed and fed with a normal diet (CE-2; CLEA Japan, Japan) under controlled conditions. The animals were maintained in a specific-pathogen free (SPF) facility under controlled conditions of temperature (e.g., 23±2° C.), humidity (e.g., 45±10%), lighting (e.g., 12-hour artificial light and dark cycles; light from 8:00 to 20:00) and air exchange. A high pressure was maintained in the experimental room to prevent contamination of the facility. The animals were housed in TPX cages (CLEA Japan) with a maximum of 4 mice per cage. Sterilized Paper-Clean (Japan SLC) was used for bedding and replaced once a week. Sterilized solid normal diet was provided ad libitum, being placed in a metal lid on the top of the cage. Pure water was also provided ad libitum from a water bottle equipped with a rubber stopper and a sipper tube. Water bottles were replaced once a week, cleaned, and sterilized in an autoclave and reused. Mice were identified by ear punch and each cage was labeled with a specific identification code.

Measurement of Kidney Biochemistry: To quantify kidney hydroxyproline content, frozen left kidney samples were processed by an alkaline-acid hydrolysis method as follows: kidney samples were dissolved in 2 normal (N) sodium hydroxide (NaOH) at 65° C. and autoclaved at 121° C. for 20 minutes. The lysed samples (400 µL) were acid-hydrolyzed with 400 µL of 6N hydrochloride acid (HCl) at 121° C. for 20 minutes, and neutralized with 400 µL of 4N NaOH containing 10 mg/mL of activated carbon. An AC buffer (e.g., 2.2M acetic acid/0.48M citric acid, 400 µL) was added to the samples, followed by centrifugation to collect the supernatant. A standard curve of hydroxyproline was constructed with serial dilutions of trans-4-hydroxy-L-proline (Sigma-Aldrich, USA) starting at 16 µg/mL. The prepared samples and standards (e.g., each 400 µL) were mixed with 400 µL chloramine T solution (Wako Pure Chemical Industries, Japan) and incubated for 25 minutes at room temperature. The samples were then mixed with Ehrlich's solution (e.g., 400 µL) and heated at 65° C. for 20 minutes to develop the color. After samples were cooled on ice and centrifuged to remove precipitates, the optical density of each supernatant was measured at 560 nanometers (nm). The concentrations of hydroxyproline were calculated from the hydroxyproline standard curve. Protein concentrations of kidney samples were determined using a bicinchoninic (BCA) protein assay kit (Thermo Fisher Scientific, USA) and used to normalize the calculated hydroxyproline values. Kidney hydroxyproline contents were expressed as microgram (µg) per mg protein.

Histopathological analysis: To visualize collagen deposition, kidney sections were stained using picro-Sirius red solution (Waldeck, Germany). For quantification of interstitial fibrosis area, bright field images in the corticomedullary region were captured using a digital camera (e.g., DFC295; Leica Microsystems, Germany) at 200-fold magnification, and the positive areas in 5 fields/section were measured using ImageJ software (National Institute of Health, USA).

Quantitative RT-PCR: Total ribonucleic acid (RNA) was extracted from kidney samples using RNAiso (Takara Bio, Japan) according to the manufacturer's instructions. One µg of RNA was reverse-transcribed using a reaction mixture containing 4.4 micromolar (mM) of magnesium chloride ($MgCl_2$) (F. Hoffmann-La Roche, Switzerland), 40 U RNase inhibitor (Toyobo, Japan), 0.5 mM dNTP (Promega, USA), 6.28 µM random hexamer (Promega), 5× first strand buffer (Promega), 10 mM dithiothreitol (Invitrogen, USA) and 200 U MMLV-RT (Invitrogen) in a final volume of 20 µL. The reaction was carried out for 1 hour at 37° C., followed by 5 minutes at 99° C. Real-time PCR was performed using real-time PCR DICE and TB Green™ Premix Ex Taq™ II (Takara Bio). To calculate the relative microRNA (mRNA) expression level, the expression of each gene (e.g., α-SMA, TIMP-1, TGF-β and Collagen Type 1) was normalized to that of reference gene 36B4 (gene symbol: Rplp0). Information regarding the PCR-primer sets and the plate layout are described in Tables 1 and 2.

TABLE 1

FOR Primers for the Quantitative RT-PCR Measurements

| SEQ ID NO. | Gene | Set ID | | Sequence |
|---|---|---|---|---|
| 1 | 36B4 | MA057856 | forward | 5'-TTCCAGGCTTTGGGCATCA-3' |
| 2 | | | reverse | 5'-ATGTTCAGCATGTTCAGCAGTGTG-3' |
| 3 | Alpha- | MA057911 | forward | 5'-AAGAGCATCCGACACTGCTGAC-3' |
| 4 | SMA | | reverse | 5'-AGCACAGCCTGAATAGCCACATAC-3' |
| 5 | TIMP-1 | MA098519 | forward | 5'-TGAGCCCTGCTCAGCAAAGA-3' |
| 6 | | | reverse | 5'-GAGGACCTGATCCGTCCACAA-3' |
| 7 | TGF-β | MA030397 | forward | 5'-GTGTGGAGCAACATGTGGAACTCTA-3' |
| 8 | | | reverse | 5'-TTGGTTCAGCCACTGCCGTA-3' |

TABLE 1-continued

FOR Primers for the Quantitative RT-PCR Measurements

| SEQ ID NO. | Gene | Set ID | | Sequence |
|---|---|---|---|---|
| 9 | Collagen | MA075477 | forward | 5'-CCAACAAGCATGTCTGGTTAGGAG-3' |
| 10 | Type 1 | | reverse | 5'-GCAATGCTGTTCTTGCAGTGGTA-3' |

36B4: Ribosomal protein, large, P0 (Rplp0)
Alpha-SMA: Actin, alpha 2, smooth muscle, aorta (Acta2)
TIMP-1: Tissue inhibitor of metalloproteinase 1 (Timp1)
TGF-β: Transforming growth factor, beta 1 (Tgfb1)
Collagen Type 1: Collagen, type 1, alpha 2 (Col1a2)

TABLE 2

Specifics Regarding the PCR Plates for the Quantitative RT-PCR Measurements

| Plate Mouse ID | 1<br>101-308 | 2<br>401-608 | 3<br>701-708 |
|---|---|---|---|
| Alpha-SMA | Plate 1-2 | Plate 2-2 | Plate 3-2 |
| 36B4 | Plate 1-1 | Plate 2-1 | Plate 3-1 |
| TIMP-1 | Plate 1-3 | Plate 2-3 | Plate 3-2 |
| 36B4 | Plate 1-1 | Plate 2-1 | Plate 3-1 |
| TGF-β | Plate 1-4 | Plate 2-4 | Plate 3-3 |
| 36B4 | Plate 1-1 | Plate 2-1 | Plate 3-1 |
| Collagen Type 1 | Plate 1-5 | Plate 2-5 | Plate 3-3 |
| 36B4 | Plate 1-1 | Plate 2-1 | Plate 3-1 |

Sample Collection: For serum samples, non-fasting blood was collected in serum separate tubes without anticoagulant through direct cardiac puncture and centrifuged at 3,500×g for 4 minutes at 4° C. The supernatant was collected and stored at −80° C. for shipping. For kidney samples, the left kidney was collected and cut into 2 pieces horizontally. Superior part of left kidney was fixed in Bouin's solution and then embedded in paraffin. Paraffin blocks were stored at room temperature for histological analyses. The inferior part of left kidney was cut into 2 pieces coronally. The anterior part of left kidney was snap frozen in liquid nitrogen and stored at −80° C. for gene expression assay. The posterior part of left kidney was snap frozen in liquid nitrogen and stored at −80° C. for kidney biochemistry.

Statistical Tests: Statistical analyses were performed using Bonferroni Multiple Comparison Test on GraphPad Prism 6 (GraphPad Software Inc., USA). P values <0.05 were considered statistically significant. A trend or tendency was assumed when a one-tailed t-test returned P values <0.1. Results were expressed as mean±SD.

1.2 Experimental Design and Treatment

The study design included the following study groups:
Group 1 (Sham Control): Eight sham-operated mice kept without any treatment until sacrifice.
Group 2 (Vehicle): Eight UUO mice were orally administered vehicle [0.5% HPMC] in a volume of 10 mL/kg once daily from Day 0 to Day 13.
Group 3 (DS109 Low): Eight UUO mice were orally administered vehicle supplemented with DS109 at a dose of 5 mg/kg once daily from Day 0 to Day 13.
Group 4 (DS109 Middle): Eight UUO mice were orally administered vehicle supplemented with DS109 at a dose of 50 mg/kg once daily from Day 0 to Day 13.
Group 5 (DS109 High): Eight UUO mice were orally administered vehicle supplemented with DS109 at a dose of 250 mg/kg once daily from Day 0 to Day 13.
Group 6 (DS102 Low): Eight UUO mice were orally administered vehicle supplemented with DS102 at a dose of 50 mg/kg once daily from Day 0 to Day 13.
Group 7 (DS102 High): Eight UUO mice were orally administered vehicle supplemented with DS102 at a dose of 500 mg/kg once daily from Day 0 to Day 13.

Table 3 summarizes the treatment schedule for each of Groups 1-7 during the study.

TABLE 3

Summary of the Treatment Schedule

| Group | No. mice | Model | Test substance | Dose (mg/kg) | Volume (mL/kg) | Regimen | Sacrifice (Day) |
|---|---|---|---|---|---|---|---|
| 1 | 8 | Sham | — | — | — | Day 0-Day 13 | 14 |
| 2 | 8 | UUO | Vehicle | — | 10 | PO, QD, Day-Day 13 | 14 |
| 3 | 8 | UUO | DS109 | 5 | 10 | PO, QD, Day-Day 13 | 14 |
| 4 | 8 | UUO | DS109 | 50 | 10 | PO, QD, Day 0-Day 13 | 14 |
| 5 | 8 | UUO | DS109 | 250 | 10 | PO, QD, Day 0-Day 13 | 14 |
| 6 | 8 | UUO | DS102 | 50 | 10 | PO, QD, Day 0-Day 13 | 14 |
| 7 | 8 | UUO | DS102 | 500 | 10 | PO, QD, Day 0-Day 13 | 14 |

Animal Monitoring and Sacrifice: The viability, clinical signs and behavior for the mice were monitored daily. Individual body weight was measured daily before treatment during the treatment period. Mice were observed for significant clinical signs of toxicity, moribundity and mortality approximately 60 minutes after each administration. The animals were sacrificed by exsanguination through direct cardiac puncture under isoflurane anesthesia (Pfizer Inc.) at Day 14.

1.3 Results

Figure 2:
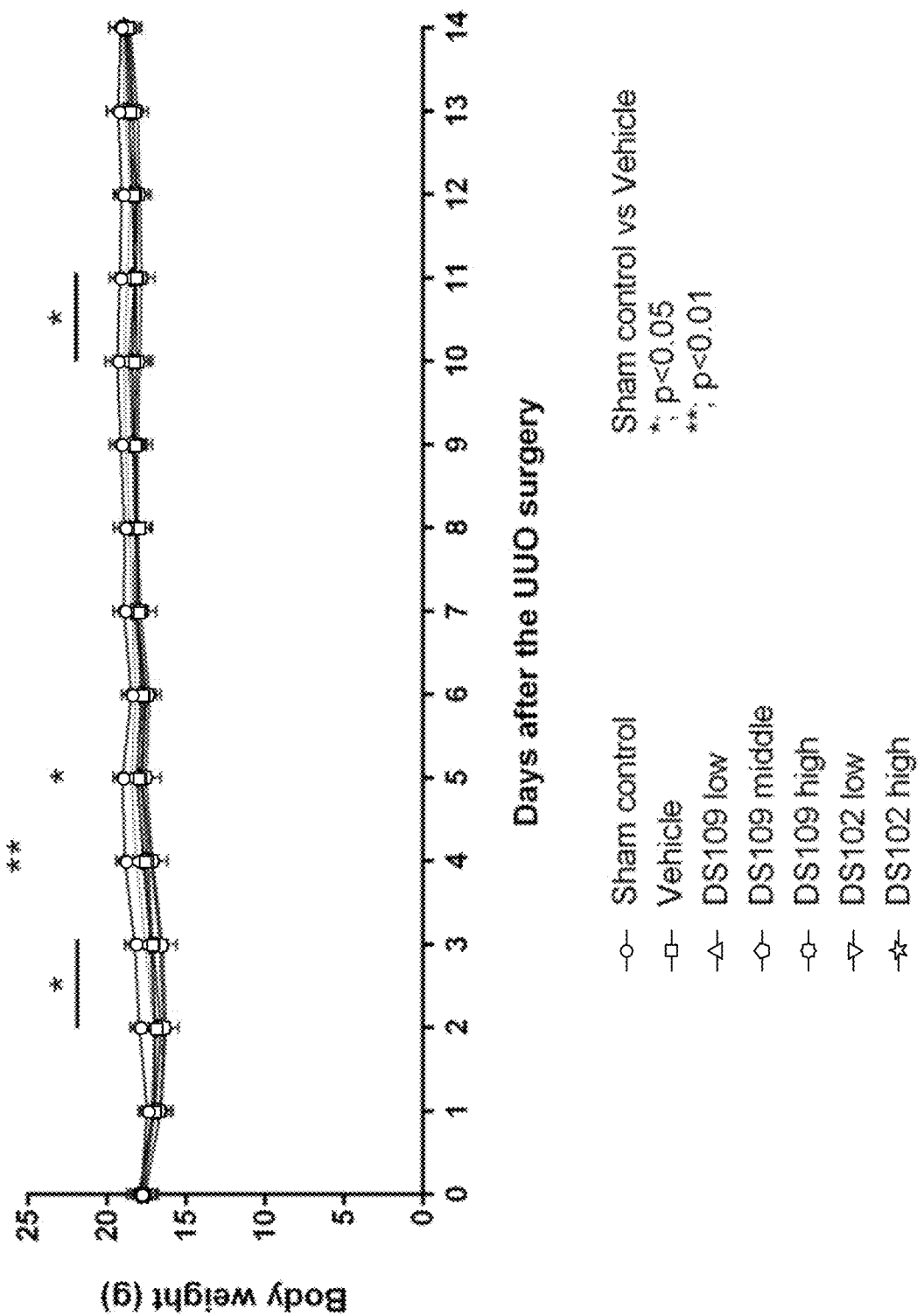
FIG. 2 shows the body weight changes of the animals according to the study described in Example 1.

Body weight changes and general considerations: FIG. 2 shows the body weight changes for all animals. In all the animals, body weight decreased after surgery, and recovered gradually during the treatment period. Mean body weight of the Vehicle group was significantly lower than that of the Sham control group from Day 2 to Day 5 and from Day 10 to Day 11. There were no significant changes in mean body weight at any day during the treatment period between the Vehicle group and the treatment groups. There were no dead animals in all groups during the treatment period. In the present study, none of the animals showed deterioration in general condition.

Figure 3:
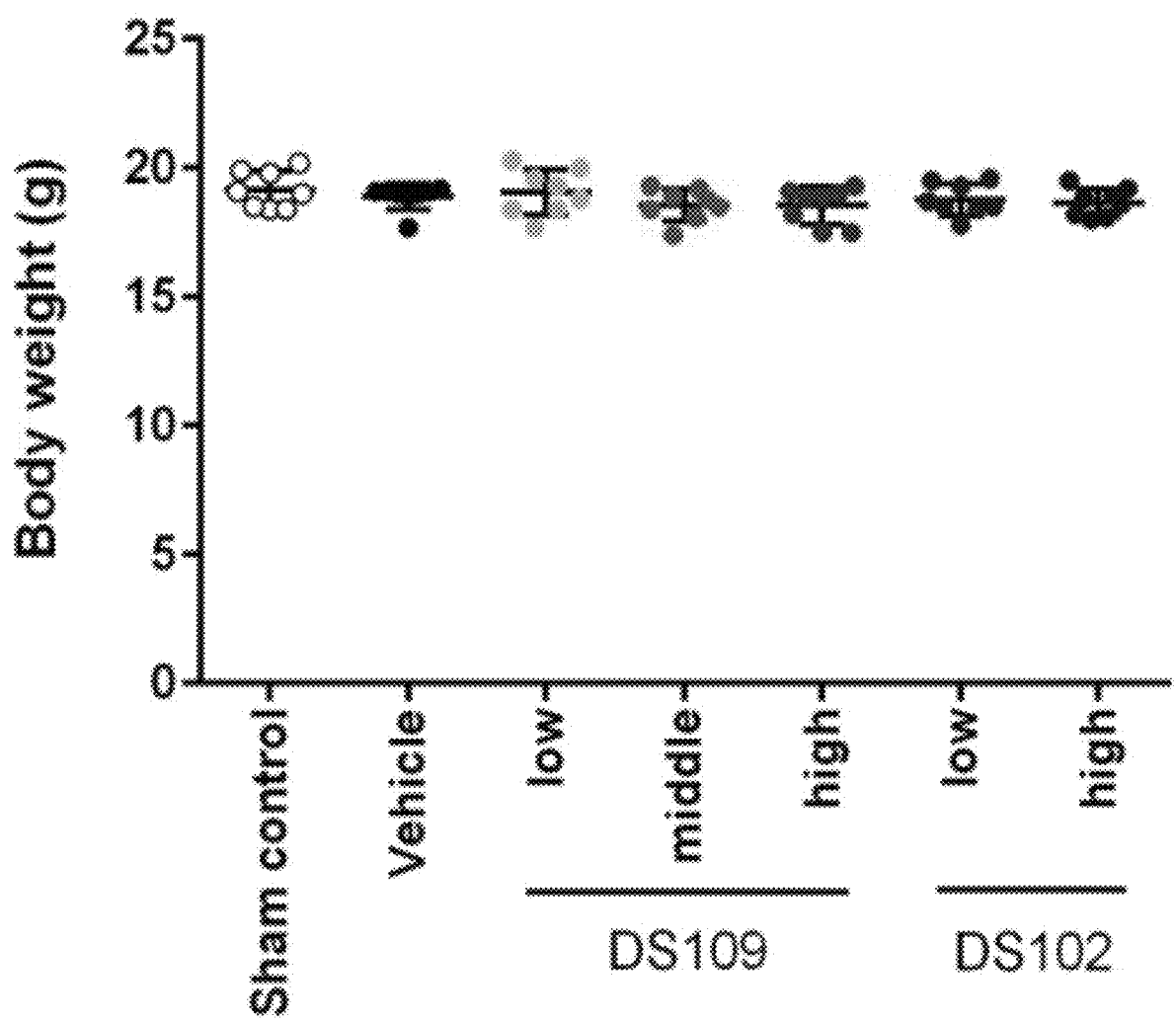
FIG. 3 shows the body weight on the day of sacrifice of the animals according to the study described in Example 1.
Figure 4A:
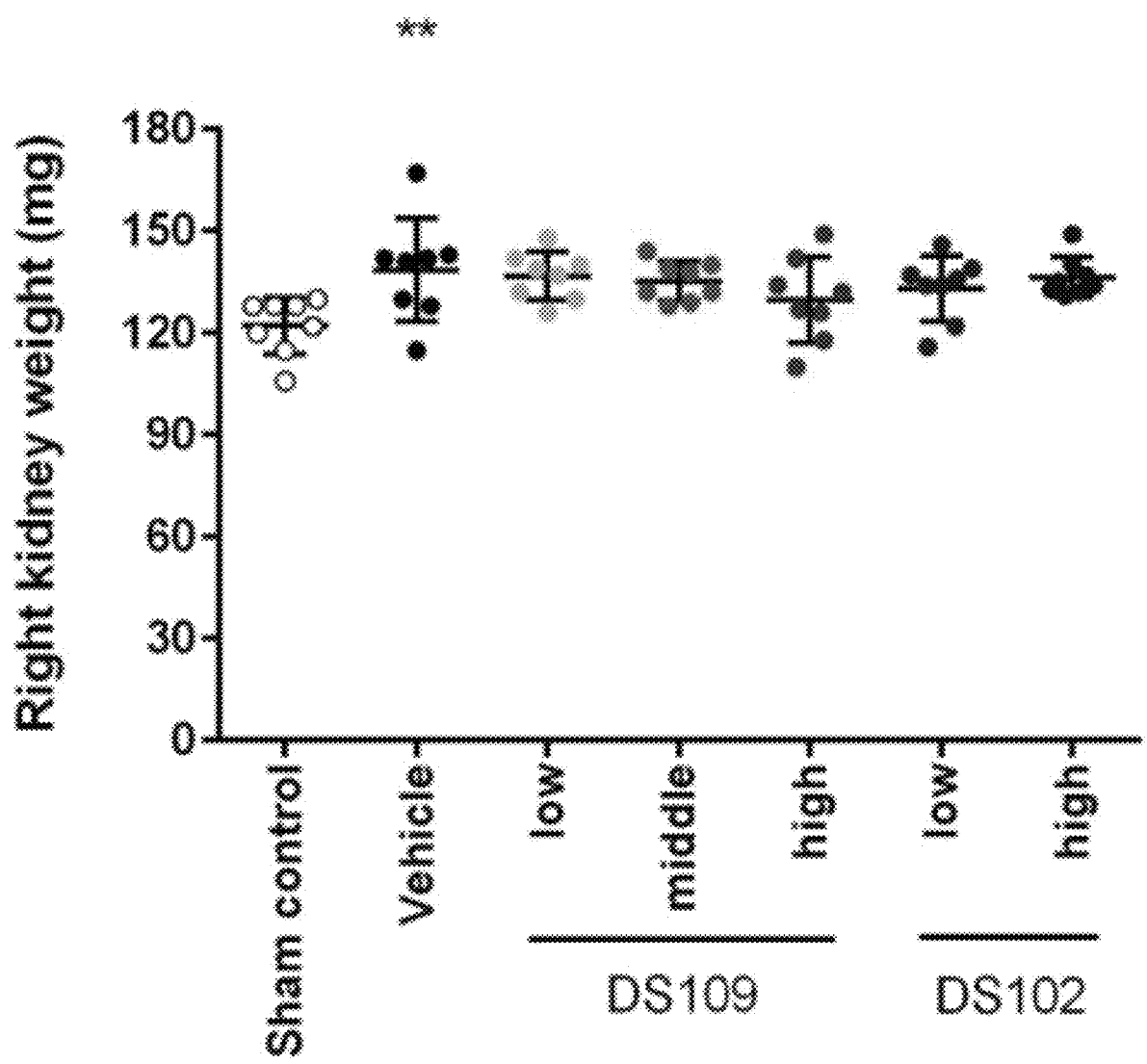
FIGS. 4A-4D show the kidney weight and kidney-to-body weight ratio of the animals on the day of sacrifice according to the study described in Example 1.
Figure 4B:
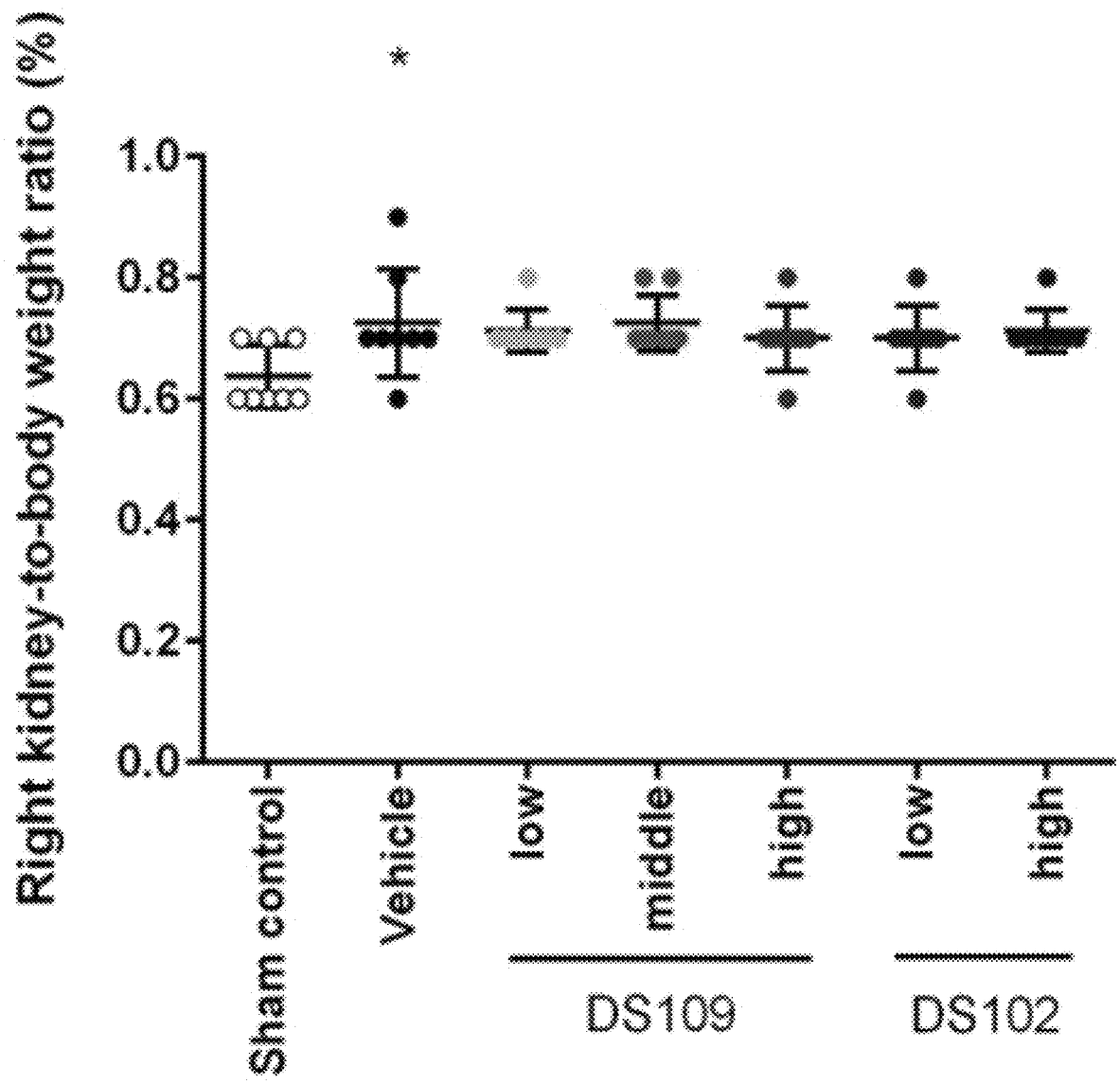
Figure 4C:
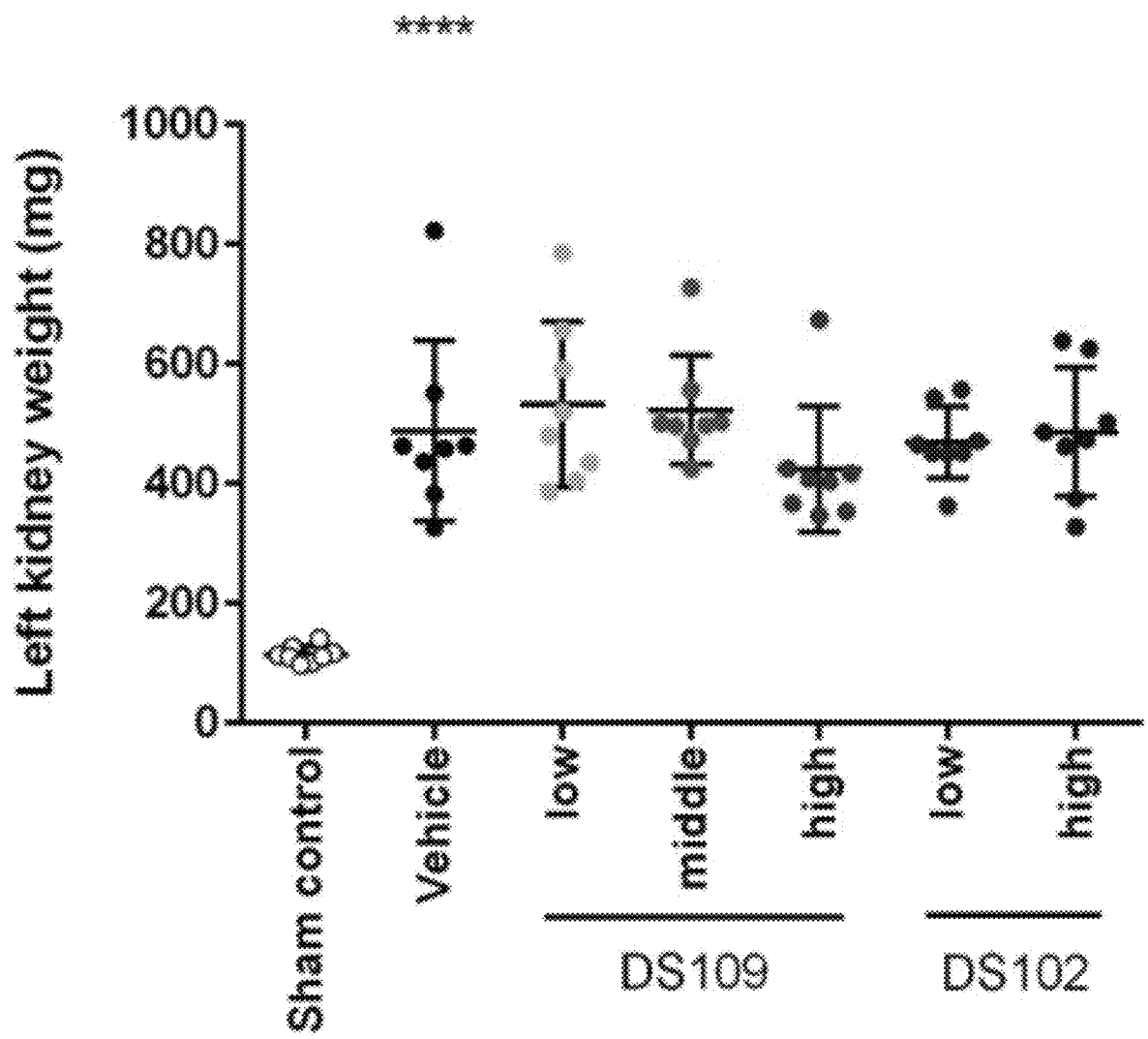
Figure 4D:
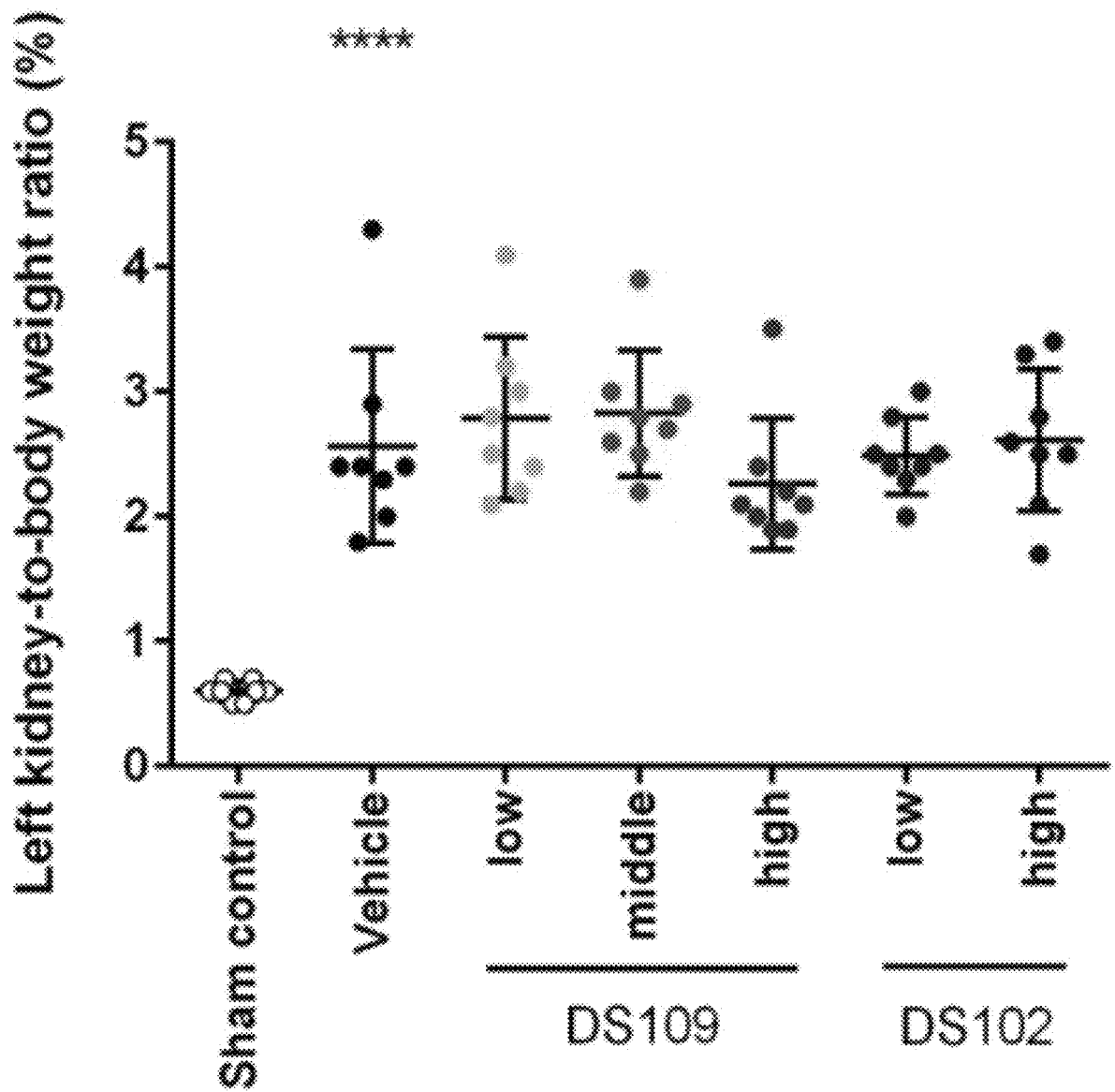

Body and kidney weight on the day of sacrifice: FIG. 3 and Table 4 show the body weight of the animals on the day of sacrifice. There was no significant difference in mean body weight on the day of sacrifice between the Sham control group and the Vehicle group. There were no significant differences in mean body weight on the day of sacrifice between the Vehicle group and the treatment groups.

TABLE 4

Body Weight on the Day of Sacrifice

| Group | Body Weight (g) | Right Kidney Weight (mg) | Right Kidney-to-Body Weight Ratio (%) | Left Kidney Weight (mg) | Left Kidney-to-Body Weight Ratio (%) |
|---|---|---|---|---|---|
| Sham control, (n = 8) | 19.2 ± 0.7 | 122 ± 8 | 0.64 ± 0.05 | 115 ± 14 | 0.60 ± 0.08 |
| Vehicle, (n = 8) | 18.9 ± 0.5 | 139 ± 15 | 0.73 ± 0.09 | 488 ± 150 | 2.56 ± 0.77 |
| DS109 low, (n = 8) | 19.1 ± 0.9 | 137 ± 7 | 0.71 ± 0.04 | 533 ± 138 | 2.79 ± 0.65 |
| DS109 middle, (n = 8) | 18.6 ± 0.6 | 135 ± 6 | 0.73 ± 0.05 | 523 ± 91 | 2.83 ± 0.50 |
| DS109 high, (n = 8) | 18.6 ± 0.7 | 130 ± 13 | 0.70 ± 0.05 | 425 ± 105 | 2.26 ± 0.53 |
| DS102 low, (n = 8) | 18.8 ± 0.6 | 133 ± 10 | 0.70 ± 0.05 | 469 ± 60 | 2.49 ± 0.30 |
| DS102 high, (n = 8) | 18.7 ± 0.5 | 136 ± 6 | 0.71 ± 0.04 | 487 ± 108 | 2.61 ± 0.57 |

FIGS. 4A-4D and Table 4 show the kidney weight and kidney-to-body weight ratio of the animals on the day of sacrifice. The Vehicle group showed a significant increase in mean right kidney weight compared with the Sham control group. However, there were no significant differences in mean right kidney weight between the Vehicle group and the treatment groups. The Vehicle group also showed a significant increase in mean right kidney-to-body weight ratio compared with the Sham control group. There were no significant differences in mean right kidney-to-body weight ratio between the Vehicle group and the treatment groups. The Vehicle group also showed a significant increase in mean left kidney weight compared with the Sham control group. There were no significant differences in mean left kidney weight between the Vehicle group and the treatment groups. Lastly, the Vehicle group showed a significant increase in mean left kidney-to-body weight ratio compared with the Sham control group, but there were no significant differences in mean left kidney-to-body weight ratio between the Vehicle group and the treatment groups.

Figure 5:
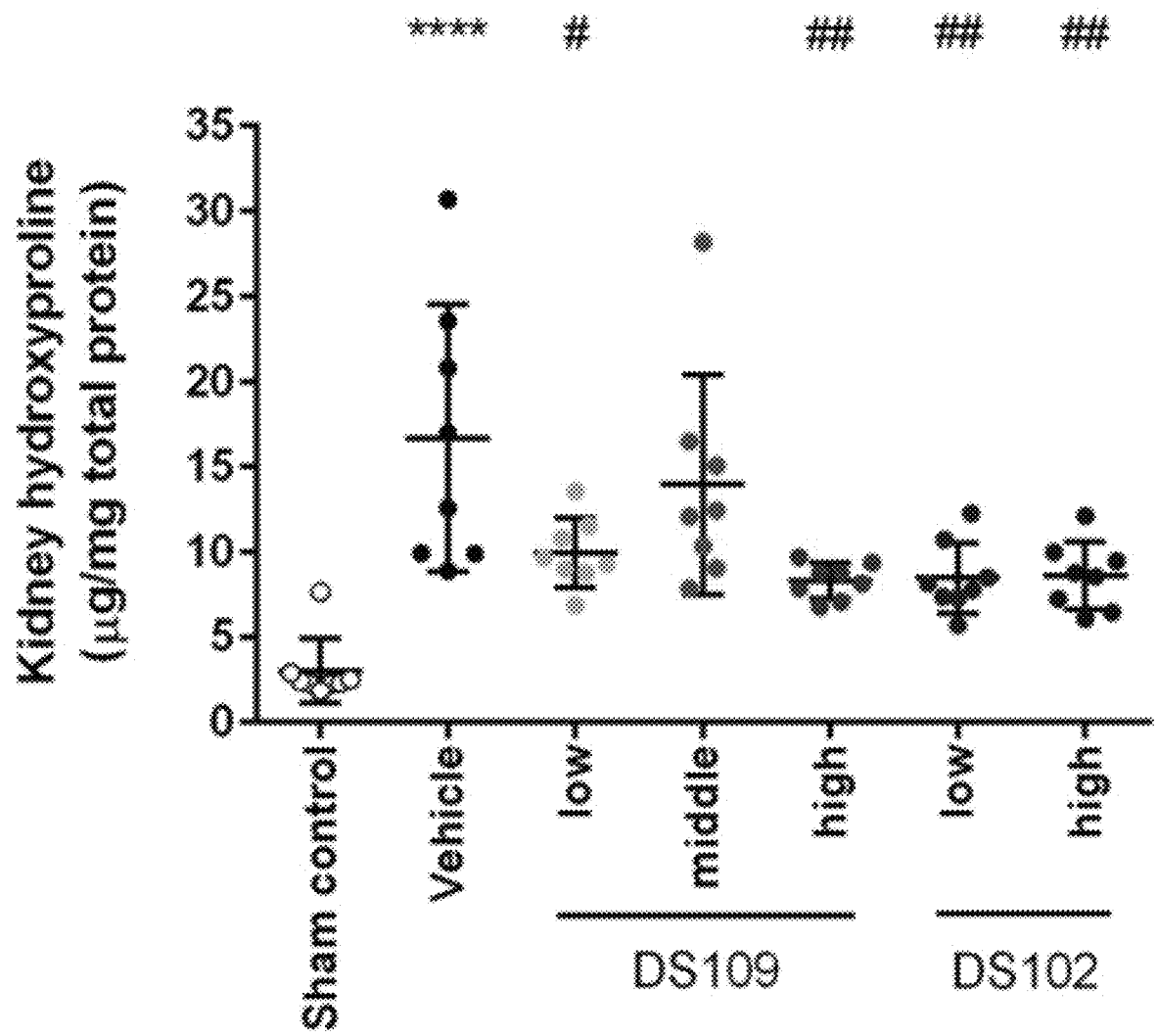
FIG. 5 shows the kidney hydroxyproline content for the animals according to the study described in Example 1.

Kidney Chemistry: FIG. 5 and Table 5 show the kidney hydroxyproline content for the animals. The Vehicle group showed a significant increase in kidney hydroxyproline contents compared with the Sham control group. The DS109 low, DS109 high, DS102 low and DS102 high groups showed significant decreases in kidney hydroxyproline contents compared with the Vehicle group. There was no significant difference in kidney hydroxyproline contents between the Vehicle group and the DS109 middle group.

TABLE 5

The Kidney Hydroxyproline Content

| Group | Kidney hydroxyproline (µg/mg total protein) |
|---|---|
| Sham control, (n = 8) | 3.02 ± 1.89 |
| Vehicle, (n = 8) | 16.67 ± 7.83 |
| DS109 low, (n = 8) | 9.94 ± 2.02 |
| DS109 middle, (n = 8) | 13.94 ± 6.44 |
| DS109 high, (n = 8) | 8.30 ± 1.04 |
| DS102 low, (n = 8) | 8.47 ± 2.08 |
| DS102 high, (n = 8) | 8.59 ± 1.99 |

Figure 6A:
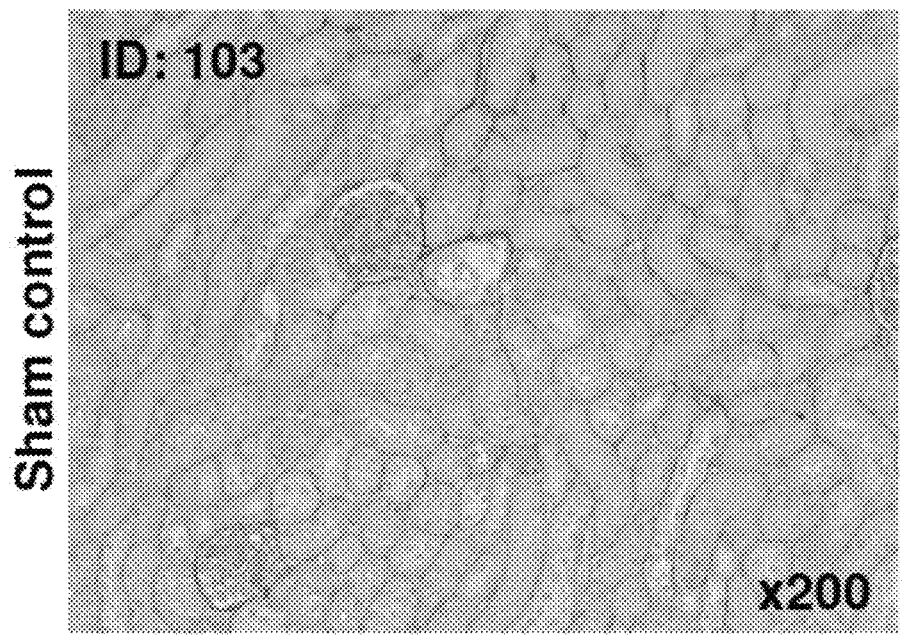
FIGS. 6A-6G show the Sirius red staining of the animals according to the study described in Example 1.
Figure 6B:
Figure 6C:
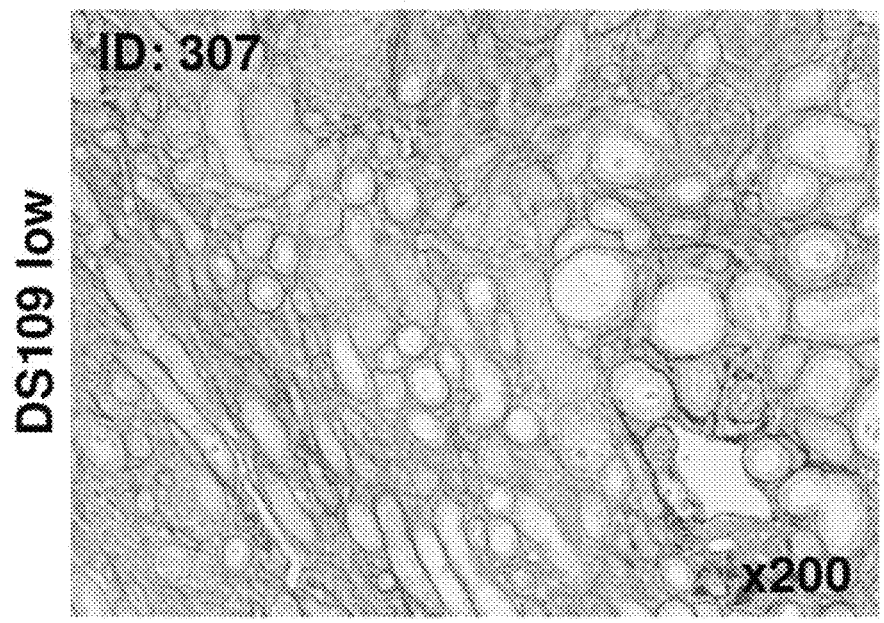
Figure 6D:
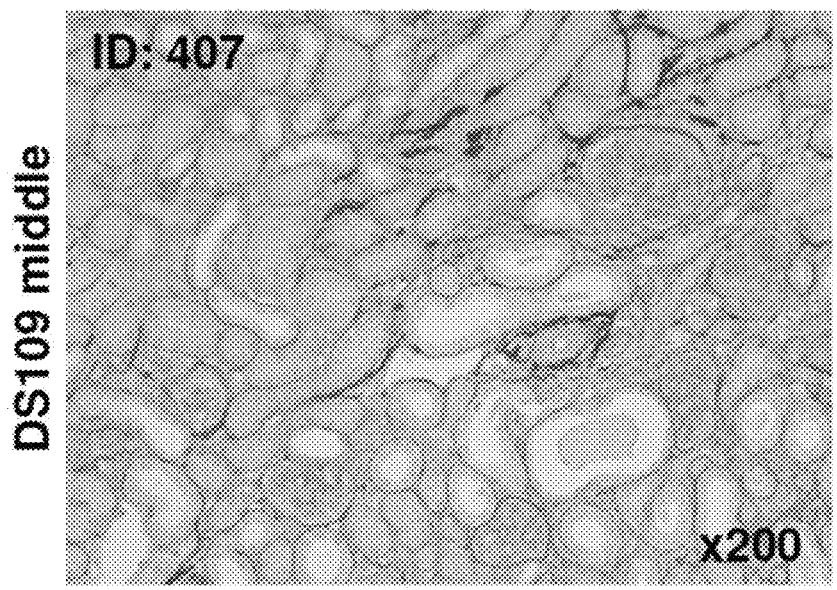
Figure 6E:
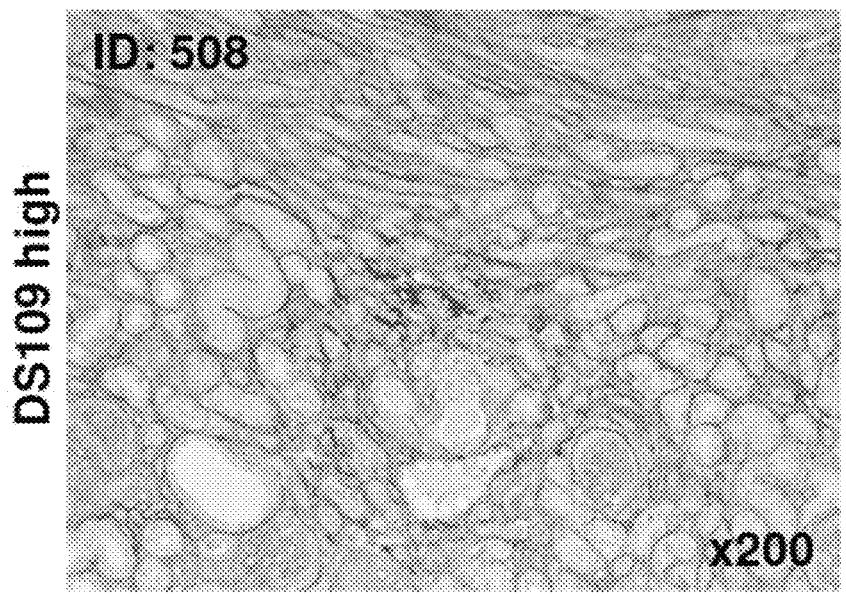
Figure 6F:
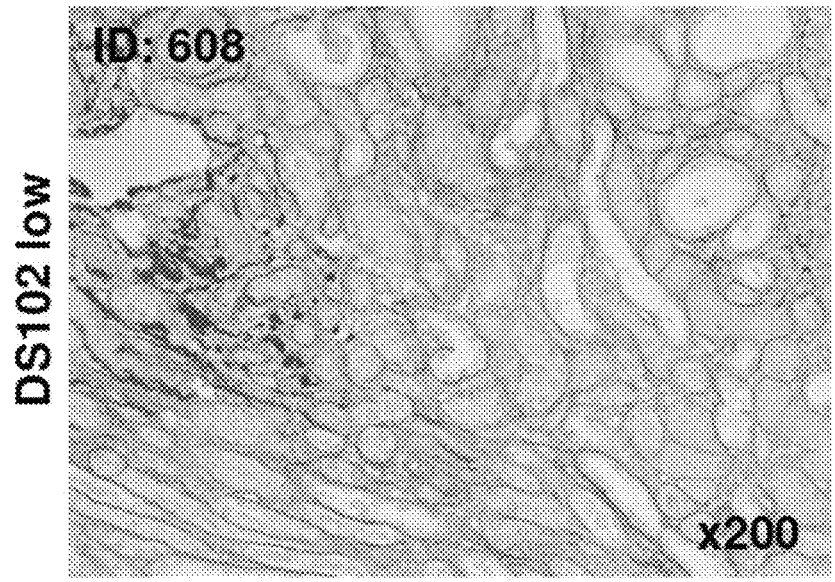
Figure 6G:
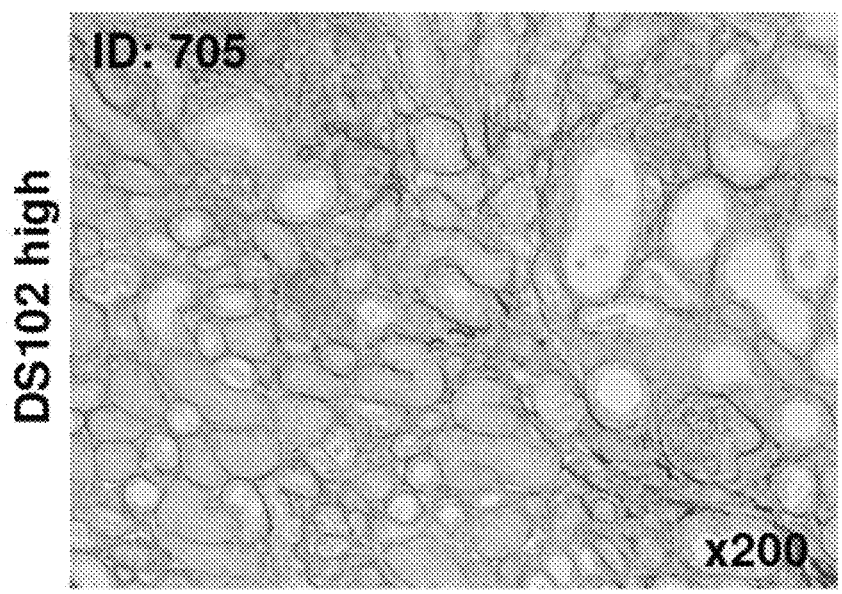
Figure 7:
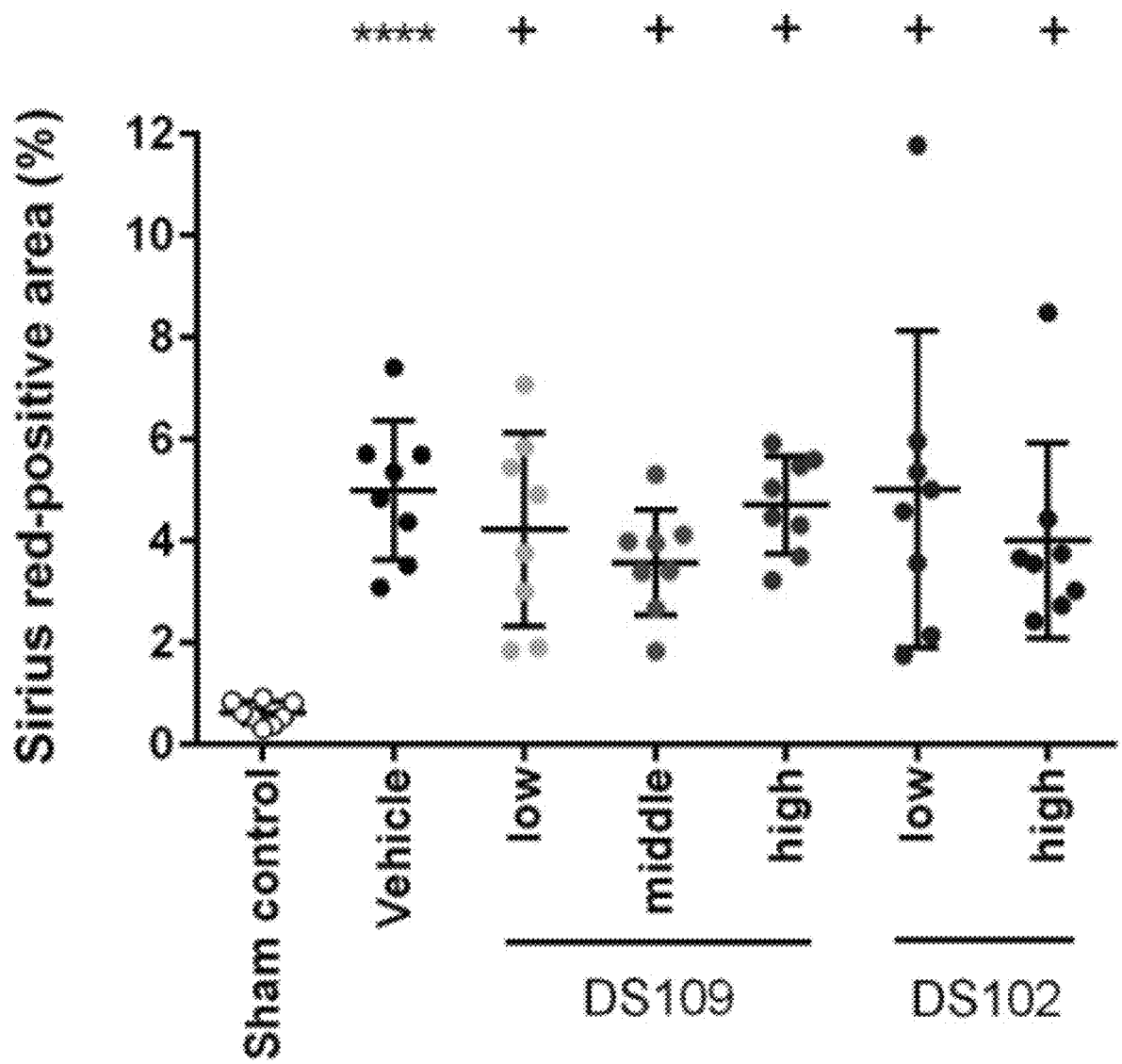
FIG. 7 shows a plot depicting the Sirius red-positive area (%) of the animals according to the study described in Example 1.
Figure 8A:
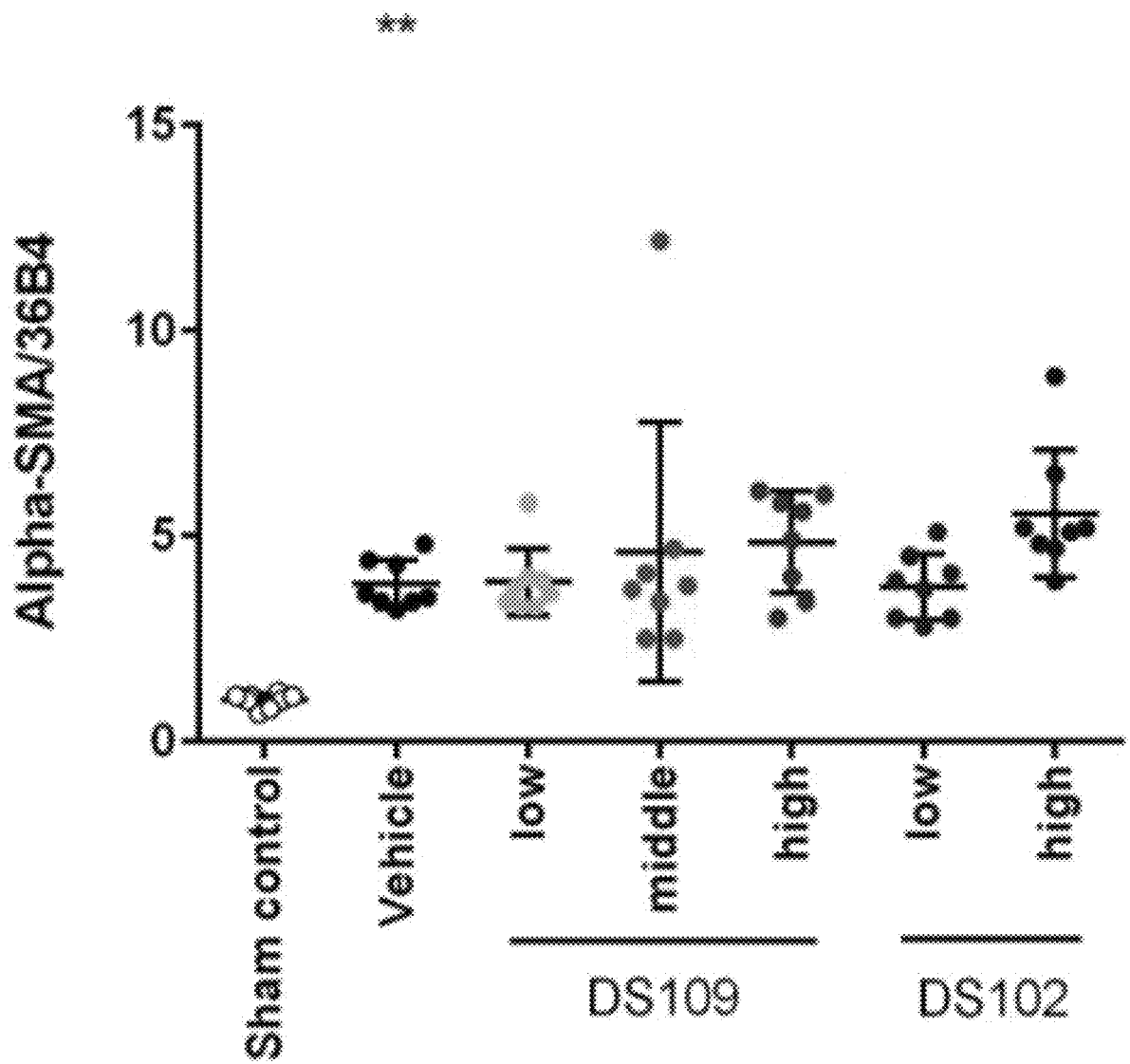
FIGS. 8A-8D show the gene expression analyses for α-SMA, TIMP-1, TGF-β, and Collagen Type 1 of the animals according to the study described in Example 1, respectively.
Figure 8B:
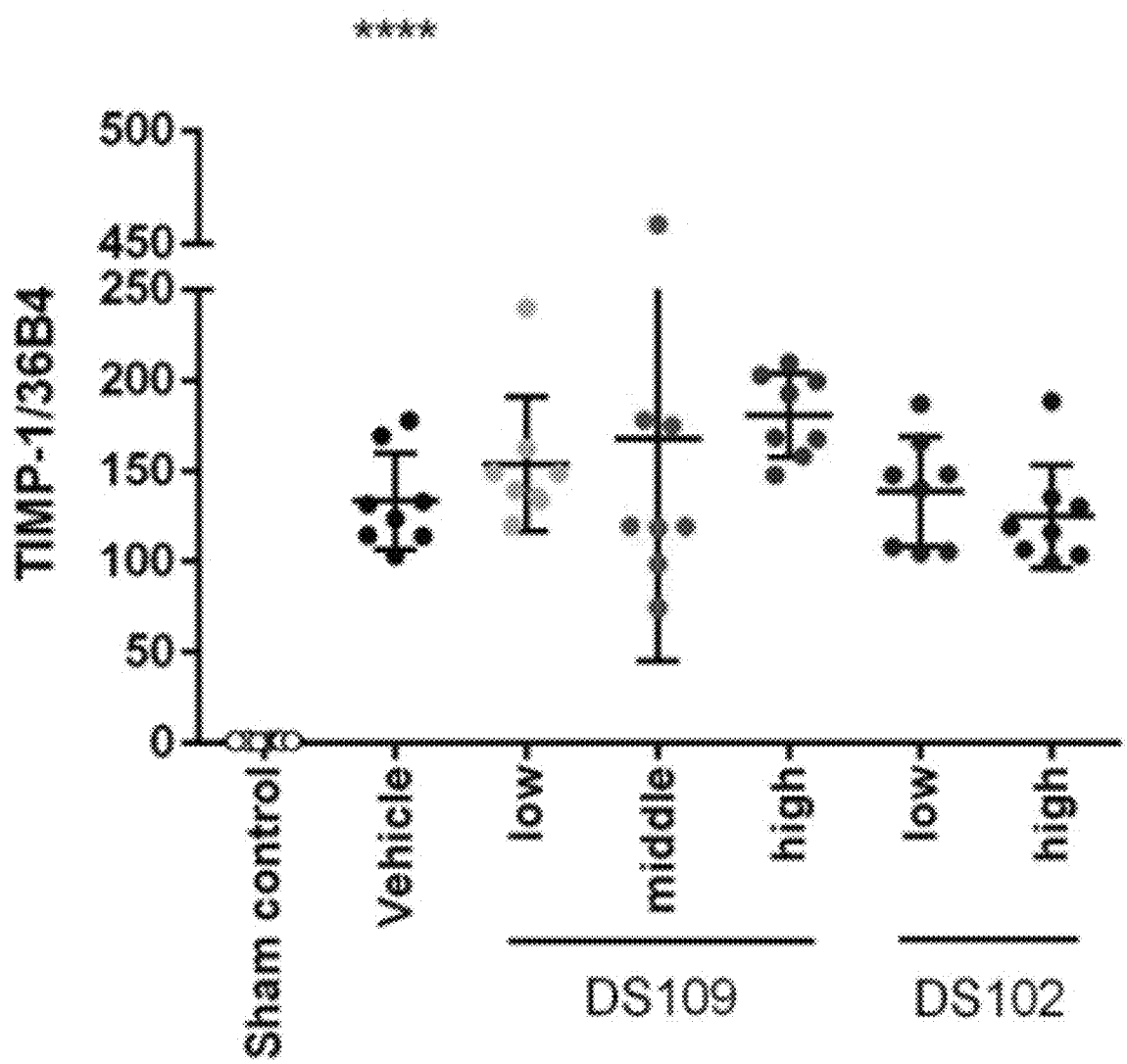
Figure 8C:
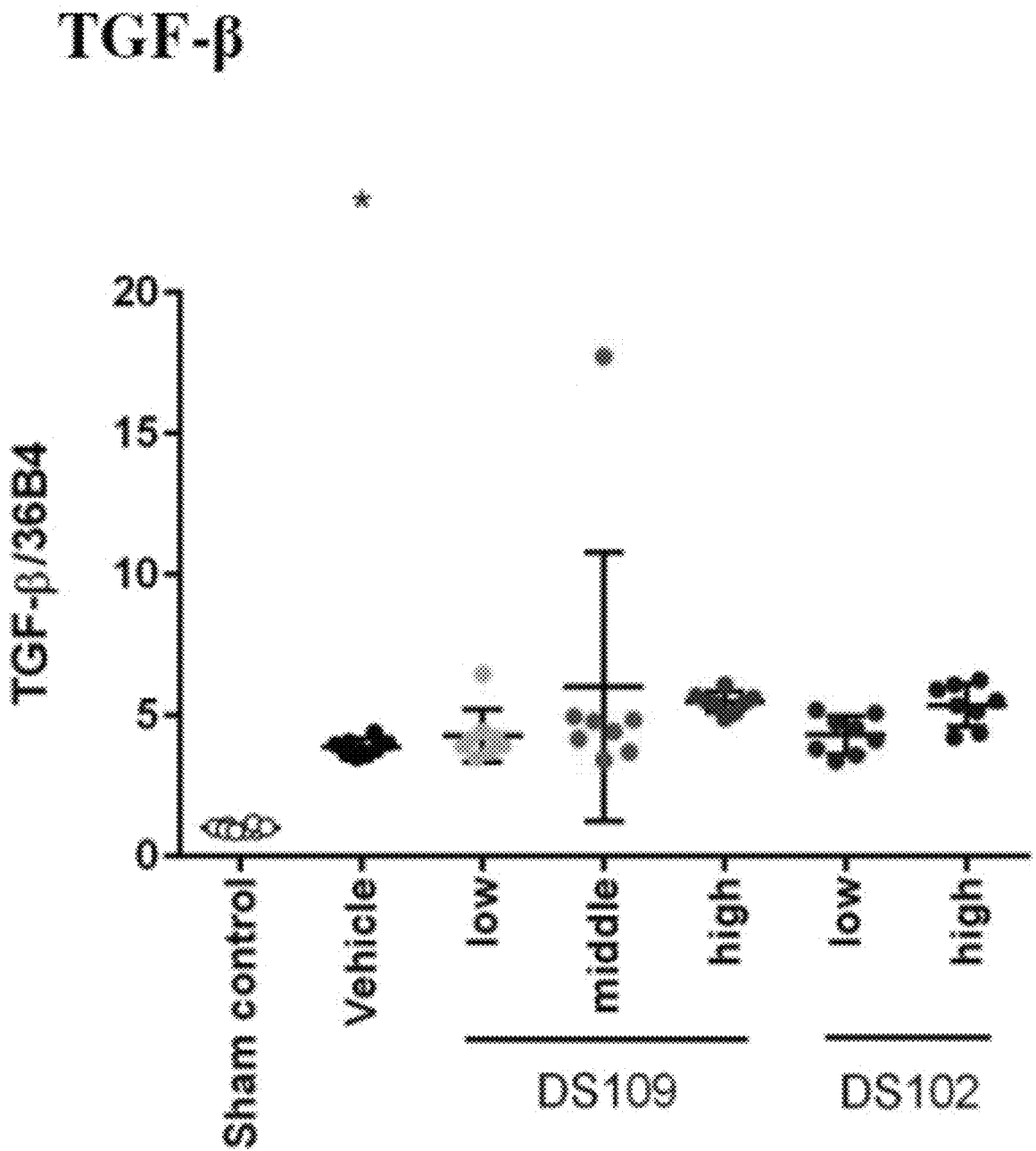
Figure 8D:
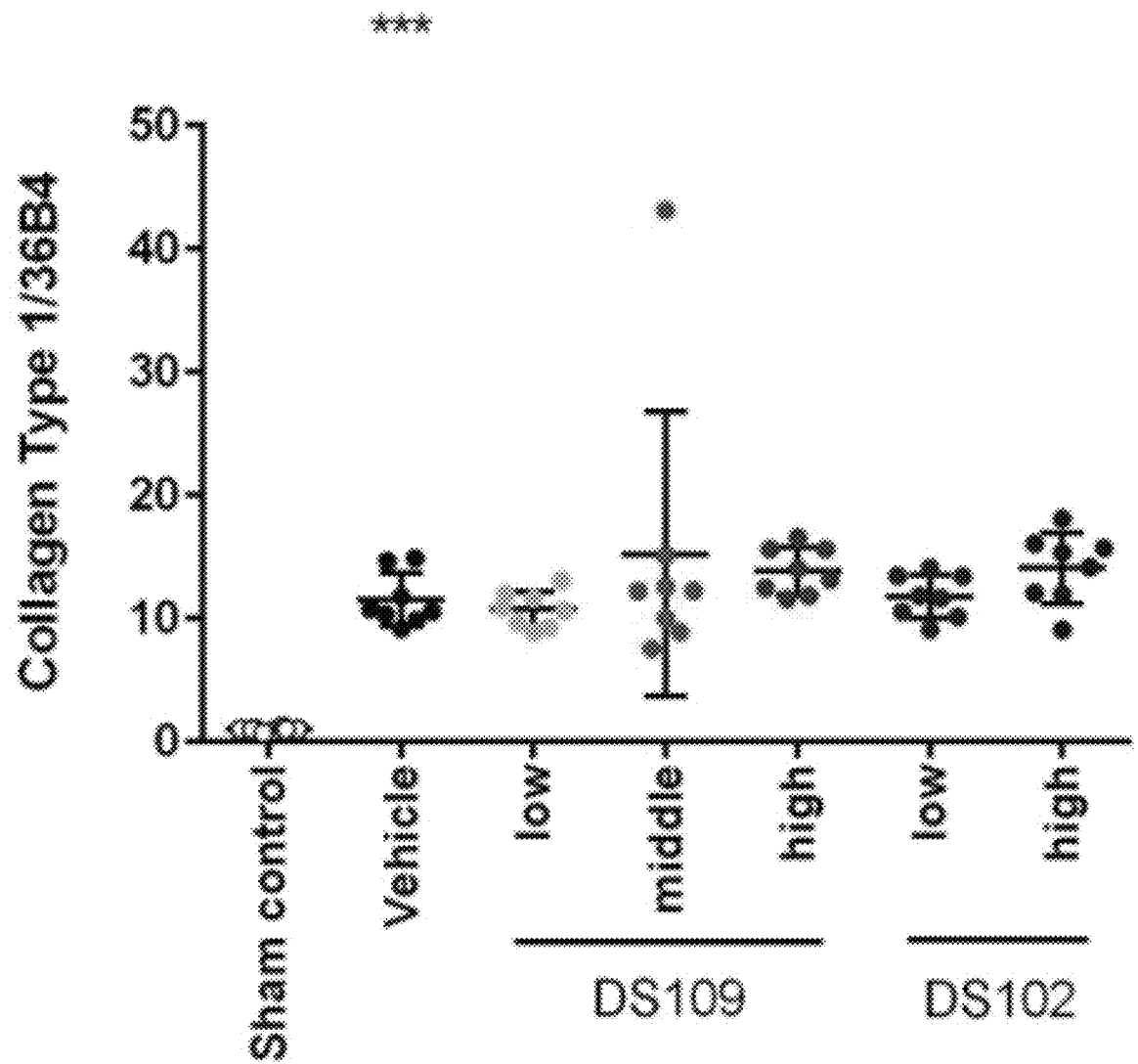

Histological Analysis: FIGS. 6A-6G and Table 6 show the Sirius red staining and FIG. 7, the fibrosis area of the animals. FIG. 6A displays representative photomicrographs of Sirius red-stained kidney sections. The Vehicle group showed a significant increase in the percentage of fibrosis area (Sirius red-positive area) compared with the Sham control group. Bonferroni Multiple Comparison revealed that the fibrosis area in the DS109 middle group tended to decrease compared with the Vehicle group. There were no significant differences in fibrosis area between the Vehicle group and the other treatment groups. Mann-Whitney U test was conducted due to the presence of notable outliers and revealed that the DS109 low, DS109 middle, DS109 high, DS102 low and DS102 high groups fibrosis area tended to decrease ($p<0.1$) compared with the Vehicle group.

TABLE 6

Fibrosis Area of the Animals

| Group | Sirius red-positive area (%) | Sirius red-positive area (%) _Median |
|---|---|---|
| Sham control, (n = 8) | 0.63 ± 0.22 | 0.51 ± 0.15 |
| Vehicle, (n = 8) | 5.00 ± 1.37 | 4.55 ± 0.94 |
| DS109 low, (n = 8) | 4.23 ± 1.90 | 3.22 ± 1.47 |
| DS109 middle, (n = 8) | 3.58 ± 1.04 | 3.28 ± 1.41 |
| DS109 high, (n = 8) | 4.71 ± 0.96 | 3.76 ± 0.81 |
| DS102 low, (n = 8) | 5.01 ± 3.11 | 4.19 ± 3.33 |
| DS102 high, (n = 8) | 4.01 ± 1.92 | 3.08 ± 1.16 |

Gene Expression Analyses: Gene expression analyses for alpha-SMA, TIMP-1, TGF-β, Collagen Type 1 are shown in FIG. 8A-8D and Table 7.

TABLE 7

Gene Expression Analysis

| Group | Alpha-SMA | TIMP-1 | TGF-β | Collagen Type 1 |
|---|---|---|---|---|
| Sham control, (n = 8) | 1.00 ± 0.18 | 1.00 ± 0.14 | 1.00 ± 0.09 | 1.00 ± 0.13 |
| Vehicle, (n = 8) | 3.82 ± 0.58 | 133.20 ± 26.86 | 3.88 ± 0.30 | 11.52 ± 2.15 |
| DS109 low, (n = 8) | 3.87 ± 0.82 | 153.60 ± 37.12 | 4.29 ± 0.93 | 10.76 ± 1.45 |
| DS109 middle, (n = 8) | 4.61 ± 3.15 | 167.70 ± 122.60 | 6.01 ± 4.77 | 15.23 ± 11.52 |
| DS109 high, (n = 8) | 4.85 ± 1.22 | 180.90 ± 23.12 | 5.48 ± 0.36 | 13.88 ± 1.91 |
| DS102 low, (n = 8) | 3.74 ± 0.81 | 138.30 ± 30.39 | 4.31 ± 0.69 | 11.80 ± 1.78 |
| DS102 high, (n = 8) | 5.54 ± 1.54 | 124.80 ± 28.60 | 5.37 ± 0.76 | 14.09 ± 2.88 |

Alpha-SMA: The Vehicle group showed a significant increase in α-SMA mRNA expression level compared with the Sham control group. There were no significant differences in α-SMA mRNA expression level between the Vehicle group and the treatment groups.

TIMP-1: The Vehicle group showed a significant increase in TIMP-1 mRNA expression level compared with the Sham control group. There were no significant differences in TIMP-1 mRNA expression level between the Vehicle group and the treatment groups.

TGF-β: The Vehicle group showed a significant increase in TGF-β mRNA expression level compared with the Sham control group. There were no significant differences in TGF-β mRNA expression level between the Vehicle group and the treatment groups.

Collagen Type 1: The Vehicle group showed a significant increase in Collagen Type 1 mRNA expression level compared with the Sham control group. There were no significant differences in Collagen Type 1 mRNA expression level between the Vehicle group and the treatment groups.

1.4 Summary

As shown by Sirius-red staining and kidney hydroxyproline content, renal fibrosis was established in the Vehicle group in the present study.

DS109: Treatment with DS109 at low dose showed significant decreases (p<0.05) in kidney hydroxyproline contents and a reduction trend (p<0.1) in fibrosis area compared with the Vehicle group. Treatment with DS109 at middle dose showed reduction trend (p<0.1) in the fibrosis area compared with the Vehicle group. Lastly, treatment with DS109 at high dose showed significant decreases (p<0.05) in kidney hydroxyproline contents and a reduction trend (p<0.1) in fibrosis area compared with the Vehicle group.

DS102: Treatment with DS102 at low dose showed a significant decrease in kidney hydroxyproline contents (p<0.05), and a reduction trend (p<0.1) in fibrosis area compared with the Vehicle group. Treatment with DS102 at high dose showed significant decreases in kidney hydroxyproline contents (p<0.05), and a reduction trend (p<0.1) in fibrosis area compared with the Vehicle group.

In conclusion, the results from this study suggest that DS109 and DS102 have a suppressive effect on renal fibrogenesis and potential as therapeutic agents for chronic renal diseases that progress to fibrosis.

Example 2

Cholestatic Liver Disease and/or Liver Fibrosis Bile Duct Ligation (BDL) Study

The objective of this study was to examine the effects of DS012 on cholestasis induced by BDL.

Figure 9:
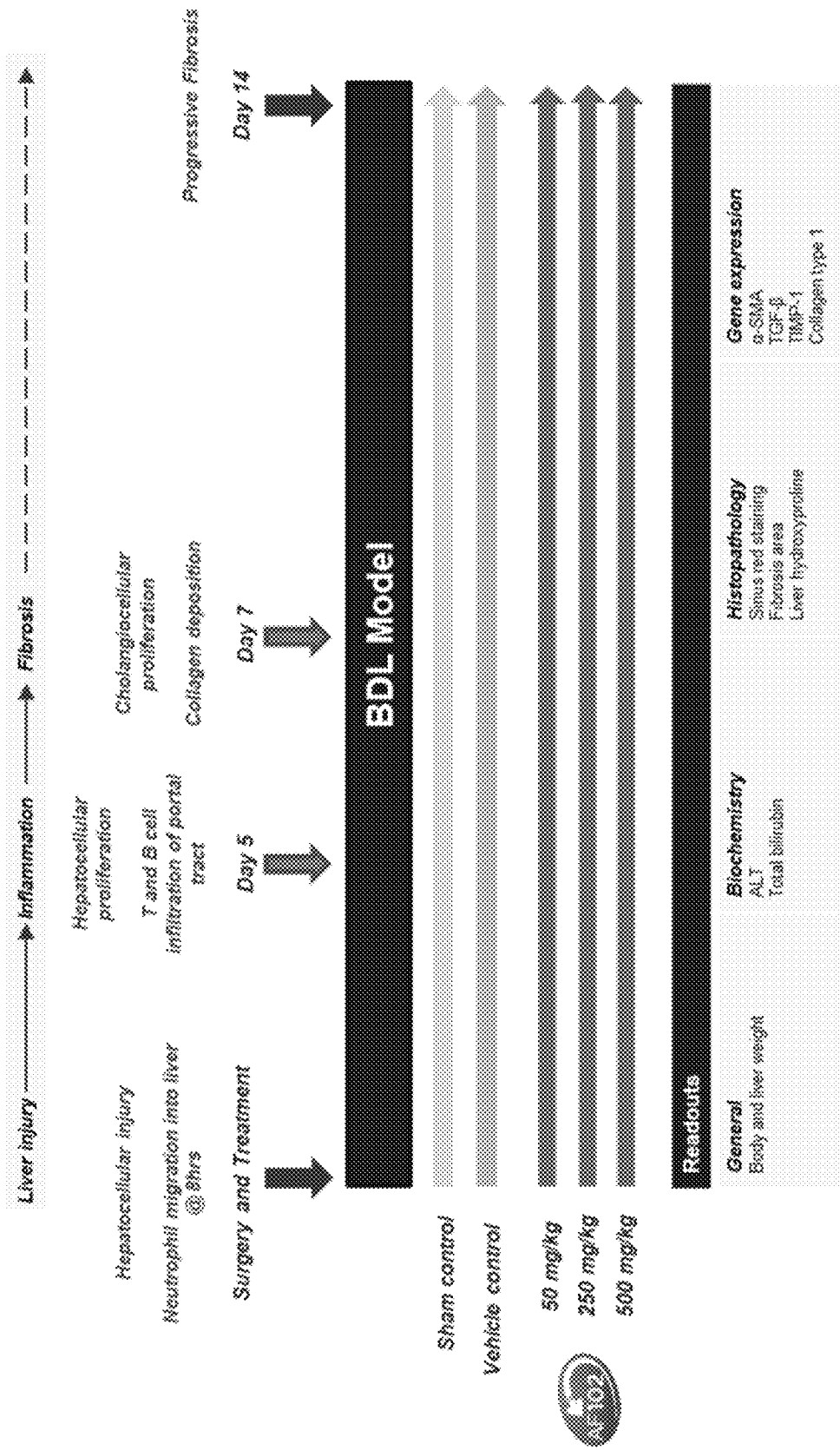
FIG. 9 is a schematic diagram of the study described in Example 2 and its duration.

FIG. 9 depicts the study design from surgery and treatment to day 14 of the study.

1.1 Materials and Methods

Test Substance: The test substance for this study was DS102. To prepare dosing solutions of each substance, DS102 was diluted in a vehicle of 0.5% hydroxypropyl methyl cellulose (HPMC).

BDL Surgery: On Day 0 of the study, BDL surgery was performed under pentobarbital (Kyoritsu Seiyaku, Japan) anesthesia. The mouse's hair was first shaved, the abdominal cavity cut open, and the common bile duct was ligated twice with 7-0 surgical silk. The mouse's peritoneum and the skin were closed with sutures, and the mice were transferred to a clean cage (e.g., resting cage) until recovered from anesthesia. Sham operated mice had their common bile duct exposed but not ligated.

Drug Administration: DS102 was administered to orally in a volume of 10 milliliters (mL)/kilogram (Kg).

Treatment Doses: DS102 was administered at 3 dose levels of 50, 250, and 500 milligram (mg)/Kg once daily from Day 0 to Day 13 of the study.

Animals: Pathogen-free 6 weeks of age male C57BL/6J mice were obtained from Japan SLC, Inc. (Japan). The animals were maintained in a specific-pathogen free (SPF) facility under controlled conditions of temperature (e.g., 23±2° C.), humidity (e.g., 45±10%), lighting (e.g., 12-hour artificial light and dark cycles; light from 8:00 to 20:00) and air exchange. A high pressure was maintained in the experimental room to prevent contamination of the facility. The animals were housed in TPX cages (CLEA Japan) with a maximum of 4 mice per cage. Sterilized Paper-Clean (Japan SLC) was used for bedding and replaced once a week. Sterilized solid normal diet was provided ad libitum, being placed in a metal lid on the top of the cage. Pure water was also provided ad libitum from a water bottle equipped with a rubber stopper and a sipper tube. Water bottles were replaced once a week, cleaned, and sterilized in an autoclave and reused. Mice were identified by ear punch and each cage was labeled with a specific identification code.

Measurement of Serum Biochemistry: To visualize collagen deposition, Bouin's fixed liver sections were stained using picro-Sirius red solution (Waldeck, Germany). For quantitative analysis of fibrosis area, bright field images of Sirius red-stained sections were captured using a digital camera (DFC295; Leica, Germany) at 100-fold magnification, and the positive areas in 5 fields/section were measured using ImageJ software (National Institute of Health, USA).

Histological analysis: To visualize collagen deposition, kidney sections were stained using picro-Sirius red solution (Waldeck, Germany). For quantification of interstitial fibrosis area, bright field images in the corticomedullary region were captured using a digital camera (e.g., DFC295; Leica Microsystems, Germany) at 200-fold magnification, and the positive areas in 5 fields/section were measured using ImageJ software (National Institute of Health, USA).

Quantitative RT-PCR: Total ribonucleic acid (RNA) was extracted from liver samples using RNAiso (Takara Bio, Japan) according to the manufacturer's instructions. One µg of RNA was reverse-transcribed using a reaction mixture containing 4.4 mM magnesium chloride ($MgCl_2$) (F. Hoffmann-La Roche, Switzerland), 40 U RNase inhibitor (Toyobo, Japan), 0.5 mM dNTP (Promega, USA), 6.28 µM random hexamer (Promega), 5× first strand buffer (Promega), 10 mM dithiothreitol (Invitrogen, USA) and 200 U MMLV-RT (Invitrogen) in a final volume of 20 µL. The reaction was carried out for 1 hour at 37° C., followed by 5 minutes at 99° C. Real-time PCR was performed using real-time PCR DICE and TB Green™ Premix Ex Taq™ II (Takara Bio). To calculate the relative mRNA expression level, the expression of each gene (α-SMA, TIMP-1, TGF-β and Collagen Type 1) was normalized to that of reference gene 36B4 (gene symbol: Rplp0). Information regarding the PCR-primer sets and the plate layout are described in Tables 8 and 9.

collected and cut into 6 pieces. Two pieces of left lateral lobe were fixed in Bouin's solution and then embedded in paraffin. Samples were stored at room temperature for histological analysis. The other 2 pieces of left lateral lobe were embedded in O.C.T. compound and quick frozen in liquid nitrogen. Samples were stored at −80° C. The remaining pieces of left lateral lobe was snap frozen in liquid nitrogen and stored at −80° C. for gene expression analyses. Right medial lobe, left medial lobe, right lobe and caudate lobe were snap frozen in liquid nitrogen and stored at −80° C. for shipping.

Statistical Tests: Statistical analyses were performed using Bonferroni Multiple Comparison Test on GraphPad Prism 6 (GraphPad Software Inc., USA). P values <0.05 were considered statistically significant. A trend or tendency was assumed when a one-tailed t-test returned P values <0.1. Results were expressed as mean±SD.

1.2 Experimental Design and Treatment

The study design included the following study groups:
Group 1 (Sham Control): Eight sham-operated mice kept without any treatment until sacrifice.

TABLE 8

FOR Primers for the Quantitative RT-PCR Measurements

| SEQ ID NO. | Gene | Set ID | | Sequence |
|---|---|---|---|---|
| 1 | 36B4 | MA057856 | forward | 5'-TTCCAGGCTTTGGGCATCA-3' |
| 2 | | | reverse | 5'-ATGTTCAGCATGTTCAGCAGTGTG-3' |
| 3 | Alpha-SMA | MA057911 | forward | 5'-AAGAGCATCCGACACTGCTGAC-3' |
| 4 | | | reverse | 5'-AGCACAGCCTGAATAGCCACATAC-3' |
| 5 | TIMP-1 | MA098519 | forward | 5'-TGAGCCCTGCTCAGCAAAGA-3' |
| 6 | | | reverse | 5'-GAGGACCTGATCCGTCCACAA-3' |
| 7 | TGF-β | MA030397 | forward | 5'-GTGTGGAGCAACATGTGGAACTCTA- 3' |
| 8 | | | reverse | 5'-TTGGTTCAGCCACTGCCGTA-3' |
| 9 | Collagen Type 1 | MA075477 | forward | 5'-CCAACAAGCATGTCTGGTTAGGAG-3' |
| 10 | | | reverse | 5'-GCAATGCTGTTCTTGCAGTGGTA-3' |

36B4: Ribosomal protein, large, P0 (Rplp0)
Alpha-SMA: Actin, alpha 2, smooth muscle, aorta (Acta2)
TIMP-1: Tissue inhibitor of metalloproteinase 1 (Timp1)
TGF-β: Transforming growth factor, beta 1 (Tgfb1)
Collagen Type 1: Collagen, type 1, alpha 2 (Col1a2)

TABLE 9

Specifics Regarding the PCR Plates for the Quantitative RT-PCR Measurements

| Plate Mouse ID | 1<br>101-308 | 2<br>401-608 | 3<br>701-708 |
|---|---|---|---|
| Alpha-SMA | Plate 1-2 | Plate 2-2 | Plate 3-2 |
| 36B4 | Plate 1-1 | Plate 2-1 | Plate 3-1 |
| TIMP-1 | Plate 1-3 | Plate 2-3 | Plate 3-2 |
| 36B4 | Plate 1-1 | Plate 2-1 | Plate 3-1 |
| TGF-β | Plate 1-4 | Plate 2-4 | Plate 3-3 |
| 36B4 | Plate 1-1 | Plate 2-1 | Plate 3-1 |
| Collagen Type 1 | Plate 1-5 | Plate 2-5 | Plate 3-3 |
| 36B4 | Plate 1-1 | Plate 2-1 | Plate 3-1 |

Sample Collection: For serum samples, non-fasting blood was collected in serum separate tubes without anticoagulant through direct cardiac puncture and centrifuged at 3,500×g for 4 minutes at 4° C. The supernatant was collected and stored at −80° C. for biochemistry (30 µL) and shipping (all the remaining). For liver samples, left lateral lobe was Group 2 (Vehicle): Fifteen BDL-operated mice were orally administered vehicle [0.5% HPMC] in a volume of 10 mL/kg once daily from Day 0 to Day 13.

Group 3 (DS102 Low): Fifteen BDL-operated mice were orally administered vehicle supplemented with DS102 at a dose of 50 mg/kg once daily from Day 0 to Day 13.

Group 4 (DS102 Middle): Fifteen BDL-operated mice were orally administered vehicle supplemented with DS102 at a dose of 250 mg/kg once daily from Day 0 to Day 13.

Group 5 (DS102 High): Fifteen BDL-operated mice were orally administered vehicle supplemented with DS102 at a dose of 500 mg/kg once daily from Day 0 to Day 13.

Table 10 summarizes the treatment schedule for each of Groups 1-5 during the study.

TABLE 10

Summary of the Treatment Schedule

| Group | No. mice | Mice | Test substance | Dose (mg/kg) | Volume (mL/kg) | Regimen | Sacrifice |
|---|---|---|---|---|---|---|---|
| 1 | 8 | Sham | — | — | — | — | Day 14 |
| 2 | 15 | BDL | Vehicle | — | 10 | PO, QD, Day 0-13 | Day 14 |
| 3 | 15 | BDL | DS102 | 50 | 10 | PO, QD, Day 0-13 | Day 14 |
| 4 | 15 | BDL | DS102 | 250 | 10 | PO, QD, Day 0-13 | Day 14 |
| 5 | 15 | BDL | DS102 | 500 | 10 | PO, QD, Day 0-13 | Day 14 |

Animal Monitoring and Sacrifice: The viability, clinical signs and behavior for the mice were monitored daily. Individual body weight was measured daily before treatment during the treatment period. Mice were observed for significant clinical signs of toxicity, moribundity and mortality approximately 60 minutes after each administration. The animals were sacrificed at Day 14 after BDL surgery by exsanguination through direct cardiac puncture under isoflurane anesthesia (Pfizer Inc.)

1.3 Results

Figure 10:
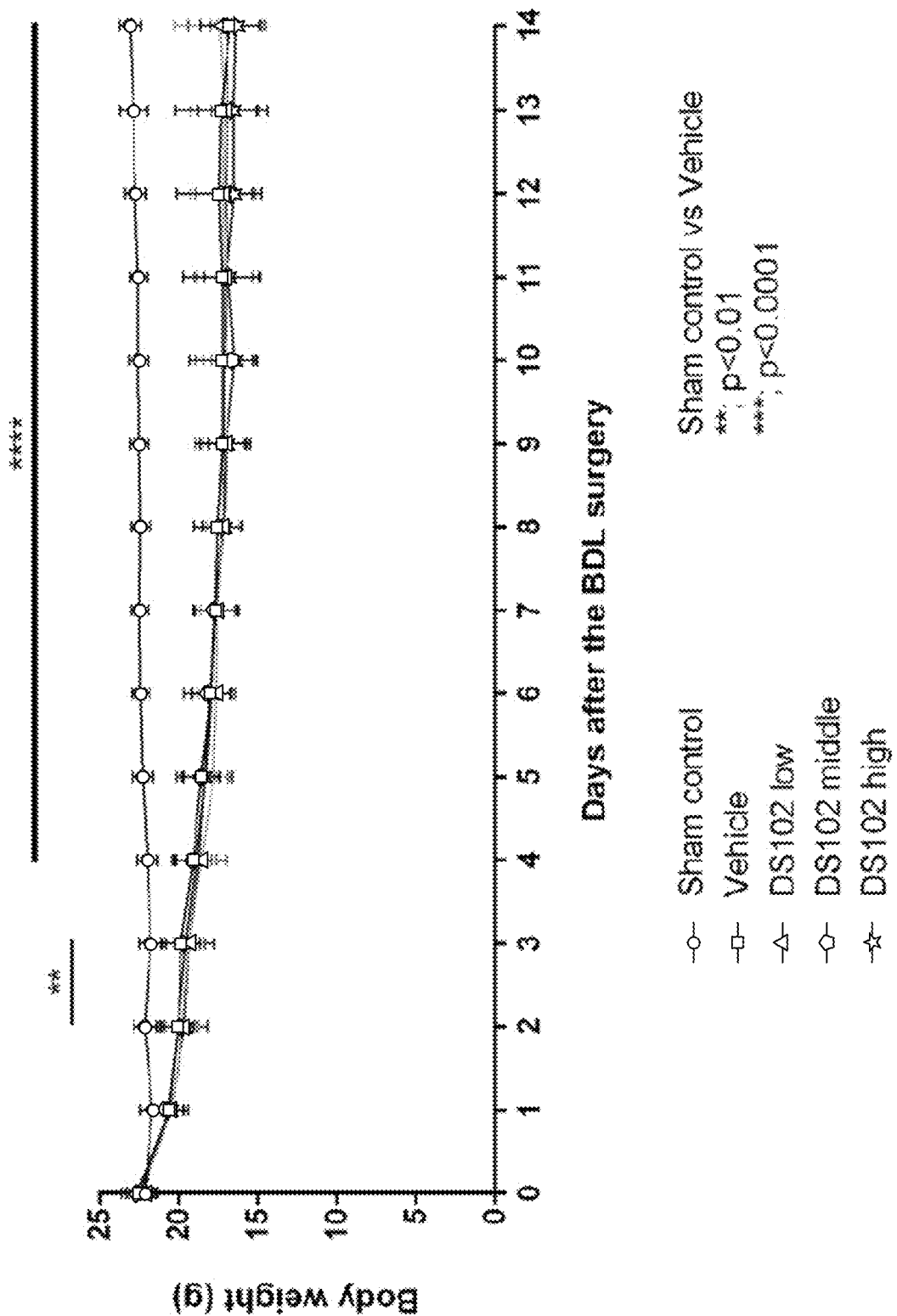
FIG. 10 shows the body weight changes of the animals according to the study described in Example 2.

Body weight changes and general considerations: FIG. 10 shows the body weight changes for all animals. Mean body weight in all groups, except of the Sham control group, gradually decreased during the study period. Mean body weight of the Vehicle group was significantly lower than that of the Sham control group from Day 2 to Day 14. There were no significant changes in mean body weight at any day during the study period between the Vehicle group and the DS102 treatment groups.

During the treatment period, mice found dead before reaching Day 14 were as follows: three out of 15 mice were found dead in the Vehicle group; seven out of 15 mice were found dead in the DS102 low, DS102, middle and DS102 high groups. In this model, a percentage of deaths are expected simply due to disease induction and the observed mortality rate is consistent with historical data.

Figure 11:
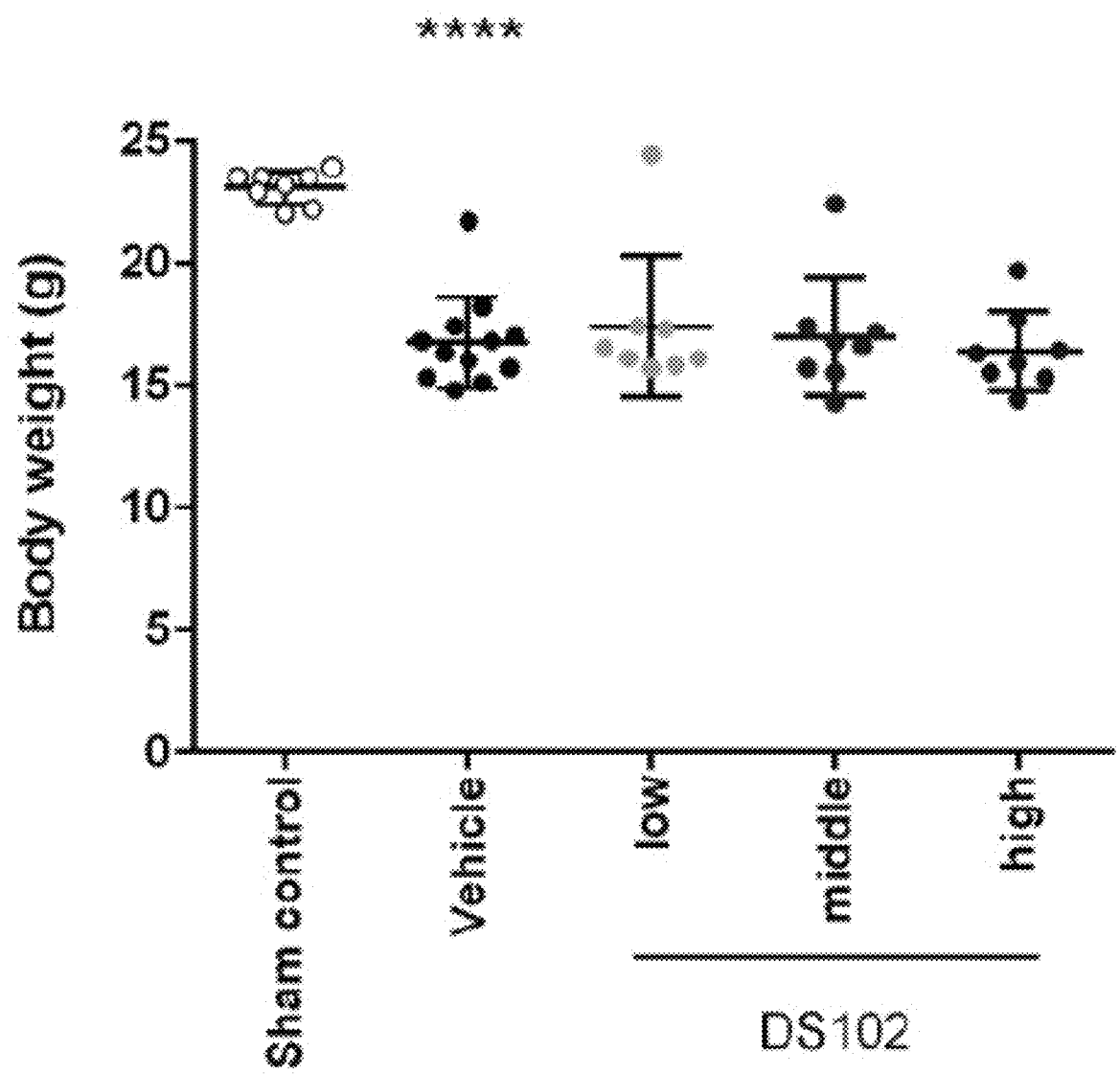
FIG. 11 shows the body weight on the day of sacrifice of the animals according to the study described in Example 2.

Body and liver weight on the day of sacrifice: FIG. 11 and Table 11 show the body weight of the animals on the day of sacrifice. The Vehicle group showed a significant decrease in mean body weight on the day of sacrifice compared with the Sham control group. There were no significant differences in mean body weight on the day of sacrifice between the Vehicle group and the DS102 treatment groups.

TABLE 11

Body Weight on the Day of Sacrifice

| Group | Body Weight (g) | Liver Weight (mg) | Liver-to-Body Weight Ratio (%) |
|---|---|---|---|
| Sham control, (n = 8) | 23.1 ± 0.7 | 1132 ± 90 | 4.9 ± 0.4 |
| Vehicle, (n = 12) | 16.8 ± 1.8 | 1438 ± 180 | 8.7 ± 1.4 |
| DS102 low, (n = 8) | 17.4 ± 2.9 | 1392 ± 328 | 8.3 ± 2.3 |
| DS102 middle, (n = 8) | 17.0 ± 2.4 | 1513 ± 182 | 9.0 ± 1.2 |
| DS102 high, (n = 8) | 16.4 ± 1.6 | 1231 ± 255 | 7.6 ± 1.5 |

Figure 12A:
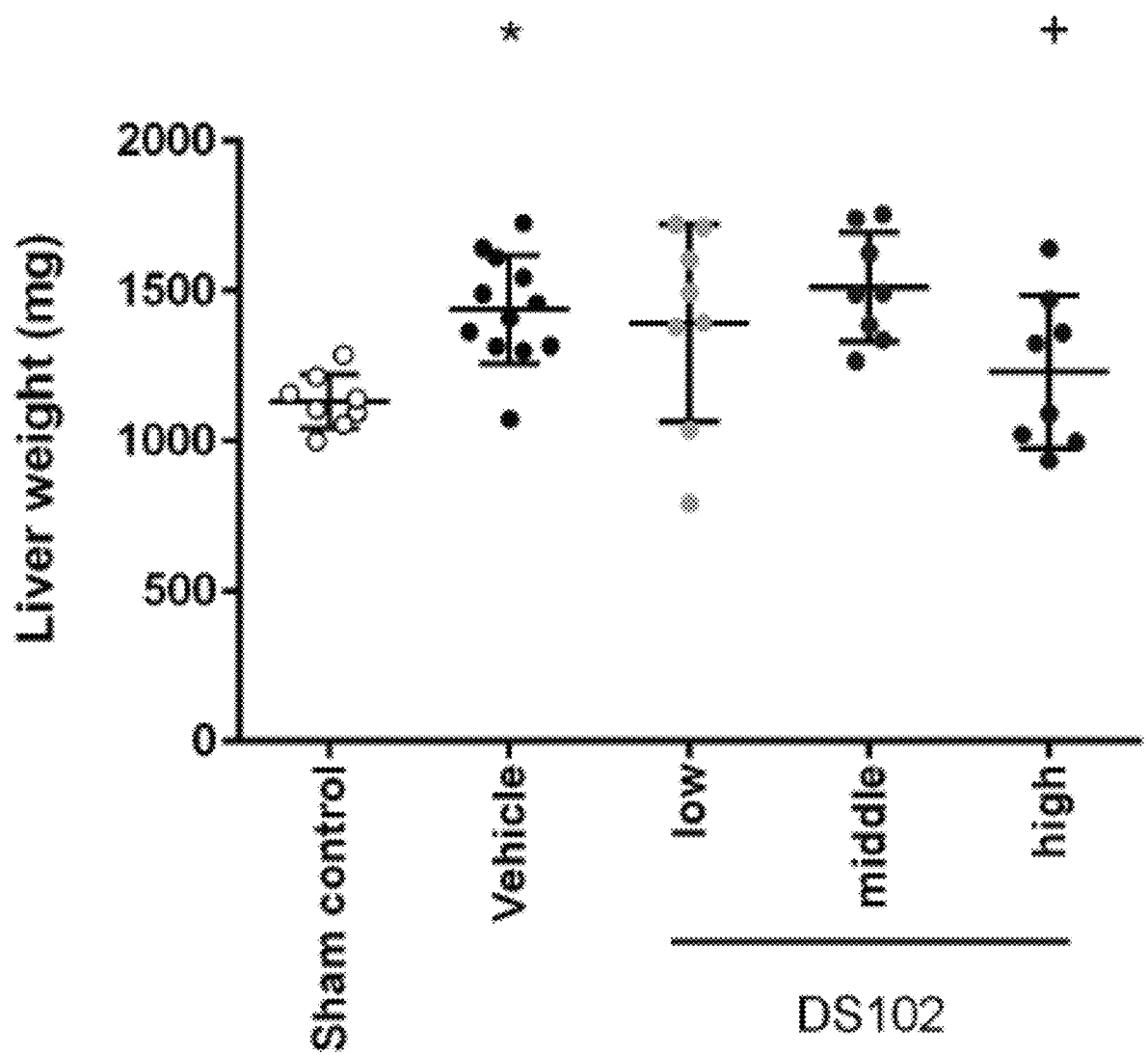
FIGS. 12A and 12B show the liver weight and liver-to-body weight ratio of the animals on the day of sacrifice according to the study described in Example 2, respectively.
Figure 12B:
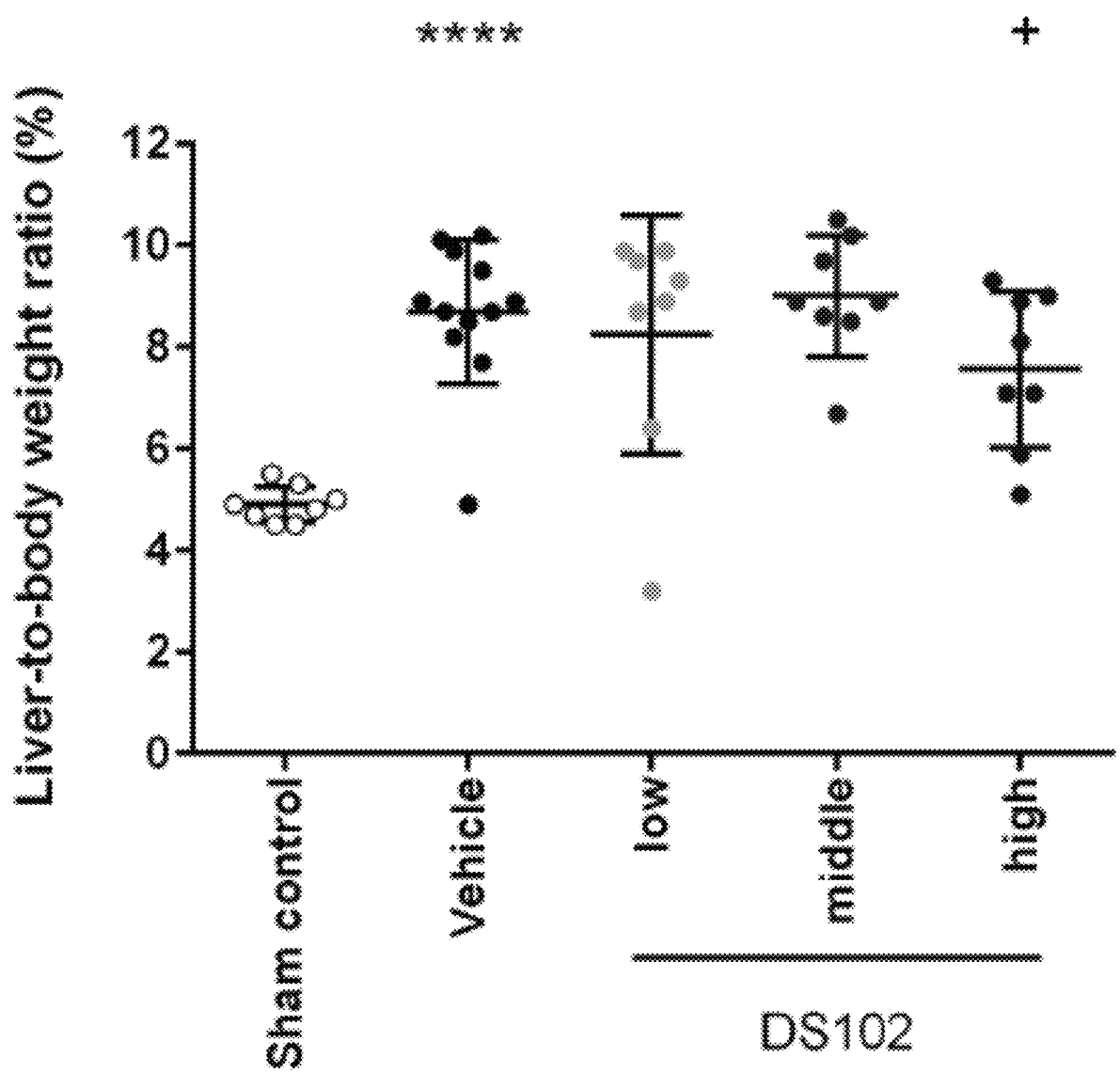

FIGS. 12A and 12B and Table 11 show the liver weight and liver-to-body weight ratio of the animals on the day of sacrifice. The Vehicle group showed a significant increase in mean liver weight compared with the Sham control group. Mean liver weight in the DS102 high group tended to decrease compared with the Vehicle group. There were no significant differences in mean liver weight between the Vehicle group and the other treatment groups. The Vehicle group showed a significant increase in mean liver-to-body weight ratio compared with the Sham control group. Mean liver-to-body weight ratio in the DS102 high group tended to decrease compared with the Vehicle group. There were no significant differences in mean liver-to-body weight ratio between the Vehicle group and the other treatment groups.

Figure 13:
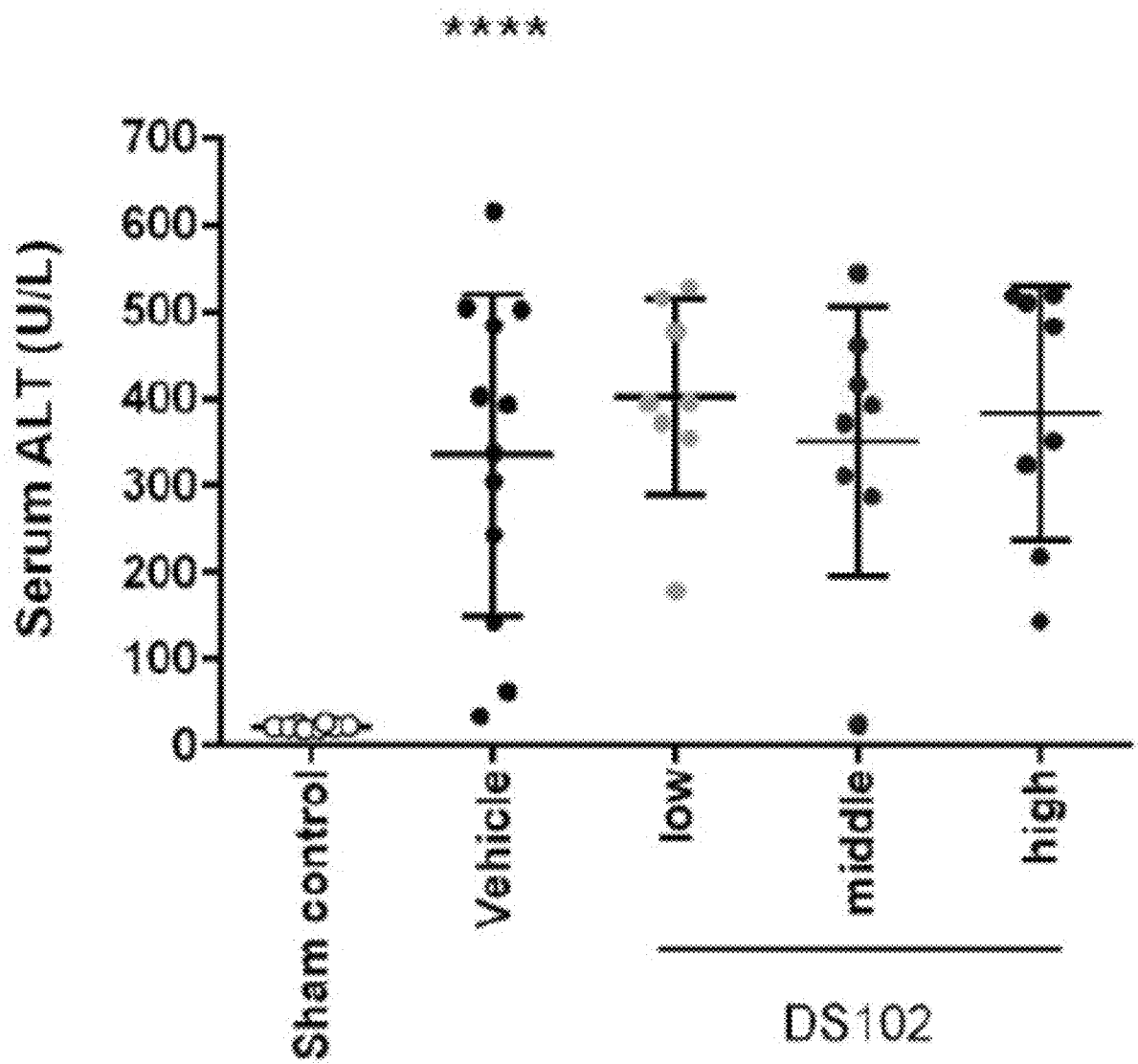
FIG. 13 shows the changes of serum ALT levels of the animals according to the study described in Example 2.

Biochemistry: FIG. 13 and Table 12 show the serum aminotransferase (ALT) for the animals. The Vehicle group showed a significant increase in serum ALT level compared with the Sham control group. There were no significant differences in serum ALT level between the Vehicle group and the DS102 treatment groups. However, from historical data for this model, ALT levels are known to decrease at Day 14 without treatment. As such, this may impact the ability to detect differences between the groups.

TABLE 12

Biochemistry

| Group | Serum ALT (U/L) | Serum Total Bilirubin (mg/dL) |
|---|---|---|
| Sham control, (n = 8) | 22 ± 2 | 0.4 ± 0.1 |
| Vehicle, (n = 12) | 335 ± 185 | 24.9 ± 9.6 |
| DS102 low, (n = 8) | 402 ± 112 | 26.8 ± 6.9 |
| DS102 middle, (n = 8) | 351 ± 155 | 23.5 ± 9.8 |
| DS102 high, (n = 8) | 383 ± 147 | 26.2 ± 6.1 |

Figure 14:
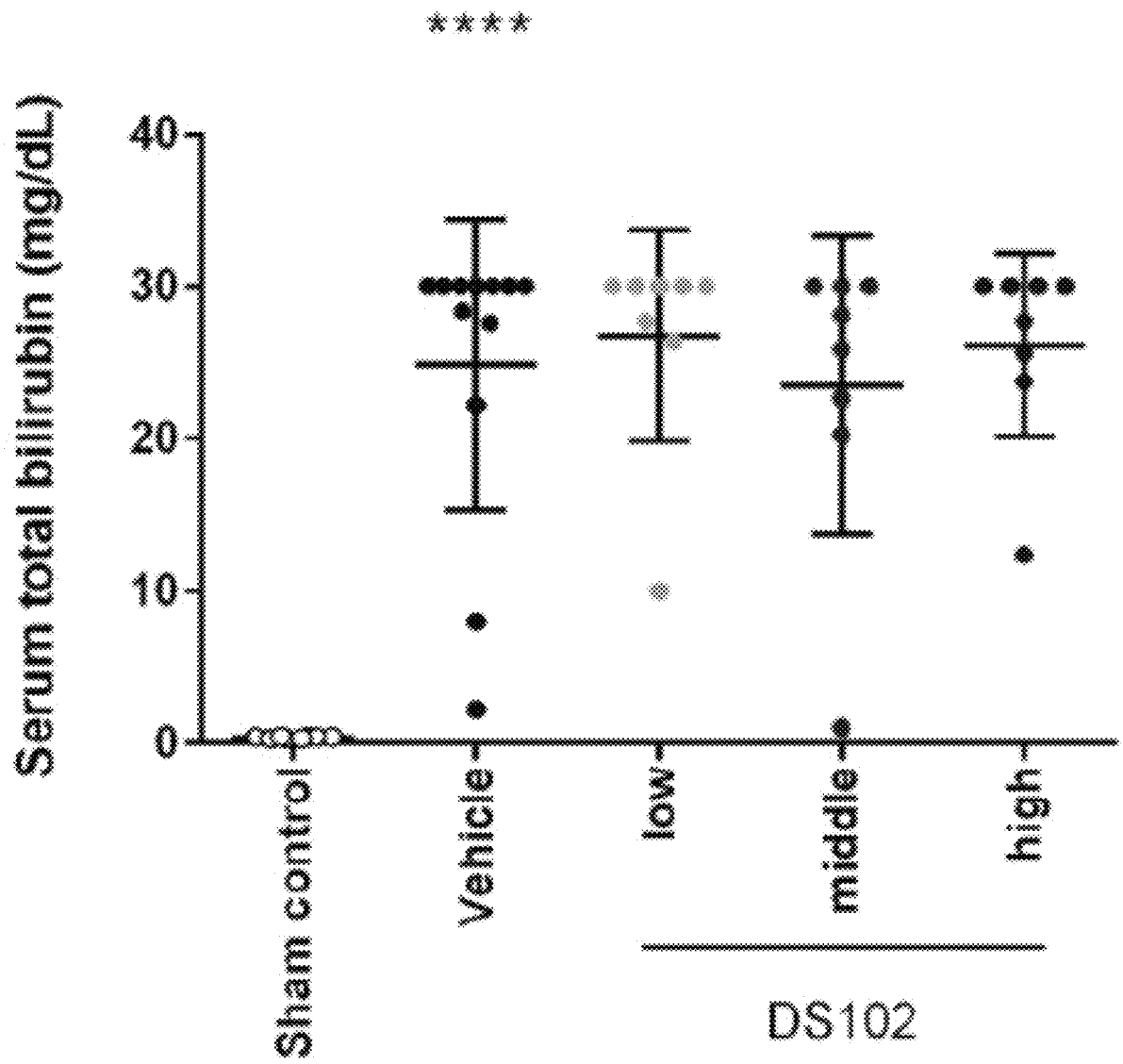
FIG. 14 shows the changes of serum total bilirubin levels of the animals according to the study described in Example 2.

FIG. 14 and Table 12 show the serum total bilirubin for the animals. The Vehicle group showed a significant increase in serum total bilirubin level compared with the Sham control group. There were no significant differences in serum total bilirubin level between the Vehicle group and the DS102 treatment groups.

Figure 15A:
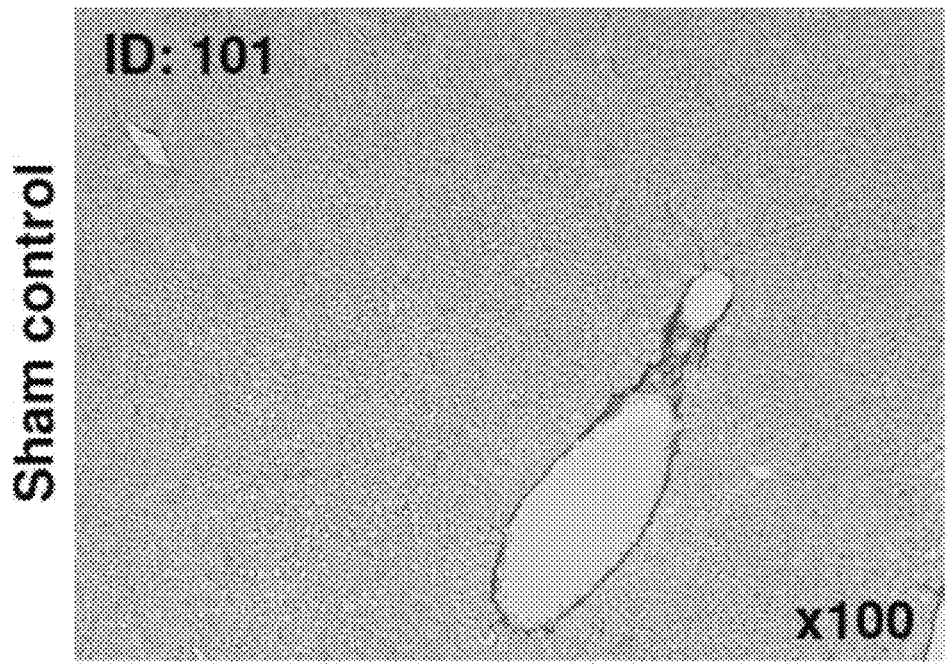
FIGS. 15A-15E show the Sirius red staining and the fibrosis area of the animals according to the study described in Example 2.
Figure 15B:
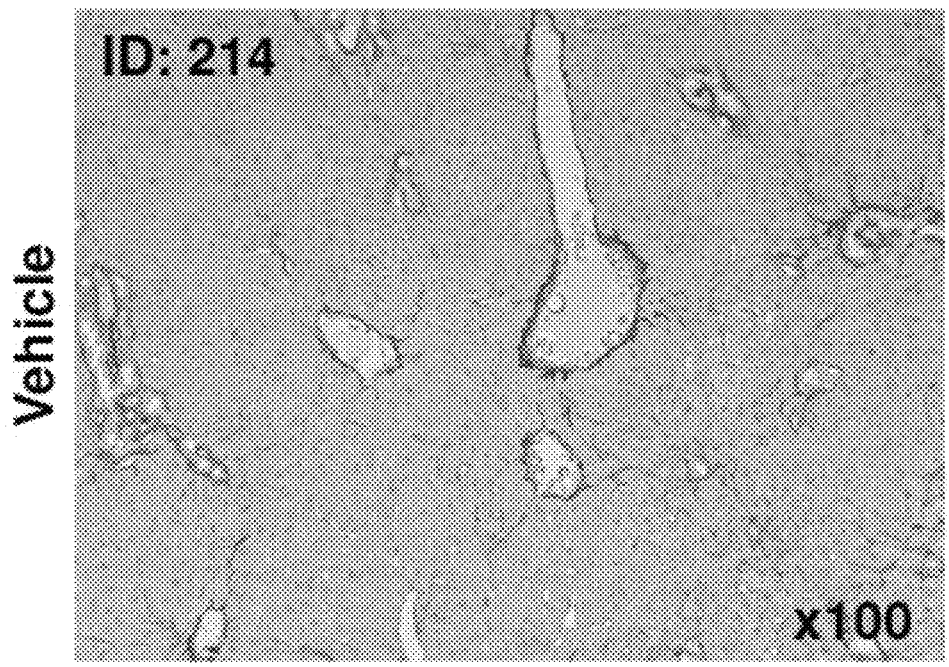
Figure 15C:
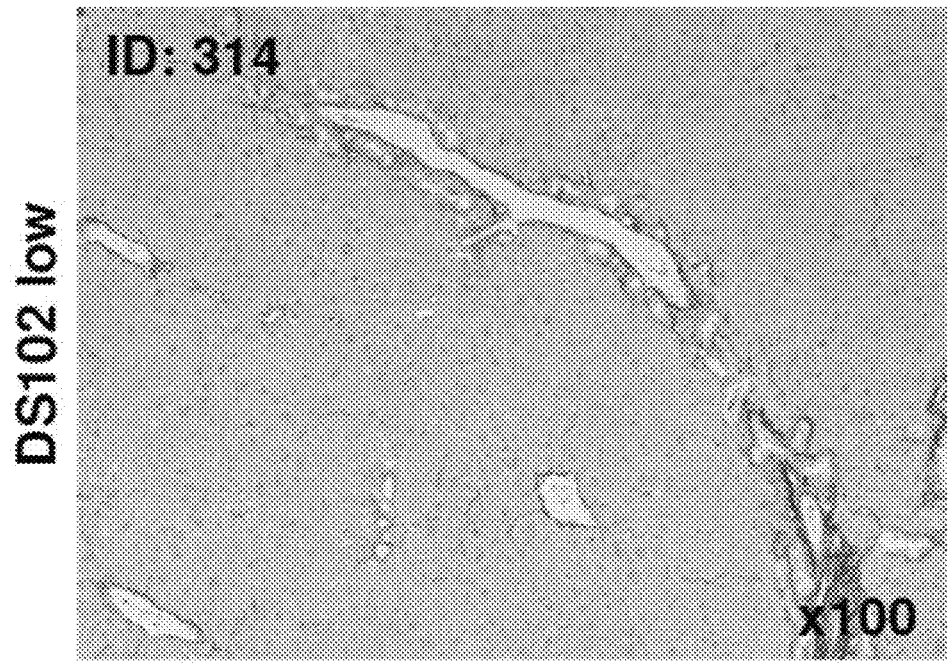
Figure 15D:
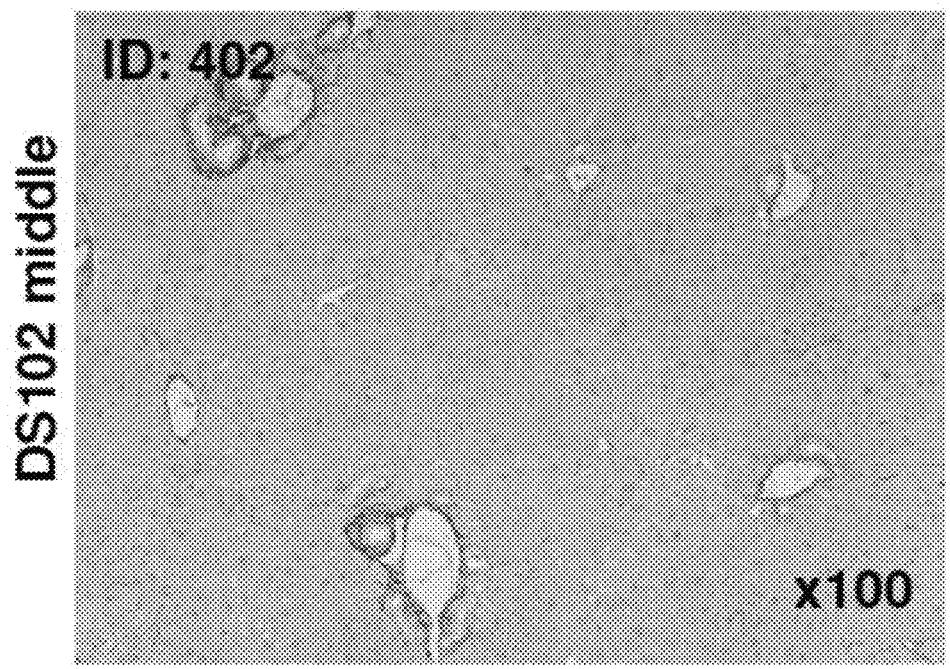
Figure 15E:
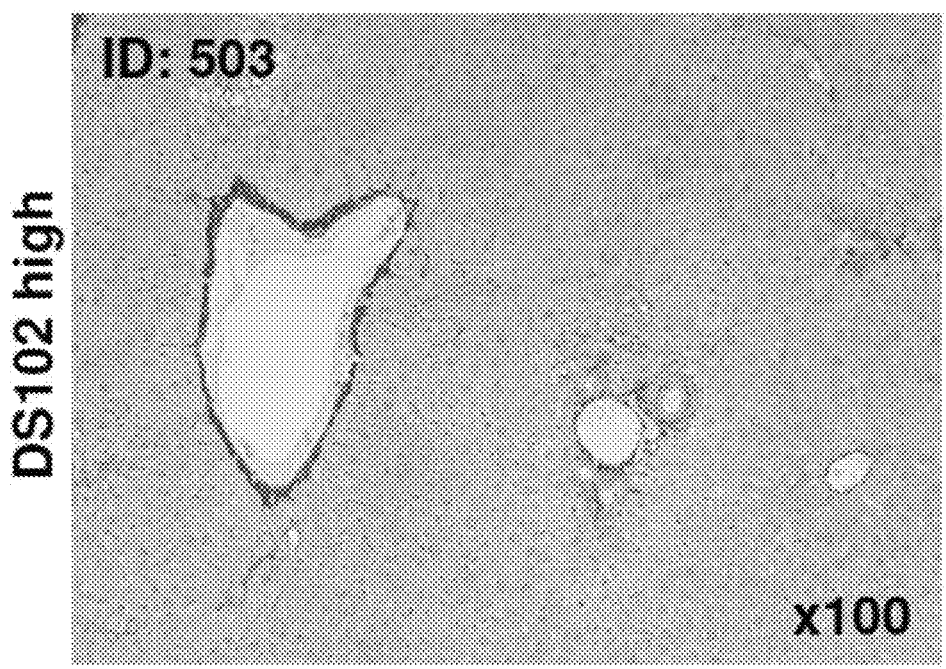
Figure 16:
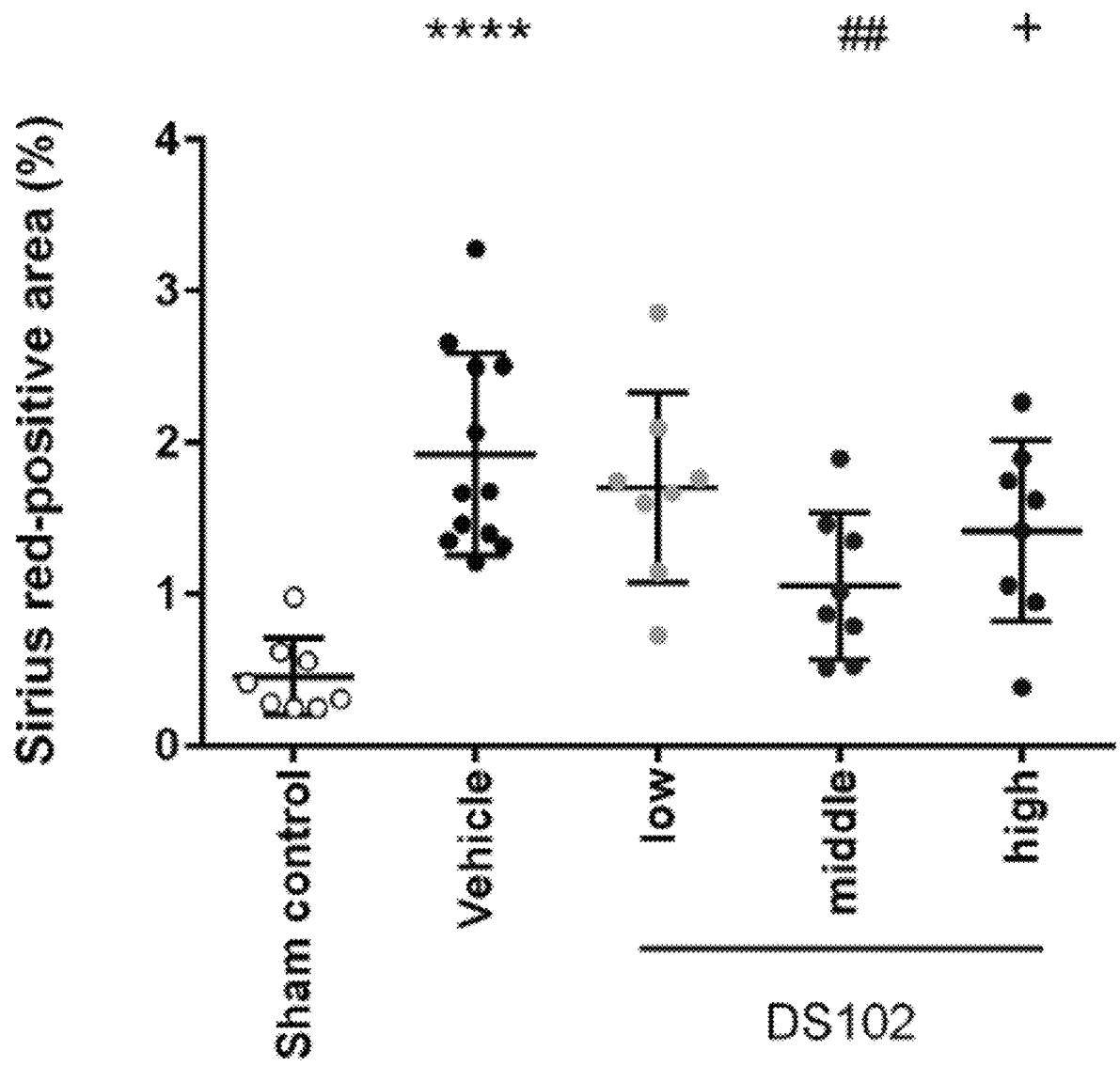
FIG. 16 shows a plot depicting the Sirius red-positive area (%) of the animals according to the study described in Example 2.
Figure 17A:
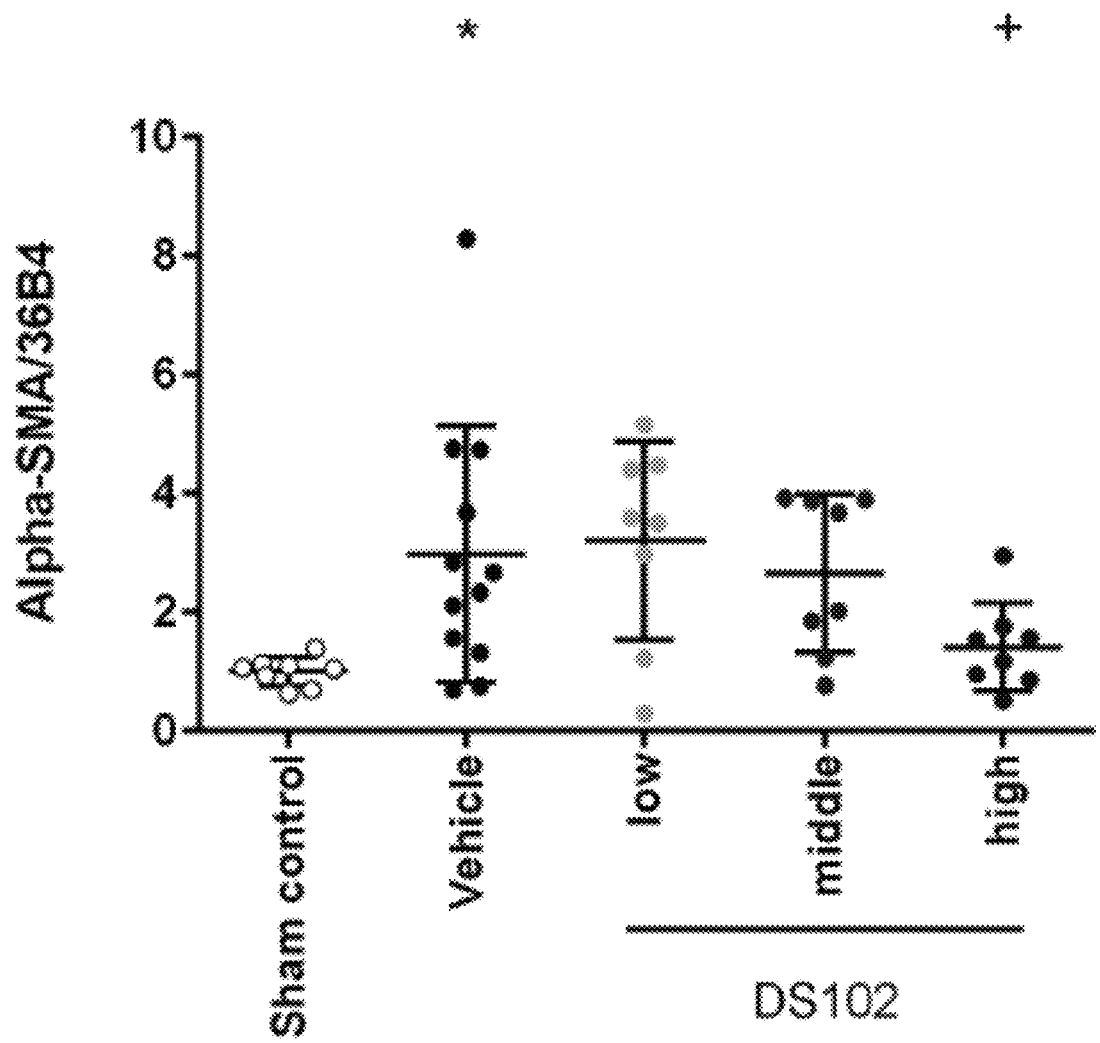
FIG. 17A-17D show the gene expression analyses for α-SMA, TIMP-1, TGF-β, and Collagen Type 1 of the animals according to the study described in Example 2, respectively.
Figure 17B:
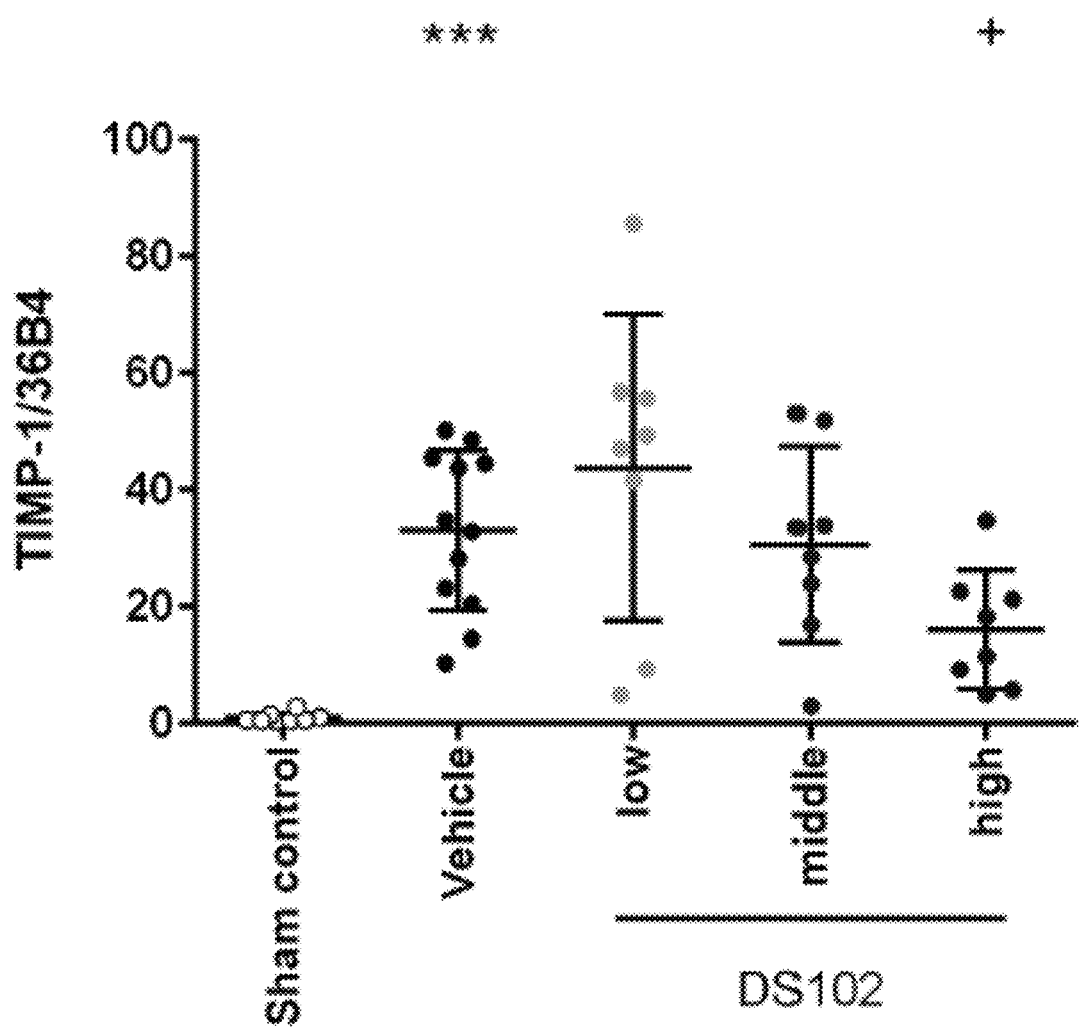
Figure 17C:
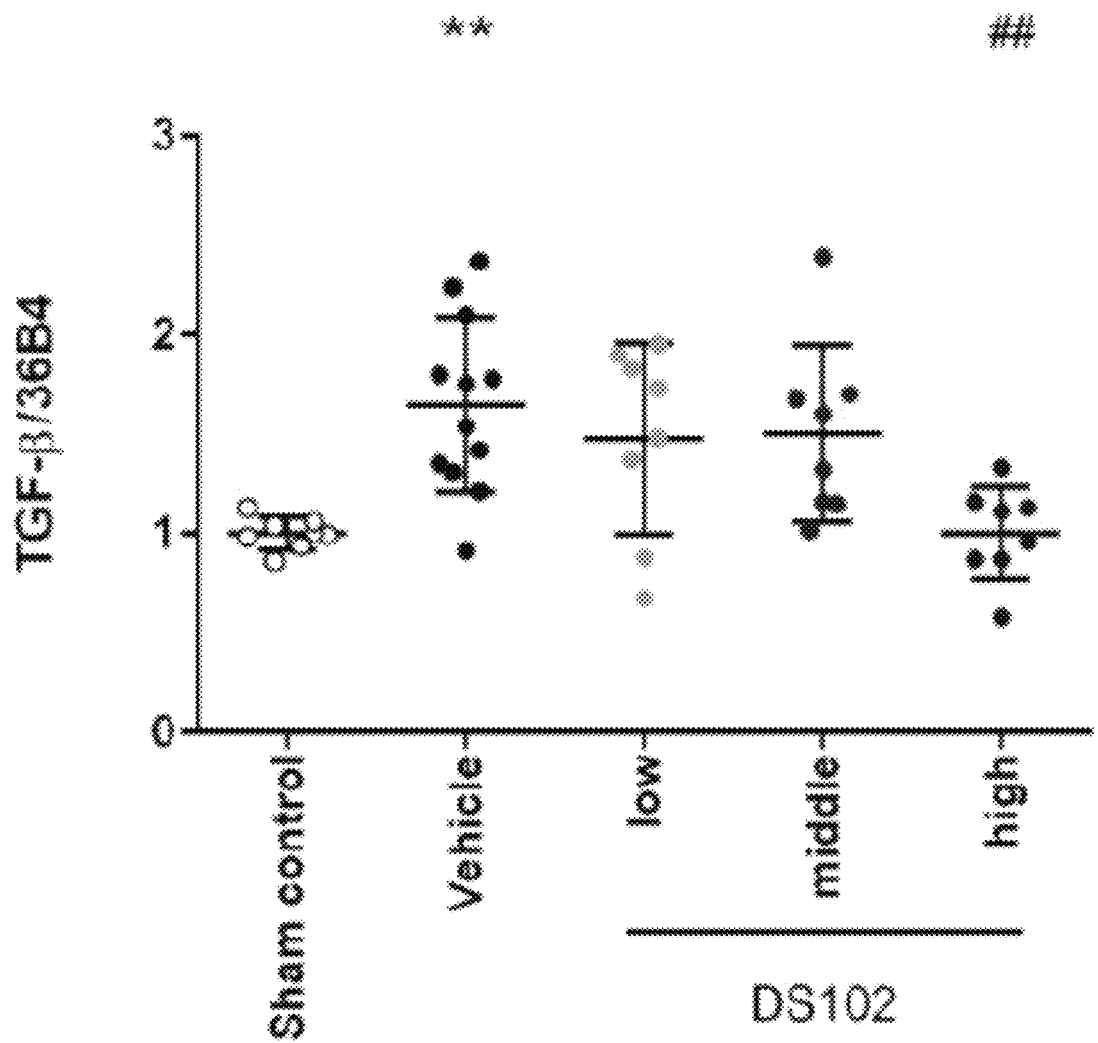
Figure 17D:
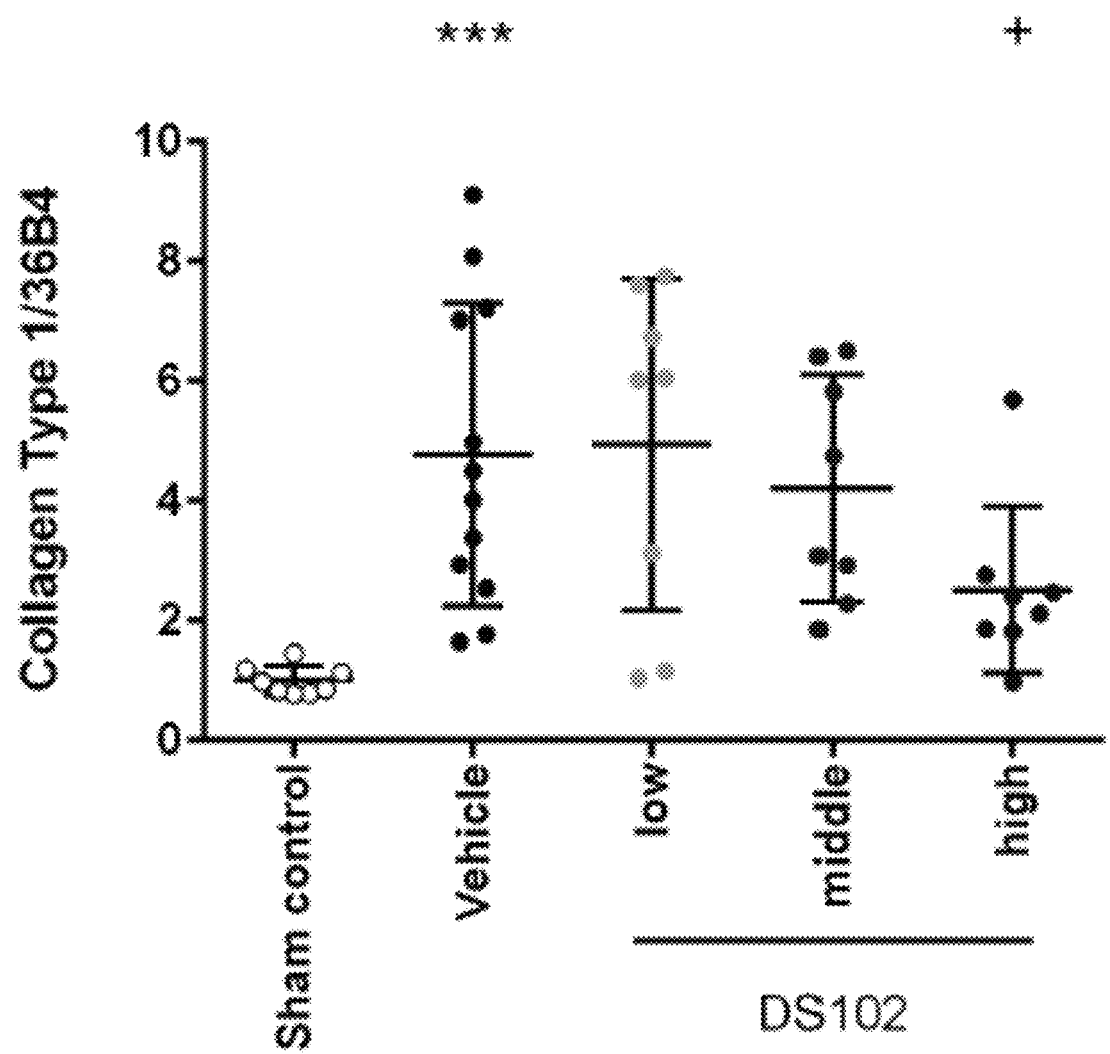

Histological Analysis: FIGS. 15A-14E and Table 13 show the Sirius red staining and FIG. 16, the fibrosis area of the animals. FIG. 14A displays representative of photomicrographs of Sirius red-stained liver sections. Liver sections from the Vehicle group showed increased collagen deposition in the portal region of liver lobule and PV-CV or PV-PV bridging fibrosis compared with the Sham control group. The Vehicle group showed a significant increase in the fibrosis area (Sirius red-positive area) compared with the Sham control group. The DS102 middle group showed a significant decrease in the fibrosis area compared with the Vehicle group. Fibrosis area in the DS102 high group tended to decrease compared with the Vehicle group. There was no significant difference in the fibrosis area between the Vehicle group and the DS102 low group.

TABLE 13

Histological Analysis

| Group | Sirius red-positive area (%) |
|---|---|
| Sham control, (n = 8) | 0.46 ± 0.25 |
| Vehicle, (n = 12) | 1.93 ± 0.67 |
| DS102 low, (n = 8) | 1.70 ± 0.63 |
| DS102 middle, (n = 8) | 1.06 ± 0.48 |
| DS102 high, (n = 8) | 1.42 ± 0.60 |

Gene Expression Analyses: Gene expression analyses for α-SMA, TIMP-1, TGF-β, and Collagen Type 1 are shown in FIGS. 17A-17D and Table 14.

TABLE 14

Gene Expression Analyses

| Group | Alpha-SMA | TIMP-1 | TGF-β | Collagen Type 1 |
|---|---|---|---|---|
| Sham control, (n = 8) | 1.00 ± 0.24 | 1.00 ± 0.82 | 1.00 ± 0.08 | 1.00 ± 0.24 |
| Vehicle, (n = 12) | 2.98 ± 2.16 | 33.09 ± 13.75 | 1.65 ± 0.44 | 4.77 ± 2.53 |
| DS102 low, (n = 8) | 3.21 ± 1.67 | 43.82 ± 26.19 | 1.48 ± 0.48 | 4.94 ± 2.76 |
| DS102 middle, (n = 8) | 2.66 ± 1.33 | 30.65 ± 16.80 | 1.50 ± 0.44 | 4.21 ± 1.90 |
| DS102 high, (n = 8) | 1.42 ± 0.75 | 16.09 ± 10.16 | 1.00 ± 0.23 | 2.51 ± 1.39 |

α-SMA: The Vehicle group showed a significant increase in the α-SMA mRNA expression level compared with the Sham control group. α-SMA mRNA expression level in the DS102 high group tended to decrease compared with the Vehicle group. There were no significant differences in α-SMA mRNA expression level between the Vehicle group and the DS102 treatment groups.

TIMP-1: The Vehicle group showed a significant increase in the TIMP-1 mRNA expression level compared with the Sham control group. TIMP-1 mRNA expression level in the DS102 high group tended to decrease compared with the Vehicle group. There were no significant differences in TIMP-1 mRNA expression level between the Vehicle group and the DS102 treatment groups.

TGF-β: The Vehicle group showed a significant increase in the TGF-β mRNA expression level compared with the Sham control group. The DS102 high group showed a significant decrease in the TGF-β mRNA expression level compared with the Vehicle group. There were no significant differences in TGF-β mRNA expression level between the Vehicle group and the DS102 treatment groups.

Collagen Type 1: The Vehicle group showed a significant increase in the Collagen Type 1 mRNA expression level compared with the Sham control group. Collagen Type 1 mRNA expression level in the DS102 high group tended to decrease compared with the Vehicle group. There were no significant differences in Collagen Type 1 mRNA expression level between the Vehicle group and the DS102 treatment groups.

1.4 Summary

In this study, biochemical parameters (e.g., ALT and total bilirubin), histological collagen deposition (e.g., fibrosis area) and gene expression levels (e.g., α-SMA, TIMP-1, TGF-β, Collagen Type 1) in the Vehicle group significantly increased compared with the Sham control group. These results suggested that cholestasis and liver fibrosis were established in the Vehicle group.

Treatment with DS102 at the middle dose showed a significant decrease (p<0.05) in fibrosis area compared with the Vehicle group. Treatment with DS102 at the high dose showed a significant decrease (p<0.05) in TGF-β mRNA expression level, and a trend approaching significance (p<0.01) for decrease in fibrosis area, liver weight, liver-to-body weight ratio, α-SMA, TIMP-1 and Collagen Type 1 mRNA expression levels compared with the Vehicle group. These results indicate that DS102 inhibits the production of multiple pro-fibrotic cytokines in the liver, has a suppressive effect on liver fibrosis and has potential as a therapeutic agent for cholestatic liver diseases.

Example 3

Effects of DS102 on TGF-β Receptors, Signaling and Induced Fibrotic Proteins The objective of this study was to examine the effects of 15-HEPE and 15-HEPE EE on the expression of TGF-β receptors, TGF-β induced intracellular signaling and pro-fibrotic epithelial mesenchymal transition proteins.

1.1 Materials and Methods

Cytotoxicity testing: The cytotoxicity of 15-HEPE free acid and ethyl ester was tested in different liver (hepatoma) cell lines to understand the concentration range in the test system.

Transcriptional activity: A promoter (Luciferase) assay was conducted to measure TGFβ-induced transcriptional activation following administration of 15-HEPE.

Sucrose gradient ultracentrifugation and confocal microscopy were used to identify 15-HEPE induced microdomain translocation of TGF-β receptors by sucrose. Sucrose density gradient analysis of TGF-β receptors was conducted in the plasma membranes of Mv1Lu cells (mink lung epithelial cell) treated with 100 μM of 15-HEPE and an equal volume of DMSO (dimethyl sulfoxide) at 37° C. for 0, 1, 4, and 24 hours, and the cell lysates from these treated cells were subjected to sucrose density gradient ultracentrifugation. The sucrose gradient fractions were then analyzed by Western blot analysis using anti-Tβ(type I TGF-β receptor), anti-TβR-II (type II TGF-β receptor), anti-TβR-III (type III TGF-β receptor, betaglycan), anti-EGFR (epidermal growth factor receptor), and anti-caveolin-1 antibodies. The lipid raft/caveolae, and non-lipid raft microdomain localization of TβR-I, TβR-II, TβR-III, EGFR and caveolin-1 in the plasma membrane of untreated cells or cells treated with 15-HEPE were assessed to determine the effects of 15-HEPE on the membrane microdomain localization of the TGF-β receptors.

1.2 Results

The effects of 15-HEPE on TGF-β-induced signaling and cellular responses were determined. To test the effect of 15-HEPE on TGF-β-induced signaling, the activities of 15-HEPE to regulate TGF-β-stimulated Smad2 phosphorylation and nuclear translocation, both of which are key signaling events leading to TGF-β-induced cellular responses, were tested. One important biological activity of TGF-β is transcriptional activation of genes responsible for epithelial-mesenchymal transition (EMT), which is a crucial event in wound healing, tissue fibrosis, and cancer progression. The effect of 15-HEPE on TGFβ-induced epithelial mesenchymal transition related proteins (such as fibronectin, PAI-1, and N-cadherin etc.) expression in HepG2 and LXR cells were assessed. HepG2 cells (human hepatoma cell line) were treated in increasing doses of 15-HEPE stage II in DMEM containing 0.1% of FBS for 1 hour and continually stimulated with or without 200 picomolar (pM) of TGF-β for 48 hours.

Figure 18A:
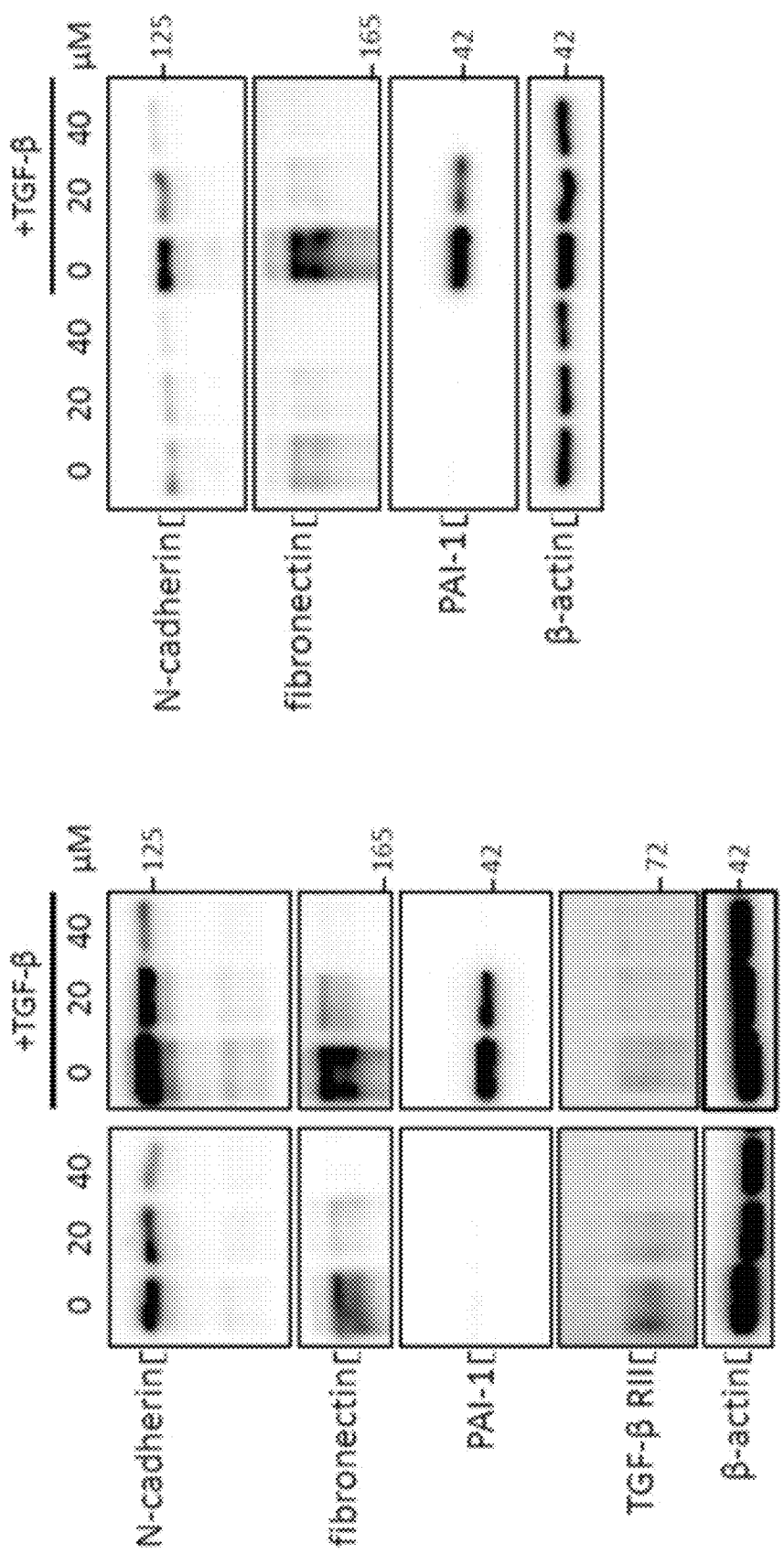
FIGS. 18A and 18B show DS102 (15-HEPE) induced inhibition of TGF-β according the study described in Example 3.
Figure 18B:
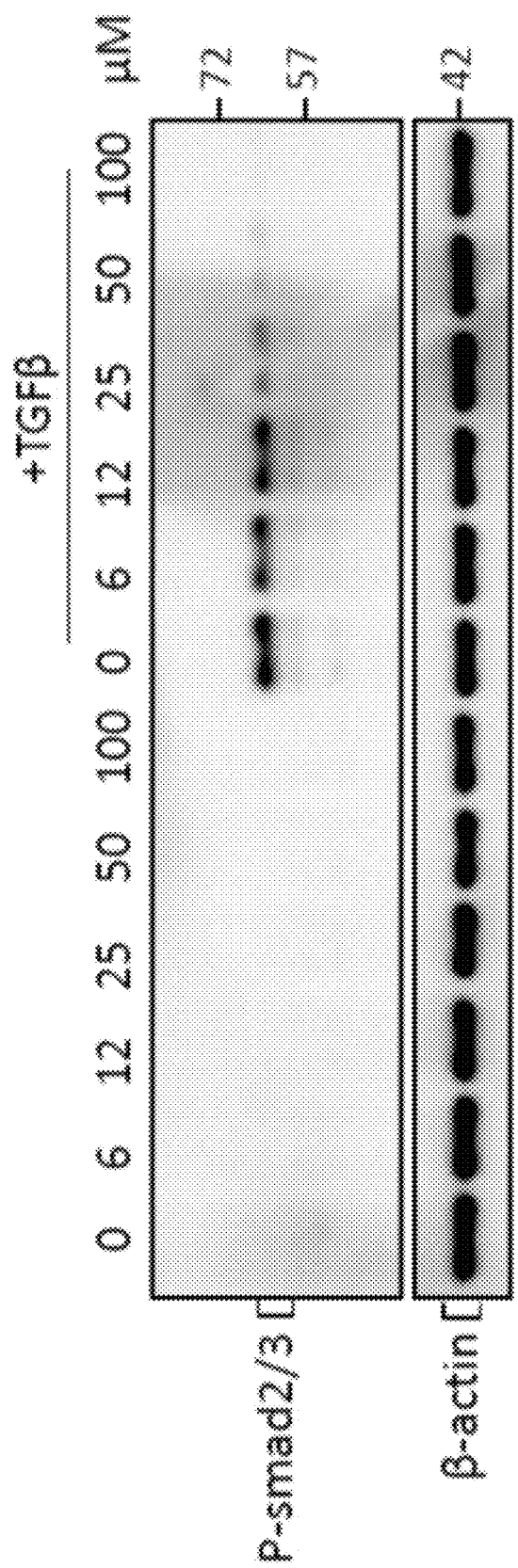

15-HEPE directly inhibited TGF-β signaling as shown in FIGS. 18A and 18B. Specifically, FIG. 18A shows that 15-HEPE induced degradation of type II TGF-β receptor and blocked TGF-β induced epithelial mesenchymal transition (EMT) (i.e., pro-fibrotic) protein production. HepG2 cells (human hepatoma cell line) were treated in increasing doses of 15-HEPE stage II in DMEM containing 0.1% of FBS for 1 hour and continually stimulated with or without 200 picomolar (pM) of TGF-β for 48 hours. The two panels shown in FIG. 18A are two separate experiments run under the same experimental conditions. The results from these separate experiments indicate that 15-HEPE blocks TGF-β induced EMT protein production and induced degradation of type II TGF-β receptor. FIG. 18A also shows the effects of 15-HEPE on plasminogen activator inhibitor-1 (PA-1), a protein induced by TGF-β and associated with increased cardiovascular risk. FIG. 18B shows that 15-HEPE inhibits TGF-β-stimulated intracellular signaling (e.g., SMAD2/3 phosphorylation) in liver stellate cells. The experiment conducted in FIG. 18B included pretreating LX2 cells (human liver stellate cells) with increasing concentrations between 0 μM to 100 μM of DS102 for 24 hours followed by 30 min of TGF-β stimulation. The results of the experiment indicated that 15-HEPE inhibit TGF-β stimulation.

Figure 18C:
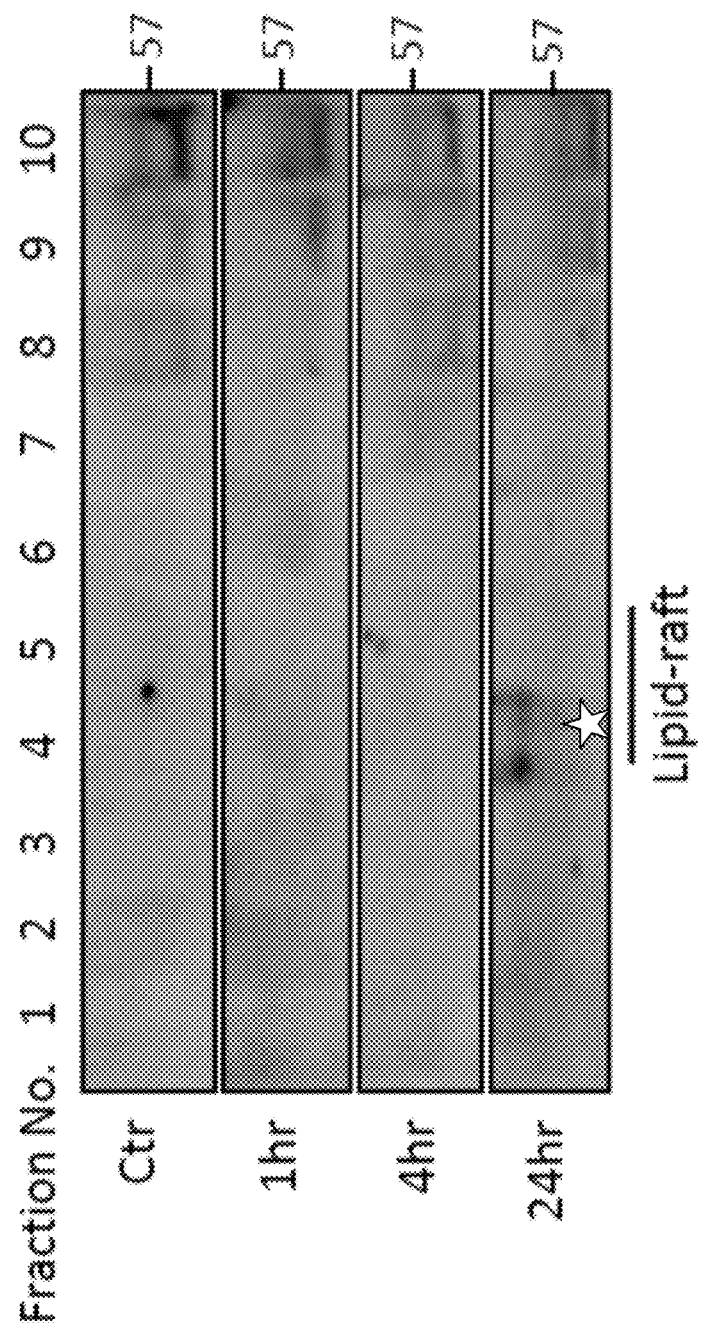
Figure 18D:
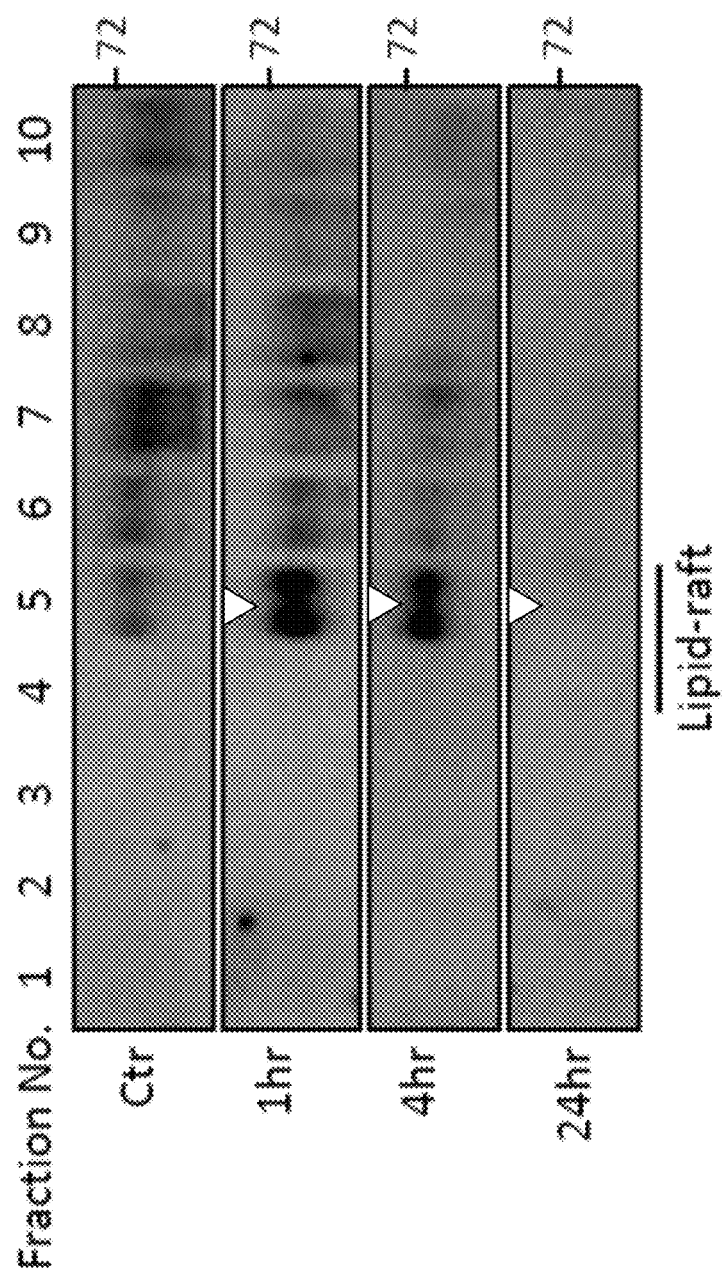
Figure 18E:
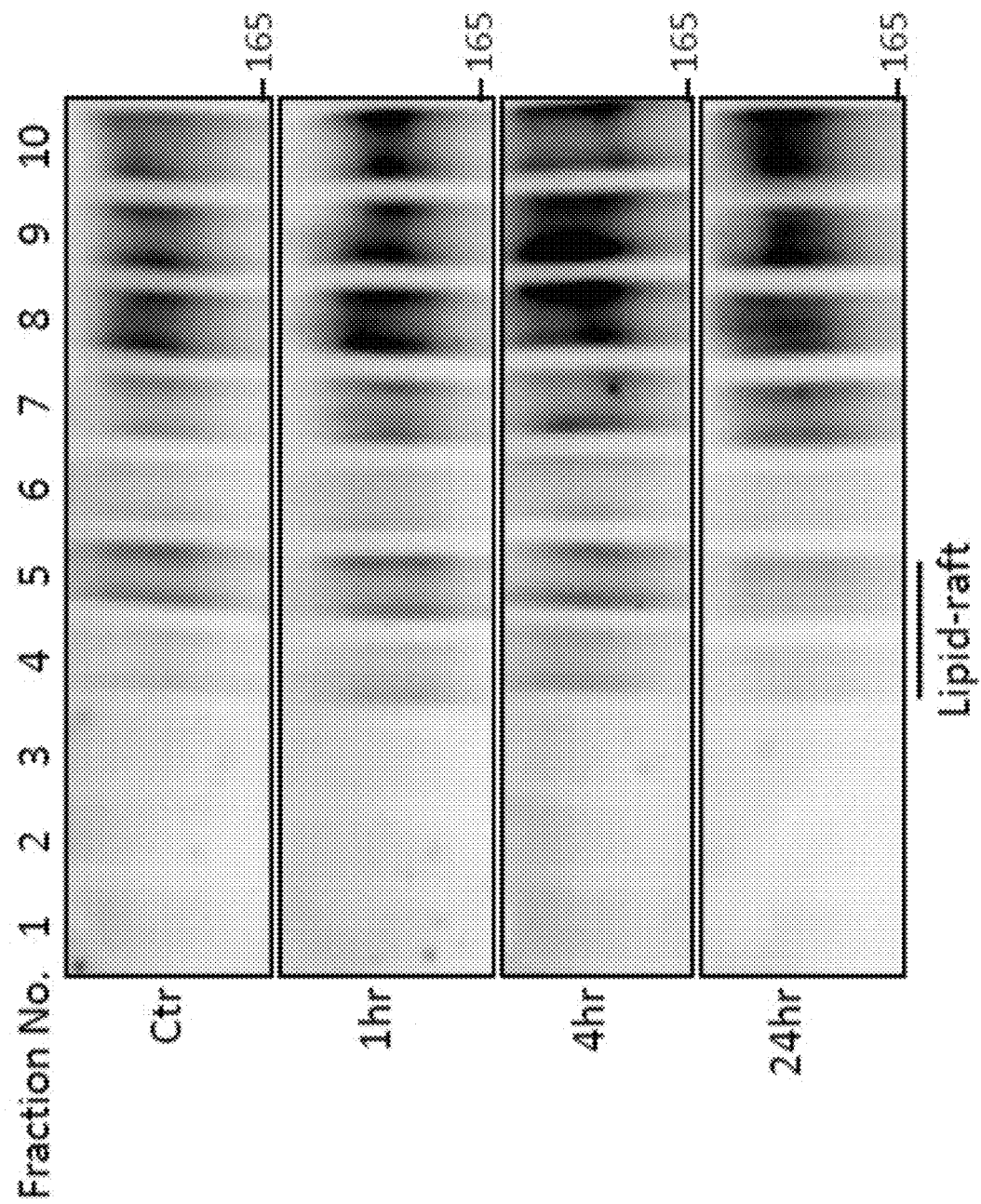
Figure 18F:
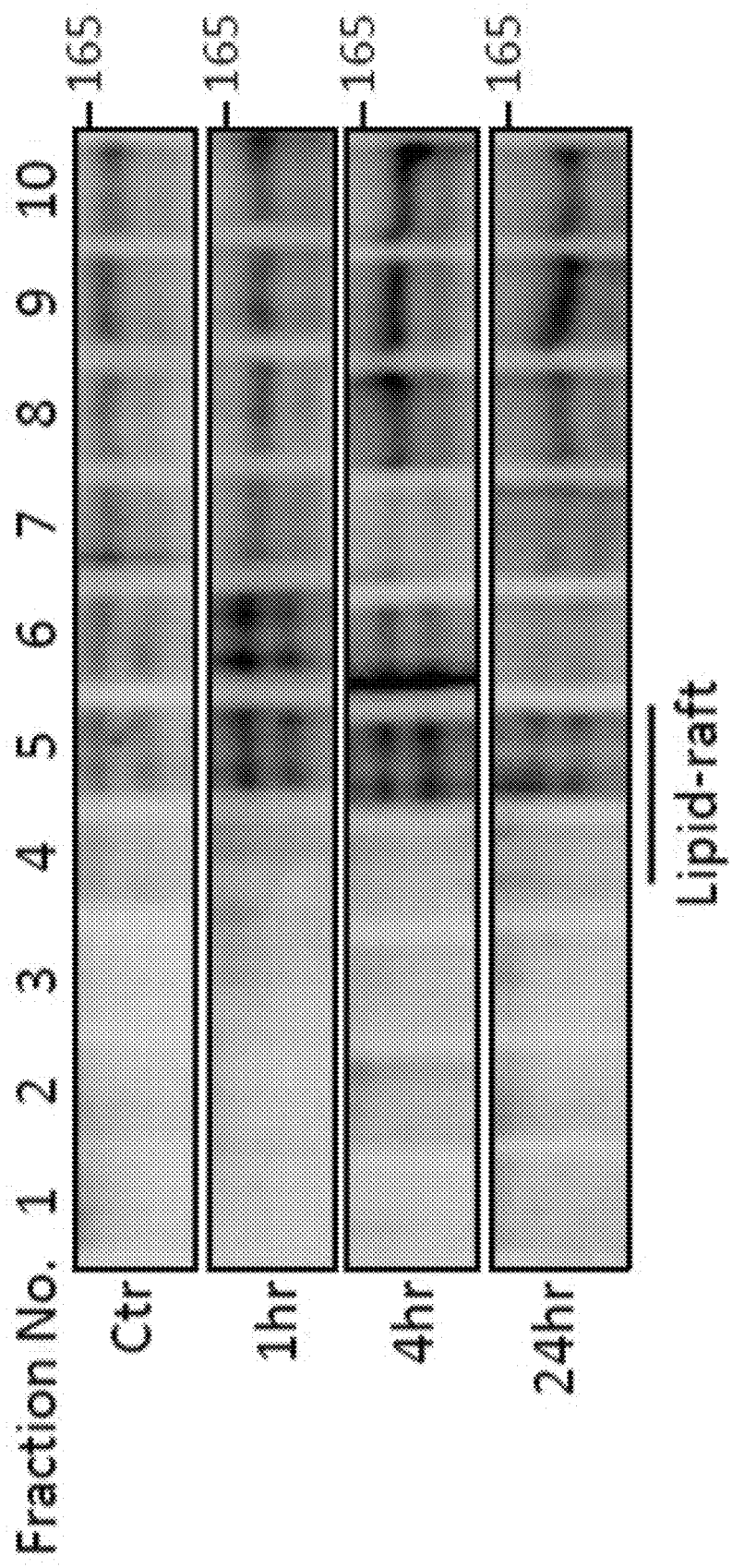
Figure 18G:
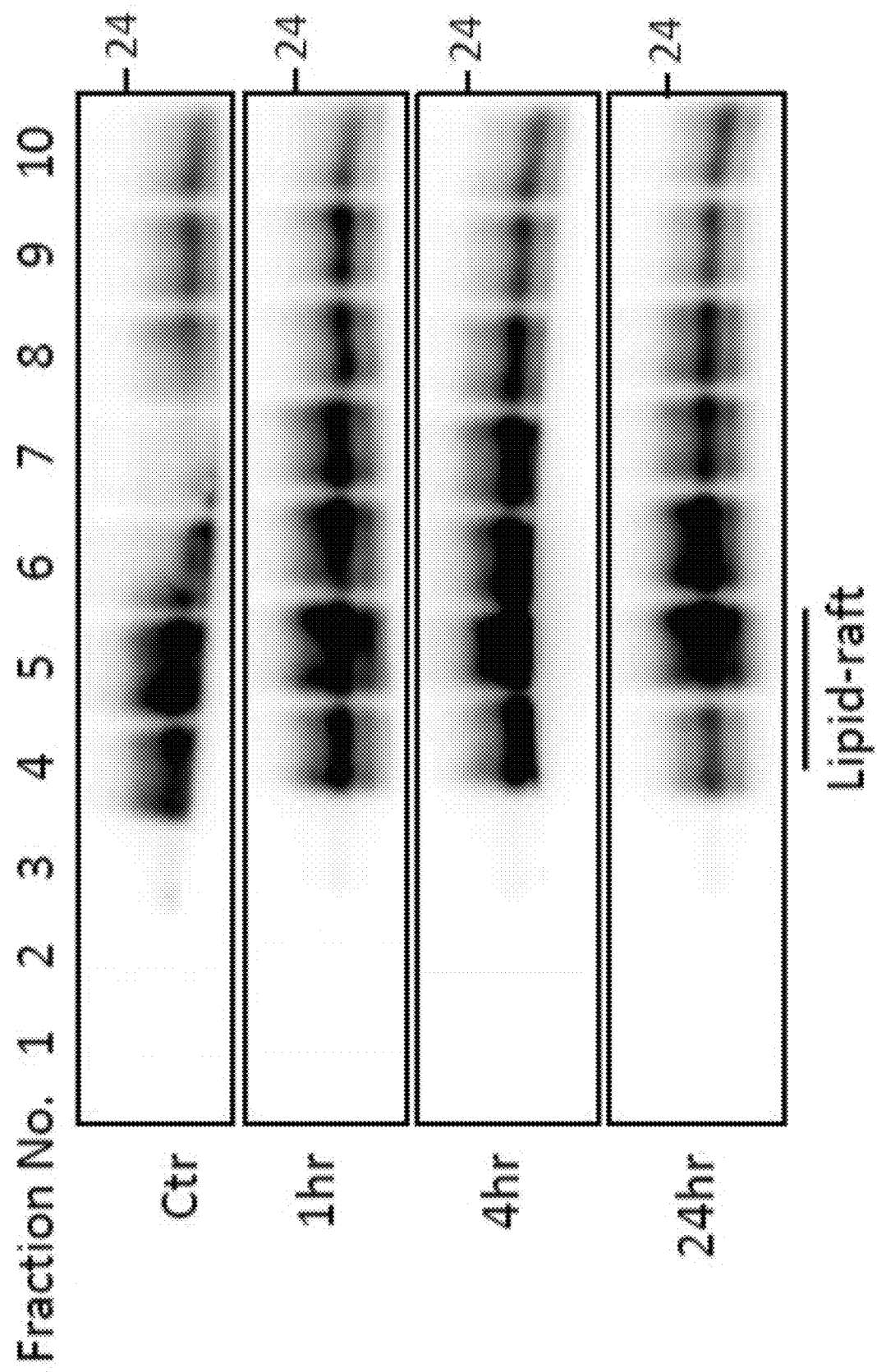

A 15-HEPE sucrose density gradient analysis of TGF-β receptors was conducted in the plasma membranes of mink lung epithelial cell (Mv1 Lu) cells treated with 100 μM of 15-HEPE and an equal volume of dimethyl sulfoxide (DMSO) at 37° C. for 0, 1, 4, and 24 hours, and the cell lysates from these treated cells were subjected to sucrose density gradient ultracentrifugation. The sucrose gradient fractions were then analyzed by Western blot analysis using anti-TβR-I (type I TGF-β receptor—FIG. 18C), anti-TβR-II (type II TGF-β receptor-FIG. 18D), anti-TβR-III (type III TGF-β receptor, betaglycan-FIG. 18E), anti-EGFR (epidermal growth factor receptor-FIG. 18F), and anti-caveolin-1 antibodies (FIG. 18G). Fractions 4 to 5 contained lipid rafts/caveolae whereas fractions 7-10 were non-lipid raft fractions. Treatment with 15-HEPE did not affect the abundance of TβR-I proteins but induced translocation of TβR-I to lipid-raft at 24 hours treatment (FIG. 18C). Stars(*) indicate 15-HEPE increased abundance of TβR-I (24 hours) in the fraction in comparison with that of the control and shorter treatment durations (FIG. 18C). 15-HEPE induced TβR-II translocation from 1 to 4 hours and further induce degradation at 24 hours treatment (FIG. 18D). The triangles (▼) indicate translocation and decreased abundance of TβR-II in the fraction in comparison with control cells (FIG. 18D). In FIGS. 18E, 18F and 18G, 15-HEPE did not change the localization and abundance of TβR-III, EGFR and caveolin-1.

1.3 Summary

Accordingly, taken together, these results demonstrate that 15-HEPE in both the free acid or ethyl ester form, induced translocation and degradation of type II TGF-β receptors, blocked TGF-β induced pro-fibrotic protein production, and inhibited TGF-β induced intracellular signaling (SMAD2/3) in liver stellate cells. As such, 15-HEPE and 15-HEPE EE can directly inhibit TGF-β signaling, results which support the therapeutic potential for 15-HEPE and 15-HEPE EE in treating multiple fibrotic diseases including non-alcoholic steatohepatitis (NASH), other fibrotic diseases, cardiometabolic diseases, as well as multiple indications for cancer.

Example 4

The Efficacy of Orally Administered DS102 in NAFLD Patients

The objective of the study was to assess the safety and efficacy of orally administered DS102 capsules versus placebo in the treatment of adult patients with Non-Alcoholic Fatty Liver Disease (NAFLD).

1.1 Study Endpoints

Primary Endpoints: The primary endpoints for this study included the efficacy as well as the safety for administering DS102. The efficacy was evaluated based on change in serum alanine aminotransferase (ALT) from baseline to Week 16 and change in liver stiffness measured by transient elastography from baseline to Week 16. The safety was evaluated on the number of treatment emergent adverse events (TEAEs) in each treatment group leading to treatment discontinuation.

Secondary Endpoints: The secondary endpoints for this study included a change in any one of the following: serum ALT from baseline to Weeks 2, 4, 8 and 12; aspartate aminotransferase (AST) from baseline to Weeks 2, 4, 8, 12 and 16; AST:ALT ratio from baseline to Weeks 2, 4, 8, 12 and 16; fibrosis-4 (FIB-4) index from baseline to Week 16; NAFLD fibrosis score (NFS) from baseline to week 16; change in hepatic fat measured by controlled attenuation parameter (CAP) from baseline to Week 16; enhanced liver fibrosis (ELF) score from baseline to Week 16; and homeostatic model assessment insulin resistance (HOMA-IR) and adipose tissue insulin resistance (adipo-IR) from baseline to Weeks 2, 4, 8, 12 and 16.

Exploratory analysis: The exploratory analysis included analysis of lipid and metabolic parameters including total cholesterol, triglycerides, very low-density lipoprotein cholesterol (VLDL-C), low density lipoprotein cholesterol (LDL-C), high density lipoprotein cholesterol (HDL-C), non-high-density lipoprotein cholesterol (non-HDL-C), remnant-like particle cholesterol (RLP-C), fasting glucose, insulin, free fatty acids and hemoglobin A1C (HbA1C). Additional exploratory analysis included high throughput lipidomics and proteomics.

1.2 Study Design

This was a randomized, placebo-controlled, double-blind, parallel group, multi-center exploratory phase IIa study to investigate the safety and efficacy of orally administered DS102 capsules and the dose-response relationship between two doses of DS102 and placebo in NAFLD patients aged 18 to 75 years. Three parallel groups of patients with confirmed NAFLD were investigated in this study to compare two different doses of DS102 with placebo over a 16-week treatment period. The study was planned to include 96 evaluable patients with 32 patients randomized per treatment group.

The study consisted of a screening period of 28 days, a 16-week treatment period and a 4 week follow up period. At the screening visit, patients were assessed using the screening examinations. Patients who meet the inclusion criteria and who do not meet the exclusion criteria were enrolled.

Figure 19:
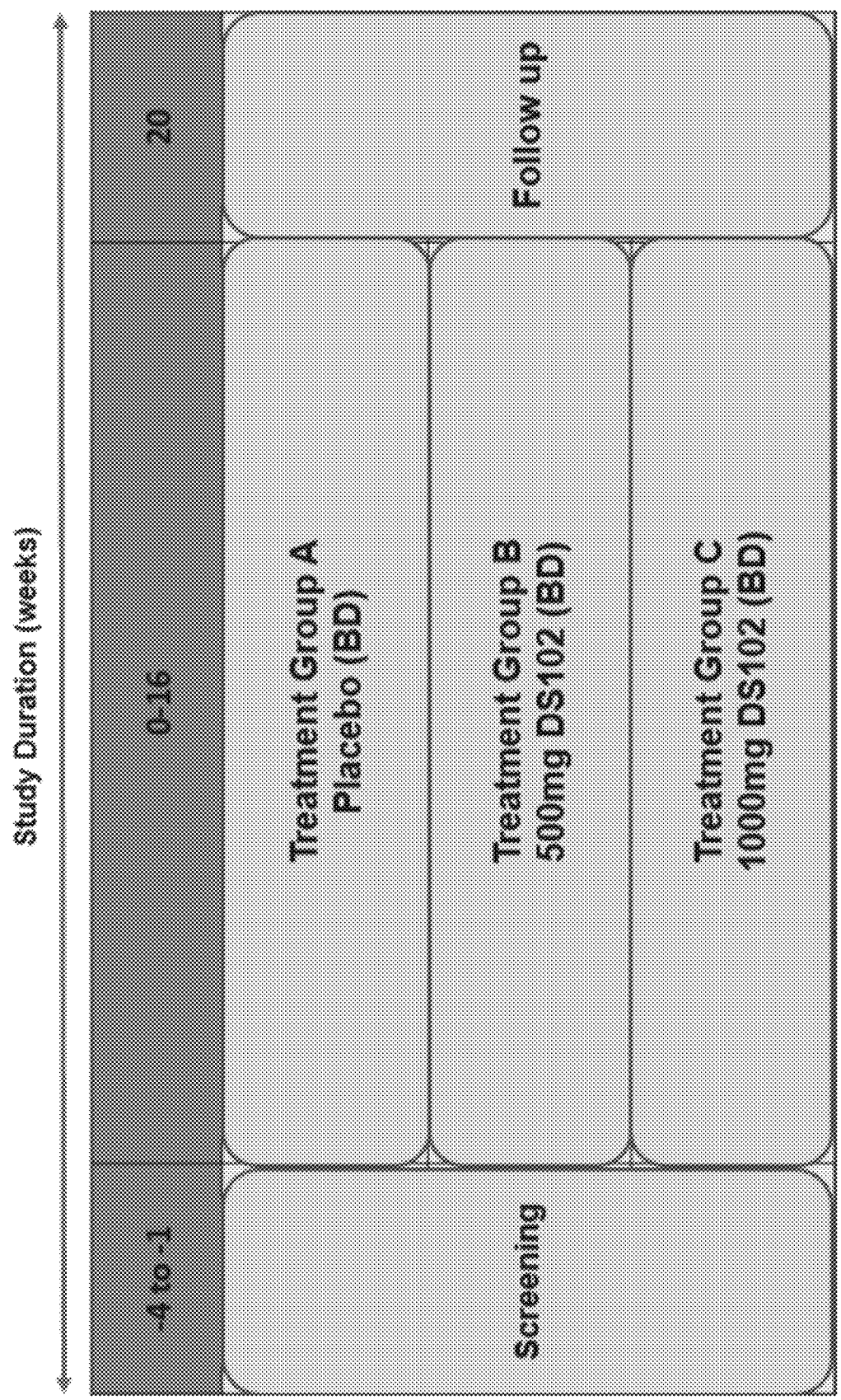
FIG. 19 is a schematic diagram of the study described in Example 4 and its duration.

A schematic diagram of the overall timeframe of the study is provided in FIG. 19. Once patients were enrolled in the study they were restricted from using any other treatment for NAFLD. Any medication (e.g., prescription as well as over the counter (OTC) drugs) or therapeutic intervention deemed necessary for the patient, and which in the opinion of the Investigator do not interfere with the safety and efficacy evaluations, were continued unless they are included in the list of 'Concomitant Medications' provided below.

Before the comparative treatment period commenced, patients returned to the site for a baseline assessment of their disease and eligible patients were randomly allocated to one of the three parallel group treatment regimens in a 1:1:1 randomization:

Treatment group A: 2× Placebo 500 mg capsules orally administered twice a day (4 capsules daily) for 16 weeks.

Treatment group B: 1×DS102 500 mg capsule & 1× Placebo 500 mg capsule orally administered twice a day (4 capsules daily) for 16 weeks.

Treatment group C: 2×DS102 500 mg capsules orally administered twice a day (4 capsules daily) for 16 weeks.

To maintain the double-blind conditions, the DS102 capsule and placebo capsule were identical in appearance.

1.3 Patients and Screening

In order to participate in this study, the patients were required to meet all of the following inclusion criteria and must not have met any of the following exclusion criteria. The inclusion and exclusion criteria were verified at the screening visit (Visit 1) and at the start of treatment/baseline visit (Visit 2).

Inclusion Criteria for this study were as follows:

Patients diagnosed with NAFLD by the presence of hepatic steatosis on imaging or histology in the absence of any secondary causes.

Patients with an ALT 1.5 ULN and <5 ULN on two occasions 7 or more days apart during screening.

Patients with historical liver biopsy showing NASH and/or F1 fibrosis or NFS ≥−1.455 or Fib-4 1.3 or Fibroscan 8 kPa within 3 months of screening.

Patients with a body mass index (BMI) between 25.0 and 40.0 kg/m$^2$. Patients with a history of controlled obesity or controlled diabetes were allowed in the study.

Patients whose pre-study clinical laboratory findings did not interfere with their participation in the study, in the opinion of the Investigator.

Patients aged between 18 and 75 years.

Female patients and male patients with female partners of child bearing potential were required to use adequate contraception or have a sterilized partner for the duration of the study. Adequate contraception is defined as: systemic hormonal contraceptives; intrauterine device or barrier method of contraception in conjunction with spermicide; or agree to sexual abstinence, defined as a patient refraining from heterosexual intercourse during the entire period of risk associated with the study treatments and in line with their preferred and usual lifestyle. Hormonal contraceptives were required to be on a stable dose for at least one month before baseline.

Patients who were able to communicate well with the Investigator, to understand and comply with the requirements of the study and understand and sign the written informed consent.

Exclusion Criteria for this study were as follows:

Patients with an unstable metabolic condition such as weight change >5% in the 3 months prior to inclusion.

Patients with medical/surgical history of gastric bypass surgery, orthotopic liver transplant (OLT) or listed for OLT.

Patients with uncontrolled diabetes mellitus type 2, i.e. HbA1c 9% (75 mmol/mol) at the time of screening.

Patients with decompensated or severe liver disease as evidenced by one or more of the following: confirmed cirrhosis or suspicion of cirrhosis, esophageal varices, ascites, suspicion of portal hypertension, hospitalization for liver disease within 60 days of screening, bilirubin 2×ULN, or ALT or AST 5×ULN. Patients with Gilbert's syndrome were eligible if the conjugated bilirubin was 1.5×ULN.

Patients with inflammatory bowel disease that was either active or requiring medical therapy.

Patients with diagnosed or suspected autoimmune diseases such as systemic lupus erythematosus (SLE) and/or rheumatoid arthritis (RA).

Patients with a history of or active non-liver malignancies other than curatively treated skin cancer (basal cell or squamous cell carcinomas).

Patients with a significant systemic or major illness other than liver disease, including coronary artery disease, cerebrovascular disease, pulmonary disease, renal insufficiency, serious psychiatric disease, respiratory or hypertensive disease, as well as diabetes and arthritis that, in the opinion of the Investigator, precluded the patient from participating in and completing the study.

Patients requiring anti-diabetic treatment (including insulin sensitizing agents), and/or lipid lowering treatment, and who were not on a stable dose for at least 3 months prior to screening were excluded. If patients were insulin dependent this treatment should have commenced at least 3 months prior to screening, however changes in dose were permitted.

Patients with known hypersensitivity to any ingredients of the study treatment.

Patients with a positive test for human immunodeficiency virus (HIV) antibodies, Hepatitis B surface antigen or Hepatitis C antibodies at screening.

Patients with liver disease of other etiologies such as drug-induced, autoimmune hepatitis, primary biliary cholangitis (PBC), primary sclerosing cholangitis (PSC), haemochromatosis, alpha-1 antitrypsin (A1AT) deficiency or Wilson's disease.

Patients with a significant history of drug/solvent abuse, in the opinion of the Investigator.

Patients with a history of alcohol abuse in the opinion of the Investigator, or who drink in excess of 21 units per week (males) or 14 units per week (females), whereby a unit consists of 10 ml or 8 mg of pure alcohol.

Patients who used dietary supplements rich in omega-3 or omega-6 fatty acids in the 4 weeks prior to baseline.

Patients who have participated in any other clinical study with an investigational drug within 3 months before the first day of administration of study treatment.

Patients who are pregnant, planning pregnancy, breast-feeding and/or were unwilling to use adequate contraception during the trial.

Patients, in the opinion of the Investigator, not suitable to participate in the study.

1.4 Study Conduct

During the study, ten visits to the clinic were scheduled after the screening visit: one at the start of the comparative treatment period/baseline (Day 0/Visit 2) and eight in the comparative treatment period (Week2/Visit 3, Week 4/Visit 4, Week 6/Visit 5, Week 8/Visit 6, Week 10/Visit 7, Week 12/Visit 8, Week 14/Visit 9, Week 16/Visit 10). A final safety follow-up visit (Visit 11) was conducted four weeks after Visit 10 or two weeks after the final visit attended if the patient did not complete the study. Table 17 describes the clinical visits for the study.

TABLE 17

Study Flow Chart of The Clinical Visits for The Study

| Study Procedure | Screening/ Visit 1 Day -28 to -1 | Baseline/ Visit 2 Day 0 | Visit 3/ Week 2 Day 14 | Visit 4/ Week 4 Day 28 | Visit 5/ Week 6 Day 42 | Visit 6/ Week 8 Day 56 | Visit 7/ Week 10 Day 70 | Visit 8/ Week 12 Day 84 | Visit 9/ Week 14 Day 98 | EOT/ Visit 10/ Week 16 Day 112 | Follow Up/ Visit 11/ Week 20 Day 140 |
|---|---|---|---|---|---|---|---|---|---|---|---|
| Visit Window | | | +/-2 days | +/-2 days | +/-2 days | +/-2 days | +/-2 days | +/-2 days | +/-2 days | +/-2 days | +/-4 days |
| Informed consent | X | | | | | | | | | | |
| Inclusion Exclusion | X | X | | | | | | | | | |
| Demography | X | | | | | | | | | | |
| Medical history | X | X | | | | | | | | | |
| Physical examination | X | X | X | X | | X | | X | | X | X |
| 12-lead ECG | X | X | | | | | | | | X | |
| Plasma PK sampling [1] | | X | X | X | | X | | X | | X | X |
| Vital signs | X | X | X | X | | X | | X | | X | X |
| Clinical laboratory tests [2] | X | X | | X | | X | | X | | X | X |
| Lipid Profile [3] | | X | | | | X | | | | X | |
| Urinalysis | | X | | | | | | | | X | |
| Virology | X | | | | | | | | | | |
| Pregnancy test [4] | X | X | | X | | X | | X | | X | X |
| ALT, AST [5] | XX | X | X | X | | X | | X | | X | X |
| HOMA-IR/Adipo-IR | | X | X | X | | X | | X | | X | X |
| ELF | | X | | | | | | | | X | |
| Liver stiffness and CAP | | X | | | | | | | | X | |
| FIB-4 | | X | | | | | | | | X | |
| NFS [including BMI] | | X | | | | | | | | X | |
| Biomarkers Blood Sample | | X | | | | X | | | | X | X |
| Exploratory Blood Sample | | X | | | | | | | | X | |
| Patient Randomisation | | X | | | | | | | | | |
| IMP/Placebo Dispensing | | X | X | X | X | X | X | X | X | | |
| Study drug/placebo administration | | X----------------------------------------------------------X | | | | | | | | | |
| IMP Accountability/ Diary Card review | | X | X | X | X | X | X | X | X | X | |
| AE assessment | | X--------------------------------------------------------------------X | | | | | | | | | |
| Concomitant medication assessment | X | | | | | | X------------------------------------------------X | | | | |

[1] Pharmacokinetics Trough only. Sample was taken pre-dose.
[2] Includes biochemistry, haematology and coagulation tests. This was taken fasting (Minimum of 8 hours).
[3] Lipid Profile was taken fasting (Minimum of 8 hours).
[4] Female Patients of child bearing potential only.
[5] ALT to be assessed on two occasions during screening 7 or more days apart.

Screening Visit (Visit 1): At the screening visiting the following

Screening Visit (Visit 1): Once informed consent was obtained, patients were assigned a Patent Screen Number. Ideally the patient was fasted. The following screening assessments/sample collections were performed: verification of inclusion/exclusion criteria; demographic data; medical history; physical examination; 12-lead electrocardiogram (ECG); Vital signs (blood pressures, heart rate and body temperature); samples for clinical laboratory safety tests (hematology, serum biochemistry, and coagulation tests); virology; pregnancy test (for female patients of child-bearing potential); ALT, AST tests (ALT measured on two occasions during screening); and concomitant medication assessment. Unscheduled visits occurred when a patient needed to make a visit in between the scheduled visit dates due to an adverse event (AE), difficulty complying with the study protocol requirements, or a significant change in their disease state. All procedures that were medically necessary were followed. If qualified, before leaving the clinic the patient was instructed not to have any breakfast before the next visit to allow a minimum fasting period of 8 hours.

Treatment Period: Following completion of a successful screening visit, patients began the comparative treatment period (16 weeks). At the start of the comparative treatment period, after confirmation of continued eligibility, patients were randomly assigned to one of the three treatment regimens. Patients took the allocated investigation medicinal product (IMP) of a DS102 capsule or placebo capsule twice-daily throughout the comparative treatment period. Each self-administration of IMP was recorded in a patient diary card. Patients were instructed to take DS102 in the morning and in the evening with or after food (except on the mornings of clinic visits 3, 4, 6, 8 and 10 when patients were instructed to abstain from taking DS102 prior to the visit and to take DS102 as soon as possible after the clinic visit). At the start of the baseline (Visit 2), Week 2 (Visit 3), Week 4 (Visit 4), Week 8 (Visit 6), Week 12 (Visit 8), Week 16 (Visit 10), and Week 20 (Visit 11), the patient was asked if they had fasted for a minimum of 8 hours prior to the visit. If this was not the case, the duration of fasting period was documented, and the patient reinstructed about the duration of the fasting period. The patient was then provided with a light breakfast (e.g. tea or orange juice and toast). At baseline (Visit 2), Week 8 (Visit 8), and Week 16 (Visit 10), the blood sampling assessment was carried out prior to the patient receiving the light breakfast. Unscheduled visits occurred when a patient needed to make a visit in between the scheduled visit dates due to an adverse event (AE), difficulty complying with the study protocol requirements, or a significant change in their disease state. All procedures that were medically necessary were followed. Patients who discontinued the study early had study procedures scheduled for Visit 10 performed as soon as possible after patient withdrawal so that all study-related information could be recorded. At the discretion of Investigator, urine DOA and alcohol breath tests were performed at any time during the conduct of the trial.

Baseline (Visit 2): Patients attended the investigational site at Visit 2. Blood sampling was the first assessment carried out. After the blood sampling, the following assessments were performed: verification of inclusion/exclusion criteria; medical history; physical examination; 12-lead ECG; pharmacokinetic sampling; vital signs (blood pressures, heart rate and body temperature); samples for clinical laboratory safety tests (haematology, serum biochemistry, and coagulation tests); lipid profile; urinalysis; pregnancy test (for female patients of child-bearing potential); ALT, AST tests; HOMA-IR/Adipo-IR; ELF; liver stiffness and CAP; FIB-4; NFS (including BMI); biomarkers blood sample; exploratory blood sample; patient randomization; study drug/placebo administration; AE assessment; and concomitant medication assessment. If all study entry criteria were satisfied the Investigator randomized the patient and provided the patient with the designated IMP or placebo from one of the patient treatment packs. The first dose of IMP or placebo was administered at site once all baseline assessments had been completed. The patient took their second dose of IMP or placebo in the evening of Day 0. The capsules were then administered twice-daily. Patients did take IMP or placebo on the morning of their return site visit (Visit 3). Before leaving the clinic, the patient was instructed not to have any breakfast before the next visit to allow a minimum fasting period of 8 hours.

Week 2 (Visit 3): Patients returned to the investigational site at Visit 3. Patients did not take IMP or placebo on the morning of Visit 3. The following assessments were performed: physical examination; pharmacokinetic sampling; vital signs (e.g., blood pressures, heart rate and body temperature); ALT, AST tests; HOMA-IR/Adipo-IR; AE assessment; and concomitant medication assessment. The IMP or placebo was returned, and further IMP or placebo was supplied to the patient. The patient took their next dose of IMP or placebo as soon as all visit assessments had been completed. The capsules continued to be administered twice-daily. On completion of this visit, patients were advised that they were required to return to the investigational site in two weeks at Visit 4. Patients did not take IMP or placebo on the morning of their return site visit (Visit 4). Before leaving the clinic, the patient was instructed not to have any breakfast before the next visit to allow a minimum fasting period of 8 hours.

Week 4 (Visit 4): Patients returned to the investigational site at Visit 4. Patients did not take IMP or placebo on the morning of Visit 4. The following assessments were performed: physical examination; pharmacokinetic sampling; vital signs (blood pressures, heart rate and body temperature); samples for clinical laboratory safety tests (haematology, serum biochemistry and coagulation tests); pregnancy test (for female patients of child-bearing potential); ALT, AST tests; HOMA-IR/Adipo-IR; AE assessment; and concomitant medication assessment. The IMP or placebo was returned, and further IMP or placebo was supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 5. Patients did not take IMP or placebo on the morning of their return site visit (Visit 5).

Week 6 (Visit 5): Patients returned to the investigational site at Visit 5. The following assessments were performed: AE assessment and Concomitant medication assessment. The IMP or placebo was returned and further IMP or was supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 6. Patients did not take IMP or placebo on the morning of their return site visit (Visit 6). Before leaving the clinic, the patient was instructed not to have any breakfast before the next visit to allow a minimum fasting period of 8 hours.

Week 8 (Visit 6): Patients returned to the investigational site at Visit 6. Patients did not take IMP or placebo on the morning of Visit 6. Blood sampling was the first assessment carried out. After the blood sampling, the following assessments were performed: physical examination; pharmacokinetic sampling; vital signs (blood pressures, heart rate and body temperature); samples for clinical laboratory safety tests (haematology, serum biochemistry and coagulation tests); lipid profile; pregnancy test (for female patients of child-bearing potential); ALT, AST tests; HOMA-IR/Adipo-IR; biomarker blood samples; ae assessment; and concomitant medication assessment. The IMP or placebo were returned and further IMP or supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 7. Patients did take IMP or placebo on the morning of their return site visit (Visit 7).

Week 10 (Visit 7): Patients returned to the investigational site at Visit 7. The following assessments were performed: AE assessment and concomitant medication assessment. The IMP or placebo were returned, and further IMP or placebo was supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 8. Patients did not take IMP or placebo on the morning of their return site visit (Visit 8). Before leaving the clinic, the patient was instructed not to have any breakfast before the next visit to allow a minimum fasting period of 8 hours.

Week 12 (Visit 8): Patients returned to the investigational site at Visit 8. Patients did not take IMP or placebo on the morning of Visit 8. The following assessments were performed: physical examination; pharmacokinetic sampling; vital signs (blood pressures, heart rate and body temperature); samples for clinical laboratory safety tests (haematology, serum biochemistry, and coagulation tests); pregnancy test (for female patients of child-bearing potential); ALT, AST tests; HOMA-IR/Adipo-IR; AE assessment; and concomitant medication assessment. The IMP or placebo was returned, and further IMP or placebo supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 9. Patients did not take IMP or placebo on the morning of their return site visit (Visit 9).

Week 14 (Visit 9): Patients returned to the investigational site at Visit 9. The following assessments were performed: AE assessment and concomitant medication assessment. The IMP or placebo were returned, and further IMP or placebo supplied to the patient. The patient took their next dose of IMP or placebo as soon as all visit assessments had been completed. The capsule continued to be administered twice-daily. On completion of this visit, patients were advised that they were required to return to the investigational site in two weeks at Visit 10 Patients should not take IMP or placebo on the morning of their return site visit (Visit 10). Before leaving the clinic, the patient was instructed not to have any breakfast before the next visit to allow a minimum fasting period of 8 hours.

Week 16 (Visit 10) or Early Withdrawal: Patients returned to the investigational site at Visit 10. Patients did not take IMP or placebo on the morning of Visit 10. Blood sampling was the first assessment carried out. After the blood sampling, the following assessments were performed: physical examination; 12-lead ECG; pharmacokinetic sampling; vital signs (blood pressures, heart rate and body temperature); samples for clinical laboratory safety tests (haematology, serum biochemistry, and coagulation tests); urinalysis; lipid profile; pregnancy test (for female patients of child-bearing potential); ALT, AST tests; HOMA-IR/Adipo-IR; ELF; liver stiffness and CAP; FIB-4; NFS [including BMI]; Biomarker blood samples; exploratory blood sample; AE assessment; and concomitant medication assessment. The IMP or placebo were returned. No further IMP or placebo blister packs or patient diary cards were issued. Following completion of the study assessments at this visit, there were continued study restrictions. On completion of this visit, patients were advised that they were required to return to the investigational site in four weeks at Visit 11 to assess any AEs since this visit and conduct safety and efficacy assessments. Before leaving the clinic, the patient was instructed not to have any breakfast before the next visit to allow a minimum fasting period of 8 hours.

Follow Up Visit (Week 20/Visit 11): Four weeks after Visit 10 (or 2 weeks after early withdrawal visit), patients returned to the investigational site. The following assessments were carried out: physical examination; pharmacokinetic sampling; vital signs (blood pressures, heart rate and body temperature); samples for clinical laboratory safety tests (haematology, serum biochemistry and coagulation tests); pregnancy test (for female patients of child-bearing potential); ALT, AST tests; HOMA-IR/Adipo-IR; biomarkers; AE assessment; and concomitant medication assessment.

1.5 Assessments

Efficacy assessments included: ALT, AST, ALT:AST ratio; HOMA-IR/Adipo-IR; ELF; liver stiffness and CAP; FIB-4 index; and NFS. A detailed description of each is provided below.

ALT, AST, ALT:AST ratio: Increased liver enzymes (ALT and AST) are a marker of liver injury and were assessed at Visit 1/Screening (on two occasions during screening 7 or more days apart), Visit 2/Baseline, Visit 3/Week 2, Visit 4/Week 4, Visit 6/Week 8, Visit 8/Week 12, Visit 10/Week16 and Follow up Visit 11/Week 20.

HOMA-IR/Adipo-IR: HOMA-IR/Adipo-IR levels are a method of measuring insulin resistance. HOMA-IR is calculated by multiplying fasting plasma insulin (FPI) by fasting plasma glucose (FPG), then dividing by the constant 405. Adipo-IR is calculated by multiplying fasting non-esterified fatty acids (NEFA)×fasting insulin. Blood samples were taken to assess HOMA-IR and Adipo-IR at Visit 2/Baseline, Visit 3/Week 2, Visit 4/Week 4, Visit 6/Week 8, Visit 8/Week 12, Visit 10/Week16 and Follow up Visit 11/Week 20. All subjects were required to have been fasted for a minimum of 8 hours prior to blood sampling. If subjects had not fasted for a minimum of 8 hours, the duration of fasting time was recorded, and subjects encouraged to fast appropriately for the next clinical visit.

ELF: An ELF score is an extracellular matrix marker set consisting of tissue inhibitor of metalloproteinases 1 (TIMP-1), amino-terminal propeptide of type III procollagen (PII-INP) and hyaluronic acid (HA). Blood samples were taken to perform this assessment at baseline (Visit 2) and Week 16 (Visit 10).

Liver stiffness and CAP: Liver stiffness and CAP were assessed using transient elastography (e.g., FibroScan® 502 Touch model or equivalent). Patients were fasted and scanned at the same time of the day, if possible, for baseline (Week 0) and Visit 10 (Week 16). For this assessment the following conditions were met: patients were lying in dorsal decubitus position with the right arm in maximal abduction behind the head, in a similar position to that used for liver biopsy (LB); the tip of the transducer was placed on the skin between the ribs over the right lobe of the liver (the physician took the measurements with the probe placed in the intercostal space); during the FibroScan® examination the choice of M+ or XL+ probe was determined by the Automatic Probe Selection tool (APS) (If, the APS tool advises to use the "XL+probe" or "switch" continuously between "M+ and XL+ probe", only the XL+ probe was used); and the operator, assisted by an ultrasonic time motion image, located a portion of the liver which is free of large vascular structures (the depth of measurement was between 35-75 mm for the XL+ probe and 25-65 mm for the M+ probe and the explored volume will be 3 $cm^3$). For each patient, the operator performed an examination including at least 10 valid measurements or a maximum of 20 attempts, with the XL+ or M+ probe, at the same spot. The entire examination lasted no more than 10-15 minutes. The final stiffness and CAP values was recorded as median values of valid measurements.

FIB-4 Index: FIB-4 index is based on age, platelet count, ALT level, and AST level and was assessed at Baseline (Visit 2) and Week 16 (Visit 10). FIB-4 score is determined as shown by the equation below.

$$FIB-4 = \frac{\text{Age (years)} \times AST\ (U/L)}{\text{Platelet count } (10^9/L) \times \sqrt{ALT\ (U/L)}}$$

NFS: The NFS is based on age, hyperglycemia, BMI, platelet count, albumin level, and AST/ALT ratio. NAFLD fibrosis score=−1.675+0.037×age (years)+0.094×BMI (kg/m2)+1.13×IFG/diabetes (yes=1, no=0)+0.99×AST/ALT ratio−0.013×platelet (×109/l)−0.66×albumin (g/dl). NFS was assessed at Baseline (Visit 2) and Week 16 (Visit 10).

Safety Assessments included the following: medical history; physical examination; ECG; vital signs; clinical laboratory safety tests (e.g., hematology, serum biochemistry, coagulation, lipid profile, and urinalysis); virology; pregnancy test; blood sampling; pharmacokinetic sampling; exploratory blood collection; biomarker blood collection; urine DOA and alcohol breath test; adverse event assessment; concomitant medication; bioanalysis; sample, storage, handling; and shipping; and restrictions. A detailed description of each is provided below.

Medical History: A complete review of the patient's medical history was undertaken by the Investigator or designee at the Screening Visit (Visit 1) and Baseline (Visit 2) to ensure that no exclusion criteria had been met. Any concomitant disease, whether considered relevant for the study or not by the Investigator, was reported. The date of diagnosis or duration of the condition was noted where possible.

Physical Examination: A physical examination (including height and weight) was performed by the Investigator as per the study flow chart in Table 19 at Visit 1/Screening, Visit 2/Baseline, Visit 3/Week 2, Visit 4/Week 4, Visit 6/Week 8, Visit 8/Week 12, Visit 10/Week16 and Follow up Visit 11/Week 20 in accordance with local practices. This examination was completed in full at baseline and symptom-directed thereafter (i.e., a standard panel of body systems was not assessed unless indicated by patient). For example, should the patient report to the Investigator the presence of 'rash' then the skin was evaluated. It was not required that additional body systems were assessed unless clinically warranted. Any abnormal results were recorded. Changes in findings of the physical examination compared with the baseline examination were recorded as an AE.

ECG: A 12-lead ECG 10 mm/1 my, 25 mm/s with a 10 second lead II rhythm strip was recorded at each time point. ECGs were recorded using the GE Mac 1200 or equivalent model. Patients were rested quietly in a fully supine position for 5 minutes before the ECG was taken. Recordings were made on the days indicated in Study Flow Chart in Table 19 at Visit 1/Screening, Visit 2/Baseline and Visit 10/Week 16.

Vital Signs: Vital signs measurements were performed as per the Study Flow Chart in Table 19 at Visit 1/Screening, Visit 2/Baseline, Visit 3/Week 2, Visit 4/Week 4, Visit 6/Week 8, Visit 8/Week 12, Visit 10/Week16 and Follow up Visit 11/Week 20. Vital signs measurements were performed before any blood samples were taken. All new findings or changes to previous findings considered clinically significant were recorded as an AE if the finding was made after the patient had signed. Vital sign measurements included: blood pressure performed as supine (e.g., after at least 5 minutes of rest) systolic and diastolic blood pressure (in mmHg); heart rate taken at rest in beats per minute (bpm), and temperature taken as per clinical practice.

Clinical Laboratory Safety Tests: Safety tests were performed for hematology, serum biochemistry, coagulation, lipid profile, and urinalysis: Blood and urine samples were taken as per the Study Flow Chart in Table 19 for routine hematology, serum biochemistry, coagulation and urinalysis tests, along with a Lipid Profile. All samples were analyzed in the central laboratory. All subjects were fasted for a minimum of 8 hours prior to blood sampling. If subjects had not fasted for a minimum of 8 hours, the duration of fasting time was recorded, and subjects encouraged to fast appropriately for the next clinical visit.

Hematology: Full blood count to include red cell count, hemoglobin, hematocrit, white cell count, differential white cell count, platelet count and reticulocyte count.

Serum biochemistry: Urea (blood urea nitrogen; BUN), creatinine, uric acid, total bilirubin, Indirect and Direct Bilirubin, sodium, bicarbonate potassium, phosphorus, calcium chloride, alkaline phosphatase (ALP), aspartate aminotransferase (AST), alanine aminotransferase (ALT), ALT/AST ratio, lactate dehydrogenase (LDH), creatine phosphokinase (CPK), albumin, total protein, cholesterol, triglycerides, glucose, C-reactive protein (CRP).

Coagulation: prothrombin time (PT), international normalized ratio (INR) and activated partial prothrombin time (APTT).

Lipid Profile: LDL, HDL, and VLDL-C.

Urinalysis: pH, protein, glucose, blood, ketones, leukocytes, leukocyte esterase, bilirubin, specific gravity, urobilinogen and nitrate. Reflex micro if blood, protein, leukocyte esterase or nitrate/nitrite are present.

Virology: A blood sample was taken to perform virology tests including HIV, Hep C and Hep B as detailed in the Study Flow Chart in Table 19.

Pregnancy Test: For female patients of childbearing potential, a pregnancy test was carried out as per the Study Flow Chart of Table 19 at Visit 1/Screening, Visit 2/Baseline, Visit 4/Week 4, Visit 6/Week 8, Visit 8/Week 12, Visit 10/Week 16 and Visit 11/Week 20.

Blood Sampling: Blood samples were obtained, and laboratory results reviewed for clinically significant values by each Investigator following sample analysis and verification. Additional blood may have been required for repeats of safety laboratory test.

Pharmacokinetic (PK) sampling: Blood samples for PK analysis were collected via direct venipuncture as per the Study Flow Chart in Table 19 at Visit 2/Baseline, Visit 3/Week 2, Visit 4/Week 4, Visit 6/Week 8, Visit 8/Week 12, Visit 10/Week16 and Follow up Visit 11/Week 20. A 1 mL blood sample was taken at each timepoint. Following centrifugation, plasma samples were split in two and a back-up sample kept at the central laboratory until bioanalytical assays had been completed.

Exploratory Blood Collection: Blood was collected as per the Study Flow Chart in Table 19 at baseline (Week 0) and Visit 10/Week 16 and stored for potential gene array analysis or additional exploratory testing at a later date.

Biomarker Blood Collection: Blood was collected as per the Study Flow Chart in Table 19 at baseline (Week 0), Visit 6/Week 8, Visit 10/Week 16 and Follow up Visit 11/Week 20 and was stored for potential biomarker analysis.

Urine DOA and Alcohol Breath Test: As clinically appropriate at the discretion of the Investigator, an alcohol breath test was performed, and a urine sample taken from patients at any time during the conduct of the trial and testing done to detect the following: amphetamine, barbiturate, benzodiazepine, cocaine, cannabinoids, and opiates.

Concomitant Medication: Patients were on a stable dose of any concomitant medications for at least 3 months prior to screening and that dose should have remained stable for the entire study duration. If patients were insulin dependent this treatment should have commenced at least 3 months prior to screening, however changes in dose were permitted.

Restrictions: The study include diet, alcohol, caffeine, and physical activity restrictions. For diet, patients avoided both during the study and for 4 weeks prior to baseline, ingesting food supplements rich in omega-3 or omega-6 fatty acids (e.g., cod liver oil capsules). For alcohol, patient avoided alcohol consumption in excess of 21 units per week (males) or 14 units per week (females), whereby a unit consists of 10 ml or 8 mg of pure alcohol. There were no caffeine restrictions either prior to or during the study. For physical activity, patients were to avoid exercise and strenuous physical activity for at least 3 to 4 hours before the safety laboratory test (e.g., biochemistry).

1.6 Investigational Drug

DS102 capsules were white, opaque hard-shelled capsules (size 0) containing 500 mg of 15-HEPE ethyl ester (EE) with 5% w/w of colloidal silicon dioxide as viscosity modifier.

DS102 placebo (paraffin oil) were white, opaque hard-shelled capsule (size 0) containing equivalent fill weight of liquid paraffin with 1% w/w of colloidal silicon dioxide as viscosity modifier.

DS102 and Placebo capsules were stored at 2-8° C. in a secure area (e.g. a locked cabinet or drug storage room), protected from unintended use. Labels were blinded to the dose and contained the randomization number.

Dosage and administration: This study involved a comparison of DS102 with placebo, administered orally twice daily for a total duration of 16 weeks. The last study drug administration occurred on the day preceding Week 16 visit/Early Termination (ET) visit. Patients were required to take the capsules with or after food. Medication(s) for other conditions that were permitted in the study were taken as usual. The walleted blister packs consisted of 7 days of 4 capsules and lastly, the patients took the assigned medication for 16 consecutive weeks.

1.7 Adverse Events and Serious Adverse Events

Adverse events (AEs) and serious adverse events (SAEs) for this study were defined as follows.

Adverse Events (AE): Any undesirable experience occurring to a patient who has taken their first dose of the study drug, whether or not considered related to the investigational IMP(s). AEs were recorded in the case report form, defining relationship to IMP and severity.

Serious Adverse Events (SAE): If a patient experienced a serious adverse event after the first dose of the study drug, the event was recorded as a SAE. A SAE is characterized as an untoward medical occurrence at any dose to include any of the following: results in death, is life threatening, requires in-patient hospitalization or prolongation of existing hospitalization, or results in persistent or significant disability/incapacity. The term "life-threatening" refers to an event in which the patient was at risk of death at the time of the event. It does not refer to an event which hypothetically might have caused death if it were more severe. Examples of important, but not life threatening, events included intensive treatment in an emergency room, allergic bronchospasm, blood dyscrasias or convulsions that did not result in hospitalization, or the development of drug dependency or drug abuse.

Unexpected Adverse Event (UAE): An experience not previously reported in the Investigator's Brochure or similar product information sheet such as the Summary of Products Characteristics (SPC).

The intensity of an AE is an estimate of the relative severity of the event made by the Investigator based on his or her clinical experience. The following definitions were used to rate the severity of an AE:

Mild: The adverse event was transient and easily tolerated.

Moderate: The adverse event caused the patient discomfort and interrupted the patient's usual activities.

Severe: The adverse event caused considerable interference with the patient's usual activities and may have been incapacitating or life-threatening.

Causality of the AE to experimental treatment was also established by taking into account the patient's history, most recent physical examination findings, and concomitant medications. The following definitions were used to determine causality of an AE:

Not related: temporal relationship of the onset of the AE, relative to the experimental treatment was not reasonable or another cause could explain the occurrence of the AE.

Related: temporal relationship of the onset of the AE, relative to the experimental treatment was reasonable, followed a known response pattern to the treatment, and an alternative cause was unlikely.

All AEs were reported for the entire study duration up to and including the follow up period.

1.8 Drug-Induced Livery Injury

Severe drug-induced liver injury (DILI): Irrespective of perceived causation, in the event of severe DILI the investigational drug was discontinued until the episode was deemed resolved. In the event the investigational drug was deemed to be the cause of the liver injury then the patient was not rechallenged with the drug. Severe DILI stipulates evidence of hepatic impairment as demonstrated by a total bilirubin >2×ULN or INR>1.5.

Patients with abnormal baseline liver biochemistry: In determining abnormal baseline liver biochemistry, a fold increase was calculated against baseline levels instead of using the ULN. Thus, a figure of 3× baseline ALT or AST (or >200 IU/L) was followed by repeat testing within 72 hours to confirm/determine if the biochemical changes were improving or worsening. AE information was collected alongside a thorough physical examination. A liver etiology screen and/or other appropriate testing was undertaken. In the event of liver dysfunction, then the patient was managed as a severe DILI. Pausing of drug treatment was considered if any of the criteria under severe DILI occurred.

1.9 Serious Adverse Reactions and Unexpected Adverse Reactions

Adverse Reaction: All noxious and unintended responses to a medicinal product related to any dose were considered adverse drug reactions. The phrase "responses to a medicinal product" means that a causal relationship between a medicinal product and an AE was at least a reasonable possibility (i.e., the relationship cannot be ruled out). For marketed medicinal products, an adverse reaction is a response to a drug which is noxious and unintended, and which occurs at doses normally used in man for prophylaxis, diagnosis, or therapy of disease or for modification of physiological function.

Unexpected Adverse Reaction: An adverse reaction, the nature or severity of which was not consistent with the applicable product information.

Suspected Unexpected Serious Adverse Reaction (SUSAR): Any serious adverse reaction that might have been related to the IMP and was unexpected according to the definition above.

1.10 Statistical Methodology and Data Management

This clinical trial employed a randomized, double-blind, placebo-controlled parallel group design. Randomization was used to minimize assignment bias and to increase the likelihood that known and unknown patient attributes (e.g. demographic characteristics) were evenly balanced across the treatment groups. Blinding was used to reduce potential bias during data collection and evaluation of safety and efficacy. The use of placebo as comparator was justified as a reasonable design to assess safety and efficacy in patients based on the brevity of the study duration and the absence of any possible long-term irreversible damage that may have had the result of placebo treatment.

Estimation of Sample Size: Assuming a 20% delta in the percentage response between active drug and placebo arms, a standard deviation of 25% and a dropout rate of 20%, this resulted in a requirement of 32 patients per group for a statistical test with 5% level of significance, and 80% power. The sample size was re-estimated at an interim analysis based on recommendation from an unblinded. The sample size could have increased to a maximum of 150 patients in total to achieve a conditional power of 80% for the primary endpoint.

Blinding and Code Breaking Instructions: All study site personnel, as well as the personnel involved in the monitoring or conduct of the study, were blinded to the individual patient treatment assignments. Randomization details were kept strictly confidential, accessible only in an emergency to authorized persons, until the time of formal unblinding. The blinded code for the trial was broken only after all patient data has been recorded and verified and the database locked.

Interim Analysis and Data Monitoring: Interim analysis safety was carried out to estimate the conditional power when at least 50% of the patients had completed their Week 16 visit. The interim analysis was based on data collected for the primary and co-primary efficacy endpoints as well as the secondary endpoints and was used to estimate the conditional power to achieve the primary study objective, to potentially re-estimate the sample size and to potentially drop the less effective treatment arm.

Clinically Meaningful Response: A higher mean or median reduction of at least 20% of ALT or liver stiffness compared to placebo and higher mean or median reduction of at least 10% of both ALT and liver stiffness compared to placebo Analysis Sets included the enrolled set, the full analysis set (FAS), per-protocol set (PPS), safety analysis set (SAS), and the pharmacokinetic (PK) set. A detailed description of each analysis set is provided below.

Enrolled Set: Patients who signed the informed consent form. Screen failures were patients from the Enrolled Population who did not meet the eligibility requirements and were withdrawn from the study prior to randomization.

FAS: Randomized patients who received at least one administration of study treatment and had at least one post-baseline measurement. Patients were analyzed according to the treatment they were assigned to at randomization, irrespective of what treatment they actually received.

PPS: A subset of the FAS consisting of those patients of FAS who had no major protocol violations. All protocol deviations were assessed and documented on a case-by-case basis prior to the database lock, and major deviations considered as having a serious impact on the efficacy results lead to the relevant patient being excluded from the PPS.

SAS: Patients who took at least one administration of study treatment. Patients were analyzed according to the treatment actually taken.

PK Set: Patients in the SAS who had at least one DS102 PK concentration. Patients were analyzed according to the treatment actually received.

Safety Analysis: Demographic, medical history and physical examination data were listed for each patient and summarized descriptively. All AEs recorded during the study were coded to system organ class and preferred terms using the current version of the Medical Dictionary for Regulatory Activities (MedDRA). AEs were tabulated and summarized by treatment, relationship to treatment, seriousness and severity. Clinical laboratory values (e.g., hematology, biochemistry, and urinalysis) were listed for each patient by treatment and day. Values outside the laboratory normal ranges were listed separately with associated comments as to their clinical significance, with potentially clinically significant abnormalities highlighted and summarized by treatment. Clinical laboratory values obtained prior to dosing were defined as baseline values. Alcohol breath test and DOA test results were listed for each patient. Individual values of vital signs were listed and summarized descriptively for each treatment and day. 12 lead ECG assessments were listed for each patient with all associated comments and summarized by treatment and day. Concomitant medications (if any), categorized by medication group and subgroup according to the latest version of the World Health Organization drug dictionary, were listed and summarized by treatment. In general, appropriate descriptive statistics according to the nature of the variable were applied. Categorical variables were presented using counts and percentage, whilst continuous variables were presented using mean, standard deviation, median, minimum, maximum, coefficient of variation and number of patients.

Pharmacokinetic Analysis: Plasma concentrations of 15(S)-HEPE were tabulated and summarized descriptively. Individual and mean plasma concentration-time profiles of 15(S)-HEPE were presented graphically.

Primary Variables: The primary efficacy variable was the change from baseline in serum ALT at Week 16 (Visit 10). The active treatment groups were compared against placebo via an analysis of covariance (ANCOVA) model, including the corresponding baseline value as covariate. The comparisons against placebo were done according to Dunnett's multiple testing procedure. For missing Week 16 values, the last value available was carried forward (LOCF). Similar methods were applied for liver stiffness. For ALT, longitudinal modelling was considered in addition.

Secondary variables: The secondary efficacy variables and their changes from baseline to Week 16 (Visit 10) were summarized with descriptive statistics per treatment group and visit. This applied to the AST, AST:ALT ratio, hepatic fat measured by CAP, liver stiffness measurements by transient elastography, FIB-4, NFS, ELF and HOMA-IR/Adipo-IR. The change from baseline for the active treatment groups was compared against placebo via an ANOVA model, including a term for center effects. The 5% level of significance was used for all treatment comparisons.

Exploratory analysis: The exploratory analysis included analysis of lipid and metabolic parameters including total cholesterol, triglycerides, very low-density lipoprotein cholesterol (VLDL-C), low density lipoprotein cholesterol (LDL-C), high density lipoprotein cholesterol (HDL-C), non-high-density lipoprotein cholesterol (non-HDL-C), remnant-like particle cholesterol (RLP-C), fasting glucose, insulin, free fatty acids and hemoglobin A1C (HbA1C). Additional exploratory analysis included high throughput lipidomics and proteomics.

1.11 Results

This study demonstrated that patients diagnosed with NAFLD and administered DS102 at a dose of either 1 g or 2 g per day, exhibited a statistically significant reduction in markers of metabolic overload and an improvement in insulin sensitivity and glycemic control.

Figure 20:
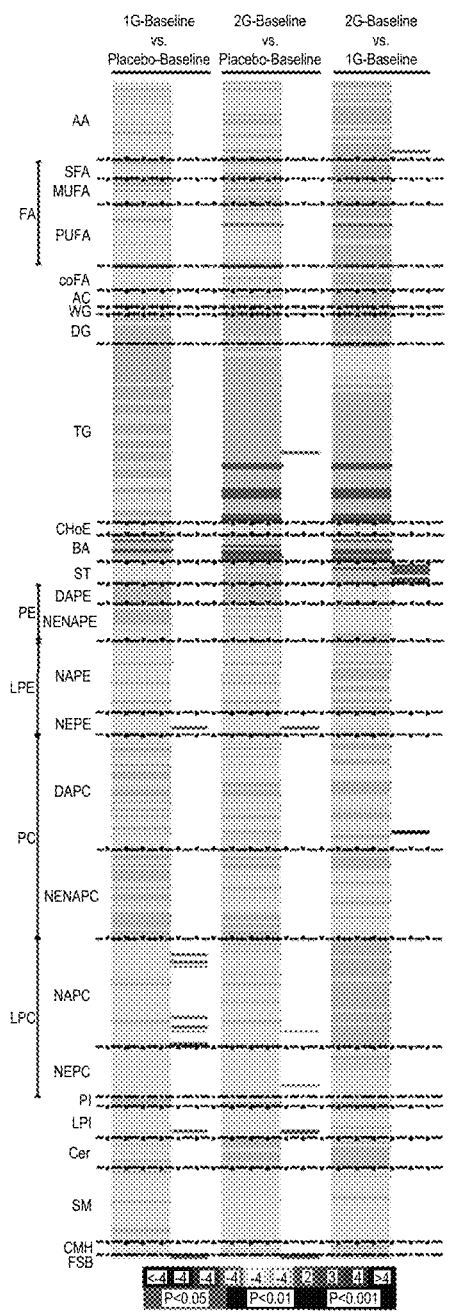
FIG. 20 shows the baseline lipidomic profile of patients according to the study described in Example 4.

FIG. 20 shows that the three treatment groups were well balanced at baseline and had similar lipidomic and metabolomic profiles. The baseline characteristics of the patients are shown in Table 18 where 10 to 13% of the patients were on a statin therapy at baseline.

TABLE 18

Baseline Characteristics of the Subjects

|  | 2 g DS102 (n = 31) | 1 g DS102 (n = 32) | Placebo (n = 30) |
|---|---|---|---|
| Age, median, years | 47.0 | 53.5 | 50.0 |
| Gender, % | | | |
| Female | 32.3 | 37.5 | 30.0 |
| Male | 67.7 | 62.5 | 70.0 |
| Race, % | | | |
| White | 100.00 | 93.75 | 90.00 |
| Other | 0.00 | 6.25 | 10.00 |
| BMI, median, kg/m$^2$ | 30.9 | 33.5 | 33.9 |
| Statin use, % | 9.7 | 12.5 | 13.3 |
| Fasting plasma glucose, mean, mg/dL | 119.1 | 110.9 | 120.3 |
| Hemoglobin A1C (%), mean | 6.3 | 6.2 | 6.2 |
| ALT, median, IU/L | 74.0 | 70.5 | 96.5 |
| Liver Stiffness, median, kPa | 7.9 | 8.2 | 8.4 |
| HOMA-IR, median | 4.4 | 5.1 | 5.0 |
| Triglycerides, median, mg/dL | 242.0 | 146.0 | 150.0 |

Figure 21A:
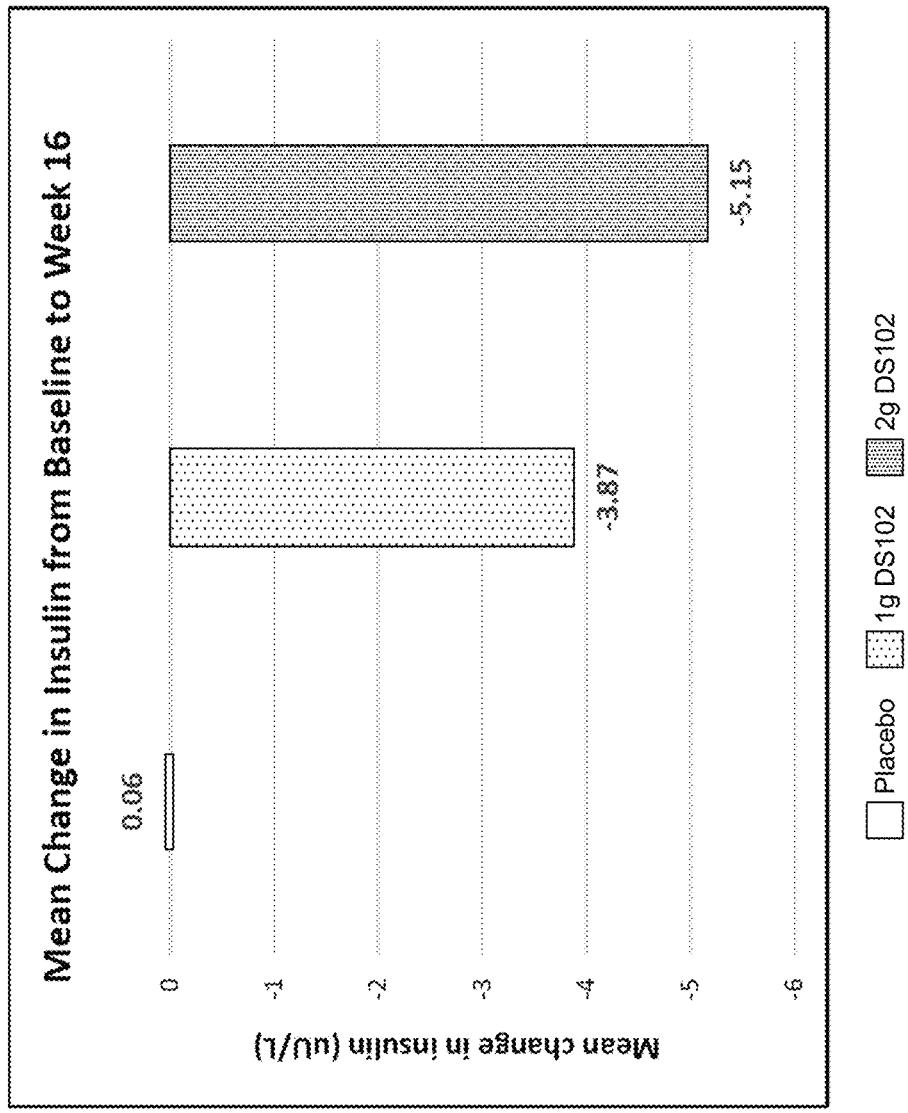
FIGS. 21A-21C are plots depicting the changes in insulin, glucose, and free fatty acid levels in patients administered Epeleuton (15-HEPE) and placebo, respectively.
Figure 21B:
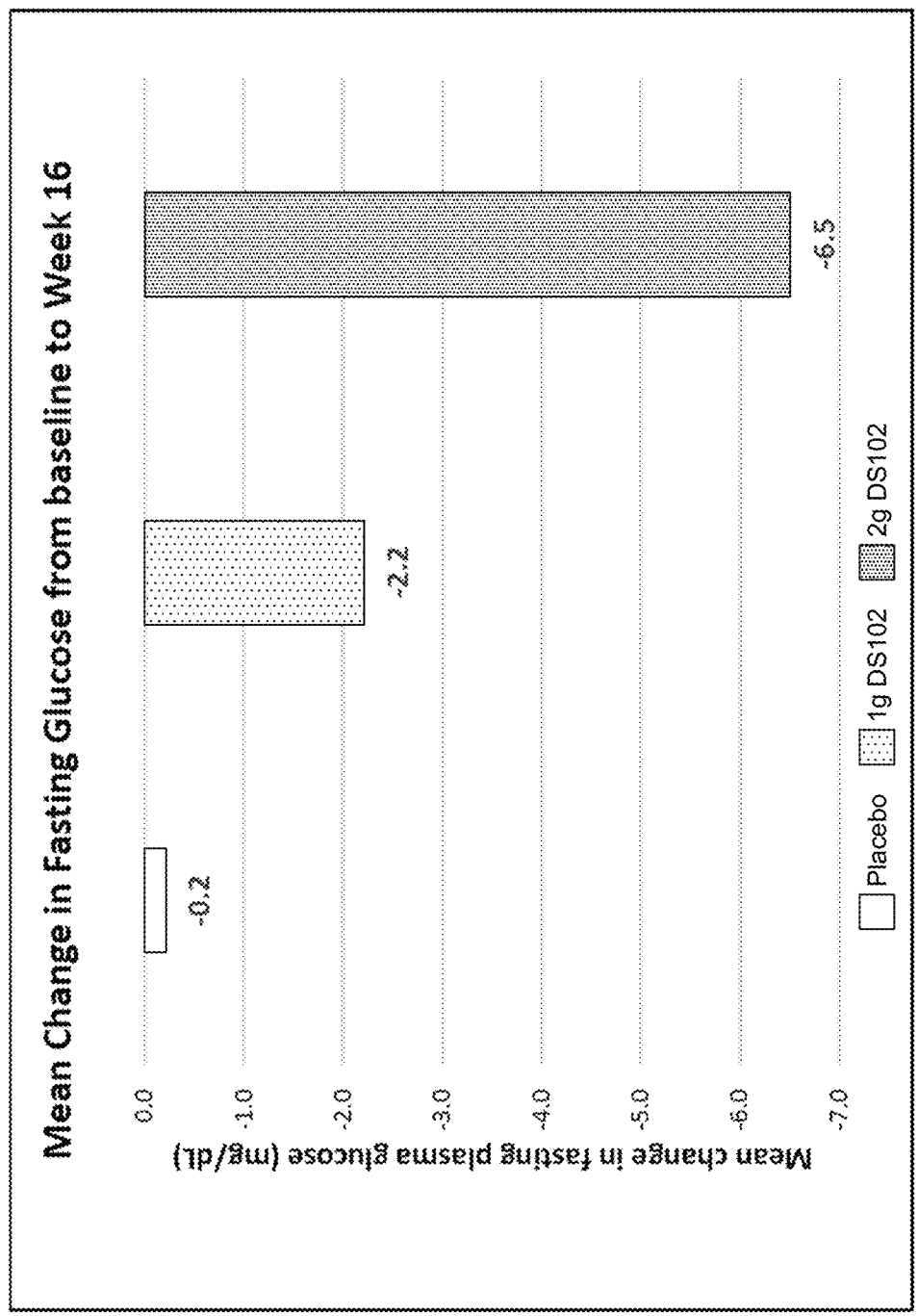
Figure 21C:
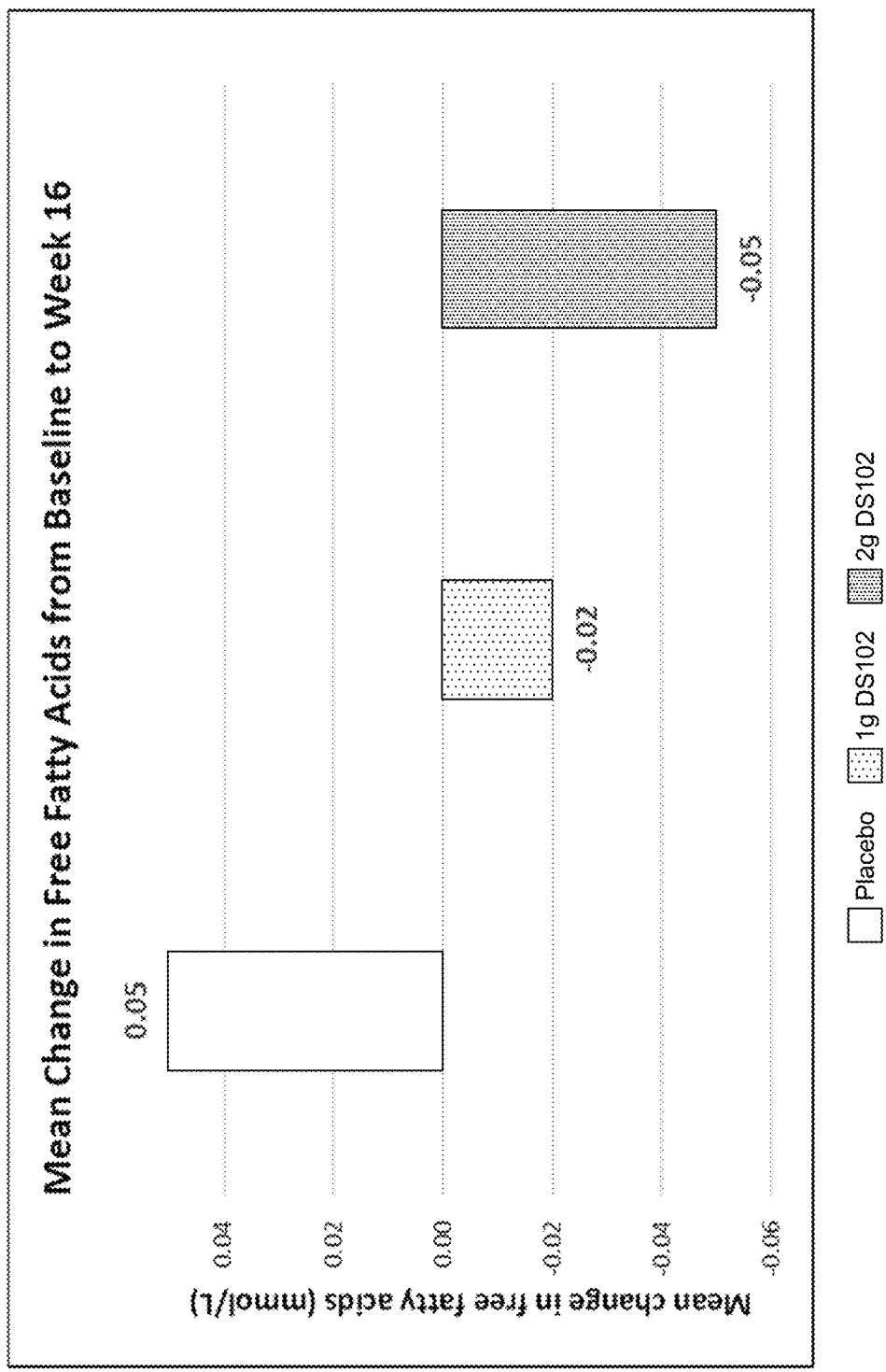

FIGS. 21A-21C depict the changes in insulin, glucose, and free fatty acid levels from baseline to Week 16 in patients administered DS102 either 1 g or 2 g per day as compared to a placebo. The reduction in insulin, glucose, and free fatty acid levels upon administration of DS102 is clinically significant as metabolic substrates including glucose, carbohydrates and free fatty acids drive the pathogenesis of NASH.

Figure 22A:
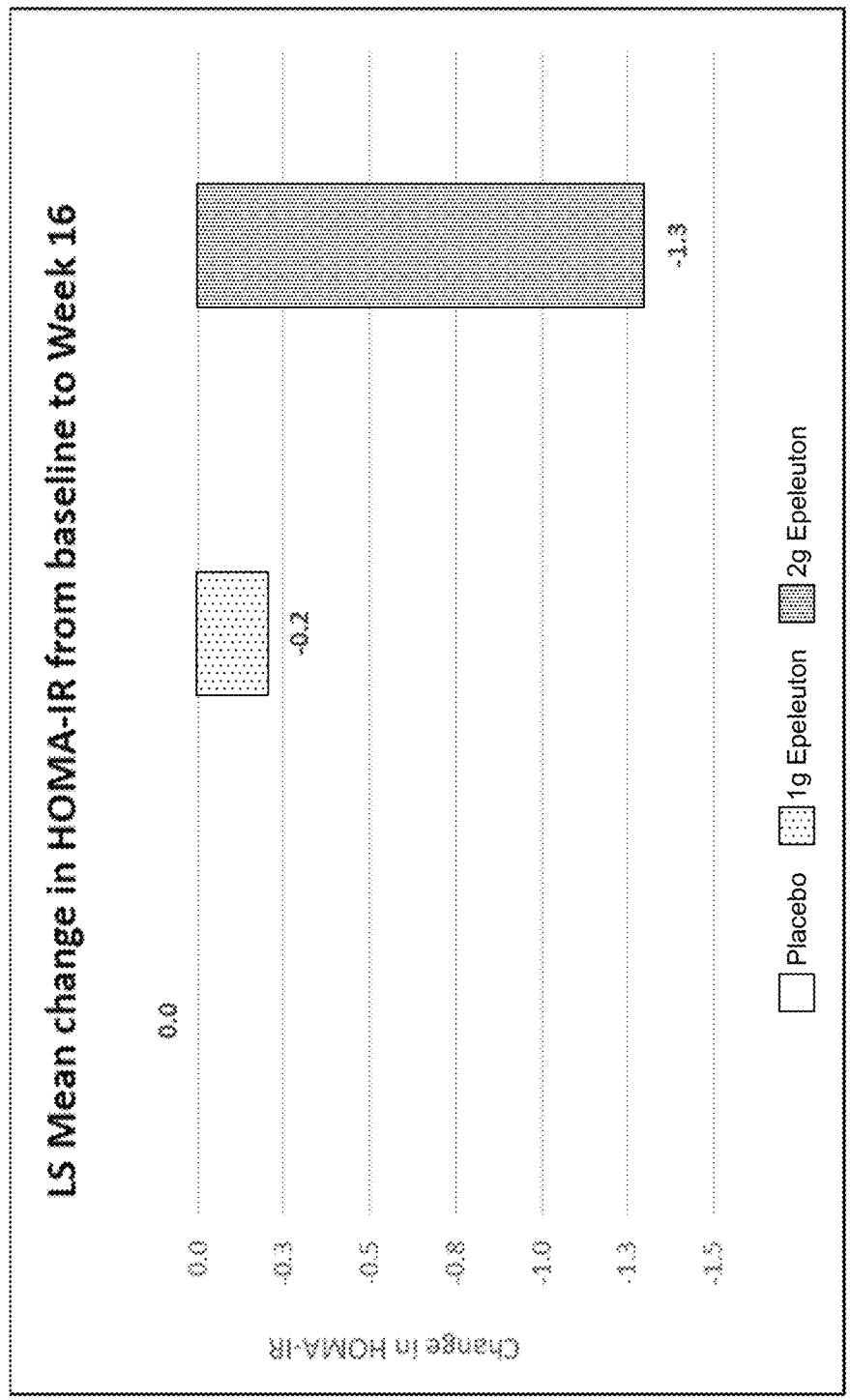
FIGS. 22A and 22B are plots depicting the changes in HOMA-IR and apido-IR levels in patients administered Epeleuton and placebo, respectively.
Figure 22B:
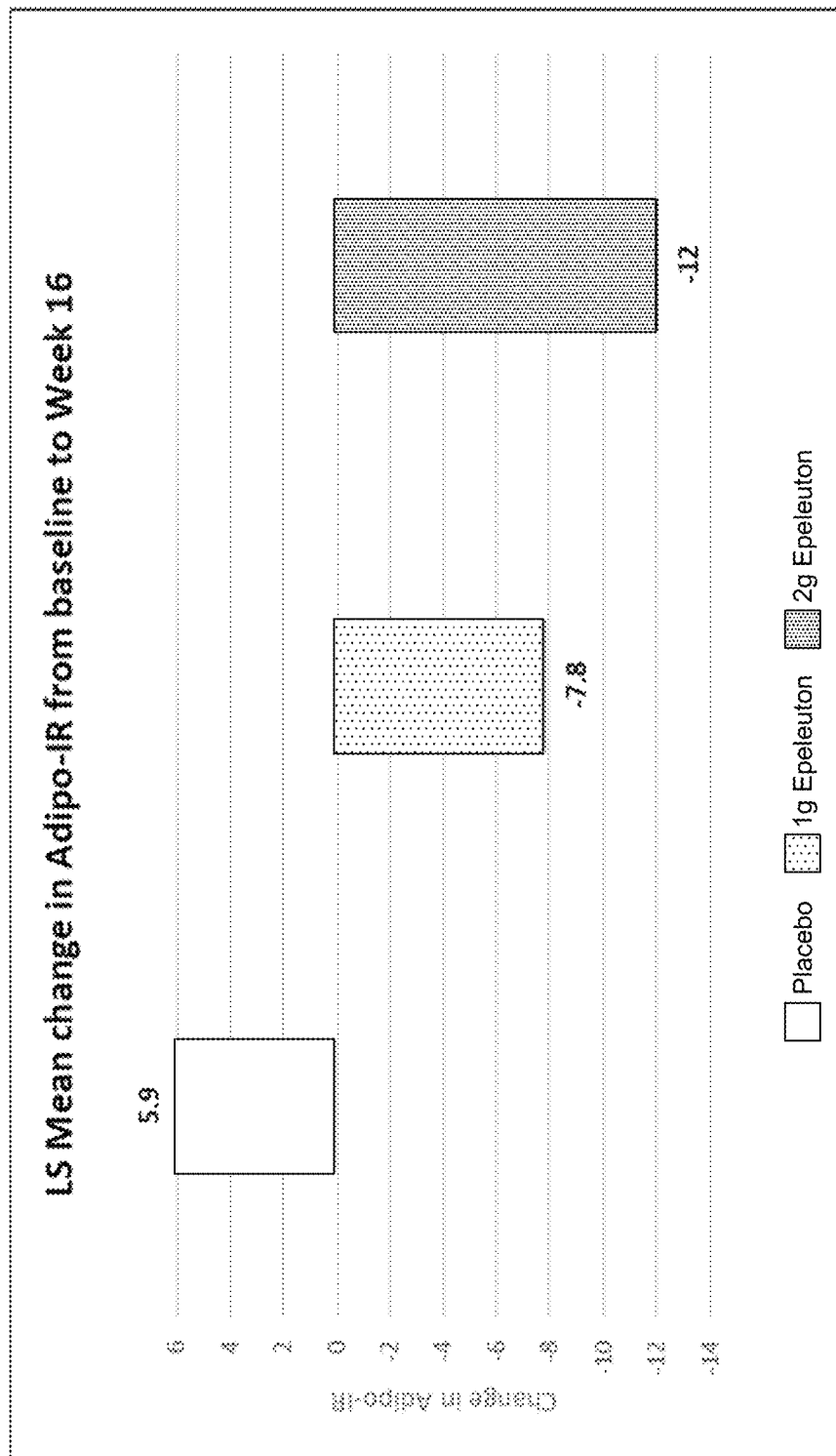

FIGS. 22A and 22B show the changes in HOMA-IR and adipo-IR levels from baseline to Week 16 in patients administered DS102 either 1 g or 2 g per day as compared to a placebo. The patients exhibited an improvement in both insulin resistance indices (e.g., a reduction in HOMA-IR and adipo-IR levels) at Week 16, with significant improvements in the Per Protocol Set (PPS) observed for those patients administered 2 g of DS102.

Figure 23A:
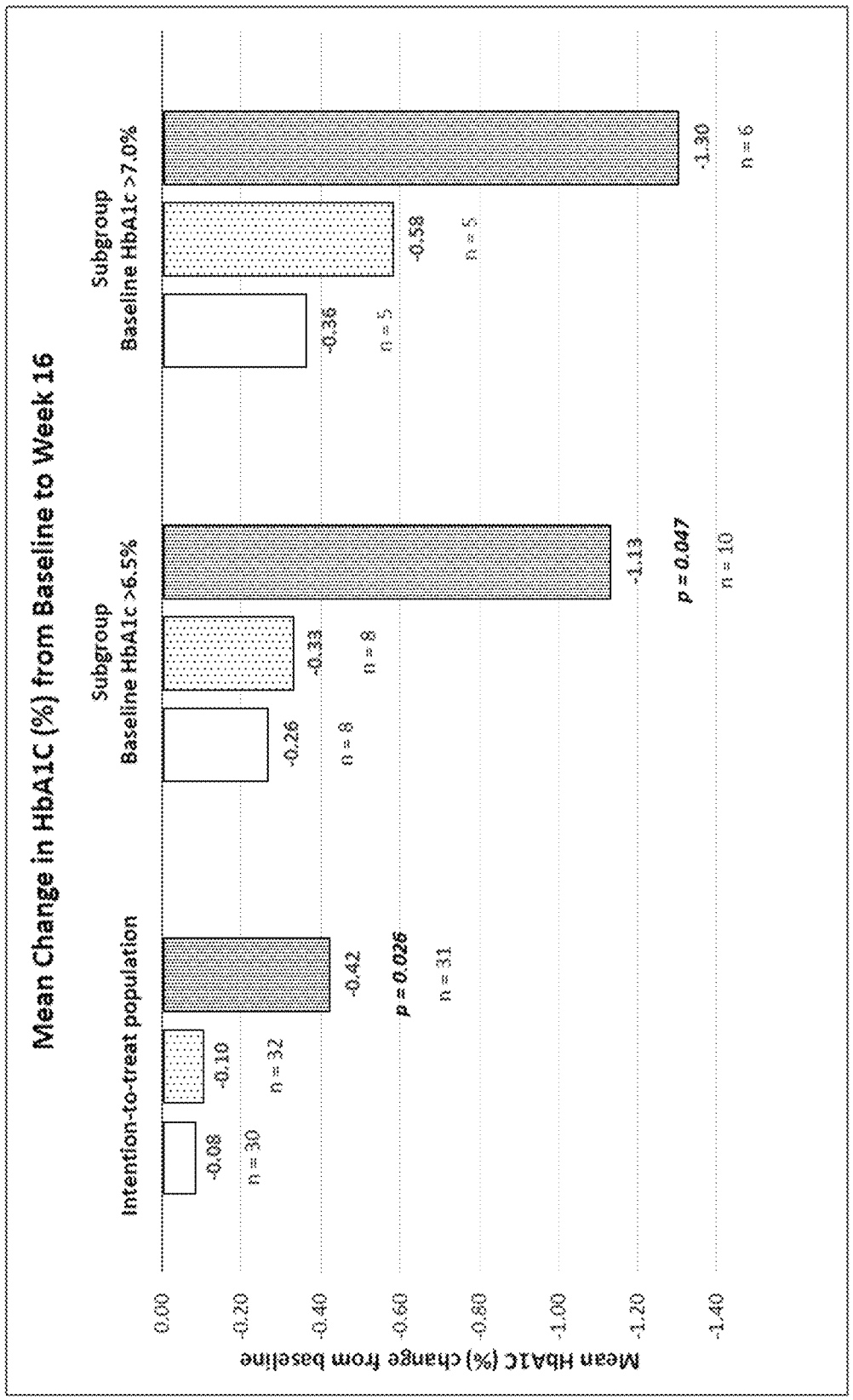
FIGS. 23A and 23B are plots depicting the changes in mean HbA1C levels in patients and proportion of patients having HbA1C levels 6.5% at week 16 administered Epeleuton and placebo, respectively.
Figure 23B:
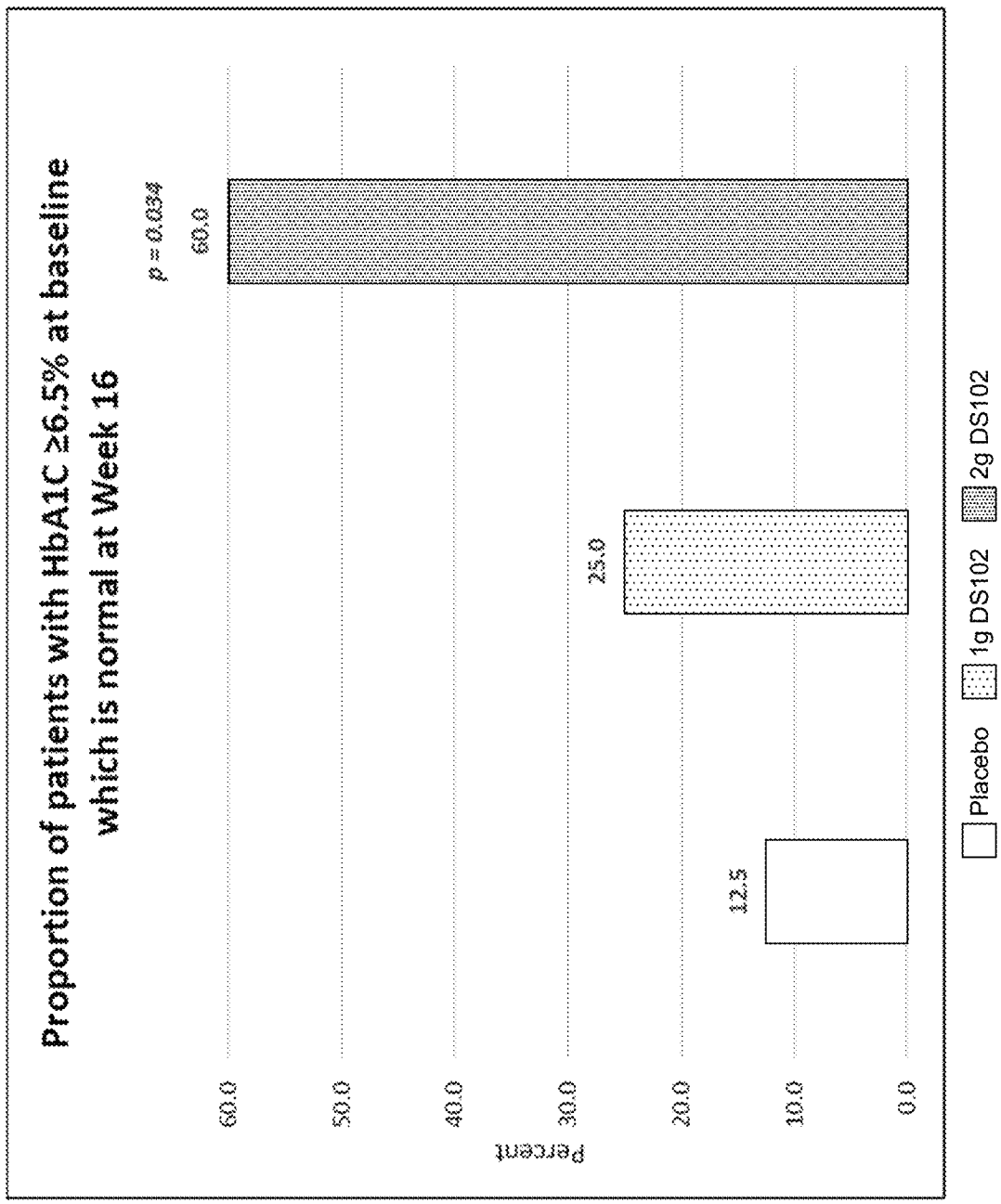

FIGS. 23A and 23B depict the changes in glycosylated hemoglobin (e.g., HbA1c) levels from baseline to Week 16 in patients administered DS012 either 1 g or 2 g per day as compared to a placebo. Specifically, FIG. 23A shows the change in HbA1c levels and FIG. 23B shows the change in HbA1c levels in the proportion of patients who had high HbA1c levels at baseline but achieved normal levels at Week 16. Since Hb1Ac is a measure of the amount of glucose attached to the body's red blood cells and a surrogate for long-term glycemic control, these results indicate the administration of DS102 provides clinically significant improvements and normalizes glycemic control in a dose-dependent manner.

Figure 24A:
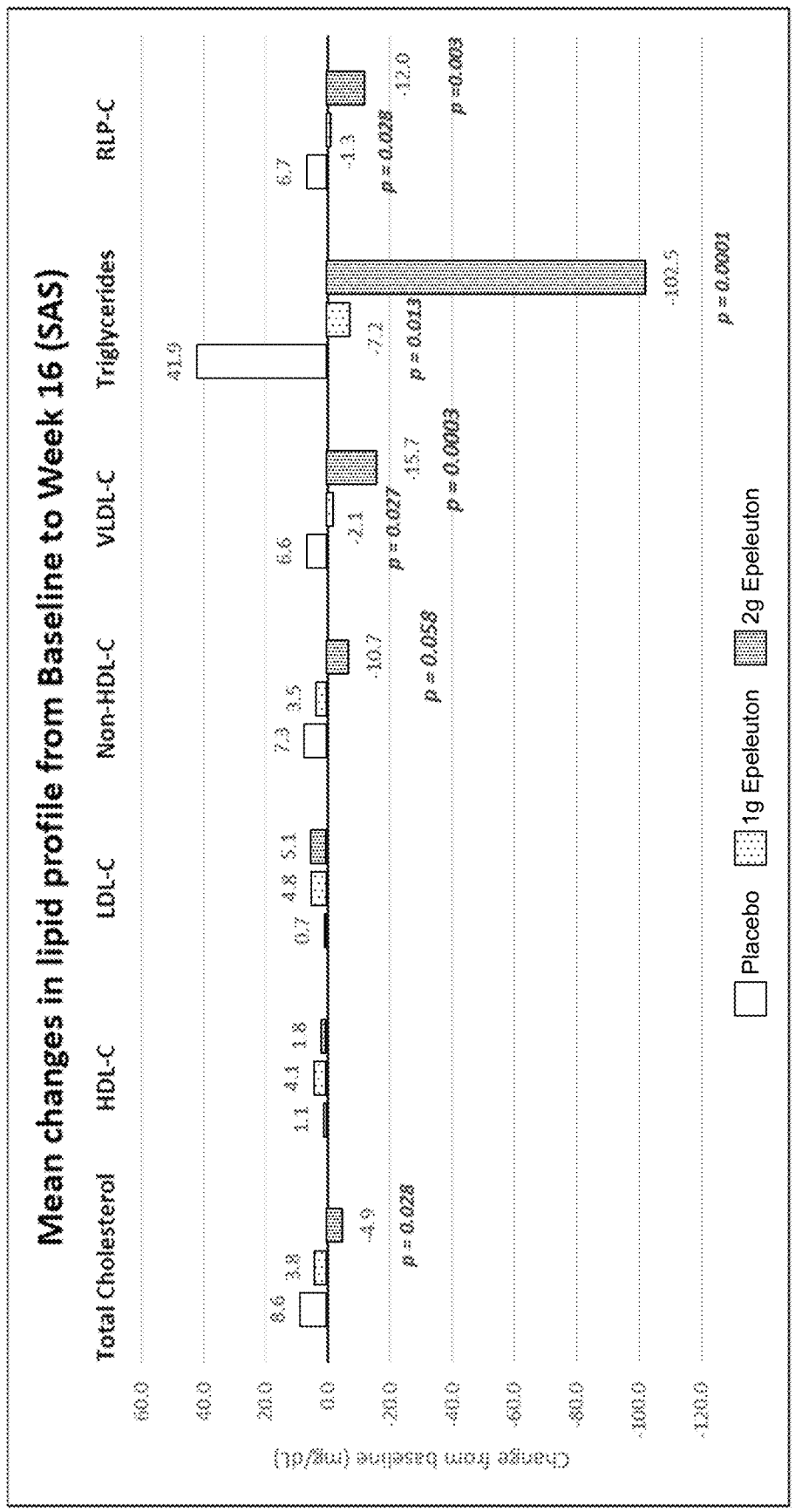
FIGS. 24A and 24B are plots depicting the mean change and median (%) change in the lipid profile of patients administered Epeleuton and placebo, respectively.
Figure 24B:
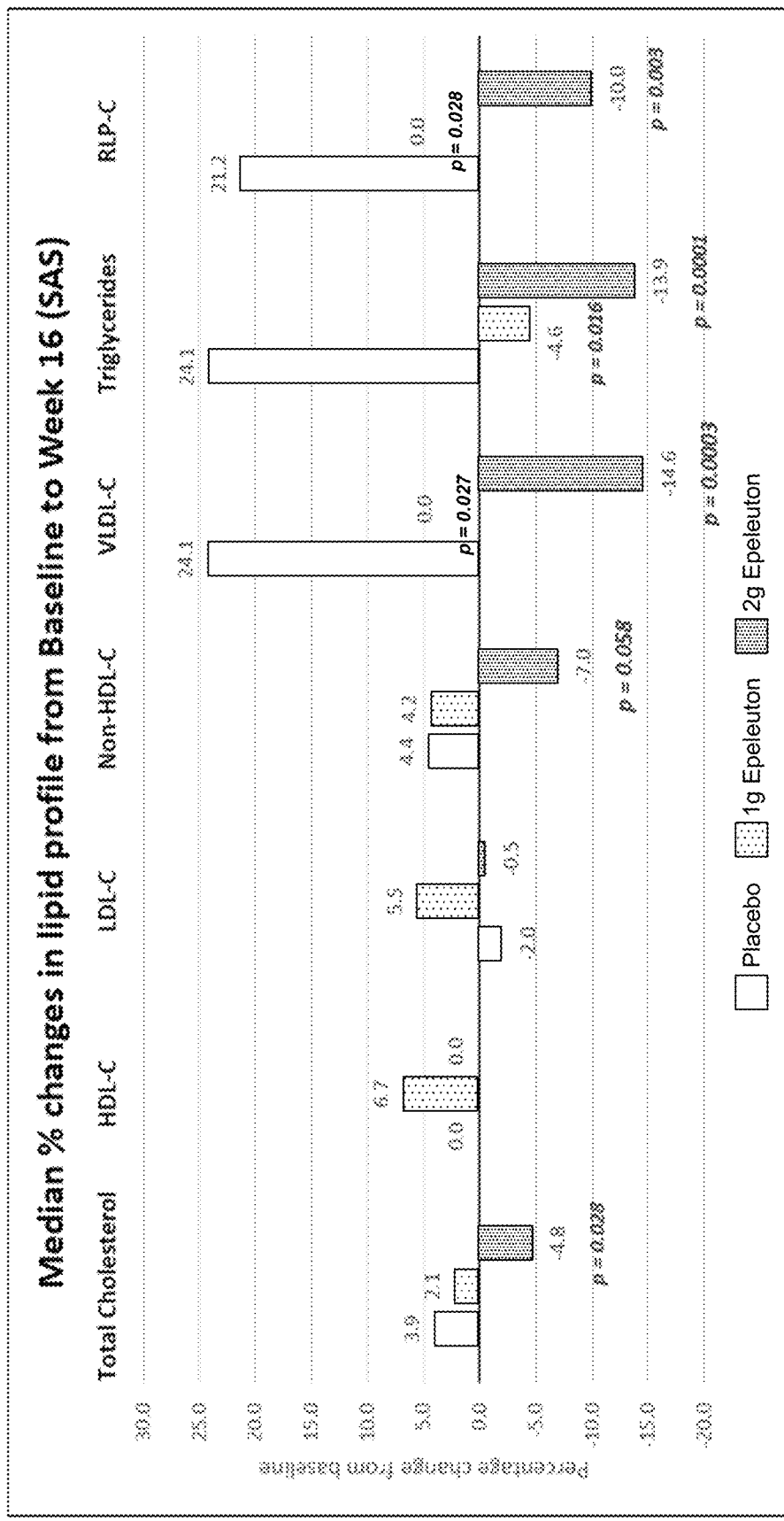
Figure 25A:
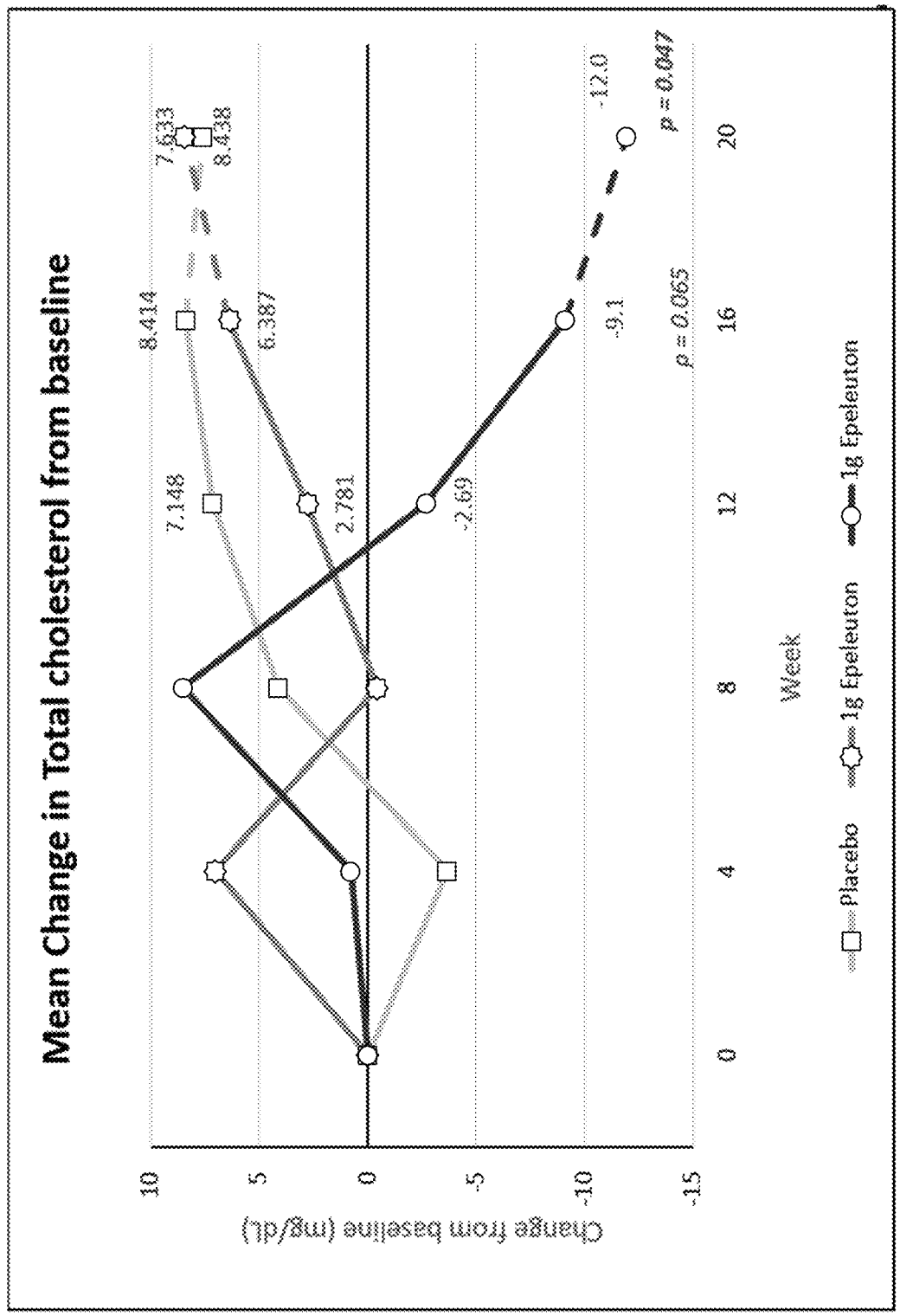
FIGS. 25A-25C are plots depicting the changes in cholesterol, triglyceride, and VLDL-C levels in patients administered Epeleuton and placebo, respectively.
Figure 25B:
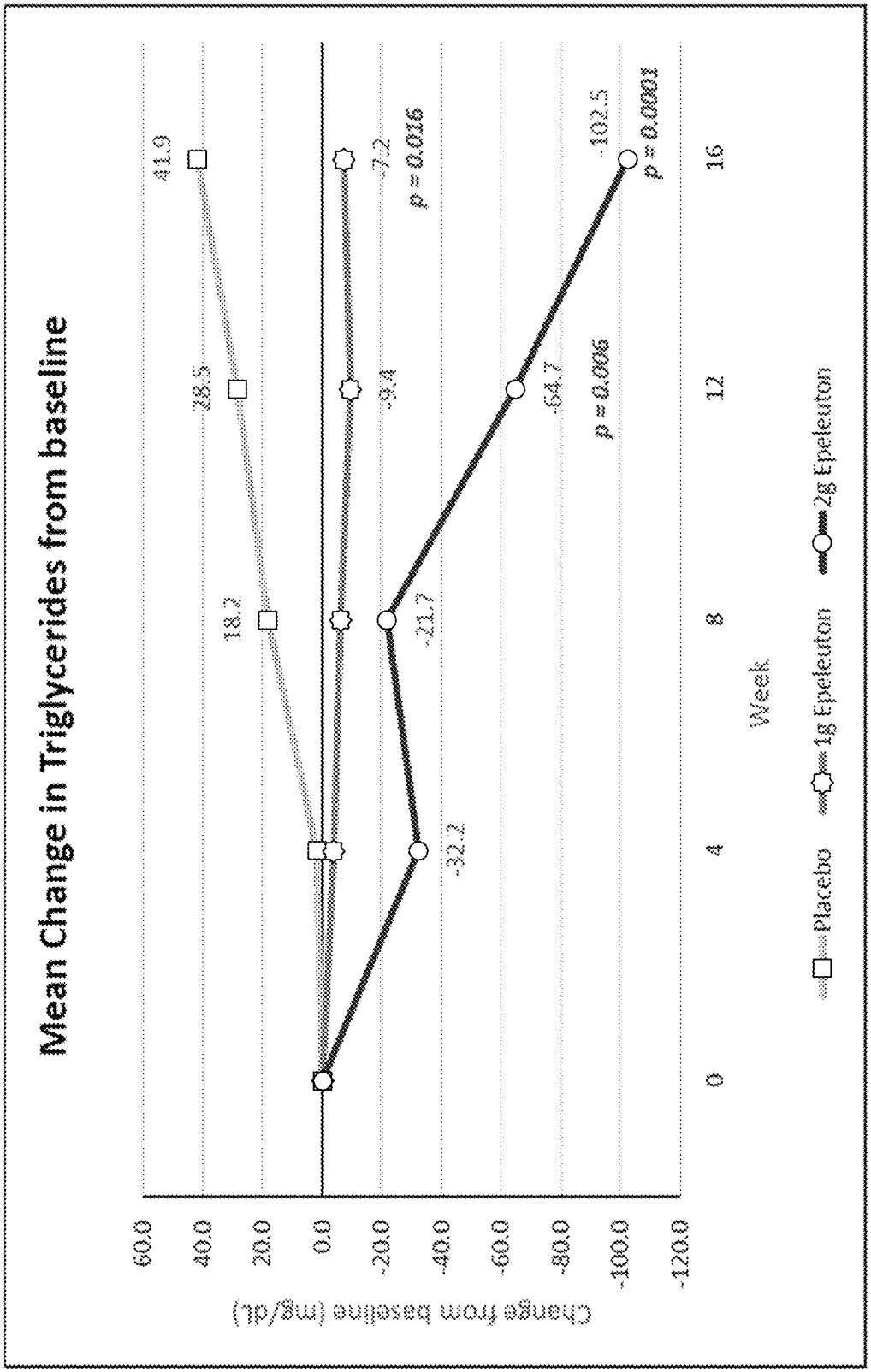
Figure 25C:
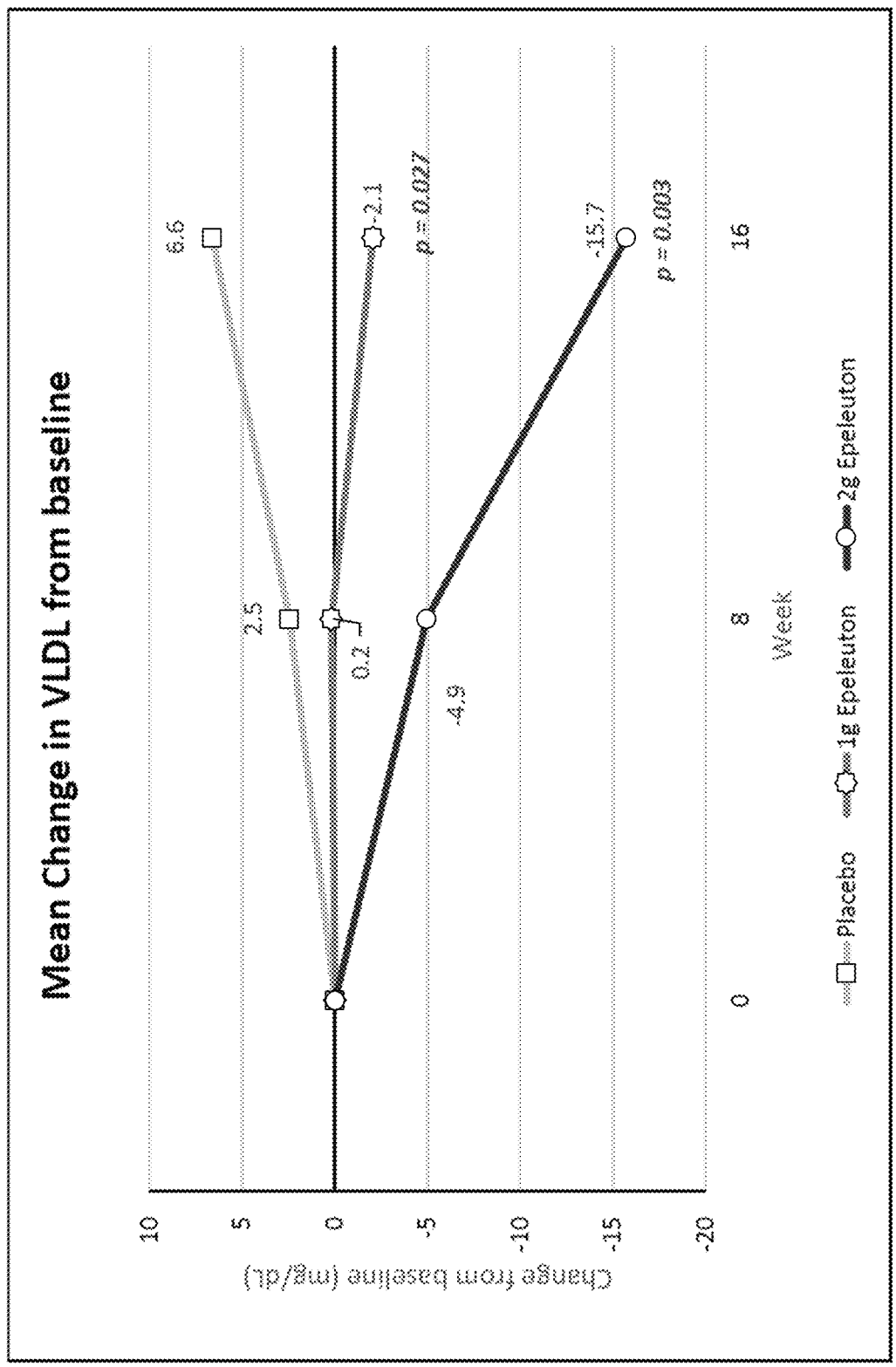

FIGS. 24A and 24B show the mean change and median (%) change in the patient's lipid profile at Week 16 in the safety analysis set (SAS). These results are further depicted in FIGS. 25A-25C and illustrate that the administration of DS102 significantly improved patient's lipid profile by either sustaining or reducing total cholesterol, VLDL-C, non-HDL-C, remnant-like particle (RLP) cholesterol and triglyceride levels in the patients. Significantly, the reductions did not plateau at Week 16, suggesting that the administration DS102 might induce even larger changes in studies of longer duration.

As shown in FIG. 26 the administration of DS102 also reverses the hepatotoxic lipid signature of NASH and improves multiple lipid classes that are altered in patients diagnosed with NASH. Specifically, the administration of 2 g of DS102 significantly decreased levels of multiple hepatotoxic diglycerides and significantly increased levels of multiple glycerophospholipid groups. This finding is important as patients with NASH have low levels of hepatic and plasma glycerophospholipids.

Figure 27:
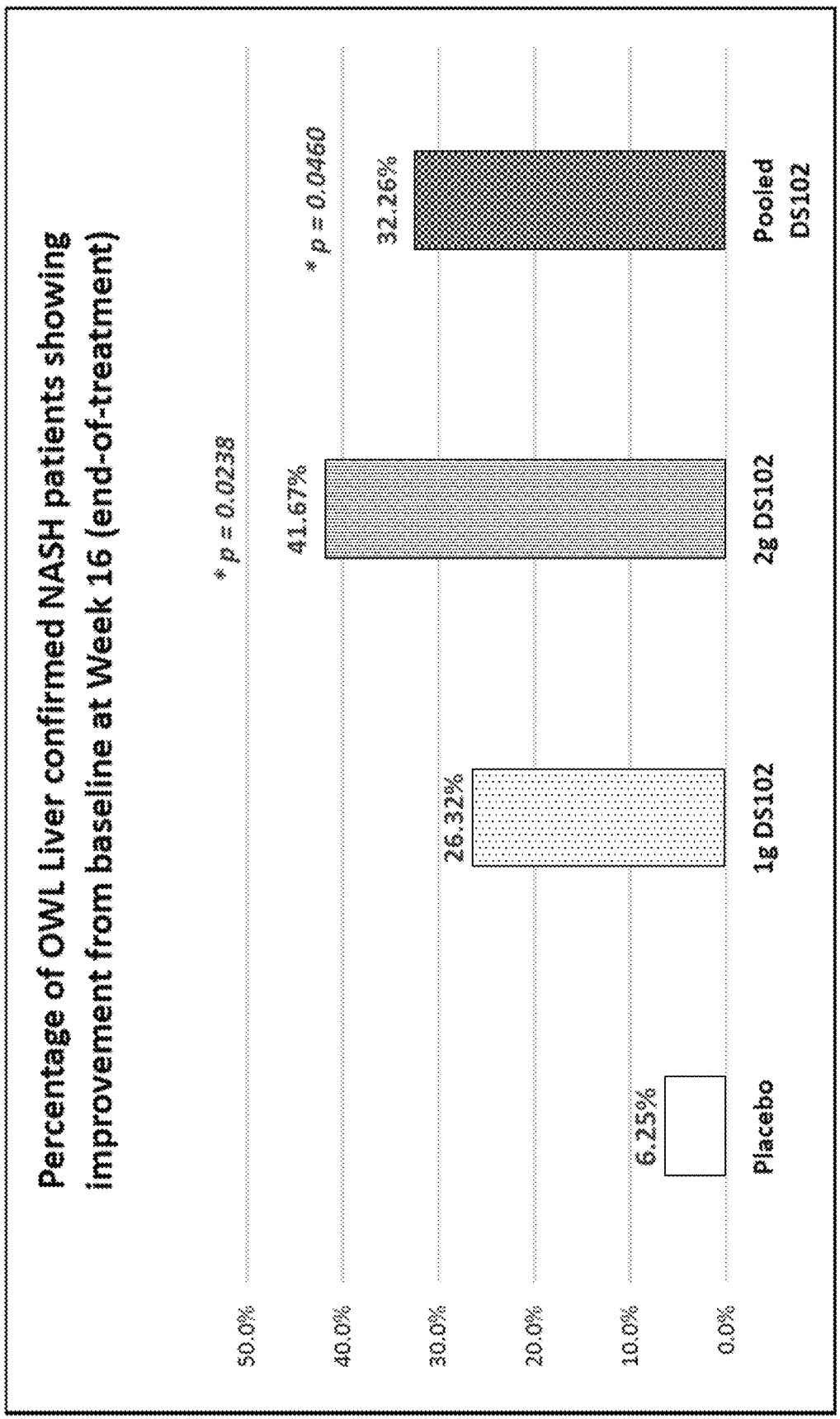
FIG. 27 are plots that validate that administration DS102 resolves NASH using the OWL liver care test.

FIG. 27 shows that the administration of DS102 also resolved NASH based on validated diagnostic tests such as the OWL liver care non-invasive diagnostic test for NASH. OWL Liver Care is a test that was developed based on the plasma lipidomics in biopsy-confirmed NASH patients and provides high predictive values. OWL Liver Care has an area under the curve (AUC) of 0.88 for distinguishing NAFLD and normal liver patients and an AUC of 0.79 for distinguishing NAFLD without steatohepatitis and NASH patients. The administration of DS102 significantly improved and normalized OWL liver care diagnosed NASH in a dose dependent manner as compared to placebo at Week 16. Table 19 shows the test diagnoses at baseline for each treatment group and demonstrates that most patients were classified as NASH or NAFLD at baseline with a lower percentage of the patients in the 2 g DS102 group.

TABLE 19

OWL Test Diagnoses at Baseline

| Arm | Diagnosis | Baseline | Change in Diagnosis (Week 16 vs. baseline) | | |
|---|---|---|---|---|---|
| | | | Improvement | Stable | Worsening |
| Placebo | NASH | 16 | 1 | 15 | — |
| | Steatosis | 7 | 1 | 4 | 2 |
| | No NAFLD | 3 | — | 1** | 2 |

TABLE 19-continued

OWL Test Diagnoses at Baseline

| Arm | Diagnosis | Baseline | Change in Diagnosis (Week 16 vs. baseline) | | |
|---|---|---|---|---|---|
| | | | Improvement | Stable | Worsening |
| 1 g DS102 | NASH | 19 | 5 | 14 | — |
| | Steatosis | 5 | — | 2 | 3 |
| | No NAFLD | 4 | — | 3 | 1 |
| 2g DS102 | NASH | 12 | 5 | 7 | — |
| | Steatosis | 14 | 1 | 9 | 4 |
| | No NAFLD | 3* | — | 2*, ** | 1 |

Figure 28:
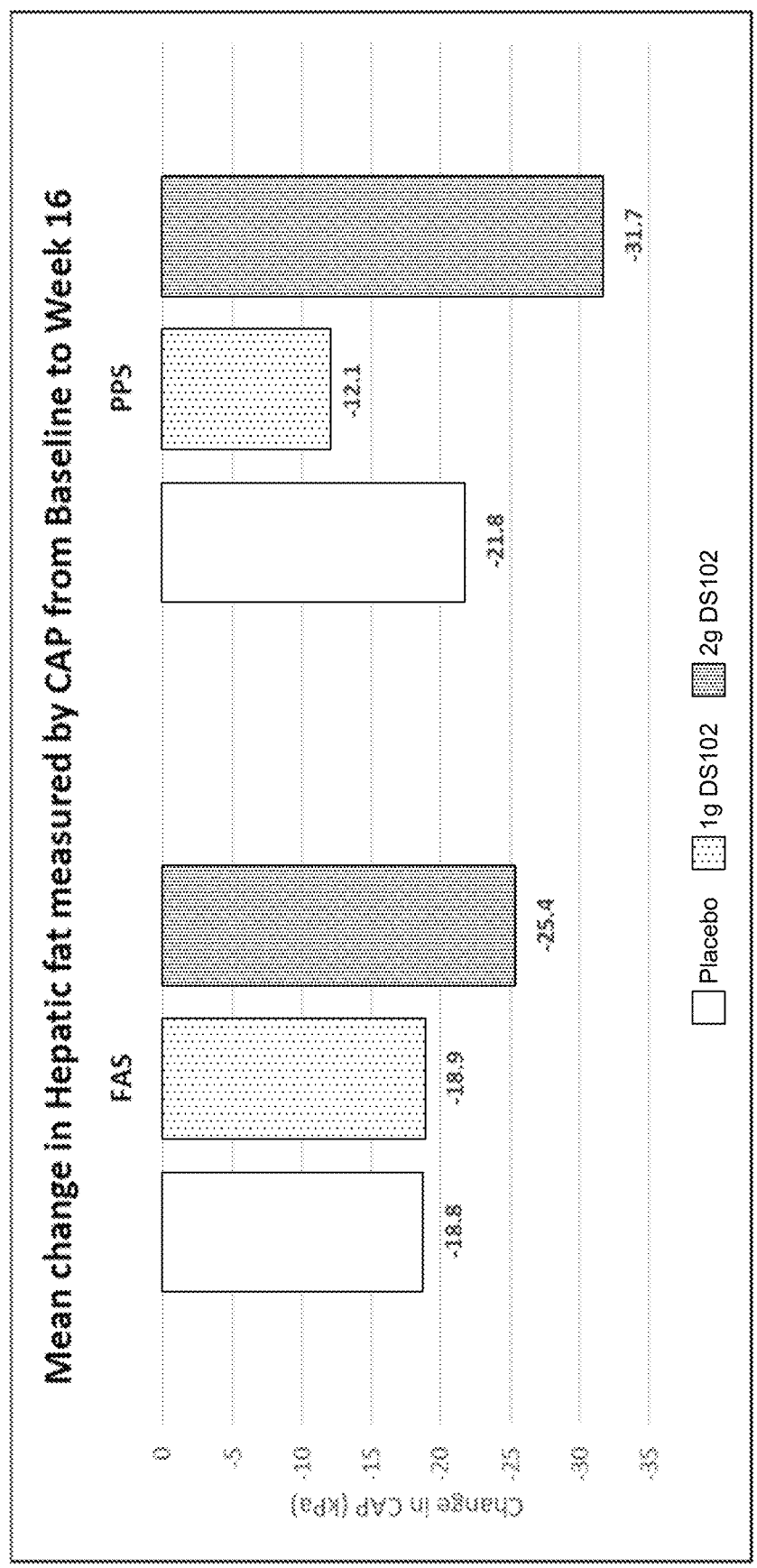
FIG. 28 are plots depicting the changes in hepatic fat content by CAP in patients administered DS102 and placebo.

The administration of DS102 also reduced hepatic fat content as assessed by CAP in patients diagnosed with NAFLD as shown in FIG. 28. It is further contemplated that DS102 is expected to induce larger changes in hepatic content in studies of longer duration and when assessed by more sensitive methods.

The administration of DS102 also lowered triglyceride levels in patients as shown in Table 20 and it is thus contemplated that DS102 would also be effective at lowering cardiovascular risk.

TABLE 20

Changes Triglyceride Levels of Patients Administered DS102 at Week 16

| DS102 (2 g) | Triglycerides (median placebo-corrected % change from baseline) |
|---|---|
| Full Analysis Set | −40.2 |
| Subgroup: Triglycerides > Upper Limit Normal (>150 mg/dL) | −39.0 |
| Subgroup: High Triglycerides (>200 mg/dL) | −20.4 |

Figure 29A:
FIGS. 29A-29C is a chart depicting that changes in inflammatory and pro-fibrotic protein levels in patients administered DS102 and placebo.
Figure 29B:
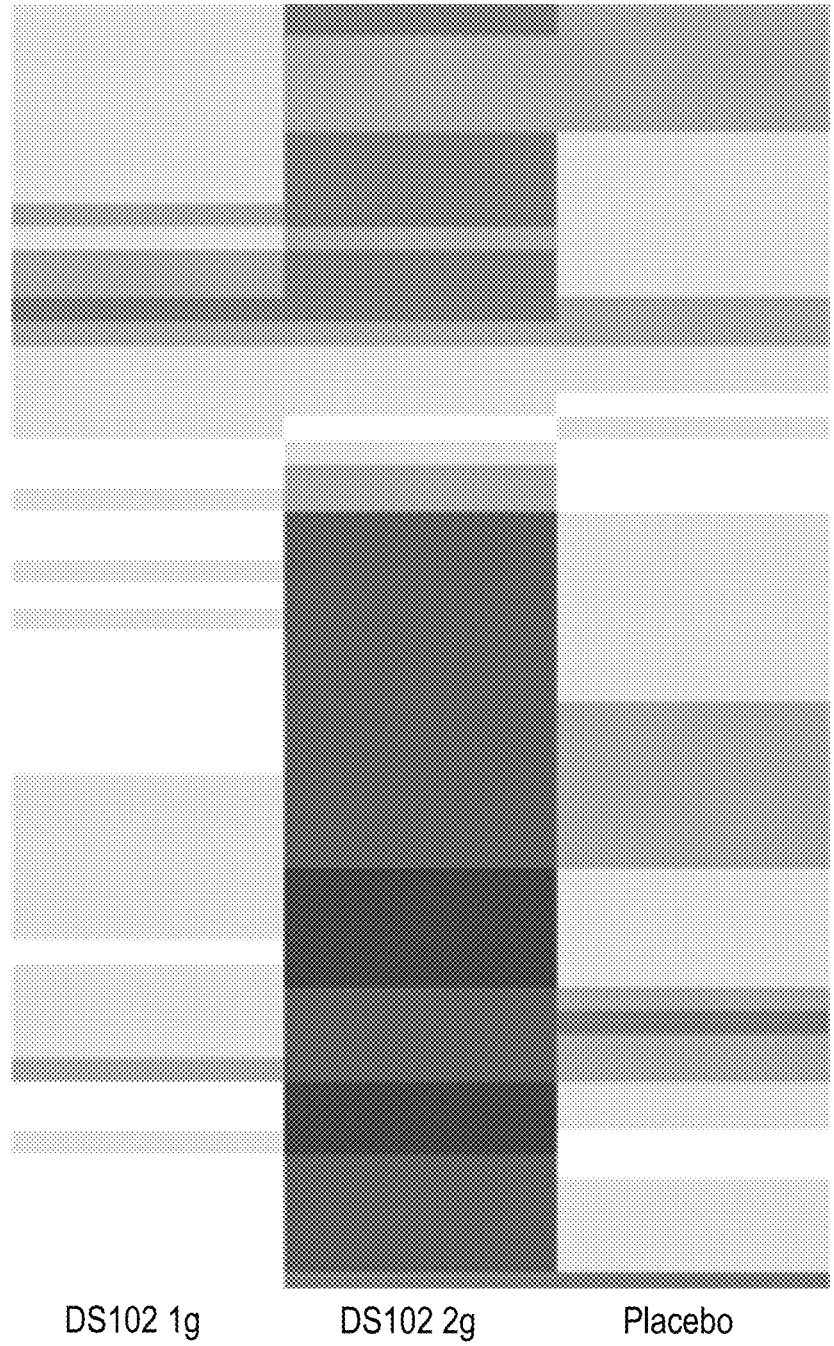
Figure 29C:
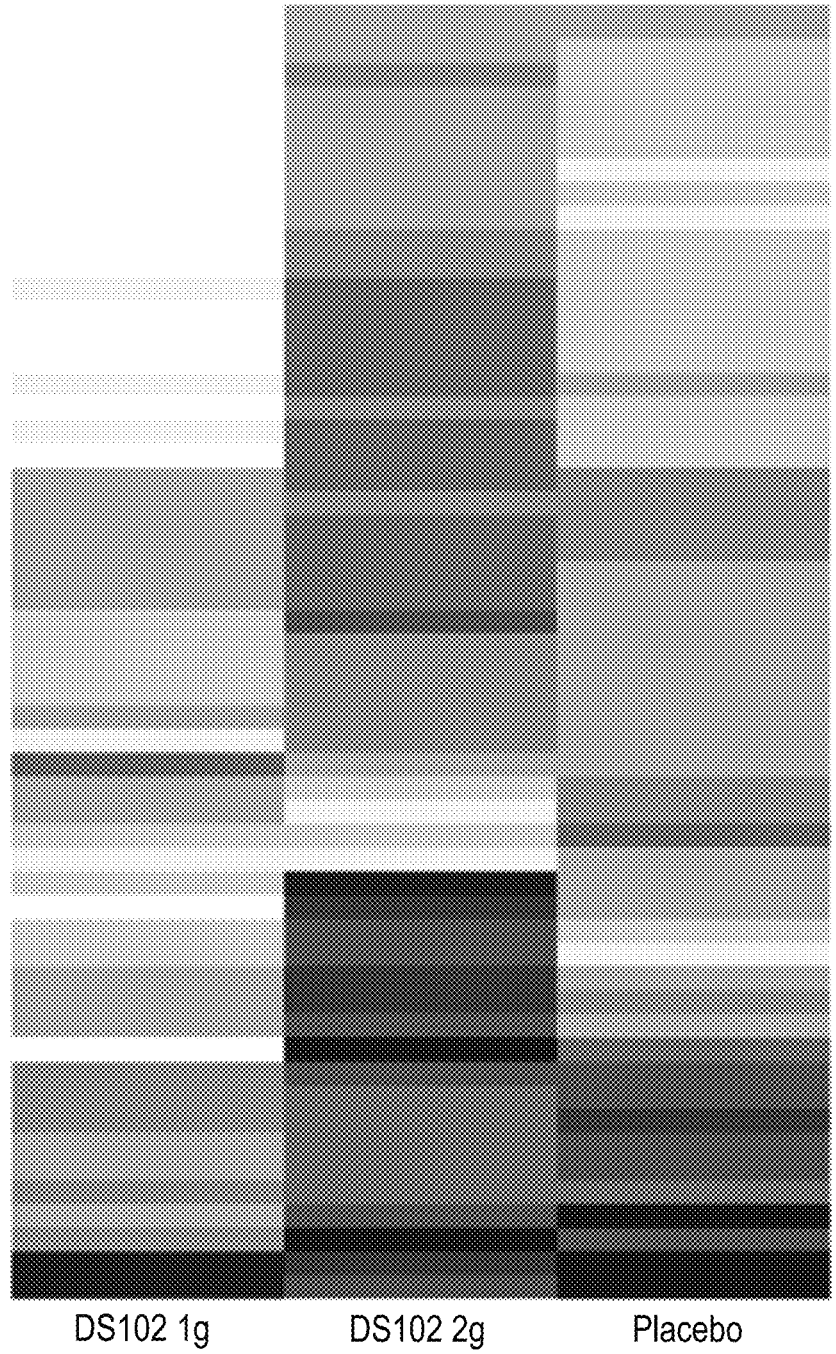

FIGS. 29A-29C shows that the administration of DS102 decreases inflammatory and pro-fibrotic proteins. For this assessment, blood samples before and after treatment with DS102 were analyzed for a panel of greater than 350 different protein biomarkers. Treatment with 2 g of DS102 significantly downregulated the expression of over 150 markers associated with inflammation, fibrosis, lipid metabolism, apoptosis, and chemotaxis. The resolution of metabolic overload and lipotoxicity was observed following treatment with DS102, which prevents subsequent cell stress, inflammation, and fibrosis. The reduction in the inflammatory and pro-fibrotic proteins suggests the potential of DS102 to provide resolution for NASH and the prevention of fibrosis.

Figure 30:
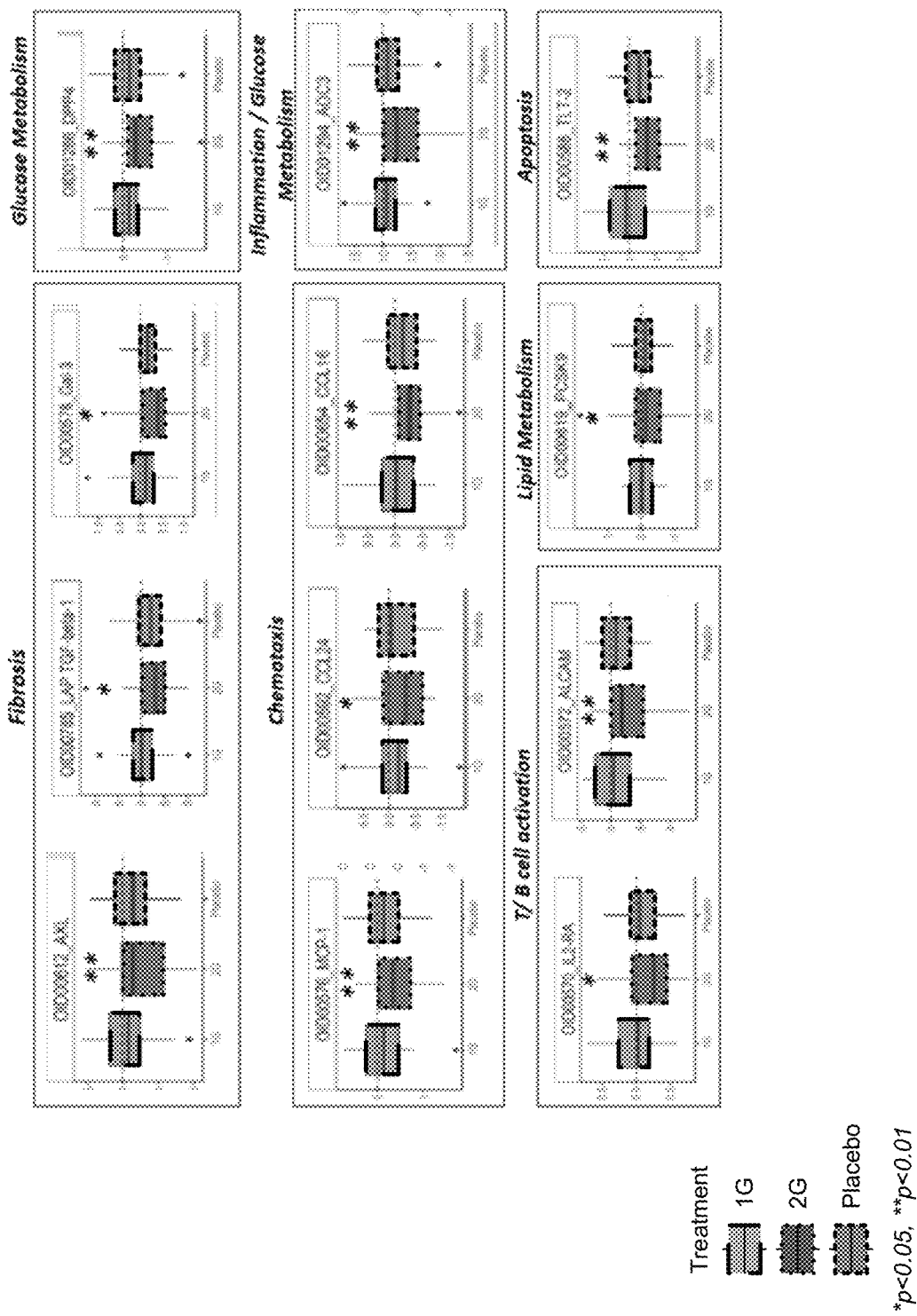
FIG. 30 are plots depicting the changes in the protein expression including of NASH development targets in patients administered DS102 and placebo.

The administration of DS102 also decreased the expression of multiple NASH development targets as shown in FIG. 30. In particular, the administration of 2 g of DS102 decreased the NASH drug development targets to include CCR215 signaling (Cenicriviroc—Allergan), Galectin3 (GR-MD-02—Galectin), and AOC3 (Boehringer Ingelheim).

Figure 31:
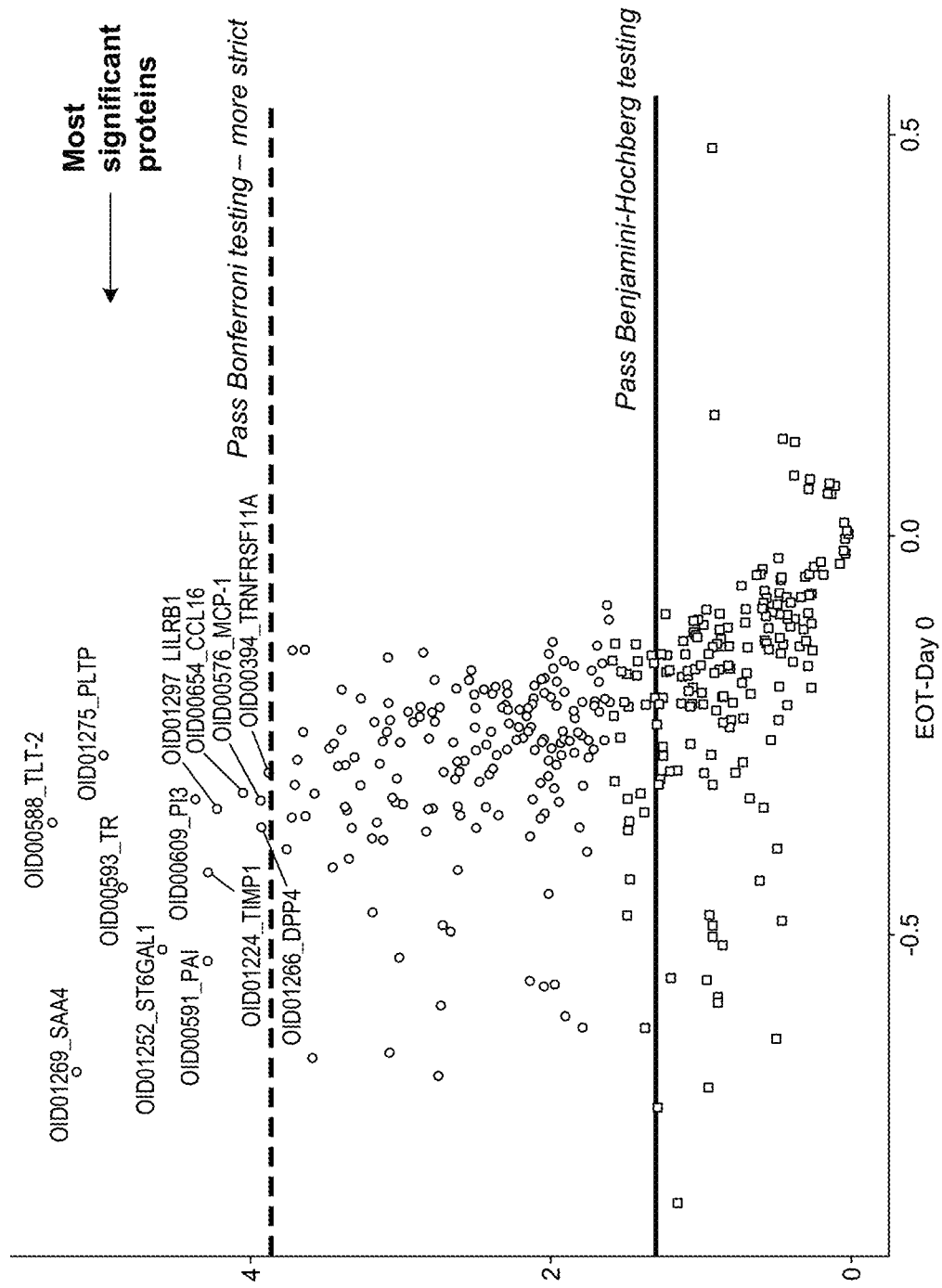
FIG. 31 is a volcano plot depicting a reduction in inflammatory and pro-fibrotic proteins in patients administered DS102 and placebo.

The volcano plot in FIG. 31 (data with Bonferroni and Benjamini-Hochberg testing) shows that the administration of 2 g of DS102 decreased inflammatory and pro-fibrotic proteins based on changes in protein expression. Table 21 shows the most significant inflammatory and pro-fibrotic protein reductions based on Bonferroni Testing.

TABLE 21

Significant Proteins based on Bonferroni Testing

| Protein | Description |
|---|---|
| PAI-1 | TGF-β induced protein, increased in metabolic syndrome, atherosclerosis, fibrosis |
| TIMP-1 | Pro-fibrotic |
| DPP4 | T-cell activation, DPP4 inhibition increases GLP-1 |
| TLT2 | Enhances T-cell activation, clearance of apoptotic cells |
| CCL16 | chemokine that binds to CCR 1,2,5,8. Cenicriviroc (Allergen) is a CCR2/5 antagonist |
| MCP-1 (CCL2) | chemokine that binds to CCR 2, 4. Cenicriviroc (Allergen) is a CCR2/5 antagonist. Increased in NASH, atherosclerosis etc. |
| SAA4 | Apolipoprotein |
| PI3/Elefin | Increased in graft versus host disease |
| TR | Iron homeostasis |
| LILRB1 | Receptor for class I MHC antigens |
| TNRSF11A | T-cell/dendritic cell interaction |

Administration of 1 g of DS102 also showed significant reductions for TR. Table 22 shows the most significant inflammatory and pro-fibrotic protein reductions based on an analysis with a linear model.

TABLE 22

Significant Proteins based on the Linear Model

| Protein | Description |
|---|---|
| TL12 | Enhances T-cell activation, clearance of apoptotic cells |
| AOC3 | Impairs glucose homeostasis. Increased in NASH, atherosclerosis. |
| PRSS2 | Expressed in pancreas, involved in cell adhesion |

This analysis also indicated that 1 protein in 1 g DS107 group and 0 proteins in Placebo group passed the $1^{st}$ threshold based on the Benjamini-Hochberg testing.

Figure 32:
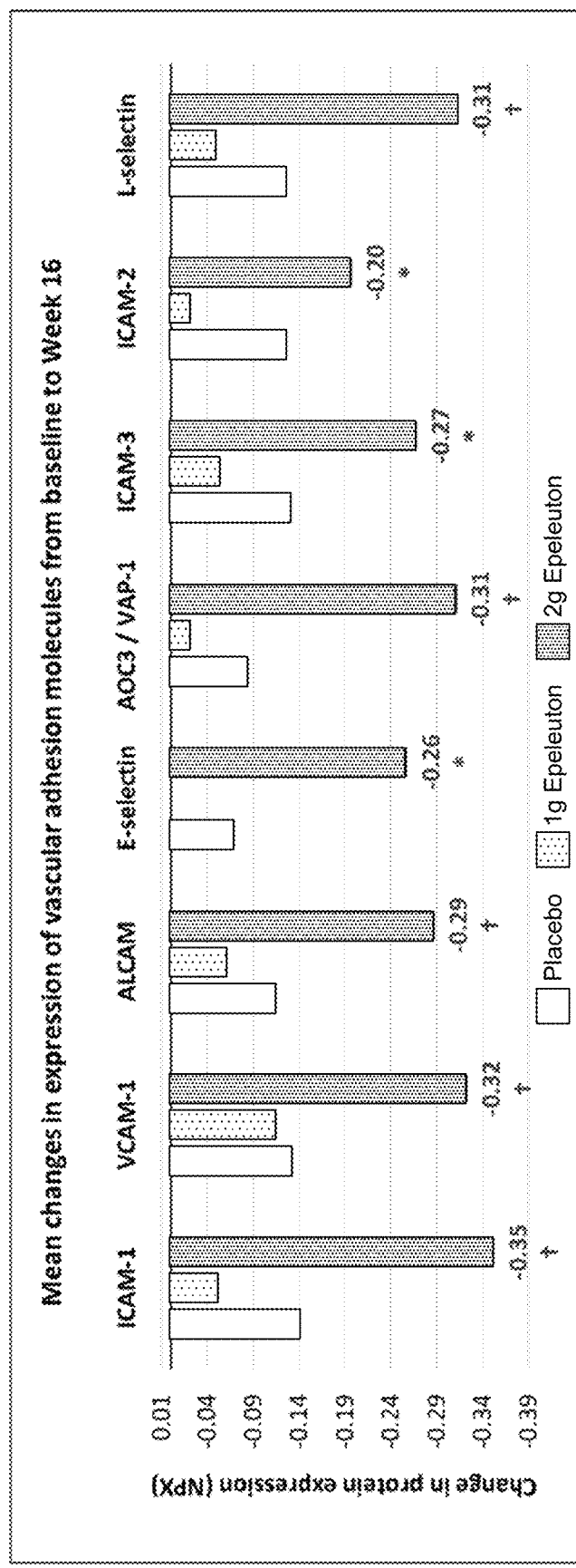
FIG. 32 are plots depicting the changes in vascular adhesion molecules in patients administered DS102 and placebo.
Figure 33:
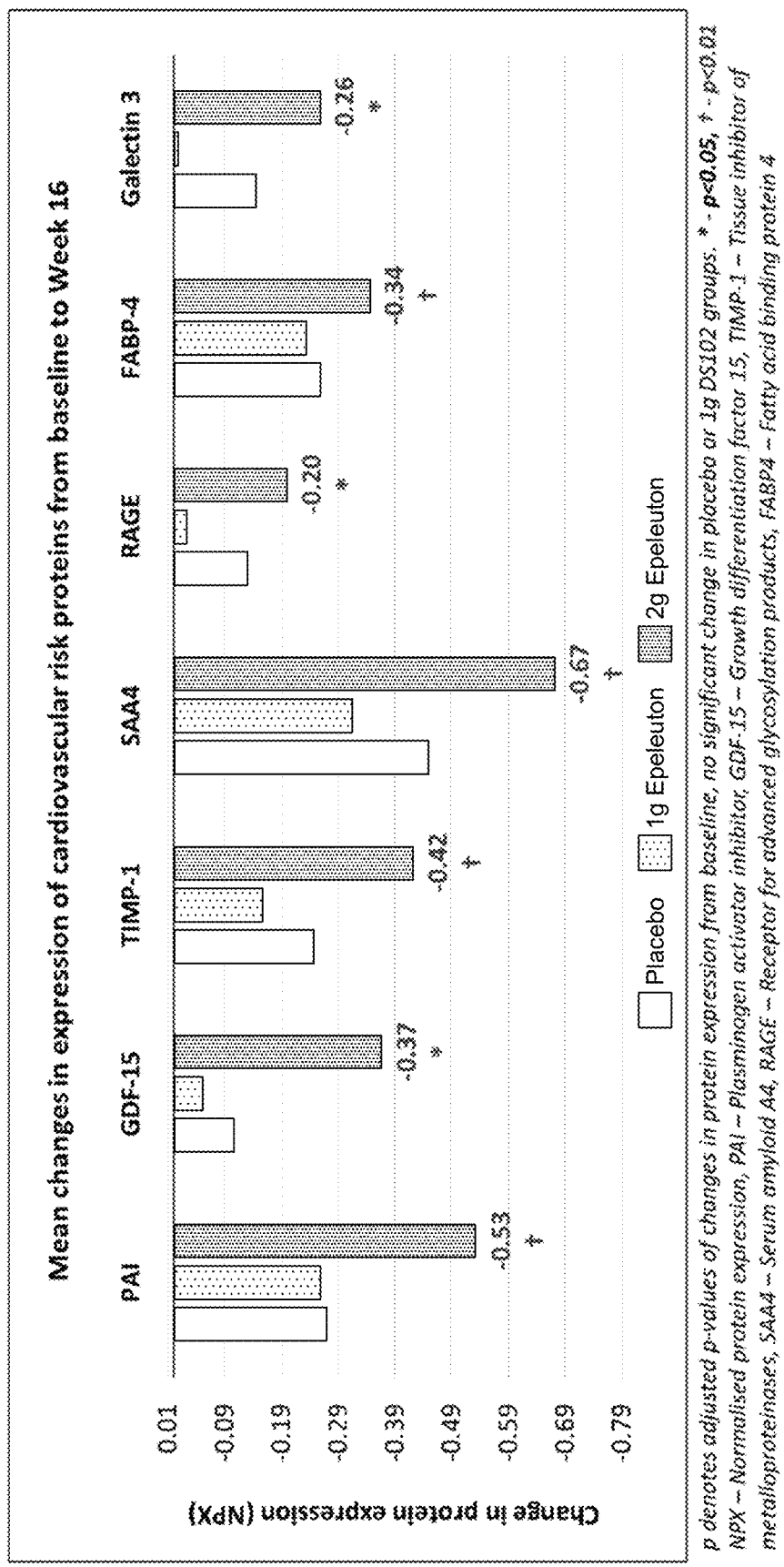
FIG. 33 are plots depicting the changes in cardiovascular risk proteins in patients administered DS102 and placebo.

The administration of DS102 also decreased the expression of multiple vascular adhesion molecules as shown in FIG. 32. Vascular adhesion molecules are implicated in atherosclerosis and their circulating levels are associated with cardiovascular risk The administration of DS102 also decreased the expression of multiple proteins that are associated with increased cardiovascular risk as shown in FIG. 33.

Figure 34:
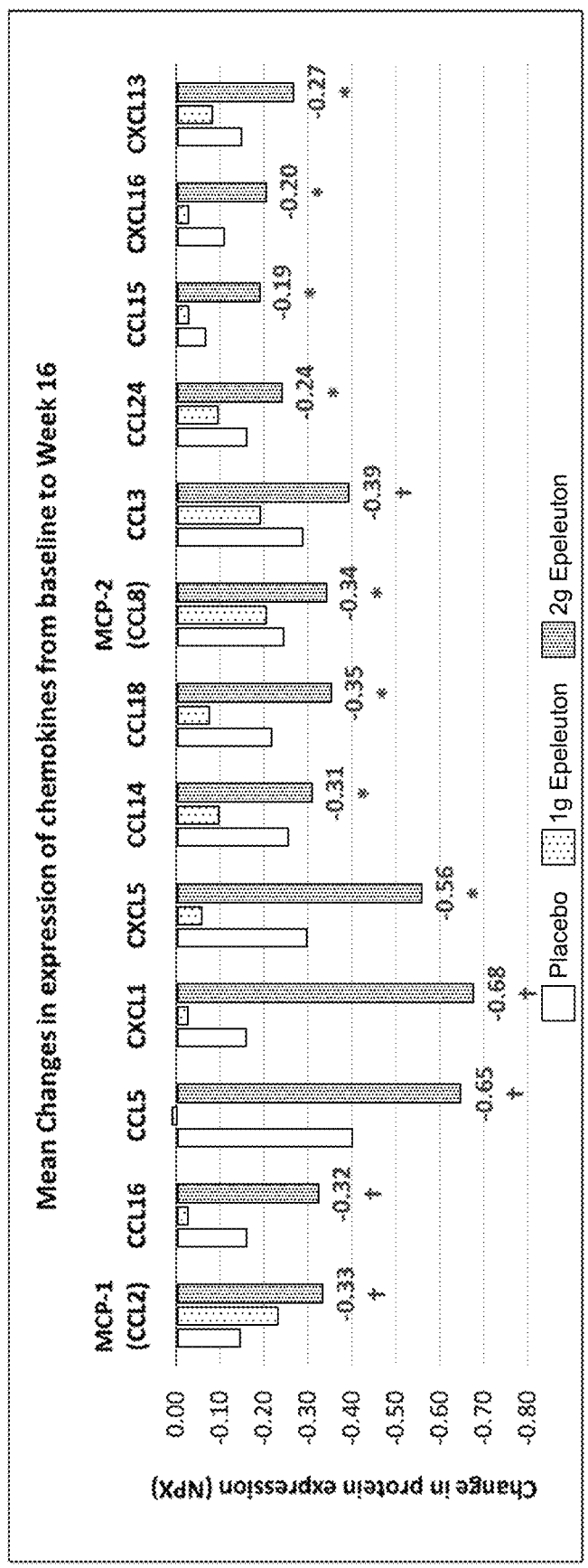
FIG. 34 are plots depicting the changes in chemokines in patients administered DS102 and placebo.

The administration of DS102 also decreased the expression of multiple circulating chemokines as shown in FIG. 34. Chemokines are important drivers of the chronic inflammation of atherosclerosis.

Figure 35:
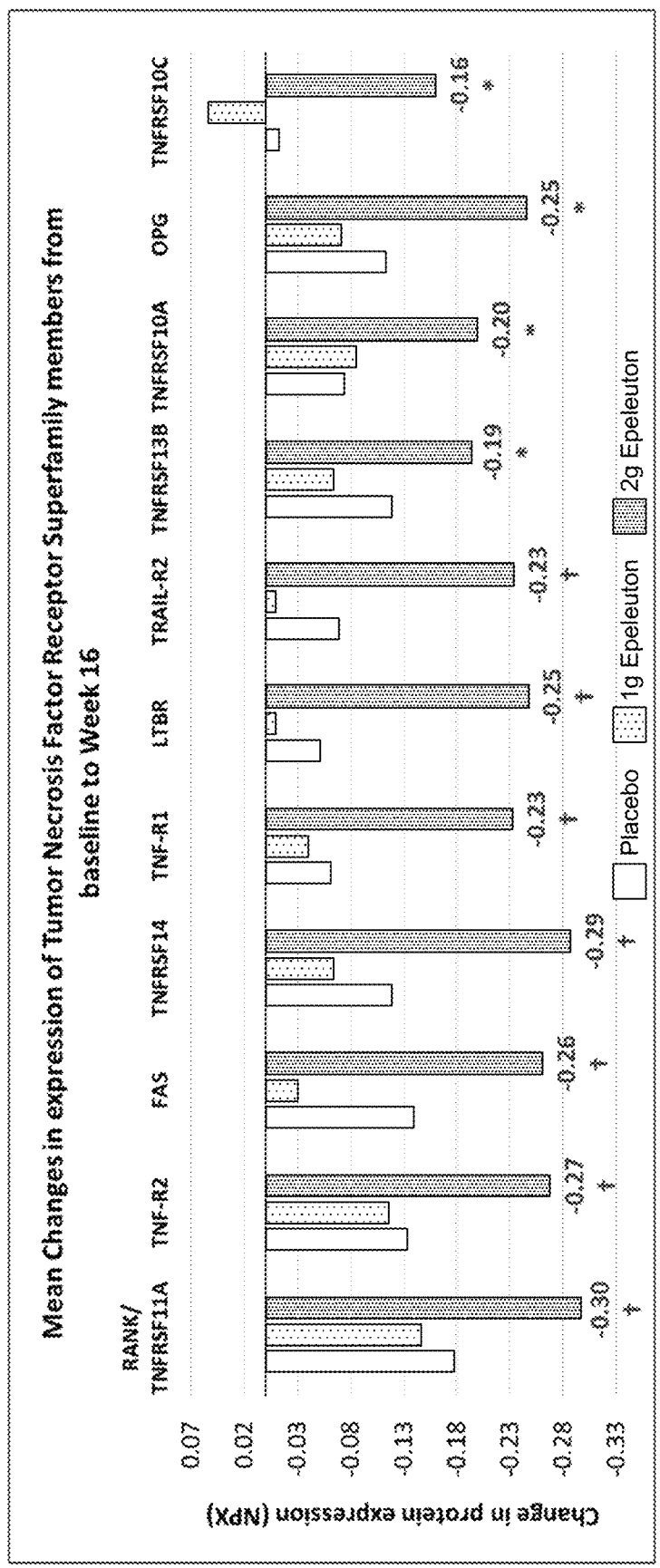
FIG. 35 are plots depicting the changes in tumor necrosis factor receptor superfamily members in patients administered DS102 and placebo.

The administration of DS102 also decreased the expression of multiple tumor necrosis factor receptor superfamily members as shown in FIG. 35. Tumor necrosis factor receptor superfamily members are implicated in inflammation and atherosclerosis.

DS102 was also proven to be safe and well tolerated, with no observed safety and tolerance differences as compared to placebo. There was no drug related serious adverse events (SAEs) and a low incidence in adverse events (AEs), which was consistent across all treatment groups. Most AEs were mild to moderate as well as transient and no patients experienced an AEs that lead to treatment discontinuation. The safety profile across each treatment group is shown in Table 23.

TABLE 23

Safety Profile for Study Groups

| Patients, n (%) | 2 g DS10 (n = 30) | 1 g DS102 (n = 32) | Placebo (n = 31) |
|---|---|---|---|
| ≥1 AE | 15 (50.0) | 19 (59.4) | 17 (54.8) |
| ≥1 AE related to study drug | 3 (10.0) | 2 (6.3) | 4 (12.9) |
| ≥1 SAE | 1 (3.3) | 0 | 1 (3.2) |
| AEs leading to treatment discontinuation | 0 | 0 | 1 (3.2) |
| SAEs related to drug study | 0 | 0 | 0 |
| Death | 0 | 0 | 0 |

Figure 36A:
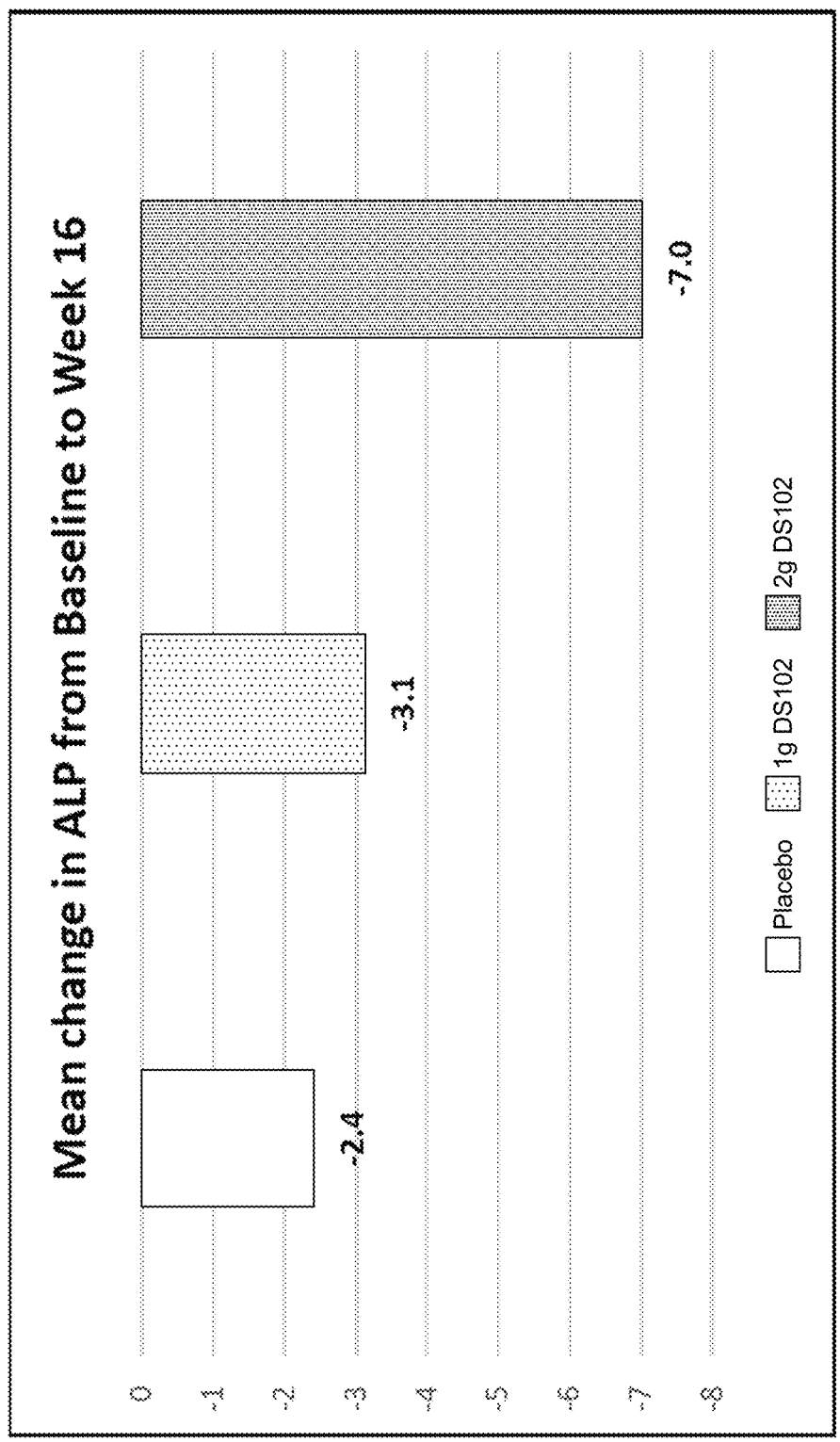
FIGS. 36A and 36B are plots depicting the reduction in ALP levels in patients administered DS102 and placebo.
Figure 36B:
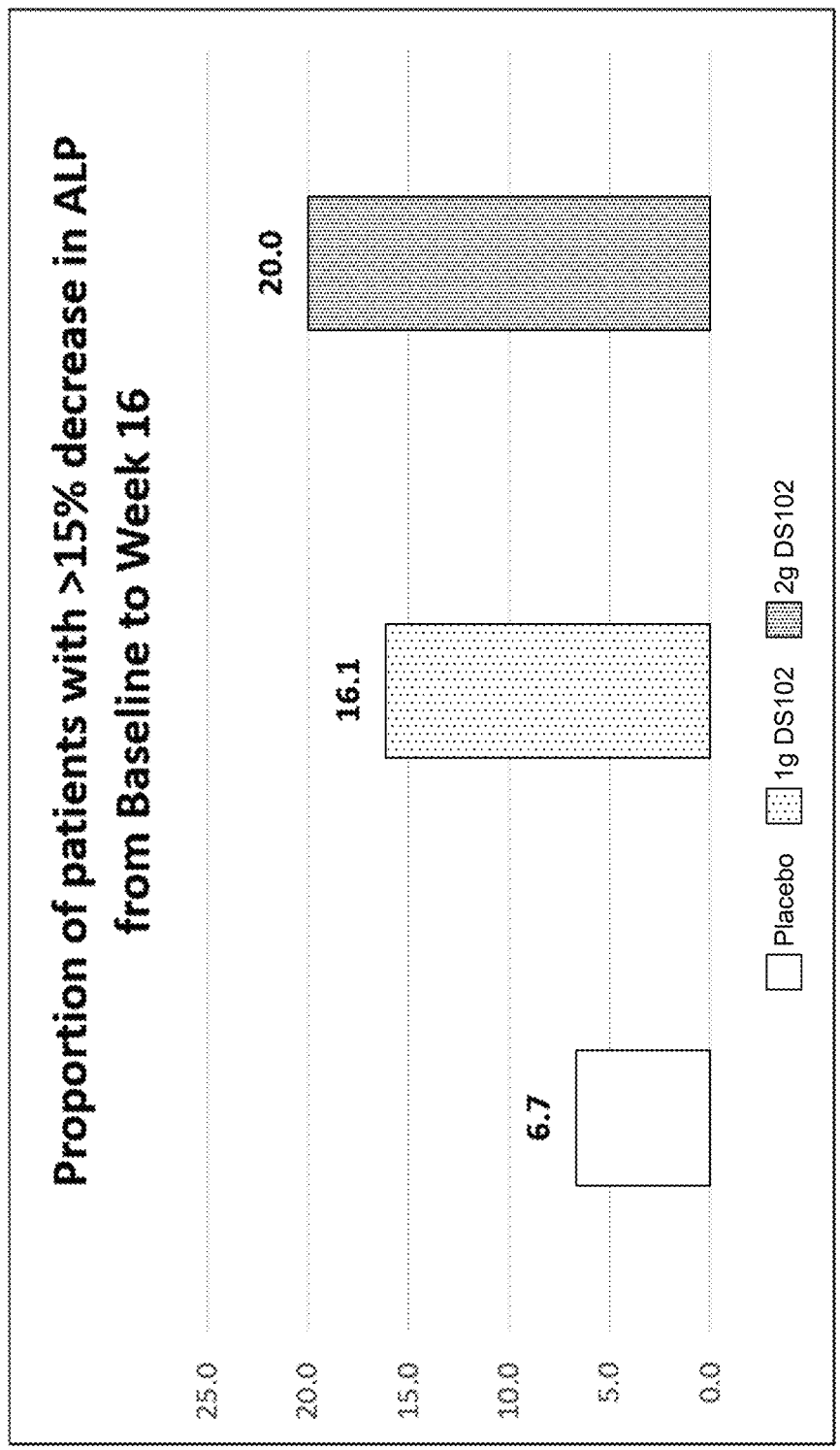

DS102 was also evaluated for potential efficacy in improving the related indications, primary biliary cirrhosis (PBC) and primary sclerosing cholangitis (PSC) as shown in FIGS. 36A and 36B. Importantly, administration of 2 g of DS102 reduced alkaline phosphate (ALP) as well as multiple markers for liver fibrosis suggesting that DS102 will also be effective in treating PBC and PSC.

Figure 37:
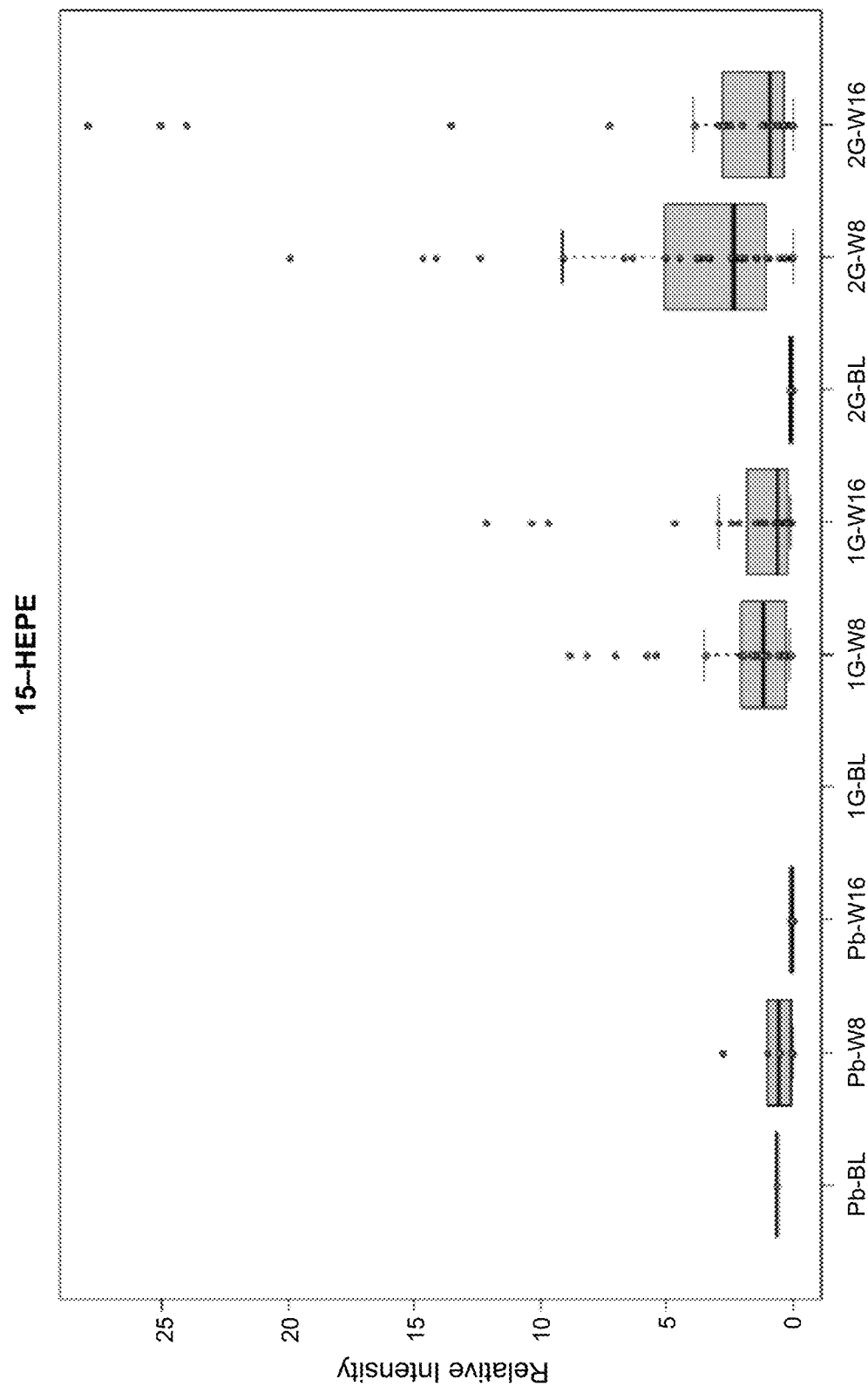
FIG. 37 is a boxplot of 15-HEPE ethyl ester trough plasma relative concentrations.

FIG. 37 is a boxplot of 15-HEPE ethyl ester (EE) trough plasma relative concentrations, which indicates that there was a higher systematic exposure in the DS102 treatment group at Weeks 8 and 16 as expected.

1.12 Summary

Overall, these results indicate that DS102 targets multiple stages of NASH pathology by significantly reducing metabolic load and improving insulin sensitivity. The administration DS102 also improved patient's lipid profiles by reversing the lipid accumulation levels associated with NASH. Specifically, those patients administered DS102 exhibited a reduction the accumulation of the hepatotoxic lipid levels to include total cholesterol, non-HDL cholesterol, RLP cholesterol, triglycerides, diglycerides, and VLDL-C as well as an increase of glycerophospholipid levels. These effects are significant as patients diagnosed with NASH are characterized by high total cholesterol, triglyceride, diglyceride, and VLDL-C levels and low glycerophospholipid and omega-3 PUFA levels. Additionally, changes to multiple lipids are expected to confer a reduction of cardiovascular risk and improvement of multiple aspects of metabolic syndrome.

The results also suggested that there is a dose dependent effect in favor of administration 2 g or higher of DS102 with large and statistically significant improvements as compared to placebo.

In conclusion, DS102 is well suited as either monotherapy or part of combination therapy for treating NASH and is contemplated to reduce cardiovascular risk, including in patients diagnosed with NASH or cardiometabolic diseases including metabolic syndrome.

Example 5

A 26 Week Toxicity Study of 15(S)-HEPE EE by Oral Gavage in Rats with a 4 Week Recovery Period The objectives of this study were to determine (1) the potential toxicity of 15(S)-HEPE EE, an omega-3 fatty acid used in the treatment of hepatic and pulmonary diseases, when given by oral gavage for 26 weeks to rats and to evaluate the potential reversibility of any findings; and (2) the toxicokinetic characteristics of 15(S)-HEPE EE.

1.1 Study Design

The test and control items were administered to the appropriate animals by once daily oral gavage 7 days a week for a minimum of 26 weeks. The volume for each animal was based on the most recent body weight measurements. The doses were given using a syringe with attached gavage cannula. The first day of dosing was designated as Day 1. The dosing formulations were removed from the refrigerator and stirred for at least 30 minutes before dosing. The dosing formulations were also stirred continuously during dosing.

Due to the onset of clinical signs, including hunched posture, erect fur and abnormal gait and body weight loss, animals 3206M, 3515F and 3703F were given a dosing holiday from Day 45 and remaining Group 3 animals were given a dosing holiday from Day 48. Animals will start dosing at the lower dose level (3000 mg/kg/day) from Day 64. The following tables illustrate the treatments (Table 23) and animal groupings (Table 24) that were used in the study.

TABLE 24

Treatment Chart

| Group No. | Treatment | Dose Level (mg/kg/day) | Dose Volume (mL/kg) | Dose Concentration (mg/mL) | Adjusted Dose Concentration (mg/mL) | Number of Animals |||||| 
|---|---|---|---|---|---|---|---|---|---|---|---|
| | | | | | | Main Study || Recovery || Toxicokinetic ||
| | | | | | | M | F | M | F | M | F |
| 1 | Control | 0 | 10 | 0 | 0 | 15 | 15 | 5 | 5 | 3 | 3 |
| 2 | 15(S)-HEPE EE | 2000 | 10 | 200 | 206$^a$/204$^c$ | 15 | 15 | 5 | 5 | 9 | 9 |
| 3 | 15(S)-HEPE EE | 6000$^a$ | 10 | 600 | 618$^b$ | 15 | 15 | 5 | 5 | 9 | 9 |
| 4 | 15(S)-HEPE EE | 3000$^a$ | 10 | 300 | 309$^b$/306$^c$ | 15 | 15 | 5 | 5 | 9 | 9 |

$^a$Due to the onset of clinical signs, including hunched posture, erect fur and abnormal gait and body weight loss, animals were given a dosing holiday from Day 48. Animals will start dosing at the lower dose level (3000 mg/kg/day) from day 64.
$^b$Adjusted concentration for batches 2540M-1801 and 2540M-1802.
$^c$Adjusted concentration for batches 2540M/1901 and 2540M/1902.

TABLE 25

| | Animal Groupings | | | | | |
|---|---|---|---|---|---|---|
| | Main Study | | Recovery | | Toxicokinetic | |
| Group No. | Males | Females | Males | Females | Males | Females |
| 1 | 1001-1015 | 1501-1515 | 1101-1105 | 1601-1605 | 1201-1203 | 1701-1703 |
| 2 | 2001-2015 | 2501-2515 | 2101-2105 | 2601-2605 | 2201-2209 | 2701-2709 |
| 3 | 3001-3015 | 3501-3515 | 3101-3105 | 3601-3605 | 3201-3209 | 3701-3709 |

Spare animals will be numbered 4001M, 4002M, 4002M and 4501F, 4502F.

Recovery Period: On completion of the dosing period, the designated recovery animals were retained for a minimum 4 week recovery period.

Justification of Route and Dosage Levels: The oral route of administration was selected for this study as this route is the intended route of human dosing. A previous 26-week oral toxicity in rats dosed once daily showed no adverse effects at the highest dose tested (1 mg/kg/day). See Warren, H (2017). A 26 Week Study of 15(S)-HEPE EE by Oral (Gavage) in Rats with a 4 Week Recovery Period. Charles River Study No. 529123. Given that no dose-limiting toxicity was seen on that study, an additional 28-day dose ranging study determined an oral maximum tolerated dose (MTD) of 6 g/kg/day. See Murie, E (ongoing). A Pilot 28-Day Study of DS102 by Oral Gavage in Rats. Charles River Study No. 506611. This current study was conducted to evaluate the chronic toxicity potential of 15(S)-HEPE EE (DS102) at this MTD to comply with ICH M3 (R2). See ICH Harmonised Tripartite Guideline M3 (R2). *Nonclinical Safety Studies for the Conduct of Human Clinical Trials and Marketing Authorisation for Pharmaceuticals.*

1.2 In-Life Procedures, Observations, and Measurements

The in-life procedures, observations, and measurements were performed for all main study and recovery animals. Toxicokinetic animals were weighed and had clinical observations recorded at the same timepoints as the main study animals.

Mortality/moribundity checks were made daily. Animals were observed for general health/mortality and moribundity. Animals were not removed from the cage during observation, unless necessary for identification or confirmation of possible findings.

Clinical Observations:

Cage side observations were made daily. Animals were not removed from the cage during observation, unless for identification or confirmation of possible findings.

Detailed clinical observations were made weekly. Animals were removed from the cage for examination.

Post-dose observations were made regularly throughout the day. All animals were examined for reaction to treatment. The onset, intensity, and duration of these signs were recorded; particular attention was paid to the animals during and for the first hour after dosing.

Body weight measurements were made twice during the pretreatment period; once daily during the dosing period; and twice weekly during the recovery period. Animals were individually weighed. A weight was recorded on the first day of scheduled necropsy (for main and recovery animals only).

Food consumption was quantitatively measure weekly, beginning at week 1 through the dosing and recovery periods.

Water consumption was made regularly throughout the study by visual inspection of the water bottles.

Ophthalmic examinations were performed using an indirect ophthalmoscope after the application of a mydriatic agent (1% Tropicamide, Mydriacy). During pretreatment, all main study and recovery animals were examined. During weeks 13 and 26, main study animals (control and high dose) were examined. During week 30, all recovery animals were examined.

1.3 Laboratory Evaluations

Clinical Pathology

Sample Collection: Blood was collected via the tail vein unless immediately prior to necropsy, when blood was collected from the orbital sinus under non-recoverable isoflurane anesthesia. Blood was collected in ascending animal order unless samples were collected prior to necropsy where the order of euthanasia was followed. Additional blood samples were obtained (e.g. due to clotting of non-serum samples) if permissible sampling frequency and blood volume were not exceeded. After collection, samples were transferred to the appropriate laboratory for processing. Samples were collected according to the following table.

TABLE 26

Samples for Clinical Pathology Evaluation

| Group Nos. | Time Point | Haematology | Coagulation | Clinical Chemistry | Urinalysis |
|---|---|---|---|---|---|
| Main Study and Recovery animals | Week 26 | — | — | — | X |
| Recovery | Day 183 | X | X | X | — |
| Main Study | Immediately Prior to Necropsy | X | X | X | — |
| Recovery animals | Week 30 | — | — | — | X |
| | Immediately Prior to Necropsy | X | X | X | — |
| Unscheduled euthanasia (when possible) | Before euthanasia | X | X | X | — |

X = sample to be collected, — = not applicable

Hematology: A 0.5 mL blood sample was collected using the anticoagulant $K_2$EDTA. Blood smears were labelled, stained, and stored. The blood smears were analyzed according to the following parameters.

TABLE 27

Hematology Parameters

| | |
|---|---|
| Red blood cell count | White blood cell count |
| Haemoglobin concentration | Neutrophil count (absolute) |
| Haematocrit | Lymphocyte count (absolute) |

TABLE 27-continued

Hematology Parameters

| | |
|---|---|
| Mean corpuscular volume | Monocyte count (absolute) |
| Red Blood Cell Distribution Width | Eosinophil count (absolute) |
| Mean corpuscular haemoglobin | Basiphil count (absolute) |
| Reticulocyte count (absolute) | Large unstained cells(absolute) |
| Platelet count | |

Coagulation: A 0.5 mL blood sample was collected using the anticoagulant 3.8% (w/v) trisodium citrate for processing to plasma. To assess coagulation the following coagulation parameters were measured.

TABLE 28

Coagulation Parameters

| | |
|---|---|
| Activated partial thromboplastin time | Prothrombin time |
| Fibinogen | Sample Quality |

Clinical Chemistry: A 0.7 mL blood sample was collected using the anticoagulant lithium heparin for processing to plasma. To assess the clinical chemistry the following parameters were measured:

TABLE 29

Clinical Chemistry Parameters

| | |
|---|---|
| Alamine aminotransferase | Total protein |
| Aspartate aminotransferase | Albumin |
| Alkaline phosphatase | Globulin |
| Gamma-glutamyltransferase | Albumin/globulin ratio |
| Creatine Kinase | Glucose |
| Total bilirubin[a] | Cholesterol |
| Urea | Triglycerides |
| Creatinine | Sodium |
| Calcium | Potassium |
| Phosphate | Cloride |
| | Sample Quality |

[a]When total bilirubin is >8.55 µmol/L, indirect and direct bilirubin will also be measured Urinalysis: Urine was collected from animals over a period of 6 hours (+/−30 min) with the absence of food and the presence of water. After collection, samples were transferred to the appropriate laboratory for processing. To assess the urinalysis, the following parameters were measured:

TABLE 30

Urinalysis Parameters

| | |
|---|---|
| Colour | Protein |
| Appearance/Clarity | Glucose |
| Specific gravity | Bilirubin |
| Volume | Ketones |
| pH | Blood |

Bone Marrow Smear Analysis: Bone marrow was collected from all animals and preserved in 10% neutral buffered formalin.

Bioanalysis and Toxicokinetic Evaluation

Bioanalytic Sample Collection: A 0.5 mL blood sample was collected using the anticoagulant K₂EDTA via the jugular vein (or the tail vein if the jugular was not assessable) using sterile needles and disposable syringes. At completion of the blood collection schedule, the toxicokinetic animals were euthanized, and the carcasses were discarded without examination. Samples were collected according to the following table.

TABLE 31

Toxicokinetic Evaluation Sample Collection Schedule

| Group No. | Animal Numbers | No. of animals | Sample Collection Time Points (Time Postdose) on Day 1 and Week 26 | | | | | |
|---|---|---|---|---|---|---|---|---|
| | | | 0 h[a] | 1 h | 2 h | 4 h | 8 h | 24 h |
| 1 | 1201-1203 1701-1703 | 3M/3F | — | — | — | X | — | — |
| 2 | 2201-2203 2701-2703 | | X | — | — | X | — | — |
| | 2204-2206 2704-2706 | | — | X | — | — | X | — |
| | 2207-2209 2707-2709 | | — | — | X | — | — | X |
| 3 | 3201-3203 3701-3703[b] | | X | — | — | X | — | — |
| | 3204-3206 3704-3706[b] | | — | X | — | — | X | — |
| | 3207-3209 3707-3709[b] | | — | — | X | — | — | X |

X = sample to be collected, — = not applicable.
[a]Sample will be collected before dosing
[b]Animal 3702F had Day 1 samples collected, however on Day 44 this animal was euthanised for humane reasons. Extra samples will be collected at Week 26 from animals 3707F (0 h[a] collection) and 3704F (4 h collection) to cover the missing timepoints for animal 3702F.

Bioanalytical Sample Processing: Samples were mixed gently and kept on crushed wet ice until centrifugation within 60 minutes of blood withdrawal. The samples were centrifuged at 1500 g for 10 minutes at 4° C. The resultant plasma was separated, transferred to uniquely labelled clear polypropylene tubes, and frozen as soon as possible over dry ice or in a freezer set to maintain −20° C.

Bioanalytical Sample Analysis: Plasma samples were analyzed for concentration of unesterified and total HEPE using validated analytical procedures. The following was determined:

a) Unesterified (HEPE occurring in plasma as the free fatty acid or bound to plasma albumin).

b) Total (quantifies unesterified HEPE and esterified HEPE (e.g. as triglycerides, cholesterol esters)) concentration at each sample time.

Incurred sample reanalysis (ISR) for unesterified HEPE was performed for this study as per the appropriate Standard Operating Procedure(s) of the bioanalytical laboratory. ISR has been successfully performed for the determination of total HEPE in rat plasma samples, using the analytical procedure referenced above, during Test Facility Study No. 527943 and is not required to be repeated in this study.

Any residual/retained bioanalytical samples were maintained for a minimum of 6 months following issue of the Draft Report after which samples were discarded. Alternatively, residual/retained samples were discarded prior to the 6 month period should the issue of the Final Report occur prior to the end of the 6 month retention period. An earlier discard of these residual/retained samples may also be requested and authorized by the Study Director.

Toxicokinetic Evaluation: Toxicokinetic parameters were estimated using Phoenix pharmacokinetic software. A non-compartmental approach consistent with the oral route of administration was used for parameter estimation. All parameters were generated from total free acid and unbound free acid of 15(S)-HEPE EE composition concentrations in plasma from Day 1 and Week 26 whenever practical. The following parameters were estimated.

TABLE 32

Parameters to be Estimated

| Parameter | Description of Parameter |
|---|---|
| Tmax | The time after dosing at which the maximum concentration was observed. |
| Cmax | The maximum observed concentration measured after dosing. |
| Cmax/D | The Cmax divided by the dose administered. |
| AUC(0-t) | The area under the concentration versus time curve from the start of dose administration to the last observed quantifiable concentration using the linear or linear/log trapezoidal method. |
| AITC(0-t)/D | The AUC(0-t) divided by the dose administered. |

Partial AUCs (between any given sample times) may be derived and reported to aid interpretation. Descriptive statistics (standard error for Cmax and AUC(0-t)) for appropriate grouping and sorting variables were generated using Phoenix. TK table and graphs were also generated.

1.4 Terminal Procedures

The following table summarizes the terminal procedures used in the study.

TABLE 33

Terminal Procedures for Main Study Animals

| Group Number | Number M | F | Scheduled Euthanasia Day | Necropsy Procedures Necropsy | Tissue Collection[a] | Organ Weights[a] | Histology[a] | Histopathology[a] |
|---|---|---|---|---|---|---|---|---|
| 1 | 15 | 15 | 183/184 | X | X | X | Full Tissue | Full Tissue |
| 2 | 15 | 15 | | | | | Gross Lesions Target Tissues[b] | Gross Lesions Target Tissues[b] |
| 3 | 15 | 15 | | | | | Full Tissue | Full Tissue |
| 1 | 5 | 5 | 211 | | | | Gross Lesions Target Tissues[b] | Gross Lesions Target Tissues[b] |
| 2 | 5 | 5 | | | | | Gross Lesions Target Tissues[b] | Gross Lesions Target Tissues[b] |
| 3 | 5 | 5 | | | | | Gross Lesions Target Tissues[b] | Gross Lesions Target Tissues[b] |
| Unscheduled Deaths | | | | X | X | — | Full Tissue | Full Tissue |

X = procedure to be conducted, — = not applicable
[a]See Tissue Collection and Preservation table for listing of tissues.
[b]Target tissues are liver (male and female), thyroid (male and female), kidney (female only), bone marrow sternum (male only).

Unscheduled Deaths: If a main study or recovery animal died during the study, a necropsy was performed and specified tissues were saved. If necessary, the animals were refrigerated to minimize autolysis. Main study or recovery animals were euthanized for humane reasons as per Test Facility SOPs. The body weight was recorded and samples for evaluation of clinical pathology parameters, were obtained if possible. These animals were necropsied, and specified tissues were retained. If necessary, the animals were refrigerated to minimize autolysis. Toxicokinetic animals that died during the study or were euthanized for humane reasons were subjected to a limited necropsy examination. The examination consisted of an evaluation of the organs and tissues in the thoracic, abdominal, and pelvic cavities, with no tissues retained. During the limited necropsy examination, special attention was directed to evidence of possible gavage trauma. The body weight was recorded and samples for evaluation of toxicokinetic analysis were collected.

Scheduled Euthanasia: Main study and recovery animals that survived until scheduled euthanasia were euthanized by exposing the animal to a rising level of carbon dioxide; a terminal body weight was recorded and the animal was subsequently exsanguinated. When possible, the animals were euthanized in a rotating order across dose groups such that similar numbers of animals from each group, including controls were necropsied throughout the day. Animals were not fasted before their scheduled necropsy. Toxicokinetic animals that survived until scheduled euthanasia were euthanized by approved methods. No necropsies were performed and no tissues were collected.

Necropsy: Main study and recovery animals were subjected to a complete necropsy examination, which included evaluation of the carcass and musculoskeletal system; all external surfaces and orifices; cranial cavity and external surfaces of the brain; and thoracic, abdominal, and pelvic cavities with their associated organs and tissues. Necropsy procedures were performed by qualified personnel with appropriate training and experience in animal anatomy and gross pathology.

Organ Weights: The organs identified for weighing in the Tissues Collection and Preservation table were weighed at necropsy (unless otherwise specified) for all scheduled euthanasia animals. Organ weights were not recorded for animals found dead or euthanized in poor condition or in extremis. Paired organs were weighed together. In the event of gross abnormalities, in addition to the combined weight, the weight of each organ of a pair was taken and entered as a tissue comment. Terminal body and brain weights were used for organ weight analysis.

Tissue Collection and Preservation: Tissues collected according to the table below were preserved in 10% neutral buffered formalin.

TABLE 34

Tissue Collection and Preservation Table

| Organ | Weigh | Macroscopic Evaluation and Collection | Histology Processing | Microscopic Evaluation |
|---|---|---|---|---|
| Animal ID | — | X | — | — |
| Artery, aorta | — | X | X | X |
| Body cavity, nasal | — | X | — | — |
| Bone marrow, sternum | — | X | X | X |
| Bone marrow smear | — | X[a] | — | — |
| Bone, femur | — | X (1) | X (1) | X (1) |
| Bone, sternum | — | X | X | X |
| Brain | X | X | X | X |
| Cervix | — | X | X | X |
| Epididymis | X (2) | X (2)[b] | X (2) | X (2) |
| Esophagus | — | X | X | X |
| Eye | — | X (2)[b] | X (2) | X (2) |
| Gland, adrenal | X (2) | X (2) | X (2) | X (2) |
| Gland, clitoral | — | X (2) | — | — |
| Gland, lacrimal | — | X (2, extra-orbital) | — | — |
| Gland, Harderian | — | X (2) | X (1) | X (1) |
| Gland, mammary | — | X | X | X |
| Gland, parathyroid | — | X (2) | X (2) | X (2) |
| Gland, pituitary | X | X | X | X |
| Gland, preputial | — | X (2) | — | — |
| Gland, prostate | X | X | X | X |
| Gland, salivary, submandibular | — | X (2) | X (1) | X (1) |
| Gland, salivary, sublingual | — | X (2) | — | — |
| Gland, salivary, perotid | — | X (2) | — | — |
| Gland, seminal vesicle | — | X (2) | X (2) | X (2) |
| Gland, thyroid/Gland parathyroid | X (2)[d] | — | — | — |
| Gland, thyroid | — | X (2) | X (2) | X (2) |
| Gland, Zymbal's | — | X (2) | — | — |
| Gut-associated lymphoid tissue[c] | — | X | X | X |
| Heart | X | X | X | X |
| Joint, femorotibial | — | X (1) | X (1) | X (1) |
| Kidney | X (2) | X (2) | X (2) | X (2) |
| Large intestine, cecum | — | X | X | X |
| Large intestine, colon | — | X | X | X |
| Large intestine, rectum | — | X | X | X |
| Larynx | — | X | — | — |
| Liver | X | X | X | X |
| Lung | — | X | X | X |
| Lymph node, mandibular | — | X (2) | X (1) | X (1) |
| Lymph node, mesenteric | — | X | X | X |
| Muscle, skeletal | — | X | X | X |
| Nasopharynx | — | X | — | — |
| Nerve, optic | — | X (2)[d] | X (2) | X (2) |
| Nerve, sciatic | — | X (2) | X (1) | X (1) |
| Ovary | X (2) | X (2) | X (2) | X (2) |
| Oviduct | — | X (2) | — | — |
| Pancreas | — | X | X | X |
| Skin | — | X | X | X |
| Small intestine, duodenum | — | X | X | X |
| Small intestine, ileum | — | X | X | X |
| Small intestine, jejunum | — | X | X | X |
| Spinal cord | — | X | X | X |
| Spleen | X | X | X | X |
| Stomach | — | X | X | X |
| Testis | X (2) | X (2) | X (2) | X (2) |
| Thymus | X | X | X | X |
| Tongue | — | X | X | X |
| Trachea | — | X | X | X |
| Ureter | — | X (2) | — | — |
| Urinary bladder | — | X | X | X |
| Uterus/Cervix | X | — | — | — |
| Uterus | — | X | X | X |
| Vagina | — | X | X | X |

X = procedure to be conducted. — = Not applicable. (1) = one side. (2) = both sides.

Macroscopic abnormalities in the organs listed and in other organs will be sampled at necropsy, processed for histology and examined microscopically.

[a] Two bone marrow smears will be collected from the femur at scheduled and unscheduled necropsies (for possible examination). Smears will not be collected from animals that are found dead or from animals that were euthanised moribund and then stored in the refrigerator prior to necropsy. Bone marrow smears are allows to air dry and are not fixed in formalin.

[b] Eyes and optic nerves are preserved in Davidson's fixative. Testis and epididymides are preserved in modified Davidson's fixative.

[c] From small intestine: Peyer's patch or solitary lymphoid follicle.

[d] Weighed after fixation.

1.5 Dose Formulation and Analysis

Control Item: The control item for this study was 0.5% HPMC in Milli-Q water. The control item was prepared as required and stored in a refrigerator set to maintain 4° C. when not in use. The prepared control item was removed from the refrigerator and stirred for at least 30 minutes before dosing. The control item was also stirred continuously during dosing.

Test Item: The test item for this study was DS102 or 15(S)-HEPE EE. Test item dosing formulations were prepared based on a method established at the test facility at appropriate concentrations to meet dosage level requirements. The dosing formulations were prepared weekly and stored in a refrigerator set to maintain 4° C. and dispensed daily. The dosing formulations were removed from the refrigerator and stirred for at least 30 minutes before dosing. The dosing formulation were also be stirred continuously during dosing.

Sample Collection and Analysis

The analyzed samples were submitted within the established stability period. All analyzed samples were transferred at ambient temperature to the analytical laboratory at the test facility. Any residual/retained analytical samples were maintained for a minimum of 6 months following issue of the draft report after which samples will be discarded. Alternatively, residual/retained samples were discarded prior to the 6 month period in the situation that the issue of the final report occurred prior to the end of the 6 month retention period. An earlier discard of these residual/retained samples may also be authorized by the study director after consultation with the sponsor. Does formulation samples were collected for analysis as indicated in the following table. Additional samples may be collected and analyzed at the discretion of the study director.

TABLE 35

Dose Formulation Sample Collection Schedule

| Interval | Concentration | Homogeneity | Stability |
|---|---|---|---|
| Day 1 | All groups | Groups 2-3[a] | N/A |
| Week 2 | All groups | Groups 2-3[a] | N/A |
| Week 10 | Group 3 | Group 3 | N/A |
| Week 13 | All groups | N/A | N/A |
| Week 14 | All groups | All groups[a] | N/A |
| Week 26 | All groups | N/A | N/A |

N/A = not applicable.
[a]The homogeneity results obtained from the top, middle and bottom for the Group 2 to 3 preparation will beaveraged and utilised as the concentration results.

Analytical Method

The analysis described below was performed by UPLC with UV detection using a validated analytical procedure.

Concentration Analysis:
  Sample for Analysis: Duplicate top, middle and bottom samples (duplicate middle only for control) were sent for analysis. Where concentration only is being assessed duplicate middle only samples were collected.
  Backup Samples: Triplicate top, middle and bottom samples (triplicate middle only for control), maintained at the test facility. Backup samples may be analyzed at the discretion of the study director. Where concentration only is being assessed triplicate middle only samples will be collected.
  Sampling Containers: Appropriately sized volumetric flasks.
  Sample Volume:
    Group 1: 0.5 mL into a 50 mL volumetric flask.
    Group 2: 0.25 mL into a 50 mL volumetric flask.
    Group 3: 0.25 mL into a 50 mL volumetric flask.
    The weight of all samples was recorded.
  Storage Conditions: Kept in a refrigerator set to maintain 4° C.
  Acceptance Criteria: The criteria for acceptability was mean sample concentration results within or equal to ±10% of theoretical concentration. For homogeneity, the criteria for acceptability was a relative standard deviation (RSD) of concentrations of 10% for each group.
  Stability Analysis: Stability analyses performed previously in conjunction with Test Facility Study No. 439414 demonstrated that the test item is stable in the vehicle when prepared and stored under the same conditions at concentrations bracketing those used in the present study. See Rogers, E (2018). Validation of an Ultra High-Performance Liquid Chromatographic Method for the Determination of 15(S) HEPE EE in oral (Gavage) Dosing Formulations. Charles River Study No. 439414. Stability data was retained in the study records for Test Facility Study No. 439414. Id.

1.6 Test System

Animals: The study used male and female Sprague Dawley rats purchased from Charles River UK Limited (Margate, Kent, UK). The target age at the initial dosing was 7-8 weeks. The target weight at the initial dosing was 175-300 g (males) and 120-250 g (females). Each animal was identified using a subcutaneously implanted electronic cylindrical, "glass-sealed" TROVAN microchip.

1.7 Husbandry

Housing: The animals were allowed to acclimate to the test facility rodent toxicology accommodation for a period of up to 3 weeks before the commencement of dosing. Animals were randomly assigned to groups. Males and females were randomized separately. Animals in poor health were not assigned to groups. Animals were housed 2 or 3 per cage by sex in appropriately sized suspended polycarbonate/polypropylene cages with stainless steel grid tops and solid bottoms. Sterilized white wood shavings were used as bedding material.

Environmental Conditions: The targeted conditions for animal room environment were as follows: temperature 19-23° C.; humidity 40-70%; ventilation a minimum of 10 air changes per hour; light cycle 12 hour light and 12 hour dark. Control of light, temperature, and humidity was automatically controlled and was continuously monitored and recorded.

Diet: SDS rat and mouse (modified) no. 1 diet SQC expanded was provided ad libitum. Water from a public supply was provided ad libitum from a water bottle. The water used by the test facility was analyzed at regular intervals for dissolved materials, heavy metals, pesticide residues, pH, nitrates and nitrites. Microbiological screening was also conducted.

Animal Enrichment: Animals were socially housed for psychological/environmental enrichment and were provided with items such as a device for hiding in and an object for chewing, except when interrupted by study procedures/activities.

Veterinary Care: Veterinary care was available throughout the course of the study and animals were examined by the veterinary staff as warranted by clinical signs or other changes. All veterinary examinations and recommended therapeutic treatments, if any, were documented in the study records.

1.8 Histology and Histopathology

Histology: Tissues identified in the Tissue Collection and Preservation table were embedded in paraffin, sectioned, mounted on glass slides, and stained with hematoxylin and eosin.

Histopathology: Histopathological evaluations were performed by a board-certified veterinary pathologist or a veterinary pathologist with training and experience in laboratory animal pathology. Microscopic examination was carried out for tissues from main study control and high dose animals, unscheduled deaths and gross lesions (including from the main study low dose group and recovery animals). If treatment effects were present in the main study high dose group, microscopic examination of target tissues from the main study low dose group and recovery animals were carried out after agreement with the Sponsor and Study Director by protocol amendment.

1.9 Computerized Systems

Computerized Systems: The follow table of computerized systems were available for use in the study:

TABLE 36

Critical Computerized Systems

| System Name | Description of Data Collected and/or Analysed |
|---|---|
| Dispense | Test item receipt, accountability and/or formulation activites |
| Provantis | Applicable In-life, clinical pathology and postmortem |
| Empower 3 | Chromatography Data Collecction and Processing (Formulation Analysis) |
| Analyst | Chromatography Data Collection (Bioanalysis) |
| Watson | Chromatography Processing (Bioanalysis) |
| Phoenix | Non-compartmental analysis and descriptive statistics (Toxicokinetic Evaluation) |
| In-house reporting software Nevis 2012 (using SAS) | Applicable In-life, clinical pathology and postmortem |
| Deviation Information Library | Deviations |
| Trend 963 Secure | Continuous temperature and humidity recording. Alarms for animal rooms, refrigerators, freezers and incubators. |
| Share Document Management System | Reporting |
| Docusign | Collection of Part 11 compliant signature |

1.10 Statistical Analysis

Data collected during the pre-dose period was tabulated, summarized and statistically analyzed. All statistical analysis was performed within the respective study phase, unless otherwise noted. Numerical data collected on scheduled occasions (with the exception of data from the toxicokinetic animals) was summarized and statistically analyzed as indicated below according to sex and occasion.

Constructed Variables: Body weight changes were calculated between each scheduled interval. Organ weight relative to body weight was calculated against the terminal body weight for scheduled intervals. Organ weight relative to brain weight was calculated against the brain weight for scheduled intervals.

Descriptive Statistical Analysis: Means, standard deviations (or % coefficient of variation or standard error, when deemed appropriate), percentages, numbers, and/or incidences will be reported as appropriate by dataset.

Inferential Statistical Analysis: All statistical analysis was conducted at the 5% significance level. All pairwise comparisons were conducted using two sided tests and were reported at the 1% and 5% levels, unless otherwise noted. The pairwise comparisons of interest are listed below:

Group 2 vs. Group 1

Group 3 vs. Group 1

Analysis were performed according to the matrix below when possible, but excluded any group with less than 3 observations.

TABLE 37

Statistical Matrix

| Variables for Inferential Analysis | Statistical Method Parametric/ Non-parametric |
|---|---|
| Body Weight | X |
| Body Weight Gains | X |
| Haematology Variables | X |
| Coagulation Variables | X |
| Clinical Chemistry Varibles | X |
| Urinalysis Variable | X |
| Organ Weights | X |
| Organ Weight relative to Body Weight | X |
| Organ Weight relative to Brain Weight | X |

Parametric/Non-parametric: Levene's Test was used to assess the homogeneity of group variances. The groups were compared using an overall one-way ANOVA F-test if Levene's test is not significant or the Kruskal-Wallis test was not significant. If the overall F-test or Kruskal-Wallis test was found to be significant, then pairwise comparisons were conducted using Dunnett's or Dunn's test, respectively.

1.11 Results

Figure 38A:
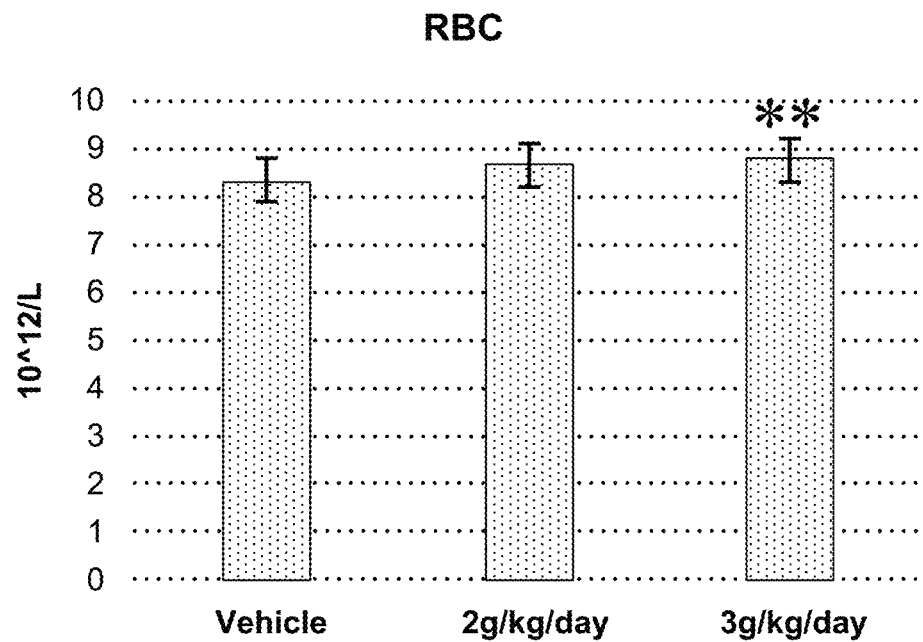
FIG. 38A-38C are bar graphs depicting mean change and standard deviation of red blood cell counts, red blood cell distribution width, and reticulocyte counts in rats administered 15(S)-HEPE EE and placebo, respectively.
Figure 38B:
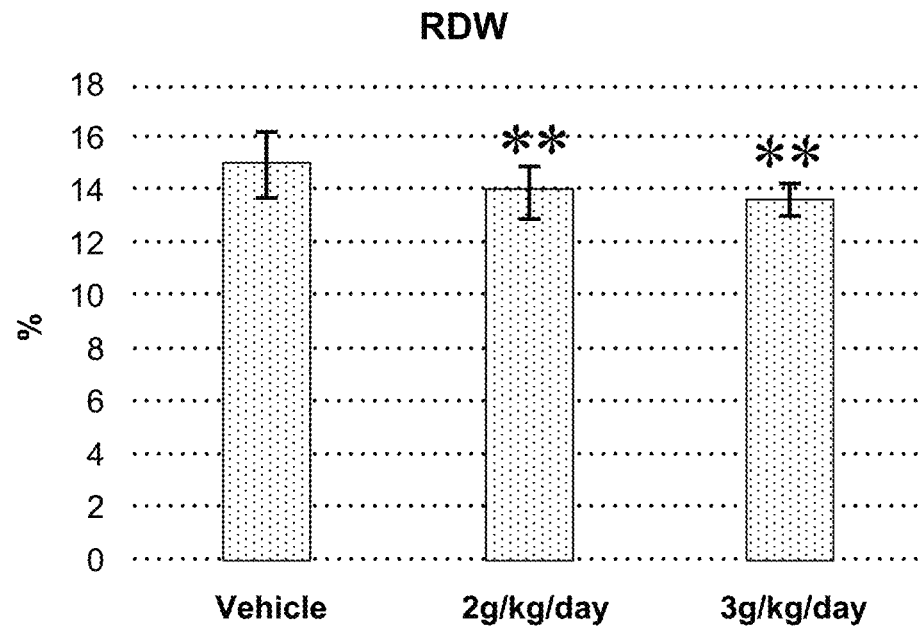
Figure 38C:
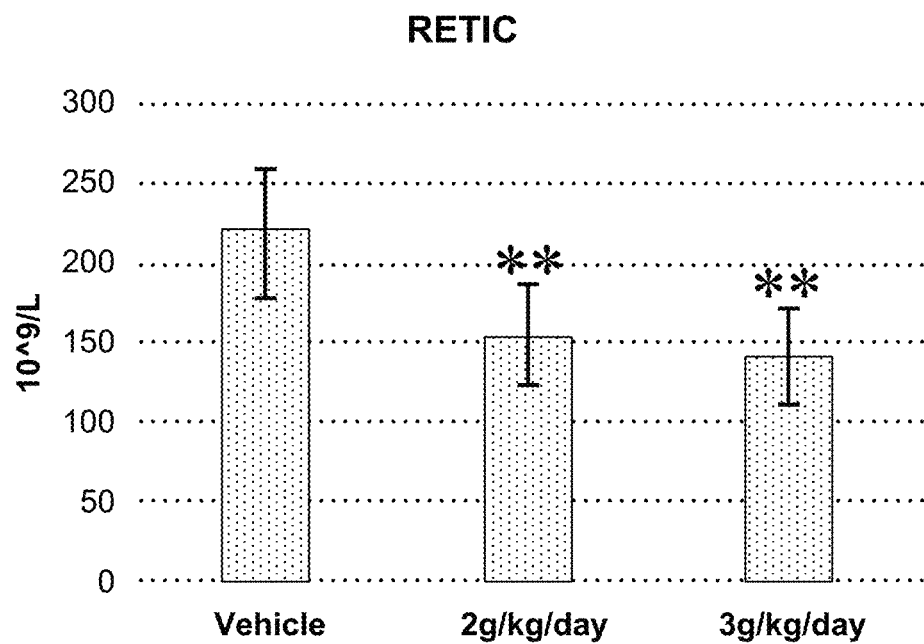

Change in red blood cell count, red blood cell distribution width, and reticulocyte count: FIG. 38A-38C shows change in red blood cell count (RBC), red blood cell distribution width (RDW), and reticulocyte count (RETIC) for rats administered 15(s)-HEPE EE or placebo. 15(S)-HEPE EE and placebo were administered once daily by oral gavage 7 days a week for a minimum of 26 weeks. The volume for each animal was based on the most recent body weight measurements. As noted in Table 38, the highest dose of 6 g/kg/day was not well tolerated and was replaced with a lower 3 g/kg/day.

TABLE 38

Change in RBC, RDW and RETIC in Rats administered 15(S)-HEPE EE

| STUDY | 26 week rat study (CRL509554) | | |
|---|---|---|---|
| 15 (S)-HEPE EE Dose (mg/kg/day) | 0 (vehicle) | 2000 | 6000/3000 |
| Red blood cell count (RBC) (10^12/L) | | | |
| Mean | 8.38 | 8.67 | 8.81** |
| (SD) | 0.42 | 0.41 | 0.42 |

TABLE 38-continued

Change in RBC, RDW and RETIC in Rats administered 15(S)-HEPE EE

| STUDY | 26 week rat study (CRL509554) | | |
|---|---|---|---|
| Red Cell Distribution Width (RDW) (%) | | | |
| Mean | 14.98 | 13.91** | 13.60** |
| (SD) | 1.23 | 0.96 | 0.57 |
| Reticulocyte count (RETIC) (10^9/L) | | | |
| Mean | 219.51 | 154.60* | 141.46** |
| (SD) | 40.41 | 32.31 | 30.57 |

Anova & Dunnett: * = p ≤ 0.05; ** = p ≤ 0.01
All presented values were observed in males
Highest dose of 6 g/kg/day was not well tolerated and was replaced with lower 3 g/kg/day dose Change in RBC: FIG. 38A and Table 38 show that administration of the 3 g/kg/day dose resulted in a significant increase in RBC compared to control.

Change in RDW: FIG. 38B and Table 38 show that administration of both the 2 g/kg/day and 3 g/kg/day doses resulted in a significant decrease in RDW compared to control.

Change in RETIC: FIG. 38C and Table 38 show that administration of both the 2 g/kg/day and 3 g/kg/day doses resulted in a significant decrease in RETIC compared to control.

These results suggest that 15-HEPE has therapeutic potential for a number of conditions that affect hemoglobin and red blood cells.

Figure 39A:
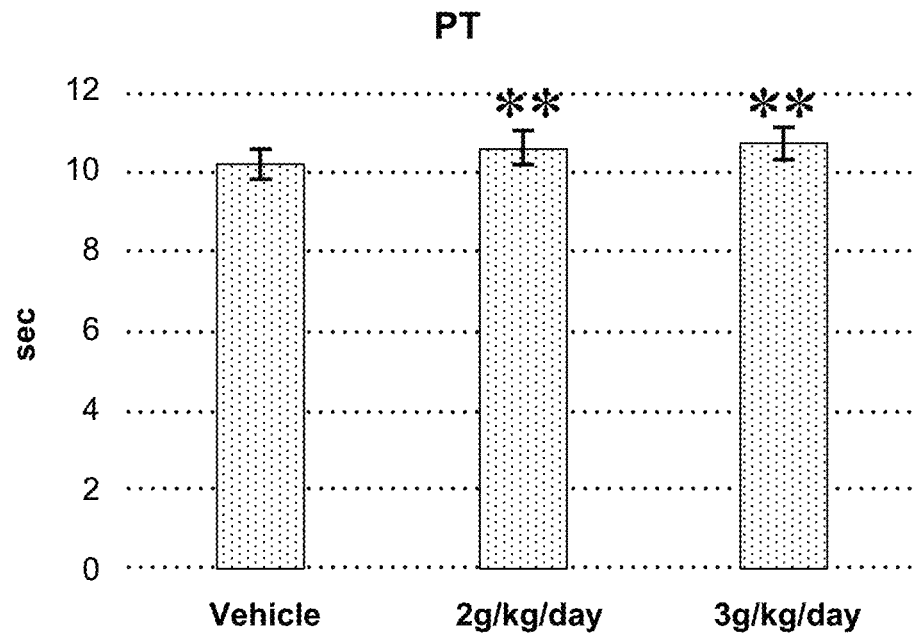
FIG. 39A-39C are bar graphs depicting mean change and standard deviation of prothrombin time, activated partial thromboplastin time, and fibrinogen concentration in rats administered 15(S)-HEPE EE and placebo, respectively.
Figure 39B:
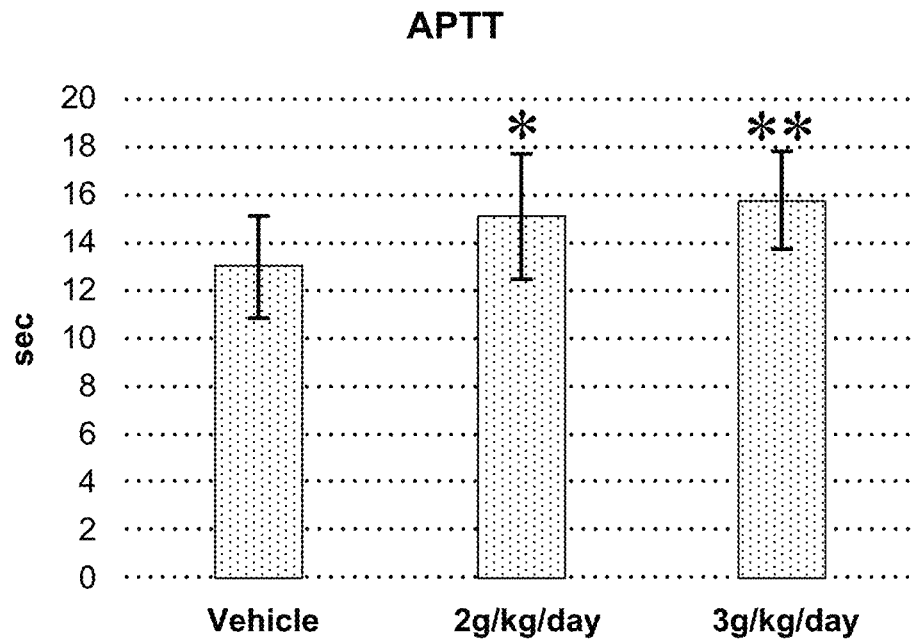
Figure 39C:
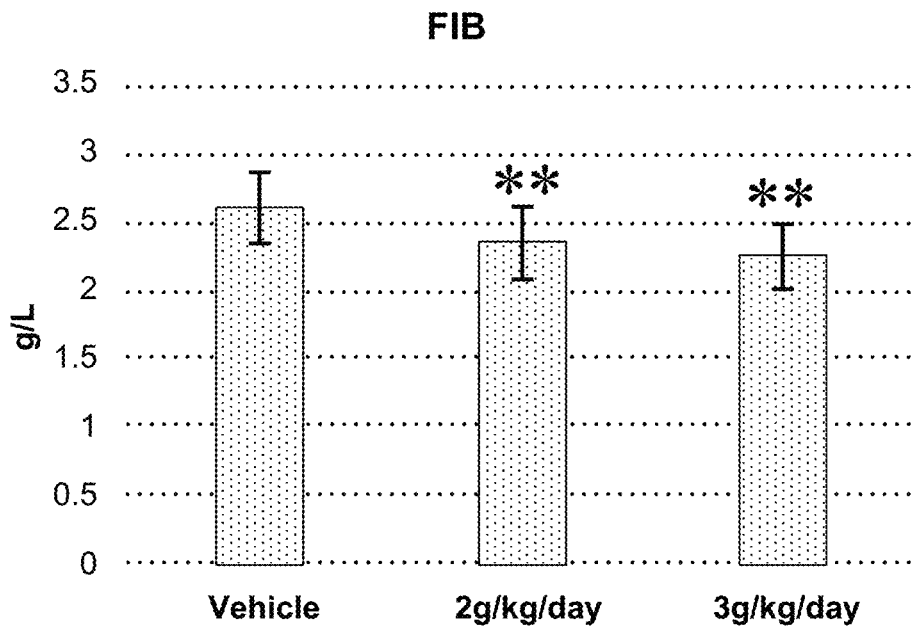

Change in prothrombin time, activated partial thromboplastin time, and fibrinogen concentration: FIG. 39A-39C shows change in prothrombin time (PT), activated partial thromboplastin time (APTT), and fibrinogen (FIB) concentration for rats administered 15(s)-HEPE EE or placebo. 15(S)-HEPE EE and placebo were administered once daily by oral gavage 7 days a week for a minimum of 26 weeks. The volume for each animal was based on the most recent body weight measurements. As noted in Table 39, the highest dose of 6 g/kg/day was not well tolerated and was replaced with a lower 3 g/kg/day.

TABLE 39

Change in PT, APTT, and FIB concentration in Rats administered 15(S)-HEP EE

| STUDY | 26 week rat study (CRL509554) | | |
|---|---|---|---|
| 15 (S)-HEPE EE Dose (mg/kg/day) | 0 (vehicle) | 2000 | 6000/3000 |
| Prothrombin Time (PT) (sec) | | | |
| Mean | 10.25 | 10.69** | 10.81** |
| (SD) | 0.34 | 0.41 | 0.47 |
| Activated Partial Thromboplastic Time (APTT) (sec) | | | |
| Mean | 12.92 | 15.03* | 15.73** |
| (SD) | 2.12 | 2.64 | 2.00 |

TABLE 39-continued

Change in PT, APTT, and FIB concentration in Rats administered 15(S)-HEP EE

| STUDY | 26 week rat study (CRL509554) | | |
|---|---|---|---|
| Fibrinogen (FIB) (g/L) | | | |
| Mean | 2.61 | 2.35** | 2.26** |
| (SD) | 0.25 | 0.29 | 0.24 |

Anova & Dunnett: * = p ≤ 0.05; ** = p ≤ 0.01
All presented values were observed in males
Highest dose of 6 g/kg/day was not well tolerated and was replaced with lower 3 g/kg/day dose Change in PT: FIG. 39A and Table 39 show that administration of both the 2 g/kg/day and 3 g/kg/day dose resulted in a significant increase in PT compared to control.

Change in APTT: FIG. 39B and Table 39 show that administration of both the 2 g/kg/day and 3 g/kg/day doses resulted in a significant increase in APTT compared to control.

Change in FIB concentration: FIG. 39C and Table 39 show that administration of both the 2 g/kg/day and 3 g/kg/day doses resulted in a significant decrease in FIB concentration compared to control.

These results suggest that 15-HEPE has anticoagulant and antithrombotic effects.

Various embodiments of the present disclosure are set forth herein below:

Para. A. A method of treating and/or preventing metabolic syndrome in a subject in need thereof, the method comprising administering to the subject 15-HEPE, 15-HETrE, or a composition comprising 15-HEPE and/or HETrE.

Para. B. A method of treating and/or preventing cardiometabolic disease in a subject in need thereof, the method comprising administering to the subject 15-HEPE, 15-HETrE, or a composition comprising 15-HEPE and/or HETrE.

Para. C. A method of treating and/or preventing metabolic syndrome and/or cardiometabolic disease in a subject in need thereof, the method comprising administering to the subject up to about 8 g of a composition comprising 15-HEPE and/or 15-HETrE, wherein the 15-HEPE and/or 15-HETrE represents at least about 90%, by weight, all fatty acids in the composition.

Para. D. A method of treating and/or preventing metabolic syndrome and/or cardiometabolic disease in a subject in need thereof, the method comprising administering to the subject up to about 8 g of a composition comprising 15-HEPE, wherein the 15-HEPE represents at least about 90%, by weight, all fatty acids in the composition and, wherein the subject exhibits one or more of: a reduction in diglyceride, glycerophospholipid, hepatic fat, blood pressure, waist circumference, and/or free fatty acid levels; and/or an increase in glycerophospholipid levels.

Para. E. A method of preventing a first stage of non-alcoholic steatohepatitis (NASH) from progressing to a second stage of NASH in a subject, the method comprising administering to the subject up to about 8 g of a composition comprising 15-HEPE.

Para. F. The method of Para. E, wherein the first stage is metabolic overload, increased hepatic fat content and lipotoxicity, cell stress apoptosis, inflammation, and/or fibrogenic remodeling.

Para. G. The method as in Para. E or Para. F, wherein the second stage is increased hepatic fat content and lipotoxicity, cell stress apoptosis, inflammation, and/or fibrogenic remodeling.

Para. H. A method of treating and/or preventing cardiovascular disease in a subject having non-alcoholic fatty liver disorder (NAFLD), metabolic syndrome, and/or cardiometabolic disease in a subject in need thereof, the method comprising administering to the subject 15-HEPE, 15-HETrE, or a composition comprising 15-HEPE and/or HETrE.

Para. I. A method of treating and/or preventing cardiovascular disease in a subject having non-alcoholic fatty liver disorder (NAFLD), metabolic syndrome, or cardiometabolic disease in a subject in need thereof, the method comprising administering to the subject up to about 8 g of a composition comprising 15-HEPE, wherein the 15-HEPE represents at least about 90%, by weight, all fatty acids in the composition.

Para. J. The method as in any one of Paras. A to I, wherein the subject exhibits a reduction in one or more of: α-smooth muscle action (α-SMA), metallopeptidase inhibitor-1 (TIMP-1), transforming growth factor beta-β (TGF-β), and/or Collagen Type 1 levels.

Para. K. The method as in any one of Paras. A to C or E to J, wherein the subject exhibits a reduction in diglyceride, hepatic fat, blood pressure, waist circumference, and/or free fatty acid levels and/or an increase in glycerophospholipid levels.

Para. L. The method as in any one of Paras. A to K, wherein the subject exhibits a reduction in alkaline phosphate (ALP) levels.

Para. M. The method as in any one of Paras. A to L, wherein the subject exhibits a reduction in serum alanine aminotransferase (ALT), aspartate aminotransferase (AST), and/or bilirubin (BUN) levels.

Para. N. The method as in any one of Paras. A to M, wherein the subject exhibits a reduction in fibrosis area.

Para. O. The method as in any one of Paras. A to N, wherein the subject exhibits a reduction in hemoglobin A1C (HbA1C), homeostatic model assessment of insulin resistance (HOMA-IR), and/or adipose tissue insulin resistance (adipo-IR) levels.

Para. P. The method as in any one of Paras. H to O, wherein the NAFLD is non-alcoholic steatohepatitis (NASH).

Para. Q. The method as in any one of Paras. B to D or F to P, wherein the cardiometabolic disease or the cardiovascular disease is one or more of: dyslipidemia, hyperlipidemia, hypercholesterolemia, hypertriglyceridemia, primary hypercholesterolemia, primary hyperlipidemia, common primary hyperlipidemia, common hypercholesterolemia, familial hyperlipidemia, familial primary hyperlipidemia, familial hypercholesterolemia, familial hypertriglyceridemia, familial combined hyperlipidemia, familial defective apolipoprotein b-100, secondary hyperlipidemia, mixed hyperlipidemia, cardiovascular disease, residual cardiovascular risk, prevention of atherosclerotic plaque formation/progression, microvascular disease, macrovascular disease, atherosclerosis, coronary atherosclerosis, diastolic dysfunction, reduction of cardiovascular risk, prevention of major coronary events, prevention of major adverse cardiovascular events, prevention of ischemic events, secondary/primary prevention of cardiovascular events, prevention of cardiovascular death, myocardial infarction, stroke, angina, restoration of normal endothelial function, diabetes, diabetes mellitus, insulin resistance, hyperinsulinemia, hyperglycemia, dysglycemia, induction of glycemic control, impaired glucose tolerance, and impaired fasting glucose.

Para. R. The method of Para. Q, wherein the microvascular disease is retinopathy, nephropathy, neuropathy, or combination thereof.

Para. S. The method of Para. Q, wherein the macrovascular disease is stroke, peripheral vascular disease, limb ischemia, heart disease, or combination thereof.

Para. T. The method as in any one of Paras. A to S, wherein the subject exhibits a reduction in very low-density lipoprotein cholesterol (VLDL-C), non-high-density lipoprotein cholesterol (non-HDL-C), and/or remnant-like particle cholesterol (RLP-C) and/or a high-density lipoprotein cholesterol (HDL-C) levels.

Para. U. The method as in any one of Paras. A to T, wherein the subject exhibits a reduction in liver stiffness, fibrosis-4 (FIB-4), enhanced liver fibrosis (ELF) score and/or NAFLD score (NFS).

Para. V. The method as in any one of Paras. A to U, wherein the subject exhibits a reduction in inflammatory and pro-fibrotic proteins selected from the group consisting of plasminogen activator inhibitor-1 (PAI-1), metallopeptidase inhibitor-1 (TIMP-1), dipeptidyl peptidase 4 (DPP4), trem-like transcript 2 (TLT2), chemokine (C—C motif) ligand 16 (CCL16), monocyte chemoattractant protein-1 (MCP-1), serum amyloid A4 (SAA4), phosphoinositide 3 (PI3), thioredoxin reductase (TR), leukocyte immunoglobulin like receptor B1 (LILBR1), amine oxidase, copper containing 3 (AOC3), serine protease 2 (PRSS2), and tumor necrosis factor ligand superfamily member 11A (TNRSF11A).

Para. W. A method of treating or preventing cholestatic liver disease in a subject, the method comprising administering to the subject 15-HEPE, 15-HETrE, or a composition comprising 15-HEPE and/or 15-HETrE.

Para. X. The method of Para. W, wherein the cholestatic liver disease is primary biliary cholangitis (PBC), primary sclerosing cholangitis (PSC), progressive familial intrahepatic cholestasis, or combination thereof.

Para. Y. The method of Para. W. or Para. X, wherein the cholestatic liver disease is caused by a drug induced liver injury, total parenteral nutrition (TPN), viral and alcoholic hepatitis, cholestasis secondary to systemic diseases, graft dysfunction, post liver transplant cholestasis, pancreatitis, choledocholithiasis, Mirizzi syndrome, genetic diseases, malignancy, or combination thereof.

Para. Z. The method of Para. Y, wherein the malignancy is a hepatocellular carcinoma, a bile duct tumor, pancreatic carcinoma, or combination thereof.

Para. AA. The method as in any one of Paras. W to Z, wherein the subject exhibits a reduction in cytokines and/or chemokines selected from the group consisting α-smooth muscle action (α-SMA), metallopeptidase inhibitor-1 (TIMP-1), transforming growth factor beta-β (TGF-β), and Collagen Type 1 levels.

Para. BB. A method of treating or preventing kidney disease in a subject, the method comprising administering to the subject 15-HEPE and/or 15-HETrE or a composition comprising 15-HEPE and/or 15-HETrE, wherein the subject has at least one risk factor for kidney disease.

Para. CC. The method of Para. BB, wherein the kidney disease is selected from the group consisting of kidney fibrosis, tubulointerstitial fibrosis, chronic kidney disease, severe interstitial fibrosis, renal interstitial fibrosis, and end stage renal disease.

Para. DD. The method of Para. CC, wherein the kidney disease leads to fibrosis.

Para. EE. The method as in any one of Paras. BB to DD, wherein the at least one risk factor for a kidney disease is selected from the group consisting of diabetes, high blood pressure, cardiovascular disease, glomerulonephritis, and polycystic kidney disease.

Para. FF. The method as in any one of Paras. BB to EE, wherein the subject exhibits a reduction in kidney hydroxyproline levels.

Para. GG. The method as in any one of Paras. BB to FF, wherein the subject exhibits no increase in α-SMA, TIMP-1, TGF-β, and/or Collagen Type 1 levels.

Para. HH. The method as in any one of Paras. BB to GG, wherein the subject exhibits a reduction in α-SMA, TIMP-1, TGF-β, and/or Collagen Type 1 levels.

Para. II. The method as in any one of Paras. AA to HH, wherein the subject exhibits a reduction in pro-fibrotic cytokines in the liver.

Para. JJ. The method of Para II, wherein the pro-fibrotic cytokines are one or more of α-SMA, TIMP-1, TGF-β, Collagen Type 1, interleukin 1β (IL-1β), interleukin-6 (IL-6), interleukin-6 (IL-8), interleukin-13 (IL-13), tumor necrosis factor (TNF-α), TNF-like ligand 1A (TL1A), aryl hydrocarbon receptor (AhR), interleukin-17 (IL-17), interleukin-23 (IL-23), interleukin-11 (IL-11), and/or interleukin-33 (IL-33).

Para. KK. The method as in any one of Paras. A to JJ, wherein the subject exhibits a reduction in vascular adhesion molecules and/or chemokines and/or tumor necrosis factor receptor superfamily members.

Para. LL. The method as in any one of Paras, A to KK, wherein the 15-HEPE, 15-HETrE, or the composition comprising 15-HEPE and/or 15-HETrE is orally administered.

Para. MM. The method as in any one of Paras. A to LL, wherein the 15-HEPE and/or 15-HETrE is in free acid form, esterified form, or salt form.

Para. NN. The method of Para. MM, wherein the esterified form is an alkyl ester form or a triglyceride form.

Para. OO. The method as in any one of Paras. A to NN, wherein the 15-HEPE comprises 15(S)-HEPE, 15(R)-HEPE, or combinations thereof and/or the 15-HETrE comprises 15(S)-HETrE, 15(R)-HETrE, or combinations thereof.

Para. PP. The method as in any one of Paras. A to OO, wherein the composition comprises about 1 g to about 2 g of 15-HEPE and/or 15-HETrE.

Para. QQ. The method as in any one of Paras. A to PP, wherein the composition comprises about 2 g or more of 15-HEPE and/or 15-HETrE.

Para. RR. The method as in any one of Paras. A to QQ, wherein the composition comprises about 1 g or about 2 g of 15-HEPE and/or 15-HETrE.

Para. SS. The method as in any one of Paras. A to RR, wherein the composition comprises about 10 mg to about 10,000 mg of 15-HEPE and/or 15-HETrE.

Para. TT. The method as in any one of Paras. A to SS, wherein the composition comprises about 5 mg/kg, about 50 mg/kg, about 250 mg/kg, or about 500 mg/kg of 15-HEPE and/or 15-HETrE.

Para. UU. The method as in any one of Paras. A to TT, wherein the 15-HEPE and/or 15-HETrE represents at least about 90%, by weight, of all fatty acids present in the composition.

Para. W. The method as in any one of Paras. A to UU, wherein the composition is administered in 1 to 8 capsules per day.

Para. WW. The method as in any one of Paras. A to C or H to W, wherein the method comprises administering to the subject 15-HEPE or a composition comprising 15-HEPE.

Para. XX. The method as in any one of Paras. A to C or H to VV, wherein the method comprises administering to the subject 15-HETrE or a composition comprising 15-HETrE.

Para. YY. A method of treating and/or preventing a hematologic disorder in a subject in need thereof, the method comprising administering to the subject 15-hydroxyeicosapentaenoic acid (15-HEPE) or a composition comprising 15-hydroxyeicosapentaenoic acid (15-HEPE).

Para. ZZ. The method of Para. YY, wherein the hematologic disorder is selected from the group consisting of anemia, blood cancer, and coagulation defects.

Para. AB. The method of Para. ZZ, wherein the anemia is selected from the group consisting of nutritional anemias and non-nutritional anemias.

Para. AC. The method of Para. ZZ, wherein the blood cancer is selected from the group consisting of lymphoma, leukemia, and myeloma.

Para. AD. The method of Para. ZZ, wherein the coagulation defect is selected from the group consisting of thrombophilia, hemophilia, Von Willebrand disease, and thrombocytopenia.

Para. AE. A method of treating and/or preventing a hemoglobin disorder in a subject in need thereof, the method comprising administering to the subject 15-HEPE or a composition comprising 15-hydroxyeicosapentaenoic acid (15-HEPE).

Para. AF. A method of treating and/or preventing a red blood cell disorder in a subject in need thereof, the method comprising administering to the subject 15-HEPE or a composition comprising 15-hydroxyeicosapentaenoic acid (15-HEPE).

Para. AG. A method of treating and/or preventing a hemoglobin disorder and/or a red blood cell disorder in a subject in need thereof, the method comprising administering to the subject up to about 8 g of a composition comprising 15-HEPE, wherein the 15-HEPE represents at least about 90% by weight, of all fatty acids in the composition.

Para. AH. A method of treating and/or preventing a hemoglobin disorder and/or a red blood cell disorder in a subject in need thereof, the method comprising administering to the subject up to about 8 g of a composition comprising 15-HEPE, wherein the 15-HEPE represents at least about 90% by weight, of all fatty acids in the composition, and wherein the subject exhibits one or more of:
(a) an increase in red blood cell count;
(b) a decrease in red cell distribution width; and/or
(c) a decrease in reticulocyte count.

Para. AI. The method Para. AH, wherein where the subject has an increase in red blood cell count of at least 10%, at least 15%, at least 20%, at least 25%, or at least 30% compared to a control subject not receiving the composition.

Para. AJ. The method of Para. AI, wherein the control subject has a red blood cell count of about $4 \times 10^{12}$ red blood cells/L.

Para. AK. The method of Para. AH, wherein the subject has a decrease in red blood cell distribution width of about 15-20%, of about 20-25%, of about 25-30%, of about 30-35%, or of about 35-40% compared to a control subject not receiving the composition.

Para. AL. The method of Para. AK, wherein the control subject has a red blood cell distribution width greater than 15%.

Para. AM. The method of Para. AH, wherein the subject has a decrease in reticulocyte count of at least about 5%, at least about 10%, at least about 15%, or at least about 20% compared to a control subject not receiving the composition.

Para. AN. The method of Para. AM, where the control subject has a reticulocyte count greater than 5% of the total number of red blood cells.

Para. AO. A method of treating and/or preventing hemolytic anemia in a subject in need thereof, the method comprising administering to the subject up to about 8 g of a composition comprising 15-HEPE, wherein the 15-HEPE represents at least about 90% by weight, of all fatty acids in the composition.

Para. AP. The method of Para. AO, wherein the hemolytic anemia is inherited hemolytic anemia or acquired hemolytic anemia.

Para. AQ. The method of Para. AP, wherein the inherited hemolytic anemia is selected from the group consisting of sickle cell disease, sickle cell anemia, β-thalassemia, and hereditary spherocytosis.

Para. AR. The method of Para. AP, wherein the acquired hemolytic anemia is selected from the group consisting of secondary to infection, medication, hematological malignancy, autoimmune disease, hypersplenism, mechanical heart valves, and blood transfusions.

Para. AS. The method of Para. AQ, wherein the sickle cell disease and sickle cell anemia are associated with sickle cell crisis, vaso-occlusive crisis, and/or splenic sequestration.

Para. AT. The method of any one of the preceding Paras. YY to AS, wherein the 15-HEPE is in the form of an ethyl ester (15-HEPE EE) or the 15-HEPE is in the form of an optically active ester (15(S)-HEPE EE).

Para. AU. A method of any one of Paras. AE to AN, wherein the hemoglobin disorder and/or the red blood cell disorder are selected from the group consisting of inherited hemolytic anemia, acquired hemolytic anemia, Fanconi anemia, iron deficiency anemia, folate deficiency, B12 deficiency, and myelodysplastic syndrome.

Para. AV. The method of any one of Paras. YY to AG, or AO to AT, wherein the subject exhibits an increase in red blood cell count, a decrease in reticulocyte count, and a decrease in red cell distribution width.

Para. AW. A method of treating and/or preventing a hematologic disorder and/or a blood disorder in a subject in need thereof, the method comprising administering to the subject up to about 8 g of a composition comprising 15-HEPE, wherein the 15-HEPE represents at least about 90% by weight, of all fatty acids in the composition.

Para. AX. The method of Para. AW, wherein the 15-HEPE is in the form of an ethyl ester (15-HEPE EE) or the 15-HEPE is in the form of an optically active ester (15(S)-HEPE EE).

Para. AY. The method of Para. AW, wherein the hematologic disorder and/or the blood disorder are selected from the group consisting of inherited hemolytic anemia, acquired hemolytic anemia, Fanconi anemia, iron deficiency anemia, folate deficiency, B12 deficiency, and myelodysplastic syndrome.

Para. AZ. The method of Para. AY, wherein the hemolytic anemia is inherited hemolytic anemia or acquired hemolytic anemia.

Para. BA. The method of Para. AZ, wherein the inherited hemolytic anemia is selected from the group consisting of sickle cell disease, sickle cell anemia, β-thalassemia, and hereditary spherocytosis.

Para. BC. The method of Para. AZ, wherein the acquired hemolytic anemia is selected from the group consisting of secondary to infection, medication, hematological malignancy, autoimmune disease, hypersplenism, mechanical heart valves, and blood transfusions.

Para. BD. The method of Para. BA, wherein the sickle cell disease and sickle cell anemia are associated with sickle cell crisis, vaso-occlusive crisis, and/or splenic sequestration.

Para. BE. The method of any one of Paras AW to BD, wherein the subject exhibits an increase in red blood cell count, a decrease in reticulocyte count, and a decrease in red cell distribution width.

Para. BF. A method of treating and/or preventing thrombophilia disorder in a subject in need thereof, the method comprising administering to the subject 15-HEPE or a composition comprising 15-hydroxyeicosapentaenoic acid (15-HEPE).

Para. BG. A method of treating and/or preventing thrombophilia in a subject in need thereof, the method comprising administering to the subject up to about 8 g of a composition comprising 15-HEPE, wherein the 15-HEPE represents at least about 90% by weight, of all fatty acids in the composition.

Para. BH. A method of treating and/or preventing thrombophilia in a subject in need thereof, the method comprising administering to the subject up to about 8 g of a composition comprising 15-HEPE, wherein the 15-HEPE represents at least about 90% by weight, of all fatty acids in the composition, and wherein the subject exhibits one or more of:
(a) an increase in prothrombin time;
(b) an increase in activated partial thromboplastin time; and/or
(c) a decrease in fibrinogen concentration.

Para. BI. A method of treating and/or preventing a venous thromboembolism in a subject in need thereof, the method comprising administering to the subject up to about 8 g of a composition comprising 15-HEPE, wherein the 15-HEPE represents at least about 90% by weight, of all fatty acids in the composition.

Para. BJ. A method of treating and/or preventing an arterial thrombosis in a subject in need thereof, the method comprising administering to the subject up to about 8 g of a composition comprising 15-HEPE, wherein the 15-HEPE represents at least about 90% by weight, of all fatty acids in the composition.

Para. BK. A method of preventing an embolism in a subject in need thereof, the method comprising administering to the subject up to about 8 g of a composition comprising 15-hydroxyeicosapentaenoic acid (15-HEPE), wherein the 15-HEPE represents at least about 90% by weight, of all fatty acids in the composition.

Para. BL. The method of Paras. BI to BK, wherein the first stage is formation of a thrombus.

Para. BM. The method of any one of Paras. BF to BG or BI to BL, wherein the subject exhibits an increase in prothrombin time, an increase in activated partial thromboplastin time, and a decrease in fibrinogen concentration.

Para. BN. The method of any one of Paras. YY to BM, wherein the 15-HEPE is orally administered.

Para. BO. The method of any one of Paras. YY to BN, wherein the composition is administered in 1 to 8 capsules per day.

Para. BP. The method of any one of Pars. YY to BO, wherein the 15-HEPE is in free acid form, esterified form, or salt form.

Para. BQ. The method of any one Paras. YY to BP, wherein the composition comprises about 1 g to about 2 g of 15-HEPE.

Para. BR. The method of any one of Paras. YY to BQ, wherein the composition comprises about 2 g to more of 15-HEPE.

Para. BS. The method of any one Paras. YY to BR, wherein the composition comprises about 5 mg/kg, about 50 mg/kg, about 250 mg/kg, or about 500 mg/kg or 15-HEPE.

We claim:

1. A method of treating a red blood cell disorder in a subject in need thereof, the method comprising administering to the subject a therapeutically effective amount of 15-HEPE ethyl ester or a composition comprising 15-HEPE ethyl ester, wherein the red blood cell disorder is an inherited hemolytic anemia or an acquired hemolytic anemia.

2. The method of claim 1, wherein the subject has an increase in red blood cell count, a decrease in red blood cell distribution width, and/or a decrease in reticulocyte count compared to a control subject not receiving the 15-HEPE ethyl ester or the composition.

3. The method of claim 1, wherein the subject has an increase in red blood cell count of at least 10%, at least 15%, at least 20%, at least 25%, or at least 30% compared to a control subject not receiving the 15-HEPE ethyl ester or the composition.

4. The method of claim 3, wherein the control subject has a red blood cell distribution width greater than 15%.

5. The method of claim 4, wherein the subject has a decrease in reticulocyte count of at least about 5%, at least about 10%, at least about 15%, or at least about 20% compared to a control subject not receiving the 15-HEPE ethyl ester or the composition.

6. The method claim 5, where the control subject has a reticulocyte count greater than 5% of the total number of red blood cells.

7. The method of claim 1, wherein the inherited hemolytic anemia is selected from the group consisting of sickle cell disease, sickle cell anemia, β-thalassemia, and hereditary spherocytosis.

8. The method of claim 1, wherein the acquired hemolytic anemia is acquired from a disorder or condition selected from the group consisting of a condition secondary to a primary infection, a medication, a hematological malignancy, an autoimmune disease, hypersplenism, positioning of a mechanical heart valve, and a blood transfusion.

9. The method of claim 7, wherein the sickle cell disease and sickle cell anemia are associated with sickle cell crisis, a vaso-occlusive crisis, and/or splenic sequestration.

* * * * *